US009493842B2

(12) United States Patent
Giaccone et al.

(10) Patent No.: US 9,493,842 B2
(45) Date of Patent: Nov. 15, 2016

(54) USE OF GTF21 MUTATIONS IN THE PROGNOSIS OF THYMIC CANCERS

(71) Applicant: The United States of America, as represented by the Secretary, Department of Health and Human Services, Washington, DC (US)

(72) Inventors: Giuseppe Giaccone, Bethesda, MD (US); Yisong Wang, Columbia, MD (US); Iacopo Petrini, Pisa (IT)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/676,987

(22) Filed: Apr. 2, 2015

(65) Prior Publication Data
US 2015/0284807 A1 Oct. 8, 2015

Related U.S. Application Data

(60) Provisional application No. 61/975,222, filed on Apr. 4, 2014.

(51) Int. Cl.
*C12Q 1/68* (2006.01)
*C07H 21/04* (2006.01)
*A61K 39/395* (2006.01)
*C12Q 1/70* (2006.01)
*G01N 33/574* (2006.01)
*A61N 5/10* (2006.01)

(52) U.S. Cl.
CPC .............. *C12Q 1/6886* (2013.01); *A61N 5/10* (2013.01); *G01N 33/57407* (2013.01); *C12Q 2600/118* (2013.01); *C12Q 2600/156* (2013.01); *G01N 2333/4703* (2013.01)

(58) Field of Classification Search
None
See application file for complete search history.

(56) References Cited

U.S. PATENT DOCUMENTS

2003/0092019 A1* 5/2003 Meyer .................... C07K 14/47
435/6.14
2006/0121497 A1* 6/2006 Morse .................. C12Q 1/6883
435/6.16

OTHER PUBLICATIONS

Malenfant (J Autism Dev Disord (2012) vol. 42 pp. 1459-1469 pre-pub online Nov. 3, 2011).*
GenBank dbSNP rs202059251 (added with build 137 on Jun. 26, 2012).*
Hegele (Arterioscler Throm Vasc Biol 2002 vol. 22 pp. 1058-1061).*
Lucentini (The Scientist 2004 vol. 18 pp. 1-3).*
Mummidi et al (Journal of Biological Chemistry 2000 vol. 275 No. 25 pp. 18946-18961).*
Girard (Clin Cancer Res 2009; 15(22) Nov. 15, 2009 pp. 6790-6799).*
Nishida (BMC Genomics 2008 9:431).*
Belinsky (Genes, Chromosomes & Cancer 48:886-896 (2009).*
Adzhubei et al., "A method and server for predicting damaging missense mutations," *Nat. Methods*, 7 (4), 248-249 (2010), author manuscript.
Arbajian et al., "A novel GTF2I/NCOA2 fusion gene emphasizes the role of NCOA2 in soft tissue angiofibroma development," *Genes Chromosomes Cancer*, 52, 330-331 (2013).
Ashworth et al., "Phase specific functions of the transcription factor TFII-I during cell cycle," *Cell Cycle*, 8 (4), 596-605 (2009).
Bailey et al., "Recent segmental duplications in the human genome," *Science*, 297, 1003-1007 (2002).
Benson, "Tandem repeats finder: a program to analyze DNA sequences," *Nucleic Acids Res.*, 27 (2), 573-580 (1999).
Berendsen et al., "Molecular dynamics with coupling to an external bath," *J. Chem. Phys.*, 81 (8), 3684-3690 (1984).
Beroukhim et al., "Assessing the significance of chromosomal aberrations in cancer: Methodology and application to glioma," *PNAS*, 104 (50), 20007-20012 (2007).
Chen et al., "Enhanced growth inhibition by combined DNA methylation/HDAC inhibitors in lung tumor cells with silenced CDKN2A," *Int. J. Oncol.*, 37 (4), 963-971 (2010).
Chiaromonte et al., "Scoring pairwise genomic sequence alignments," *Pac. Symp. Biocomput.*, 115-126 (2002).
Cingolani et al., "A program for annotating and predicting the effects of single nucleotide polymorphisms SnpEff: SNPs in the genome of *Drosophila melanogaster* strain $w^{1118}$; iso-2; iso-3," *Fly*, 6 (2), 80-92 (2012).
Darden et al., "Particle mesh Ewald: An N log(N) method for Ewald sums in large systems," *J. Chem. Phys.*, 98 (12), 10089-10092 (1993).
Desgranges et al., "Inhibition of TFII-I-Dependent Cell Cycle Regulation by p53," *Mol. Cell Biol.*, 25 (24), 10940-10952 (2005).
Ge et al., "FusionMap: detecting fusion genes from next-generation sequencing data at base-pair resolution," *Bioinformatics*, 27 (14), 1922-1928 (2011).
Genbank Accession No. AA641906.1 (Jan. 7, 2011).
Genbank Accession No. ABBA1063881.1 (May 22, 2007).
Genbank Accession No. ABBA1063882.1 (May 22, 2007).
Genbank Accession No. AC004883.3 (Mar. 23, 2002).
Genbank Accession No. AC005231.3 (Apr. 26, 2003).
Genbank Accession No. AC083884.6 (Jan. 31, 2004).
Genbank Accession No. AC211433.4 (Jan. 27, 2009).
Genbank Accession No. AF015553.1 (Sep. 20, 1997).
Genbank Accession No. AF035737.1 (Mar. 28, 1998).
Genbank Accession No. AF038967.1 (Mar. 28, 1998).
Genbank Accession No. AF038968.1 (Mar. 28, 1998).
Genbank Accession No. AF038969.1 (Mar. 28, 1998).
Genbank Accession No. AK057670.1 (Jan. 9, 2008).
Genbank Accession No. AK093663.1 (Jan. 9, 2008).
Genbank Accession No. AK096095.1 (Jan. 9, 2008).

(Continued)

*Primary Examiner* — Amanda Haney
(74) *Attorney, Agent, or Firm* — Leydig, Voit & Mayer

(57) ABSTRACT

Disclosed are methods of determining the prognosis of thymic cancer in a subject comprising detecting a mutation in the general transcription factor IIi (GTF2I) genetic sequence or protein. The presence of a GTF2I mutation indicates that the thymic cancer is indolent.

19 Claims, No Drawings

(56) References Cited

OTHER PUBLICATIONS

Genbank Accession No. AK292832.1 (Jan. 9, 2008).
Genbank Accession No. AK294935.1 (Jul. 24, 2008).
Genbank Accession No. AK297238.1 (Jul. 24, 2008).
Genbank Accession No. BC004472.2 (Mar. 8, 2005).
Genbank Accession No. BC070484.1 (Jul. 15, 2006).
Genbank Accession No. BC099907.1 (Jul. 15, 2006).
Genbank Accession No. BT007450.1 (May 13, 2003).
Genbank Accession No. CB118501.1 (Jul. 20, 2010).
Genbank Accession No. CH471200.2 (Mar. 23, 2015).
Genbank Accession No. DC346283.1 (Jan. 10, 2008).
Giaccone et al., "Phase II of the Belinostat in Patients With Recurrent or Refractory Advanced Thymic Epithelial Tumors," *J. Clin. Oncol.*, 29 (15), 2052-2059 (2011).
Jurka, "Repbase update: a database and an electronic journal of repetitive elements," *Trends Genet.*, 16 (9), 418-20 (2000).
Kelly et al., "Thymic Malignancies: From Clinical Management to Targeted Therapies," *J. Clin. Oncol.*, 29, 4820-4827 (2011).
King et al., "Mutagenic Analysis of the Destruction Signal of Mitotic Cyclins and Structural Characterization of Ubiquitinated Intermediates," *Mol. Biol. Cell.*, 7, 1343-57 (1996).
Koboldt et al., "VarScan: variant detection in massively parallel sequencing of individual and pooled samples," *Bioinformatics*, 25 (17), 2283-2285 (2009).
Kumar et al., "Predicting the effects of coding non-synonymous variants on protein function using the SIFT algorithm," *Nat. Protoc.*, 4 (8), 1073-1081 (2009).
Li et al., "Fast and accurate short read alignment with Burrows—Wheeler Transform," *Bioinformatics*, 25 (14), 1754-1760 (2009).
Li et al., "Transformation potential of Ras isoforms correlates with activation of phosphatidylinositol 3-kinase but not ERK," *J. Biol. Chem.*, 279 (36), 37398-37406 (2004).
Masaoka et al., "Follow-Up Study of Thymomas with Special Reference to Their Clinical Stages," *Cancer*, 48 (11), 2485-2492 (1981).
McKenna et al., "The Genome Analysis Toolkit: A MapReduce framework for analyzing next-generation DNA sequencing data," *Genome Res.*, 20, 1297-1303 (2010).
McPherson et al., "An Algorithm for Gene Fusion Discovery in Tumor RNA-Seq Data," *PLoS Comput. Biol.*, 7 (5), e1001138, 1-16 (2011).
Ostrovnaya et al., "A classification model for distinguishing copy number variants from cancer-related alterations," *BMS Bioinformatics*, 11, 297, 1-13 (2010).
Perez Jurado et al., "A duplicated gene in the breakpoint regions of the 7q11.23 Williams—Beuren syndrome deletion encodes the initiator binding protein TFII-I and BAP-135, a phosphorylation target of BTK," *Human Molecular Genetics*, 7 (3), 325-334 (1998).
Petrini et al., "A specific missense mutation in GTF21 occurs at high frequency in thymic epithelial tumors," *Nat Genet.*, 46 (8), 844-849 (2014).
Petrini et al., "Copy number aberrations of BCL2 and CDKN2A/B identified by array-CGH in thymic epithelial tumors," *Cell Death Dis.*, 3, e351, 1-11 (2012).
Rajan et al., "Cixutumumab for patients with recurrent or refractory, advanced thymic epithelial tumors: a multicentre, open-label, phase 2 trial," *Lancet Oncol.*, 15, 191-200 (2014) author manuscript.
Rajan et al., "Treatment of Advanced Thymoma and Thymic Carcinoma," *Current Treatment Options in Oncology*, 9, 277-287 (2008).
Roy, "Biochemistry and biology of the inducible multifunctional transcription factor TFII-I: 10 Years Later," *Gene*, 492, 32-41 (2012) author manuscript.
Saunders et al., "Strelka: accurate somatic small-variant calling from sequenced tumor—normal sample pairs," *Bioinformatics*, 28 (14), 1811-1817 (2012).
Trapnell et al., "TopHat: discovering splice junctions with RNA-Seq," *Bioinformatics*, 25 (9), 1105-1111 (2009).
Travis et al., *Pathology and Genetics: Tumors of the lung, pleura, thymus, and heart*, IARC Press, Lyon, France (2004).
Wang et al., ANNOVAR: functional annotation of genetic variants from high-throughput sequencing data, *Nucleic Acids Res.*, 38 (16), e164, 1-7 (2010).
Zucali et al., "Reproducibility of the WHO classification of thymomas: practical Implications," *Lung Cancer*, 79 (3), 236-241 (2013) author manuscrip.

\* cited by examiner

US 9,493,842 B2

USE OF GTF2I MUTATIONS IN THE PROGNOSIS OF THYMIC CANCERS

CROSS-REFERENCE TO RELATED APPLICATION

This patent application claims the benefit of U.S. Provisional Patent Application No. 61/975,222, filed Apr. 4, 2014, which is incorporated by reference in its entirety herein.

INCORPORATION-BY-REFERENCE OF MATERIAL SUBMITTED ELECTRONICALLY

Incorporated by reference in its entirety herein is a computer-readable nucleotide sequence listing submitted concurrently herewith and identified as follows: One 260,721 Byte ASCII (Text) file named "720112ST25.TXT," dated Mar. 11, 2015.

BACKGROUND OF THE INVENTION

While some thymic cancers may be relatively benign, there are some subtypes that may be aggressive. The currently available histological classification and staging systems may not be sufficiently informative about the prognosis of these cancers. Accordingly, there is a need for improved methods of determining the prognosis of thymic cancers.

BRIEF SUMMARY OF THE INVENTION

An embodiment of the invention provides a method of determining the prognosis of thymic cancer in a subject, the method comprising: obtaining genetic material from the subject; assaying the genetic material to detect a mutation in at least one copy of general transcription factor IIi (GTF2I) genetic sequence; and correlating the presence of a GTF2I mutation with the prognosis of thymic cancer in the subject, wherein the presence of the mutation indicates that the thymic cancer is indolent.

Another embodiment of the invention provides a method of determining the prognosis of thymic cancer in a subject, the method comprising: obtaining a sample from the subject; assaying the sample to detect a mutation in GTF2I protein; and correlating the presence of a mutation in the GTF2I protein with the prognosis of thymic cancer in the subject, wherein the presence of the mutation indicates that the thymic cancer is indolent.

Another embodiment of the invention provides a method for detecting a GTF2I mutation in a subject, wherein the subject has thymic cancer, the method comprising: obtaining genetic material from the subject; and assaying the genetic material to detect a mutation in at least one copy of GTF2I genetic sequence.

Still another embodiment of the invention provides a method for detecting a mutated GTF2I protein in a subject, wherein the subject has thymic cancer, the method comprising: obtaining a sample from the subject; and assaying the sample to detect a mutation in GTF2I protein.

DETAILED DESCRIPTION OF THE INVENTION

It has been discovered that a mutation in the general transcription factor IIi (GTF2I) gene is present in indolent thymic tumors and is rarely found in more aggressive thymic tumors. GTF2I is a transcription factor that regulates the transcription of genes that control cell proliferation (e.g., c-FOS), the cell cycle (e.g., cyclin-D1), and developmental processes. GTF2I binds specifically to several DNA sequences and mediates growth factor signaling. Human GTF2I is assigned Gene NCBI Gene ID No. 2969, and an Mendelian Inheritance in Man (MIM) No. 601679. The human GTF2I gene is found on chromosome 7 at 7q11.23. A wild type genomic GTF2I DNA sequence comprises SEQ ID NO: 1. Five (wild type) transcriptional variants include the GTF2I alpha (α) isoform (SEQ ID NO: 3), beta (β) isoform (SEQ ID NO: 4), gamma (γ) isoform (SEQ ID NO: 5), delta (δ) isoform (SEQ ID NO: 6), and epsilon (∈) isoform (SEQ ID NO: 7).

An embodiment of the invention provides a method of determining the prognosis of thymic cancer in a subject, the method comprising: obtaining genetic material from the subject; assaying the genetic material to detect a mutation in at least one copy of GTF2I genetic sequence; and correlating the presence of a GTF2I mutation with the prognosis of thymic cancer in the subject, wherein the presence of the mutation indicates that the thymic cancer is indolent. The inventive methods may provide many advantages. For example, the inventive methods may, advantageously, help the clinician decide whether treatment is needed (for example, additional treatment after surgery) or what type of treatment is needed (such as, for example, an aggressive course of treatment for more aggressive cancers). The inventive methods are also, advantageously, more objective than currently available histological classification and staging systems.

The thymic cancer may be any thymic cancer. In an embodiment of the invention, the thymic cancer is a thymic epithelial tumor (TET). Preferably, the TET is a thymic carcinoma (TC) or a thymoma. According to the 2004 World Health Organization (WHO) classification system, thymomas are further classified into A, AB, B1, B2 and B3 types according to their histological features (Travis et al., *Pathology and genetics: Tumors of the lung, pleura, thymus and heart*, IARC Press, Lyon, France (2004)). Type A and AB thymomas have the best prognosis, with 10-year survival rates close to 100%, wheras TCs are the most aggressive TETs with 50% 10-year survival (Kelly et al., *J Clin. Oncol.*, 29: 4820-7 (2011)). Preferably, the subject is a human.

In an embodiment, the method comprises obtaining genetic material from the subject. Obtaining genetic material from the subject may be carried out in any suitable manner known in the art. In an embodiment of the invention, the genetic material is obtained from tumor tissue. The genetic material may be obtained, for example, from tumor resection material or a tumor biopsy.

In an embodiment, the inventive method involves assaying genetic material obtained from a test subject to detect a mutation in at least one copy of the GTF2I genetic sequence. The genetic material can be, for example, DNA (for example, genomic DNA or complementary DNA (cDNA)) or RNA (e.g., (messenger RNA (mRNA)). In an embodiment of the invention, the genetic material is cDNA or mRNA of a GTF2I isoform selected from the group consisting of the GTF2I α isoform, GTF2I β isoform, GTF2I γ isoform, GTF2I δ isoform, and GTF2I ∈ isoform.

The genetic material may be obtained directly from a tumor of the test subject, or the genetic material can be copied or amplified from genetic material within the test subject's tumor cells (e.g., via polymerase chain reaction (PCR), reverse transcription polymerase chain reaction (RT-PCR), or other suitable technique). For example, epithelial cells can be harvested from the tumor tissue to obtain genetic material. To ensure that a sufficient quantity of genetic material is available for testing, genetic material may be amplified from cells obtained from the test subject, and the amplified genetic material is assayed in accordance with the inventive method. Preferably, a PCR or RT-PCR strategy is employed using primers flanking all or a portion of the GTF2I gene, so as to amplify this sequence from the test subject for the assay. While the method may comprise amplifying and assaying one copy of the GTF2I gene, preferably, the method comprises amplifying both copies of the GTF2I gene from the test subject, so that both can be assayed in accordance with the inventive method.

However obtained, the method comprises assaying the genetic material to detect a mutation in the GTF2I gene (e.g., a mutation at least one of the two GTF2I alleles). Any test able to detect mutations appropriate to the type of genetic material (e.g., genomic DNA (gDNA), cDNA, RNA) may be employed. The assaying may comprise obtaining the sequence of at least a portion of the GTF2I genetic sequence or obtaining the sequence of substantially all of the GTF2I genetic sequence. In an embodiment, the method may further comprise comparing the sequence of the genetic material of the subject to the sequence of the wild type GTF2I genetic sequence and identifying any differences between the sequence of the genetic material of the subject and the wild type GTF2I genetic sequence to detect any mutations. Examples of wild type GTF2I genetic sequences may include, for example, SEQ ID NO: 1 (wild type GTF2I genomic DNA), SEQ ID NO: 2 (wild type GTF2I exon 15), SEQ ID NO: 3 (wild type GTF2I alpha ($\alpha$) isoform cDNA), SEQ ID NO: 4 (wild type beta ($\beta$) isoform cDNA), SEQ ID NO: 5 (wild type gamma ($\gamma$) isoform cDNA), SEQ ID NO: 6 (wild type delta ($\delta$) isoform cDNA), or SEQ ID NO: 7 (wild type epsilon ($\in$) isoform cDNA). Other examples of wild type GTF2I genetic sequences may include Genbank Accession Nos. ABBA01063881.1, ABBA01063882.1, AC004883.3, AC005231.3, AC083884.6, AC211433.4, CH471200.2, AA641906.1, AF015553.1, AF035737.1, AF038967.1, AF038968.1, AF038969.1, AK057670.1, AK093663.1, AK096095.1, AK292832.1, AK294935.1, AK297238.1, BC004472.2, BC070484.1, BC099907.1, BT007450.1, CB118501.1, and DC346283.1. In an embodiment of the invention, the assaying comprises carrying out a PCR assay that specifically detects the mutation. Examples of PCR assays that specifically detect the mutation may include any one or more of (i) carrying out PCR using primers that amplify the mutated GTF2I genetic sequence but not the wild type GTF2I genetic sequence; (ii) carrying out PCR using primers that amplify the wild type GTF2I genetic sequence but not the mutated GTF2I genetic sequence; and (iii) carrying out PCR using primers that amplify the mutated GTF2I genetic sequence, the wild type GTF2I genetic sequence, and GTF2I pseudogenes, but the sequences of the PCR products make it possible to distinguish the mutated GTF2I genetic sequence from the wild type GTF2I genetic sequence as well as GTF2I pseudogenes. In an embodiment of the invention, the primers used in the PCR assay amplify the GTF2I genetic sequence (wild type or mutated) but not GTF2I pseudogenes.

The GTF2I mutation may be any type of gene mutation. For example, the GTF2I mutation may be any one or more of a missense mutation, a nonsense mutation, an insertion, a deletion, a duplication, and a frameshift mutation. Preferably, the GTF2I mutation is a missense mutation.

The GTF2I mutation may be located anywhere in the coding sequence of the GTF2I gene. In an embodiment of the invention, the GTF2I mutation is located in exon 15 of the GTF2I gene. Preferably, the mutation is chr7:74146970 T/A.

In an embodiment of the invention, the mutation is selected from the group consisting of: (a) g.75,041T>A, with reference to SEQ ID NO: 1; (b) c.1208T>A, with reference to SEQ ID NO: 3; (c) c.1211T>A, with reference to SEQ ID NO: 4; (d) c.1271T>A, with reference to SEQ ID NO: 5; (e) c.1148T>A, with reference to SEQ ID NO: 6; and (f) c.1205T>A, with reference to SEQ ID NO: 7. The GTF2I genetic mutations g.75,041T>A, c.1208T>A, c.1211T>A, c.1271T>A, c.1148T>A, and c.1205T>A are defined herein by reference to the wild type genomic DNA sequence (SEQ ID NO: 1) or one of the five wild type isoform cDNA sequences of GTF2I (SEQ ID NO: 3-7). Thus, these GTF2I genetic mutations are described herein by reference to genomic DNA ("g.") or cDNA ("c."), followed by the particular position in the sequence at which the mutation is taking place, followed by the native nucleotide at that position, followed by the nucleotide with which the native nucleotide is being replaced.

In an embodiment of the invention, the genetic material comprising the mutation comprises a nucleotide sequence selected from the group consisting of SEQ ID NO: 8 (mutated GTF2I cDNA); SEQ ID NO: 9 (mutated GTF2I genomic DNA); SEQ ID NO: 10 (mutated GTF2I alpha isoform cDNA); SEQ ID NO: 11 (mutated GTF2I beta isoform cDNA); SEQ ID NO: 12 (mutated GTF2I gamma isoform cDNA); SEQ ID NO: 13 (mutated GTF2I delta isoform cDNA); SEQ ID NO: 14 (mutated GTF2I epsilon isoform cDNA); and a complement of any one of SEQ ID NOs: 8-14.

The method further comprises correlating the presence of a GTF2I mutation with the prognosis of thymic cancer in the subject, wherein the presence of the mutation indicates that the thymic cancer is indolent. An indolent cancer may be characterized by any one or more of slow growth, less metastasis, fewer symptoms, an earlier cancer stage (e.g., at diagnosis), a higher chance of complete resection, and a longer survival time as compared to a cancer that lacks the GTF2I mutation. In an embodiment of the invention, the absence of a GTF2I mutation indicates that the thymic cancer is aggressive. An aggressive cancer may be characterized by any one or more of fast growth, more metastasis, more symptoms, a later cancer stage, a lower chance of complete resection, and a shorter survival time as compared to a cancer that has the GTF2I mutation. In an embodiment of the invention, the prognosis indicates the likelihood of the subject's 10-year survival. In this regard, the presence of the mutation indicates that the subject will have a significantly higher chance to survive 10 years and the absence of the mutation indicates that the subject will have a significantly lower chance to survive 10 years.

In an embodiment of the invention, the presence of the mutation indicates that the thymic cancer is, or has a high likelihood of being, a thymoma histotype A or AB according to the 2004 WHO classification (Travis et al., *Pathology and genetics: Tumors of the lung, pleura, thymus and heart*, IARC Press, Lyon, France, (2004)). In an embodiment, the absence of the mutation indicates that the thymic cancer is, or has a high likelihood of being, thymoma histotype B1, B2, or B3 or a TC according to the 2004 WHO classification. As described in the Examples, the presence of GTF2I mutation has been seen significantly more frequently in histologically indolent tumors (WHO type A and AB) than in more aggressive histological tumors (WHO B3 and thymic carcinoma). In addition, aggressive tumors (such as B3 thymomas and thymic carcinomas) that have the GTF2I mutation have a better prognosis than those tumors without the mutation. According to the 2004 WHO classification, A type thymomas present bland spindle/oval epithelial tumor cells with few or no lymphocytes. Grossly, they are usually encapsulated and easily separable from the surrounding organs even in case of tumors of conspicuous dimension. Type B thymomas show epithelial cells with a predominantly round or polygonal appearance. Type B1 thymomas display tumor epithelial cells with very little atypia, scattered in a prominent population of immature non-neoplastic thymocytes that resemble the structure of normal thymus cortex. Type B2 thymomas are characterized by large polygonal epithelial tumor cells arranged in a loose network containing numerous immature T lymphocytes. B3 thymomas are composed of medium size round or polygonal epithelial tumor cells with slight atypia; these cells are mixed with a minor component of intraepithelial thymocytes. AB thymomas are composed of a lymphocyte-poor type A and a more lymphocyte-rich type B component.

In an embodiment of the invention, the presence of the mutation indicates that the cancer is, or is more likely to be, in an early stage (cancer stage I-II). In an embodiment of the invention, the absence of the mutation indicates that the cancer is, or is more likely to be, in an advanced stage (cancer stage III-IV) (Masaoka et al., *Cancer*, 48(11): 2485-92 (1981)).

Another embodiment of the invention provides a method for detecting a GTF2I mutation in a subject, the method comprising: obtaining genetic material from the subject; and assaying the genetic material to detect a mutation in at least one copy of GTF2I genetic sequence. Obtaining a sample from the subject and assaying the genetic material may be carried out as described herein with respect to other aspects of the invention. In an embodiment, the subject has thymic cancer, which may be as described herein with respect to other aspects of the invention. The GTF2I mutation may also be as described herein with respect to other aspects of the invention.

In an embodiment of the invention, the method further comprises treating thymic cancer in the subject based on the presence or absence of the mutation. The inventive methods of determining the prognosis of thymic cancer in a subject may, advantageously, make it possible for an attending clinician to determine whether a particular treatment is necessary and, if so, how much treatment is necessary. In an embodiment of the invention, the method comprises treating thymic cancer in the subject when the mutation is present by surgically removing all or part of the thymic cancer without administering one or more of, two or more of, or all three of (i) radiotherapy, (ii) chemotherapy, and (iii) immunotherapy in an amount effective to treat thymic cancer in the subject. In this regard, when the mutation is present, treating thymic cancer in the patient may comprise not treating the patient with one or more of, two or more of, or all three of (i) radiotherapy, (ii) chemotherapy, and (iii) immunotherapy. Accordingly, the inventive methods may, advantageously, make it possible for a patient with the mutation to avoid or reduce exposure to one or more of, two or more of, or all three of (i) radiotherapy, (ii) chemotherapy, and (iii) immunotherapy and the accompanying side effects. In addition, the inventive methods may, advantageously, make it possible for a patient with an indolent thymic cancer to avoid or reduce the harmful effects on the heart that are associated with radiotherapy.

In an embodiment of the invention, the method may comprise treating thymic cancer in the subject when the mutation is absent by surgically removing all or part of the thymic cancer and administering one or more of, two or more of, or all three of (i) radiotherapy, (ii) chemotherapy, and (iii) immunotherapy in an amount effective to treat thymic cancer in the subject. The chemotherapy may comprise any suitable chemotherapy. For example, the chemotherapy may comprise administering any one or more of doxorubicin (ADRIAMYCIN), epirubicin (ELLENCE), belinostat, cisplatin, carboplatin, cyclophosphamide (CYTOXAN), ifosfamide (IFEX), vincristine (ONCOVIN), etoposide (VP-16), paclitaxel (TAXOL), pemetrexed (ALIMTA), 5-fluorouracil (5-FU), methylprednisolone, octreotide, gefitinib, imatinib, and gemcitabine (GEMZAR) to the subject in an amount effective to treat thymic cancer in the subject. Belinostat has antitumor activity in heavily pretreated thymic malignancies (Giaccone et al., *J. Clin. Oncol.*, 29: 2052-2059 (2011)). The immunotherapy may comprise any suitable immunotherapy. For example, the immunotherapy may comprise administering one or both of bevacizumab and cixutumumab to the subject in an amount effective to treat thymic cancer in the subject. Cixutumumab may be useful for treating thymoma (Rajan et al., *Lancet Oncol.*, 15: 191-200 (2014)). Various treatments for thymic cancer are described in Rajan et al., *Curr. Treatment Options Oncol.*, 9: 277-287 (2008).

The term "treat," as well as words stemming therefrom, as used herein, does not necessarily imply 100% or complete treatment. Rather, there are varying degrees of treatment of which one of ordinary skill in the art recognizes as having a potential benefit or therapeutic effect. In this respect, the inventive methods can provide any amount of any level of treatment of cancer in a subject. Furthermore, the treatment provided by the inventive method can include treatment of one or more conditions or symptoms of the disease, e.g., cancer, being treated.

Another embodiment of the invention provides a method of determining the prognosis of thymic cancer in a subject, the method comprising: obtaining a sample from the subject; assaying the sample to detect a mutation in GTF2I protein; and correlating the presence of a mutation in the GTF2I protein with the prognosis of thymic cancer in the subject, wherein the presence of the mutation indicates that the thymic cancer is indolent.

In an embodiment, the method comprises obtaining a sample from the subject. In an embodiment, the sample is a tumor tissue sample. Obtaining a sample from the subject may be carried out in any suitable manner known in the art, and the sample may be from any suitable source, for example, from tumor resection material or a tumor biopsy.

The method further comprises assaying the sample to detect a mutation in GTF2I protein. For example, the GTF2I protein can be purified from the sample (either partially or substantially and assayed via immunohistological techniques (e.g., Western blotting, ELISA, immunoprecipitation, etc.) using one or more antibodies recognizing mutant GTF2I protein but not wild type GTF2I protein. In this regard, the assaying may comprise contacting the sample with an antibody that specifically binds to mutant GTF2I protein and does not bind to wild type GTF2I protein, thereby forming a complex, and detecting the complex. Alternatively, or in conjunction, the GTF2I protein sample from the test subject can be assayed using one or more antibodies recognizing wild type GTF2I protein but not mutant GTF2I protein. In this regard, the assaying may comprise contacting the sample with an antibody that specifically binds to wild type GTF2I protein and does not bind to mutant GTF2I protein, thereby forming a complex, and detecting the complex. In an embodiment, the wild type GTF2I protein comprises an amino acid sequence selected from the group consisting of SEQ ID NO: 31 (wild type alpha isoform GTF2I protein), SEQ ID NO: 32 (wild type beta isoform GTF2I protein), SEQ ID NO: 33 (wild type gamma isoform GTF2I protein), SEQ ID NO: 34 (wild type delta isoform GTF2I protein), and SEQ ID NO: 35 (wild type epsilon isoform GTF2I protein). In an embodiment, the GTF2I protein with the mutation comprises an amino acid sequence selected from the group consisting of SEQ ID NO: 15 (mutated alpha isoform GTF2I protein), SEQ ID NO: 16 (mutated beta isoform GTF2I protein), SEQ ID NO: 17 (mutated gamma isoform GTF2I protein), SEQ ID NO: 18 (mutated delta isoform GTF2I protein), and SEQ ID NO: 19 (mutated epsilon isoform GTF2I protein).

In an embodiment, the mutation is selected from the group consisting of: (a) p.Leu403His, with reference to SEQ ID NO: 31; (b) p.Leu404His, with reference to SEQ ID NO: 32; (c) p.Leu424His, with reference to SEQ ID NO: 33; (d) p.Leu383His, with reference to SEQ ID NO: 34; and (e) p.Leu402His, with reference to SEQ ID NO: 35. The GTF2I protein mutations pieu403His, p.Leu404His, p.Leu424His, p.Leu383His, and p.Leu402His are defined herein by reference to one of the five wild type isoform amino acid sequences of GTF2I (SEQ ID NO: 31-35). Thus, these GTF2I protein mutations are described herein by reference to protein ("p."), followed by the native amino acid residue being replaced, followed by the particular position in the sequence at which the mutation is taking place, followed by the amino acid residue with which the native amino acid residue is being replaced.

The method further comprises correlating the presence of a mutation in the GTF2I protein with the prognosis of thymic cancer in the subject, wherein the presence of the mutation indicates that the thymic cancer is indolent. Correlating the presence of a mutation in the GTF2I protein with the prognosis of thymic cancer in the subject may be carried out as described herein with respect to other aspects of the invention.

Another embodiment of the invention provides a method for detecting a mutated GTF2I protein in a subject, the method comprising: obtaining a sample from the subject; and assaying the sample to detect a mutation in GTF2I protein. Obtaining a sample and assaying the sample may be carried out as described herein with respect to other aspects of the invention. The mutated GTF2I protein may be as described herein with respect to other aspects of the invention. In an embodiment, the subject has thymic cancer, which may be as described herein with respect to other aspects of the invention.

In an embodiment of the invention, the method further comprises treating thymic cancer in the subject based on the presence or absence of the mutation in the GTF2I protein. Treating thymic cancer in the subject based on the presence or absence of the mutation may be carried out as described herein with respect to other aspects of the invention.

The following examples further illustrate the invention but, of course, should not be construed as in any way limiting its scope.

Examples

Materials and Methods

Tumor samples of 286 patients were collected from four different institutions: National Cancer Institute (NCI) (Bethesda Md.), Pisa University Hospital (Pisa, Italy), Padua University Hospital (Padua, Italy) and IRCCS Istituto Clinico Humanitas (Rozzano, Italy). All patients selected for this study were enrolled in protocols approved at the participating institutions and a written informed consent for genome profiling (including array comparative genomic hybridization (CGH) and sequencing) was obtained from all study participants.

Nucleic Acid Extraction:

Samples of thymic epithelial tumors were collected during surgical procedures or through an image guided tumor biopsy. The collected specimens were immediately frozen in liquid nitrogen. Samples were embedded in optimal cutting temperature compound (OCT) and 8 μm slices were cut using a cryostat. A pathologist evaluated the slices after haematoxylin and eosin (H&E) staining in order to select regions rich of tumor cells for macro-dissection. Samples were annotated with pathologist's estimation of tumor cellularity. DNA and RNA were extracted at the same time from the selected tumor portion using ALL PREP RNA/DNA kit (Qiagen, Valencia, Calif.).

From paraffin embedded (FFPE) blocks, 4 and 10 μm slices were cut using a microtome. 4 μm slides were stained with haematoxylin and eosin and a pathologist confirmed the tumor diagnosis and selected the tumor material. 10 μm slides were deparaffinized using HISTOCHOICE Clearing Agent (Sigma-Aldrich, St. Louis, Mo.) and rehydrated through alcohol series. Thereafter, the stained and the 10 μm slides, from the same block, were matched and the selected regions rich in tumor cells were scraped from the rehydrated slides. DNA was extracted using DNEASY Blood and Tissue kit (Qiagen) according to vendor's protocol but with an extended proteinase K digestion of at least 16 hours (h) at 70° C.

Patient's blood (5 mL) was collected in ethylenediaminetetraacetic acid (EDTA) tubes and frozen at −80° C. DNA was extracted from the whole blood using QIAAMP DNA Blood Maxi Kit (Qiagen).

Array Comparative Genomic Hybridization:

Tumors were chosen for array Comparative Genomic Hybridization (aCGH) depending on the availability of frozen material and on their tumor cell content: only samples rich in cancer cells (>80%) were selected. Array CGH was performed in 65 cases. Array CGH was performed as previously described (Petrini et al., *Cell Death Dis.*, 3: e351 (2012)). The reference human genome was the NCBI version 37.1. Data were analyzed using Nexus 7 (Biodiscovery Inc., El Segundo, Calif., USA) according to the following pipeline. A systematic correction was applied to the data in order to limit the wave-like artifacts due to the genomic regions rich in GC nucleotides. The bias estimations were determined using a linear model that took into account the percentage of CG content and the length of the fragments. Bias estimations were then subtracted from the Log2Ratio of the probes. Thereafter, probes were re-centered through normalization to the median Log2Ratio of the diploid regions that were determined sample by sample. Segmentation was performed using Rank Segmentation algorithm according to the following settings: a significant threshold of 5.0E-6, maximum contiguous probe spacing of 1000 kb and a minimum of 10 probes per segment. Sex chromosomes were removed from the analysis. The presence of CN aberrations, candidate drivers of the tumor growth, was assessed using GISTIC algorithm (Beroukhim et al., *PNAS*, 104: 20007-12 (2007)). Regions with a Q-bound lower than 0.25 and a G-score higher than one were considered significant. GISTIC peaks related to germline CN variations were filtered out. The Toronto database of genomic variants (Iafrate et al., *Nat. Genet.*, 36: 949-51 (2004)) was adopted to define regions of germline CN variations. If a GISTIC peak was fully mapped in one of these regions, the peak was removed from the list of significant results. Chromosome arm level CN aberrations were defined when more than 80% of a chromosome arm (p or q) was covered by CN gains or losses. For example, chromosome 1q is 100,313,968 base pairs (bp) long. A single CN gain of a portion of chromosome 1q longer than 80,251,174 bp (80% of 100'313'968) will be classified as an arm level CN gain of chromosome 1q. Also, an arm level CN gain of chromosome 1q will be described if the sum of the lengths of three regions of CN gains mapped on 1q exceeds 80,251,174 bp. As previously described (Petrini et al., *Cell Death Dis.*, 3: e351 (2012)), the 80% cutoff for the definition of chromosome arm level CN aberration was chosen based on the frequency distribution of the length of CN aberrations. A hierarchical cluster of tumors was built using complete linkage of their chromosome arm level CN aberrations.

Transcriptome Sequencing:

Samples were selected for transcriptome sequencing if their RNA integrity number was >8, the H&E staining demonstrated a proportion of cancer cells >80%, and copy number aberrations larger than 5 Mb were detected using aCGH, in order to safely exclude germline copy number variations that usually (99%) are shorter than 2.3 Mb (Ostrovnaya et al., *BMC Bioinformatics*, 11: 297 (2010)). Type A thymomas were exceptions because typically they do not present copy number aberrations. Type A thymomas were safely included upon pathology review since they always present a scant thymocyte component (non-neoplastic precursors of lymphocytes). Transcriptome sequencing was conducted at the NCI sequencing facility according to the ILLUMINA mRNA sample preparation kit (Illumina, San Diego, Calif.). Briefly, using poly-T-bound magnetic beads, poly-A mRNAs were captured from total RNA. First and second strand cDNA were serially synthetized. Overhanging fragments' ends were repaired using T4 DNA and Klenow DNA polymerases and adaptors linked using T4 DNA Ligase. Ligation products were run on an agarose gel, the 200 bp band was excised and used for DNA extraction. cDNA libraries were generated from the purified products and subsequently validated with the 2100 Agilent bioanalyzer (Agilent). According to the instructions, cDNA libraries were hybridized to a flow cell, amplified, linearized and denatured using Illumina Cluster Station, in order to generate pair-end clusters ready for sequencing. Genome Analyzer II or HiSeq2000 were used for sequencing.

Transcriptome Sequencing Data Analysis Workflow:

Human genome hg19 was chosen as reference and only sequences mapped to human chromosomes chr1-22, X, Y, and M were retained. FASTQ files were obtained directly from the sequencing machine programmed to automatically trim the adaptors and barcode sequences. The reads were mapped to the reference genome using TopHat (Trapnell et al., *Bioinformatics*, 25: 1105-11 (2009)). Quality of the RNA sequencing results was assessed using CollectRnaSeqMetrics available in Picard tools and with FASTQC software.

Estimation of Gene Expression:

Gene expression was estimated from the mapped reads using Cufflinks algorithm. The log10 transformation of the FPKM+1 values was used to cluster thymic epithelial tumors. Samples were clustered using a hierarchical cluster and uncentered Pearson Correlation. Two samples with high duplication rate and the cell lines were removed from the cluster analysis.

Prediction and Validation of Fusion Transcripts:

Candidate fusion transcripts were identified from the FASTQ files using two independent algorithms: FusionMap with MONO Version 2.10.8 (Ge et al., *Bioinformatics*, 27: 1922-28 (2011)) and DeFuse (McPherson et al., *PLoS Comput. Biol.*, 7: e1001138 (2011)). The following parameters were used according to previous reports (Ge et al., *Bioinformatics*, 27: 1922-28 (2011)): MinimalFusionAlignmentLength=25, FusionReportCutoff=1 and NonCanonicalSpliceJunctionPenalty=4. Moreover, at least 20 seed reads were required to support the predicted candidates.

Fusion candidates were identified and filtered as previously described (McPherson et al., *PLoS Comput. Biol.*, 7: e1001138 (2011)). The predicted fusion transcripts identified by both methods were evaluated using the BLAT tool from the UCSC website. Predicted fusions were excluded from the candidates' list if one fusion arm had multiple possible alignments with an identity >95% or if they overlapped a region of human chained self alignment (Chiaromonte et al., *Pac. Symp. Biocomput.*, 115-26 (2002)) or a region annotated with: segmental duplications (Bailey et al., *Science*, 297: 1003-7 (2002)), repeat maskers (Jurka et al., *Trends Genet.*, 16: 418-20 (2000)), interrupted repeats (Jurka et al., *Trends Genet.*, 16: 418-20 (2000)) and simple repeat (Benson et al., *Nucleic Acids Res.*, 27: 573-80 (1999)). The fusion transcripts included in this filtered list of candidates were validated using reverse transcription polymerase chain reaction (RT-PCR) and Sanger sequencing. In brief, reverse transcription was performed using High Capacity cDNA Reverse Transcription kit (Applied Biosystems, Foster City, Calif.). PCR primers were designed on opposite sides of the fusion junction and were tagged with M13 forward and reverse primer sequences. The reactions were carried out using Taq DNA polymerase (Invitrogen) and two negative controls: cDNA from normal thymus of two unrelated subjects were included for each fusion candidate in order to exclude nonspecific amplification. Amplicons were run on an agar gel and if the predicted size band was detected, PCR products underwent EXOSAP-IT (USB, Cleveland, Ohio) purification and Sanger sequencing. Fusions were considered validated if the forward and reverse sequences were uniquely mapped to the predicted fusion transcript and if at least one of them spanned the junction sequence. The confirmed fusion transcripts were visualized using Circus-0.64.

Exome Sequencing:

Samples were included in the exome sequencing analysis if they fulfilled the following criteria: 1) tumor and normal DNA from the same patient were available, 2) the tumor sample selected for DNA extraction presented at least 80% of tumor cells in H&E stained slides from the same specimen and 3) array CGH analysis revealed the presence of CN aberrations larger than 5 Mb. Type A thymomas were included based on pathology review only, since they usually do not present CN aberrations, but are rich in epithelial cells. Exonic sequences were enriched using different capture-based platforms. Exome capture procedures were performed according to the respective vendors' instructions. Exon-enriched libraries were subsequently paired-end sequenced using Illumina's Genome Analyzer-II or HiSeq2000.

Exome Sequencing Data Analysis Workflow:

Raw FASTQ sequence reads were firstly mapped to human genome 19 (USCS) using Novoalign and then local realignment was performed around insertions/deletions (INDELs) using Genome Analysis Tool Kit (GATK). The duplicated reads were removed using Picard tool (http://picard.sourceforge.net/) and base quality score recalibration was performed using Genome Analysis Tool Kit (GATK). Using VarScan2 (Kobolt et al., *Bioinformatics*, 25: 2283-5 (2009)), somatic mutations were identified by comparing the tumor and normal bam files of each patient. The detected somatic single nucleotide variations (SNVs) and INDELs were annotated using snpEff. Predicted SNVs and INDELs were further filtered and accepted if all of the following requirements were met: 1) at least 4 reads carrying the mutation in tumor bam file, 2) mutations present in more than 20% of the reads mapped to the mutation locus, 3) at least eight reads covering the mutation locus in the normal bam file and 4) no more than 2% of reads carrying the mutation in normal bam file. In order to further reduce the false positive calls, mutations identified as germline in at least one different patient blood control were filtered out.

The somatic mutations of the coding regions identified using exome sequencing have been further annotated using Annovar (Wang et al., *Nucleic Acids Res.*, 38: e164 (2010)) with NCBI dbSNP Build 137data, Cosmic database, SIFT (Kumar et al., *Nat. Protoc.*, 4: 1073-81 (2009)) and Polyphen2 (Adzhubei et al., *Nat. Methods*, 7: 248-9 (2010)) scores.

Confirmation and Re-Sequencing of the Selected Mutated Genes:

The exome sequencing data was validated using independently prepared libraries for high depth sequencing on MISEQ sequencers (Illumina) using a custom panel of 197 genes. DNAs were extracted and fragmented by sonication. Then, indexed DNA libraries were prepared by three successive steps of end-repair, A-tailing and adapter ligation to the DNA fragments. In subsequent PCR amplification steps, primers containing a flow cell attachment site (P5), sequencing primer sites for index read (Index SP) and application read two (Rd2 SP), unique six by indices (Index) and a second flow cell attachment site (P7), were incorporated. The indexed libraries were then pooled in groups of up to 12, target enriched (Agilent), and sequenced. Sequence data were processed with in-house variant calling pipeline, which includes BWA alignment (Li et al., *Bioinformatics*, 25: 1754-60 (2009)), GATK local realignment (McKenna et al., *Genome Res.*, 20: 1297-303 (2010)), Strelka somatic variant calling (Saunders et al., *Bioinformatics*, 28: 1811-7 (2012)), SnpEff and SnpSift variant annotation (Cingolani et al., *Fly (Austin)*, 6: 80-92 (2012)).

Sanger Sequencing of GTF2I Locus:

Sanger sequencing is able to detect mutations if present in a substantial percentage of cells (15-20%). This limits the possibility to detect GTF2I mutations if the gene and the pseudogene sequences were amplified at the same time with non-specific primers because the mutation would be present in only 1:6 (17%) of the amplicons if heterozygous. In order to design specific primers for GTF2I, the nucleotide difference in exon 15 (C in the gene and T in the pseudogenes) was noted. A forward primer (ATCCCGTAC-CCTCTTTTCC) (SEQ ID NO: 20) was designed with its last 3' base covering the C nucleotide that is specific for the GTF2I gene. The reverse primer (AGACAAGAGT-TCAACAGG) (SEQ ID NO: 21) anneals to both GTF2I and pseudogene sequences. These primers were tagged with M13 forward and reverse sequences. DNA containing exclusively GTF2I sequence or the pseudogene sequences was used for the optimization of the PCR conditions. The plasmids containing exclusively GTF2I exon-15 or the pseudogene sequences were generated during the TopoTA cloning experiments. With a melting temperature of 62.5° C. only the GTF2I sequence was amplified. PCR was performed using Taq DNA Polymerase (Invitrogen) with 1.5 mM MgCl$_2$, and 200 nM of forward and reverse primers, according to the following amplification STEPs: STEP 1: 94° C. 1:00 min; STEP2: 94° C. 30 sec, 62.5° C. 30 sec, 72° C. 45 sec (×35 times); STEP3: 72° C. 7:00 min. The amplicons were purified using ExoSap-IT (USB) and sequenced according to Sanger method with M13 Forward and M13 Reverse primers. The chr7:74146970 locus was inspected for mutations on both strands using Mac Vector.

GTF2I Deep Sequencing:

Using PCR amplification followed by direct deep sequencing, the chr7: 74146970T/A mutation of GTF2I was sequenced in 250 samples. Forward and reverse primers were tailed with Illumina Adapter tags for downstream next generation sequencing using the BioMark HD System (Fluidigm) and Access Array Integrated Fluidic Circuit (IFC) chips and kits (Fluidigm). Additionally, PCR products were indexed using an 8-mer oligo barcode. DNA was sequenced using 500-cycle MISEQ Reagent Kits V2 (Illumina) and the MISEQ Benchtop Sequencer (Illumina).

GTF2I Deep Sequencing Data Analysis:

In order to avoid potential alignment problems arising from the presence of the two pseudogenes homologous to GTF2I in the genome, a new algorithm was developed to avoid the alignment step altogether. The sequence of the primers used in the target selection/library preparation of the DirectSeq protocol are present at the 5' end of each (valid) sequencer read. Only reads with a perfect match to the first 10 nucleotides (nt) of any of the DirectSeq primers were retained for further analysis. Depending on the relative position (Tables 2 and 3) with respect to the recognized primer sequence, the nucleotide N1 discriminating between gene/pseudogene and the nucleotide N2 discriminating between variant/wild type were identified. Across the entire dataset, the number of all possible combinations was counted for N1, N2 for each primer. This count included nucleotide combinations not fitting the combinations CT (gene/WT), CA (gene/mutant), TT (pseudogene/WT), TA (pseudogene/mutant) expected in the gene/pseudogene, WT/variant model as controls. These non-canonical combinations typically made up less than 1% of the reads associated with the primer, in line with the typical error rate of Illumina sequencers. Subsequently, this number was used as an estimate for the read error rate R as long as this estimate exceeded R>0.5%, otherwise R=0.5% was used as the noise estimate. A variant was called if the number of reads compatible with a mutated gene exceeded the number of reads expected as a result of read errors by at least 5*R, i.e.

$$\frac{\#\left(\frac{mut}{gene}\right)}{\left(\#\left(\frac{mut}{gene}\right)+\#\left(\frac{wt}{gene}\right)\right)} > 5*R$$

P-values for the association of the mutation status with WHO classification and stage were estimated using a Chi-square test utilizing a flat distribution as the null-model.

Survival Analysis:

Kaplan-Meier method was used to generate survival curves. Disease Related Survival (DRS) was calculated from the date of the first histological diagnosis to the date of death due to tumor progression. DRS was chosen instead of the overall survival because, given the expected long survival, especially in the most indolent thymomas, and the advanced age of many patients, death was often not related to the tumor. Survival curves were compared by the Log Rank test. A Cox proportional hazard model was initially built for the univariate analysis, which included WHO groupings (A, AB, B1 vs B2, B3, TC), stage (I-II vs III-IV), completeness of resection (R0 vs R1-R2) and GTF2I mutation status. Subsequently, multivariate analysis was performed including prognostic factors found in the univariate analysis (p<0.1). All tests were performed using the SPSS version 20 (SPSS, Inc., Chicago, Ill.).

Structural Model and Molecular Dynamics of GTF2I:

A structural model of GTF2i was based on the solution structure of GTF2I (Brookhaven Protein Data Bank [PDB]: 2DN4). GTF2I was energy minimized using the consistent valence force field AMBER 10.0 simulation package. The cutoff for nonbonded interaction energies was set to 00 (no cutoff); other parameters were set to default. The dielectric constant was set at $\in=4$ to account for the dielectric shielding found in proteins. The minimization was conducted in two steps: the first using steepest descent minimization for 5000 cycles and then using conjugate gradient minimization until the average gradient fell to <0.01 kcal/M.

Using the energy-minimized structure of GTF2i as the initial model, three ns molecular dynamics (MD) simulations with a distant-dependent dielectric constant were conducted by using the SANDER module of the AMBER 10.0 simulation package with the PARM98 force-field parameter. MD simulations were performed using 0.001-ps time steps with temperature set at 300° K. The SHAKE algorithm was used to keep all bonds involving hydrogen atoms rigid. Temperature and pressure coupling algorithms (Berendsen et al., *J. Chem. Phys.*, 81: 3684 (1984)) were used to maintain constant temperature and pressure. Electrostatic interactions were calculated with the Ewald particle mesh method (Darden et al., *J. Chem. Phys.*, 98: 10089 (1993)), and a dielectric constant at one Rij and a nonbonded cutoff of 14 Å was used to the approximate electrostatic interactions and van der Waals interactions. Structural analyses were done using the SYBYL X.1 (Tripos International, St. Louis, Mo.) molecular modeling program.

Ectopic Expression of GTF2I Mutation:

pEBB plasmids containing GTF2I beta (NM_033000.2) and delta (NM_001518.3) isoforms were purchased from Addgene. The GTF2I sequence in the plasmid was sequenced and two synonymous and one non-synonymous mutations were identified in both isoforms. The non-synonymous mutations were corrected using site directed mutagenesis. Similarly, the chr7:74146970 T/A mutation was introduced in the plasmid using QuikChange Site-Directed Mutagenesis Kit (Agilent), according to the vendor protocol. The primers to introduce the mutation were designed using primer X and included the following: sense primer: (SEQ ID NO: 22) and antisense primer: (SEQ ID NO: 23).

A beta L404H and a delta L383H mutated isoform were generated in a pEBB plasmid. The mutated and wild type GTF2I isoforms were first moved into a donor vector (pDONR221vector) through a recombinase reaction (GATEWAY BP CLONASE II Enzyme mix, Invitrogen) and subsequently moved into a lentiviral vector (pLenti6.3/V5-DEST GATEWAY Vector kit, Invitrogen) using GATEWAY LR CLONASE II Enzyme mix (Invitrogen), according to the vendor's instructions. The pLenti6.3/V5-DEST plasmids with GTF2I WT and mutated isoforms were transfected into NIH-3T3 cells (purchased from ATCC, Manassas, Va.) using Lipofectamine LTX (Invitrogen). NIH-3T3 cells were grown in DMEM (Gibco, Invitrogen) supplemented with 50 U/mL penicillin, 50 U/mL streptomycin (Invitrogen) and 10% heat-inactivated fetal bovine serum (Invitrogen) and grown in a 37° C. incubator with humidified 5% $CO_2$ atmosphere. P-BABEpuro vector containing $HRAS^{V12H}$ was purchased from Addgene and used as positive control for softagar assay (Li et al., *J. Biol. Chem.*, 279(36): 37398-406 (2004)). Stable clones were selected using 8 μg/ml blasticidin or 1 μg/ml puromycin when appropriate (Gibco, Invitrogen). For each GTF2I isoform (both wild type (WT) and mutated), four independent stable pool transfectants were obtained. Stable ectopic GTF2I expression was confirmed by western blot using anti-V5 antibody (Invitrogen) and anti-α-Tubulin (Sigma-Aldrich) as loading control.

Cell Proliferation and Soft Agar Assay:

$HRAS^{V12H}$ and mock-transfected NIH-3T3 cells were the positive (Li et al., *J. Biol. Chem.*, 279(36): 37398-406 (2004)) and negative controls, respectively. 1000 cells/well were plated in 96-well plates and tested for cell proliferation using a luminescent method (CELLTITER-GLO Luminescent Cell Viability Assay, Promega, Madison, Wis.) at 24, 48, 72 and 96 hours. For WT and mutated GTF2I isoforms, four different stable pools were included in the experiments. Each experiment was replicated at least three times and the average of cell proliferation was calculated for both WT and mutated β- and δ-GTF2I isoforms. Soft agar assay was performed as previously described (Chen et al., *Int. J. Oncol.*, 37(4): 963-71 (2010)) using 5000 cells for each well of a 6-well plate. Experiments were performed at least three times and averages were calculated from the results of four distinct pools of each GTF2I variant. Expression of endogenous GTF2I was tested by western blot using anti-GTF2I antibody (Cell Signaling, Danvers, Mass.) in frozen primary thymic epithelial tumors for which GTF2I mutation status was available.

Sequencing of RNA from GTF2I and its Pseudogenes:

Primers were designed in order to selectively amplify the transcripts of GTF2I or of its pseudogenes. Primers specific for GTF2I were located on its exon 10 (5'-SEQ ID NO: 24) and on the junction of exon 16-17 (5'-SEQ ID NO: 25). Primers specific for the pseudogenes were on their exon 1 and on exon 5-6 junction (reverse primers have the same sequence). All the primers were flanked with M13 primer sequences. Tumor RNA was converted into cDNA using High Capacity cDNA Reverse Transcription Kit (Applied Biosystems, Foster City, Calif.). Pseudogenes and GTF2I fragment were amplified by PCR using Taq DNA Polymerase (Invitrogen) according to the following program: STEP1: 94° C. 1:00 min; STEP2: 94° C. 30 sec, 55° C. 30 sec, 72° C. 45 sec (×35 times); STEP3: 72° C. 7:00 min. Amplicons of 503 bp (delta) and 566 bp (beta) were verified with a run on a 1.2% agarose gel and then purified from unincorporated nucleotides and residual primer using EXOSAP-IT (USB). PCR products were sequenced using M13 primers and Sanger technology.

TopoTA Cloning for Detection of T/a Mutation in GTF2I Gene and Pseudogenes:

Primers able to amplify the genomic DNA of GTF2I and its pseudogenes at the same time were designed. Forward (CTCAAGCCATAAAAGCCA) (SEQ ID NO: 26) and reverse (AGACAAGAGTTCAACAGG) (SEQ ID NO: 27) primers were purchased from Integrated DNA Technologies (IDT Inc., Coralville, Iowa) in order to amplify a fragment of 218 bp containing C or T, a signature that distinguishes GTF2i gene from its pseudogenes, and the T/A mutation locus. PCR was performed using Taq DNA Polymerase (Invitrogen) according to the following amplification STEPs: STEP1: 94° C. 1:00 min; STEP2: 94° C. 30 sec, 55° C. 30 sec, 72° C. 45 sec (×35 times); STEP3: 72° C. 7:00 min. PCR amplicons were cloned into a pCR4-TOPO vector using TopoTA Cloning Kit for Sequencing (Invitrogen), according to vendor's instructions. *E. Coli* DH5α bacteria were transformed with the plasmid and plated on an LB-agar Petri dish with 100 μg/mL kanamycin selection and incubated overnight at 37° C. Colonies, selected for sequencing, were resuspended in 5 mL of LB media with 100 μg/mL kanamycin and grown overnight at 37° C. in a shaking incubator. DNA was extracted using QIAPREP Spin Miniprep Kit (Qiagen) and plasmid sequenced using M13 Forward and Reverse primers.

Example 1

This example demonstrates the identification of copy number aberrations in aggressive histotypes of thymic epithelial tumors (TETs).

Large CN aberrations, affecting an entire chromosome arm (arm level CN aberrations), were present in more aggressive histotypes, in particular in TC, B3 and B2, but uncommon in the more indolent A and AB thymomas. Two major clusters of TETs were identified according to their arm level CN aberrations, the first encompassing most of A and AB tumors, and the second including mainly the aggressive histotypes. The aberrations defined two clusters of TETs: one with few arm level CN aberrations and one rich in arm level CN aberrations. These clusters trend to correlate with WHO histotypes and with the presence GTF2I mutations. Overall, the most frequent arm level CN losses involved chromosomes 6 (6p 26%; 6q 29%), 3p (22%) and 13q (18%). The most frequent arm level CN gains affected chromosomes 1q (55%), 7 (7p 20%; 7q 15%) and 20p (17%). Of particular interest were focal CN aberrations that appeared to be within the significant peaks identified using GISTC, an analysis aimed at identifying significant regions of CN aberrations possibly driving the cancer growth. These included the focal amplification of BCL2 locus, which correlated with an increased expression of BCL2 transcript according to RNAseq data. The average fragments per kilobase of exon per million fragments mapped (FPKM) value measured with BCL2 amplification was 41.52 with a standard deviation (SD) of 12.94 (n=3), and the average FPKM value measured without BCL2 amplification was 9.13 with a SD of 7.844 (n=8) (Mann Whitney p=0.0121).

Example 2

This example demonstrates the identification of a GTF2I mutation in TETs.

Exome sequencing revealed 722 somatic single nucleotide variations (SNVs) and 68 insertions/deletions (INDELs) in the coding regions of 28 TETs. An average of 28 mutations per sample was estimated (range 3-94). Thymic carcinomas (TCs) had a significantly higher number of mutations than thymomas (Mann Whitney-U; p=0.001). Moreover, mutations in several cancer genes were observed in more than one case of TC, but they were usually single events in thymomas. A customized 197-cancer gene panel was designed to sequence 52 TETs including 26 of the 28 tumors already characterized by whole exome sequencing. The two methods were highly correlated (Chi square p<0.001).

In thymomas, recurrent mutations were frequently observed in only one gene: GTF2I. This mutation was strikingly prevalent in A and AB histotypes, and all the GTF2I mutated cases presented the same single nucleotide change T/A at the same position chr7:74146970 (Table 1). This mutation was not previously described as a polymorphism in dbSNP137 and ESP5400 databases, or as a somatic mutation in tumors (COSMIC database). The missense mutation of GTF2I led to a leucine to histidine substitution and consequently altered deleteriously the protein structure and/or function according to SIFT and Polyphen2 predictions. The mutation affects the second conserved "GTF2I repeat domain" of the protein in proximity to its DNA binding site. Sanger sequencing confirmed the presence of mutations in tumors but not in normal DNA in all the mutated cases detected by exome sequencing.

The mutation was found in GTF2I sequence but not its pseudogenes: GTF2IP1 and LOC10093631 (Tables 2 and 3; see also Examples 7 and 8). GTF2I mutation (T/A) was mapped on exon 15. This region matches exon 4 of the pseudogenes, and differs by only one nucleotide: C in GTF2I and T in pseudogene sequences. The allele frequencies theoretically present in a cell were as follows: one GTF2I mutated allele (1:6, ~17%), one GTF2I WT allele (1:6, ~17%) and four pseudogenes wild type alleles (4:6, ~67%). TopoTA cloning was performed in four tumors with GTF2I mutation. Sequencing of cloned amplicons identified the mutation only in GTF2I but not in the pseudogenes. Deep sequencing was performed on five tumors with GTF2I T/A mutation. The mutation was found in GTF2I only and not the pseudogenes, which equals the mutation rate of ~17% or 1 out of 6 alleles (2 GTF2I+4 pseudogene alleles). The mutation was not identified in the negative controls.

The data demonstrate an increasing number of mutations and CN aberrations from type A to TC with the exception of GTF2I mutations.

TABLE 1

| Number of Patients Sequenced | WHO Histotype | Frequency of GTF2I Mutation |
|---|---|---|
| 56 | A | 82% |
| 54 | AB | 74% |
| 28 | B1 | 32% |
| 32 | B2 | 22% |
| 62 | B3 | 21% |
| 36 | TC | 8% |

TABLE 2

| | WT reads | Mutation (MUT) reads |
|---|---|---|
| Normal Samples | | |
| GTF2I | 31.2% | 0.0% |
| Pseudogenes | 68.2% | 0.0% |
| WT Tumors | | |
| GTF2I | 31.2% | 0.1% |
| Pseudogenes | 67.8% | 0.1% |
| Mutated Tumors | | |
| GTF2I | 28.3% | 4.1% |
| Pseudogenes | 65.7% | 0.4% |

TABLE 3

| | | | |
|---|---|---|---|
| Normal Samples | homozygous N1/N2 = C/T | GTF2I | 33% |
| | homozygous N1/N2 = T/T | LOC100093631 GTF2IP1 | 67% |
| WT Tumors | homozygous N1/N2 = C/T | GTF2I | 33% |
| | homozygous N1/N2 = T/T | LOC100093631 GTF2IP1 | 67% |
| Mutated Tumors | N1/N2 = C/A | GTF2I | 17% |
| | N1/N2 = C/T | GTF2I | 17% |
| | homozygous N1/N2 = T/T | LOC100093631 GTF2IP1 | 67% |

Example 3

This example demonstrates the prevalence of the GTF2I mutation in TETs.

The frequency of the GTF2I mutation was assessed on a total of 274 TETs (Table 4). Tumors rich in cancer cells (>50%) were evaluated for GTF2I mutation using Sanger sequencing (199 TETs). The GTF2I mutation was further sequenced in 250 TET samples, using a deep sequencing approach, which also included 78 tumors relatively rich in non-neoplastic thymocytes (cancer cells <50%). A total of 172 cases were sequenced using both Sanger and deep sequencing that demonstrated a good concordance in mutation detection (Examples 7 and 8). GTF2I mutation (chr7: 74146970T/A) was observed in 199 of the 270 TETs evaluated (44%), and most commonly in A (82%) and AB (74%) thymoma (78% overall, Table 1). The frequency of mutation progressively decreased in more aggressive histological types to only 8% in TC (3/36). More mutations were observed in early stages (I-II, 57%) than in advanced stages of the disease (III-IV, 19%, Chi-Square p<0.001). Survival data were available for 214 patients (median follow-up 39.4 months 95% CI: 30.3-48.5). Patients with tumors bearing GTF2I mutations had a better prognosis than wild type (WT) GTF2I (96% vs 70% 10-year survival, respectively; Log-Rank p<0.001), reflecting the higher mutation frequency in less aggressive tumors. All of the three TCs with GTF2I mutation were alive with a median follow-up of 27.6 months (95% CI 0-70%). Within thymomas there was a more favorable outcome in tumors with mutated than WT GTF2I (96% vs 88% 10-year survival; Log-Rank p=0.057). In models of multivariate analysis that include only two covariates, both GTF2I status and WHO classification were prognostic factors independent of disease stage. In contrast, GTF2I status and WHO classification were dependent from each other. Combining stage, WHO classification and GTF2I status in the same model, only stage was an independent prognostic factor.

TABLE 4

| Patient characteristics | | Total | GTF2I Sequenced | MUT GTF2I | WT GTF2I | p-value |
|---|---|---|---|---|---|---|
| Total in study | | 286 | 274 | 43% | 57% | |
| Patients | | 282 | 270 | 44% | 56% | |
| Age | | median 56 | | | | range (20-86) |
| Sex | Female | 139 | 135 | 41% | 59% | 0.327 |
| | Male | 143 | 135 | 47% | 53% | |
| | uk | 4 | | | | |
| WHO | A | 58 | 56 | 82% | 18% | p < 0.001* |
| | AB | 55 | 54 | 74% | 26% | |
| | B1 | 28 | 28 | 32% | 68% | |
| | B2 | 33 | 32 | 22% | 78% | |
| | B3 | 65 | 62 | 21% | 79% | |
| | TC | 41 | 36 | 8% | 92% | |
| | NEC | 4 | 4 | 0 | 100% | |
| | Micronodular | 2 | 2 | 50% | 50% | |
| Stage | I | 41 | 40 | 58% | 42% | p < 0.001** |
| | IIA | 55 | 53 | 64% | 36% | |
| | IIB | 73 | 71 | 51% | 49% | |
| | III | 29 | 29 | 35% | 65% | |
| | IVA | 21 | 19 | 16% | 84% | |
| | IVB | 34 | 32 | 6% | 94% | |
| | uk | 33 | 30 | 37% | 63% | |
| Resection | R0 | 139 | 136 | 49% | 51% | p = 0.0267 |
| | R1 | 18 | 18 | 33% | 67% | |
| | R2 | 13 | 13 | 15% | 85% | |
| | uk | 116 | 107 | 41% | 59% | |
| Paraneoplastic Syndromes | All | 66 | 65 | 43% | 57% | p = 0.636*** |
| | Myasthenia | 63 | 62 | 45% | 55% | |
| | No | 145 | 136 | 39% | 61% | |
| | uk | 75 | 73 | 52% | 48% | |
| CGH | | 65 | 53 | 32% | 68% | |
| Whole Exome Sequencing | | 28 | 28 | 21% | 79% | |
| Transcriptome Sequencing | | 25 | 25 | 28% | 72% | |
| 197-gene Re-sequencing | | 52 | | — | — | |
| Sanger Sequencing | | 199 | 199 | 61% | 39% | |
| GTF2I Deep Sequencing | | 250 | 250 | 42% | 58% | |
| Samples Sequenced for GTF2I | | | 274 | 43% | 57% | |

Example 4

This example demonstrates the expression of the GTF2I mutation in thymomas.

RNAseq demonstrated the expression of GTF2I mutation in all thymomas evaluated (five type A and two type AB thymomas). Both the mutated and WT GTF2I alleles were expressed. The median number of reads covering the mutation locus was 1114 and the mutated allele was present in an average of 47% (range 44-49%) of total GTF2I reads. Sanger sequencing of the cDNA confirmed the mutant GTF2I in the transcripts of all these samples. There are five known isoforms of GTF2I (Roy et al., Gene, 492: 32-41 (2012)) that differ by alternative splicing of exons 10 and 12. Using transcriptome sequencing, it was demonstrated that exon 10 was almost not expressed; whereas exon 12 was expressed with approximately half of reads both in mutated and WT samples observed in the neighboring exons. Indeed, according to cufflinks estimates, the expression of β and δ isoforms was significantly higher than the other three. These results suggest that the β and δ-isoforms are predominantly expressed in TETs. Using RT-PCR and specific primers designed for β- or δ-isoforms, the expression of the two isoforms was confirmed and the T/A mutation was detected in both of them. The observed T/A mutation corresponded to L404H in β-isoform and L383H in δ-isoform of GTF2I.

Gene expression was estimated from RNAseq data. Tumors with GTF2I mutations tended to cluster together in a group rich in A and AB thymomas, similarly to what was observed in CGH results.

Example 5

This example demonstrates the functional characterization of the GTF2I mutation.

GTF2I mutation is included within the amino acid sequence RILLAKE (SEQ ID NO: 28) that may represent a non-canonical destruction box resembling the destruction box (RXXLXX[LIVM]) (SEQ ID NO: 29) found in cyclins, PLK1 and Securin (King et al., Mol. Biol. Cell, 7: 1343-57 (1996)). The RILLAKE (SEQ ID NO: 28)>RILHAKE (SEQ ID NO: 30) mutation may render GTF2I unrecognizable by the protein degradation machinery (Desgranges et al., Mol. Cell Biol., 25: 10940-52 (2005)). Mutant tumors showed higher GTF2I expression than WT tumors at protein (Table 5) but not mRNA level (Table 6). To understand the biological significance of the GTF2I mutation and the elevated protein expression in mutant tumors, L404H and L383H β- and δ-isoforms of GTF2I were created by site-directed mutagenesis. pLenti6.3/-V5Dest expression vectors carrying the WT and mutated isoforms were stably introduced into NIH-3T3 cells. All β- and δ-isoforms accelerated cell proliferation in comparison to mock-transfected cells. Both β- and δ-mutant isoforms increased cell proliferation more than their WT counterparts. In contrast, no significant differences were observed in soft-agar colony formation between the mutant and WT GTF2I-transfected cells. The mutant clones (both β- and δ-isoforms) exhibited higher levels of GTF2I protein than WT ones whereas such a difference in expression was not observed at mRNA level. These results indicate that L404H and L383H mutations may augment GTF2I expression post-transcriptionally which in turn may accelerate cell proliferation by upregulation of cell cycle control proteins (Ashworth et al., Cell Cycle, 8: 596-605 (2009)).

TABLE 5

| | histotype | Normalized quantification of GTF2I protein expression |
|---|---|---|
| WT | B2 | 4.06 |
| WT | B3 | 1 |
| WT | B3 | 0.31 |
| WT | B3 | 0.29 |
| MUT | A | 4.16 |
| MUT | A | 13.03 |
| MUT | B1 | 5.33 |
| MUT | A | 8.05 |
| WT | B1 | 0.02 |
| WT | AB | 0.01 |
| WT | B2 | 1 |
| WT | B1 | 0.02 |
| MUT | A | 3.67 |
| MUT | A | 2.56 |
| WT | B2 | 1 |
| WT | B2 | 0.07 |
| WT | TC | 0.51 |
| WT | B3 | 0.03 |
| MUT | AB | 1.07 |
| MUT | A | 2.63 |
| MUT | AB | 3.14 |

TABLE 6

| | Average of GTF2I mRNA expression (FPKM) | |
|---|---|---|
| | Mutated Tumors | Wild Type Tumors |
| Delta (NM_001518) | 140,000 | 210,000 |
| Beta (NM_033000) | 90,000 | 150,000 |

Example 6

This example demonstrates the presence of fusion genes in TETs.

The presence of fusion genes was investigated using RNAseq data and two independent algorithms: FusionMap and DeFuse. All the predicted fusions were confirmed using RT-PCR followed by Sanger sequencing. Fusion transcripts were identified in seven of the 25 tumors evaluated including the TY82 TC cell lines known to carry the BRD4-NUT fusion. In these tumors the number of fusion genes ranged between 1-16. There was an average of one fusion transcript in each case (range 0-16). A B2 thymoma presented a remarkably high number of fusion transcripts (16 fusions) compared to the other samples. Although fusion proteins of GTF2I have recently been described in angiofibromas (Arbajian et al., Genes Chromosomes Cancer, 52: 330-1 (2013)), none of the fusion transcripts observed in TETs involved GTF2I sequence.

Example 7

This example demonstrates that the T/A mutation identified in Example 2 maps to the GTF2I locus but not to its pseudogenes.

GTF2I is a gene that spans 35 exons and is mapped on the long arm of chromosome 7 (chr7:74,072,030-74,175,022). The chr7:74146970 T/A mutation identified by exome sequencing is located in exon 15 of GTF2I. The T/A mutation was aligned to the same position of GTF2I exon 15 using either BWA (data not shown) or Novoalign algorithms.

There are two known pseudogenes of GTF2I: LOC100093631 and GTF2IP1. GTF2I exon 15 sequence differs by only one nucleotide from the sequence of the two pseudogenes (According to BLAT in the UCSC website: 99.5% identity, chr7:74629125-74629308 and chr7:72593127-72593310). Both these pseudogenes map to the long arm of chromosome 7 (chr7:72569012-72621336 and chr7:74601104-74653445, respectively). GTF2IP1 maps on the negative strand of chromosome 7, whereas LOC10093631 and GTF2I reside on the positive strand.

These two pseudogenes possess exons and their transcripts are processed into mature mRNAs, but proteins are not translated from either of them (de Jong et al., Eur. J. Cancer, 44: 123-30 (2008)). The two pseudogenes have a head (exon 1) that has no homology with GTF2I sequence and a tail (exon2—3'-UTR) that is very similar (99% identical; GTF2I/GRF2IP1 31,794 bp identical on 31,929 bp of sequence and GTF2I/LOC100093631 31,782 bp identical on 31,925 bp of sequence).

The transcripts of the two pseudogenes are almost identical since their sequences differ by only three nucleotides out of 3631 bp. Part of the GTF2I RNA sequence, exon13-3'UTR, is closely related to the portion of pseudogene sequences exon2-3'UTR. GTF2I exon15-3'UTR and pseudogene exon2-3'UTR RNA sequences are 99% identical. Among 3218 bp of shared sequence, GTF2I transcript differs only by four and three nucleotides from LOC100093631 and GTF2P1, respectively. The first exon of the two pseudogenes is not related to GTF2I sequence but closely resembles the first exon of GATS (93.9% identity) and GATSL2 (98.9% identity) genes. GTF2I sequence from exon 1 to exon 12 is unique and BLAT search did not reveal close similarity to other genomic regions.

Because the chr7:74146970 T/A mutation was mapped to GTF2I exon 15, it resides in the region of high homology between the gene and the pseudogenes. Therefore, it was necessary to demonstrate that this T/A mutation really belongs to GTF2I locus rather than to the pseudogenes. At the genomic level, exon 15 of GTF2I is ~4500 bp away from the point where GTF2I and the pseudogene sequences start to differ. In contrast, at mRNA level the distance is only 217 bps apart in the 8-isoform. Therefore, it was possible to design specific primers able to distinguish mRNA sequences of GTF2I from those of the pseudogenes. The T/A mutation was observed only in GTF2I cDNA but not in the cDNA from the pseudogenes in the five samples tested. Mutations were not identified in GTF2I or in the pseudogenes in the negative controls (four samples without GTF2I mutation). To further demonstrate that the mutation belongs to GTF2I locus at the genomic level, it was noted that GTF2I exon 15 and pseudogenes exon 4 differ by one nucleotide. The nucleotide chr7:74146870 is a cytidine in GTF2I sequence whereas the corresponding chr7:72593177 and chr7:74629258 in LOC100093631 and GTF2IP1 were thymidines. Because polymorphisms have not been described in these three positions, according to dbSNP137, the C/T single nucleotide difference could be used as a marker of GTF2I and pseudogenes sequences. Therefore, if the sequenced DNA strand contains both the C/T marker and the T/A mutation, one can ascertain whether the sequences with the mutation come from the gene or from the pseudogenes. Thus, it was possible to design primers that indistinctly amplify GTF2I and pseudogene sequences and then to determine if the T/A mutation belongs to the gene or to the pseudogenes using the C/T marker. In order to sequence just one strand of DNA, two strategies were adopted. The first was based on TopoTA cloning and the second on deep-sequencing technologies (MiSeq, Illumina). For TopoTA cloning, primers were designed in order to amplify a 218 bp DNA fragment that includes the C/T (gene/pseudogenes) marker and the site of mutation (chr7:74146970 T/A). The amplicons, generated using PCR reactions, were cloned into a pCR4-TOPO plasmid so that the expression of the toxic ccdB gene in the vector backbone, was disrupted. E. Coli DH5α bacteria were transformed and plated in a Petri dish with Ampicillin selection. Only bacteria carrying the amplicons, but not those carrying the empty vector, were able to grow. Colonies (17-40 for each tumor) that carry a single copy of DNA amplicons were picked, expanded and their DNA sequenced using specific sequencing primers. According to exome sequencing results the chr7:74146970 T/A mutation was expected to be heterozygous. Because the two pseudogenes were expected to be homozygous wild type, the mutated GTF2I amplicons should be 1:6 (~17%) of the amplicon sequenced. Four different tumors have been studied using TopoTA cloning, in all of them approximately 1:3 of the colonies were from GTF2I (average 35%; range 30-40%) and included all the T/A mutations. Colonies with a copy of mutated GTF2I were about 12% (6-18%), slightly less than the 17% expected, which is compatible with some normal cell contamination of the samples.

A customized deep sequencing assay was developed in order to discriminate mutations in GTF2I or pseudogenes. It was based on two pairs of primers (P1 and P3) able to amplify a region that includes the T/A mutation site and the Gene/Pseudogene marker (C/T). An additional pair of primers (P2) was included in the deep sequencing assay exclusively for genotyping purposes and was designed in order to enrich the amplification of GTF2I sequences. Twelve samples were multiplexed on a MISEQ flow cell in order to obtain extremely high read counts over the region of interest (average number of total reads was 2,306,186 range 1,137, 605-4,122,859; average number of informative reads was 585,714 range 167,054-1,449,423). Five samples had GTF2I mutation and seven were negative controls that included three normal DNA, three tumors without GTF2I mutation and a thymic carcinoma cell line without GTF2I mutation. The deep sequencing assay demonstrated GTF2I mutation only in the five positive cases but not in the negative controls. The reads with the mutations belonged exclusively to GTF2I sequence in three cases, whereas two tumors presented 1% of the pseudogene reads with the mutation. The frequency of GTF2I reads with the mutation was close to what expected (average frequency 11.5%, range 8-18%, expected frequency 17%). The few pseudogene mutated reads (1% in two cases) did not support the presence of a pseudogene allele carrying the T/A mutations (expected 17%). These reads may be related to polymerase errors introduced in the amplification step or they can represent a real pseudogene T/A mutation present in a subclone of few tumor cells.

When all samples were evaluated, for which the GTF2I mutation was genotyped using MISEQ (n=250), the results matched the expectation (Tables 2 and 3). Results were evaluated separately for the 12 normal samples, the WT tumors and the tumors with GTF2I mutations. Normal and WT tumors have an inconspicuous proportion of mutated reads either from GTF2I or from the pseudogenes. In the tumors with GTF2I mutations, the average mutated reads were 4.01% from GTF2I and 0.4% from the pseudogenes. This low proportion of mutated GTF2I reads was expected for the presence of tumors with extensive components of non-neoplastic thymocytes. Even in the tumor with highest fraction of mutated reads belonging to the pseudogenes (2.96%), the reads from GTF2I were significantly higher (16.13%).

The results of TopoTA cloning, MISEQ and the transcript sequences demonstrated that the chr7:74146970 T/A mutation unambiguously involves the GTF2I sequence.

Example 8

This example demonstrates the frequency of the GTH2I mutation.

According to the exome sequencing and transcriptome sequencing results, GTF2I mutation was common in the A and AB subgroups of thymomas. A larger cohort of patients was then screened for GTF2I mutation using standard Sanger technology and the deep sequencing approach described above. Sanger sequencing revealed GTF2I T/A mutation in 78 (39%) out of 199 thymic epithelial tumors. The somatic nature of the mutation was confirmed by the absence of GTF2I mutation in normal DNA from patients' blood. A limitation of the standard Sanger methodology is the presence of non-neoplastic thymocytes that can outnumber the epithelial tumor cells in some histotypes (in particular some AB, B1, B2). Therefore, only tumors with at least 50% cancer cells were sequenced using Sanger technology. Alternatively, a deep sequencing approach was considered for screening for the presence of the GTF2I mutation in thymocytes-rich tumors. However, samples with an extremely high proportion of nonneoplastic thymocytes represent a challenge for the detection of GTF2I mutations even using deep sequencing. This can be the case for some B1 thymomas. According to the deep-sequencing assay, 106 tumors (42%) out of 250 had the GTF2I mutation. Sanger and deep sequencing technologies showed good concordance on the 172 samples assayed with both methods. The two methods detected GTF2I mutations in 59 cases and excluded its presence in 88 tumors. The deep sequencing approach was designed to be more sensitive than the Sanger method in lymphocyte rich tumors, where GTF2I mutation was identified in 20 additional cases. These cases were considered mutated. In five samples (3%), mutations were observed only using the Sanger method but not using the deep sequencing approach. The mutation status of these samples was considered undetermined. When discordant results were observed in cases with three different sequencing technologies, samples were considered mutated when two of these technologies detected the mutation.

Combining exome sequencing, Sanger sequencing and GTF2I deep sequencing data, GTF2I mutation was observed in 119 tumors out of the 274 evaluated (43%). The frequency of mutation was higher in thymomas (50%) than in thymic carcinomas (8%; Fisher exact test p<0.001).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for detecting a GTF2I mutation in a tumor, the method comprising:
   obtaining genetic material from the tumor;
   assaying the genetic material; and
   detecting a mutation in at least one copy of GTF2I genetic sequence, wherein the mutation is selected from the group consisting of:
   (a) the T>A mutation at position 75,041 of SEQ ID NO:1;
   (b) the T>A mutation at position 1208 of SEQ ID NO: 3;
   (c) the T>A mutation at position 1211 of SEQ ID NO: 4;
   (d) the T>A mutation at position 1271 of SEQ ID NO: 5;
   (e) the T>A mutation at position 1148 of SEQ ID NO: 6; and
   (f) the T>A mutation at position 1205 of SEQ ID NO: 7.

2. The method of claim 1, wherein the tumor is a thymic epithelial tumor (TET).

3. The method of claim 2, wherein the thymic epithelial tumor is thymoma or thymic carcinoma.

4. The method of claim 1, wherein assaying comprises carrying out a polymerase chain reaction (PCR) assay that specifically detects the mutation.

5. The method of claim 1, wherein the genetic material is genomic DNA.

6. The method of claim 1, wherein the genetic material is RNA or cDNA of GTF2I β isoform or GTF2I δ isoform.

7. The method of claim 1, wherein the genetic material is RNA.

8. The method of claim 1, wherein the genetic material comprising the mutation comprises a nucleotide sequence selected from the group consisting of SEQ ID NOs: 8-9, 11, and 13 and complements thereof.

9. The method of claim 1, wherein the genetic material comprising the mutation comprises a nucleotide sequence selected from the group consisting of SEQ ID NOs: 8-14 and complements thereof.

10. The method of claim 1, wherein the method comprises detecting the presence of the T>A mutation at position 75,041 of SEQ ID NO: 1.

11. A method for detecting a mutated GTF2I protein in a tumor, the method comprising:
    obtaining a sample from the tumor;
    assaying the sample;
    and detecting a mutation in GTF2I protein selected from the group consisting of:
    (a) the mutation of Leu to His at position 403 of SEQ ID NO: 31;
    (b) the mutation of Leu to His at position 404 of SEQ ID NO: 32;
    (c) the mutation of Leu to His at position 424 of SEQ ID NO: 33;
    (d) the mutation of Leu to His at position 383 of SEQ ID NO: 34; and
    (e) the mutation of Leu to His at position 402 of SEQ ID NO: 35.

12. The method of claim 11, wherein assaying comprises contacting the sample with an antibody that specifically binds to mutant GTF2I protein and does not bind to wild type GTF2I protein, thereby forming a complex, and detecting the complex.

13. The method of claim 11, wherein assaying comprises contacting the sample with an antibody that specifically binds to wild type GTF2I protein and does not bind to mutant GTF2I protein, thereby forming a complex, and detecting the complex.

14. The method of claim 11, wherein the tumor is a thymic epithelial tumor.

15. The method of claim 11, wherein the GTF2I protein with the mutation comprises the amino acid sequence of SEQ ID NO: 16 or 18.

16. The method of claim 11, wherein the GTF2I protein with the mutation comprises an amino acid sequence selected from the group consisting of SEQ ID NOs: 1549.

17. A method of treating a thymic epithelial tumor in a human subject, the method comprising:
 obtaining a sample from the thymic epithelial tumor;
 assaying the sample; and
 detecting one or both of (I) and (II):
  (I) a mutation in at least one copy of GTF2I genetic sequence, wherein the mutation is selected from the group consisting of:
   (a) the T>A mutation at position 75,041 of SEQ ID NO: 1;
   (b) the T>A mutation at position 1211 of SEQ ID NO:4; and
   (c) the T>A mutation at position 1148 of SEQ ID NO: 6;
  (II) a mutation in GTF2I protein selected from the group consisting of:
   (a) the mutation of Leu to His at position 404 of SEQ ID NO: 32; and
   (b) the mutation of Leu to His at position 383 of SEQ ID NO: 34; and
 treating the thymic epithelial tumor in the human subject when the mutation is present by surgically removing all or part of the thymic epithelial tumor without administering one or more of (i) radiotherapy, (ii) chemotherapy, and (iii) immunotherapy in an amount effective to treat thymic epithelial tumor in the human subject.

18. The method of claim 17, comprising treating the thymic epithelial tumor in the human subject when the mutation is absent by surgically removing all or part of the thymic epithelial tumor and administering one or more of (i) radiotherapy, (ii) chemotherapy, and (iii) immunotherapy in an amount effective to treat the thymic epithelial tumor in the human subject.

19. The method of claim 18, wherein the chemotherapy comprises administering one or more of doxorubicin, epirubicin, belinostat, cisplatin, carboplatin, cyclophosphamide, ifosfamide, vincristine, etoposide, paclitaxel, pemetrexed, 5' fluorouracil, methyiprednisolone, octreotide, gefitinib, imatinib, and gemcitabine to the human subject in an amount effective to treat the thymic epithelial tumor in the human subject.

* * * * *

SEQUENCE LISTING

```
<160> NUMBER OF SEQ ID NOS: 35

<210> SEQ ID NO 1
<211> LENGTH: 103193
<212> TYPE: DNA
<213> ORGANISM: Homo sapiens

<400> SEQUENCE: 1
ccgctgggcg gcgctgcgga tgcgcaggcg caacgcgcct tcgaggaaca aaaaaaaaaa      60
aaaaaaaaaa aaaaaaagaa aaaagaaaaa aaaaggagg aggaggagga gggtgagaga     120
gaagctggga gagcagagaa aagggggccac cggtcgcccc cccgcttccc cgcacgcgct    180
ctccagccgc ggccgcccgc ctgccgcggt caccccggcc tctgcctctg tcccccagtg    240
atcggatcaa ggcgctgagc gaggccctgc ctgcggggcg gccatgcggc ggtgacagga    300
gcgcgaccga cacgcacggg ccctcgccc cctctcgcct cccgtccgct cgccagctcc     360
cctcagccga ggctgctccg cggcggccgc agcccgcgcg cggcccacac tcgcctcccc    420
tcggcacccc cggccccgga gctgcctgga ggcggccgca ctcgggtgag tccctctcgc    480
ctcatccccg cgccccccgc ccccgcctcg ggggccattg cgagcggggg cctttattag    540
agactttgcc ccgccgggc ctgcagggac aggggcctgg gagccgcggc ccgccgcgcg     600
cggtgtgggg ccttgggggg cgcccgtgcc gcctcccct accccaccc ccaccgcctc      660
```

```
gccgggtctc gagccccgcc ggccttggca gtggccgaaa cgaggcgatg ggggtggggc      720
ggcacggacg cggtcgcggg ggacgacagt ggcacgcgcg cgcctcagtg cgcgtggggg      780
aggggcgcgc gcgccgaccg gcgtgcggtg gggggcgcc tcgcgcgtgc gatcccgcgc       840
gcgagcgagc gagcggccct gcgggctgcg catgccccgc cgcgctgatt ggccggctag      900
gcggtgcggg ggcgcgcgcg gtgccaggcc cgagccgtcg tggggtcgcg ctcgcctggt      960
gtatctgggg ctcctgcgcc ggggcagcag acgcgcggga ttggccaacc ggcgcggggg     1020
cggggccgcg cgttgcctgg taactgcggc gggcggggga gcgggagcgc tgtcccccgc     1080
cccgccccgc tcccaggtgg agtccgcagt gggctttgtc ccgggccggc ccggcgcgcc     1140
tgccccgcgg ggcctgttct ttgggggaaa taaacacaat gaccggaagg aaaacttcag     1200
ctttaggcca tgaaaattaa gccgtctggg ttcagccagc acccagacga cgggagtgca     1260
gaggaagaag gaaaatgaaa tggaaaaagc tgtctccttc ccgctccccg acttctccac     1320
ttttcttaa tccagctttt gcttttcgt gtagcgaatt ttgtcctccc taggttatgg      1380
atttgcgctg atttgcggct ggggatgttc acaggtgggg tgctgttgga gtagtgtcca     1440
ctcttggcga tgcgcagctc ttgctgactg actactgacc tccttttttt aaaaaaaatt     1500
atttgtggag atgcgttctc actttgttgc ccaggctggt cttgaactcc taggctcaag     1560
cgatcctccc accttggccc ccatagtgc tgggattaca ggtgtgagcc atcgctttcg      1620
gcttaatttt cttttttttt tttagaaaca gggtctctct atgttgccct ggctgaagcg     1680
cagagtggca caatcatagc acattgcagc ctccaacacc tgggctccag cgatcctcct     1740
gcctcagcct cctcagtggc tgggactaca ggcgcatgcc atcatgccct gctaattttt     1800
tttttttga gatggagtct cactctgtgg cccaggctga agtgcactgg tgtgatctcg      1860
gctcactgca acctctgcct cccggggttca agccgttctc ctgcctcagc ctcctgagta     1920
gctgggatta caggcgtgcc caccacgccc ggctattttt tgtatttta gtagagatgg      1980
cgtttcacca tgttggccag ctggtctccc aactcttgaa tcaagctgaa agcaatcggc     2040
ccgcctcggc ctgccaccaa agtgctggga ttacaggcgt gagccaccgc cctgggtcac     2100
gcctggctaa tttaaaattt tttttttagag atggggtctt cttgtgttgc ctaggctggt    2160
cgggaactcc tggactctgg tgatcctccc gtttaggcct cccaaagtgg tgggagtaca     2220
ggcttgagcc accacgctgg gcctcatctc ttttaaattc aactttgccg cagacaatgg     2280
cttgatcagc caacagtgca gaggagaagt ctccagtcct tcagggaaca aaaggggaag     2340
ttagtttgca aatgagaacg tgcaggtaga gtgccctgcg gaggcggggt cttctcccca     2400
ggctgaggcc tgtggtgtgg gatgaccgat tttatttcct gctacaggat ttttctgtgg     2460
ctgctacctt ggctttcgtt ctcctcctc cttgagatct tggtcttttg gctgaatga      2520
catttttcag cctatggaaa tctttcttgc tcatatgcag ccacttcctt aaggtcttct     2580
ctttttttt ttttttgct gctgttgttg agagggtttc gttctatccc ccaggctgg       2640
agtgcagtgg cgcgatcttc gctcactgca acctccacct cccgggttca agcgattttc     2700
ctgcctcagt ctcccccgag tagctgggat tacaggcgcc tgccccaag ccccgctaat     2760
atttgtattt ttaatagaga cggtgtttcg ccatgtttgt caggctggtc ttgaactcct     2820
gacttcaggt gatccgcctg cctcggtctc cgaaagtgct gggattacag gcgtgagcca     2880
ccgctcccgg cctgtggtct tctcttatat tgcatagtca gagtttgttc cttcttagtc     2940
tcccaatcaa cttgtgtgcc cttcctcgca gggcaccttt attttctctc ttttttttcc     3000
ttttcctttt tcttttcttt tcttttttttt tttttttcg gaagcggagt ttcgctctcg     3060
```

```
ttgcccaggc tggagtgcag tggcgcgatc tcggctcact gcaacctccg cctcccgggt   3120
tcaagcgatt ctcctgcttc agactcctga gtagctggga ttacaggagc gctccaccac   3180
gcccggctaa gggcactttt actttcctct gcatctggcc tagtcactgg gtgttgagct   3240
cgtaggggca gggacaagaa gccttttcct cctatgtctt tctccctcca cttcccctc    3300 cagtttggca tcgtcctcgt gccttgccgg tggtagcaat gctgcttaca tttgagtgtc   3360
ttccgtgccc cctccatggc tcttgagcgc tttggatgta cagtattttt cttatttaat   3420
ctttgtgaca agtctgtaat tctattctat agagcggaac aagtctagag aagttggaga   3480
gttctgtact cttgcttgcc tagcacatga acctggccag tgtgactcaa cccctaagcc   3540
gaggttgtga aaccaccgcg cctgggcgtc cccgggagag ctggcatgtg cggactctgc   3600
ttgctgggcc ctacctccca ggctgattct gcaggtctgg ggagttgccc cacaatttgc   3660
atttcgatta gctccccagg tggtgttgat ggtggctgct tcccggacag ccctttgaga   3720
accattcaca atggtgcaaa atgaagggag agaaatttat tggagatatt tgcttttttct  3780 tactttaaaa ttagatcttg gccgggtgcg gtggctcaca cctgtaatcc cagcactttg   3840
ggaggccgag ggaggtggaa cacctgaagt caggagttgg agaccagcct gccgacatgg   3900
cgaaaccccg tctgtactaa aaatacaaaa attagccggg tgtggtggcg tgcgtacgta   3960
gtttcagcta cttggggagg ctgaggcagg ggatctctt gaacccagga ggtgaggtt    4020 gcagtgagat gagatctcac cactgcactc cagcctgggc gacagagcga gactgtgtct   4080
caaaaaaaat aaaaataaaa ataaaataga tgttaaagaa tgaaaaataa ttcggacgac   4140
tgacggtaga ttgctcagaa aactggctga gagttgagaa ttcctgttag ccatgattag   4200
aaaagttaaa agtttcataa gtctccagtt taaaagggg ccatggattt aagtgtggaa    4260
taaaatggga aatctttgga agtttggctt ttttcccact ctgatttatt tattaattta   4320
gtcgcagcac gggcatttgt tacattatcc tcttcagatg cccaaagtct gccacaccac   4380
cacacagaag gtttgagtga taggaccaca gcttgtagtt ttggcccttg gaggtagggg   4440
ggttggggag cattgtgtgc tgagtctcct ctgccacatg cccctccagc gattcagctt   4500
actcaaatat gactacagag actgacatta aaatgtaggc tttgggggtt cttttgcgg    4560 gacagggttg ggggcaattc ttgctgagaa agattttag gttttttctt tcttttttt     4620 tttttttttt tgatggagtt tcactctgtc gcccaggctg gagtgcaatg gcacaatcag   4680
ctcactgcaa cttacgcccc cccagggtca agtgattctc ctgcctcagc ctccggagta   4740
gctgggatca taggcatgcg ccaccatgcc tggctaactt tgtattttta gtagagacgg   4800
ggtttctgca tgttggtcag gctggtctcg aactcctgac ctcaggtgat ccgcctgcct   4860
tggcctcctt aagtgctggg attacaggcg tgagccactg cacctggacc ctttttttt    4920 tttttttttt tttttttttt tttgagacac agtcttgctc tatcgcccag gcgggagtgt   4980
aggtgcgtgg tctcggctca ctgctacctc tgcctcctgg gttgaagtga ttctcctgac   5040
tgagcctcct gagtagctgg gattacaagc acgcaccacc acgcctggct aattttttgt   5100
atttttagta gacacggggt ttcatcatgc tggccaggct tgtctccaac tcctgacctt   5160
gtgatctgcc cgcctaggcc tcccaaagtg ttgggcttac aggcgccctg tgattttag    5220 gttttttaaaa ttataatgga tttctttccg gggaaaataa ccgcagatag gtgggaggaa   5280
tggttttagt ttacagttga tgaccccct cctttcccca cctacaccct taggcgagtt    5340
gtacacactc ctcagggat cccaacttcc atggccactg tcctatgttc tggcatttc     5400
```

```
gatgacccat aggtggacag gttgttatca tctaaaggag ctgaacactg aacaattact    5460
aaacacttaa ccttttctgt tattactggt taccagctat ttgcattgca tttcacctaa    5520
ttcatttcta ctgttgtttc attctttgtt gatgacatga atgttttata taaacatgag    5580
tttttgcaat atgcttcata actggggtgg tataattaac acgaaattgt tttaccactg    5640
gcttaaatag atggatgtca atcattttt atgtcagtct aagggaaagt atttatttat    5700 tttttgaga tggagtctcg ctctgtggcc caggctggag tgcagtggtg ccatctcagc    5760
tctctgcaac ctccgattcc cgggctcaag cgattcttgt gccttagcct cacgagtagc    5820
tgggattaca ggcatgtgcc accatgccca gctaattttt ttgtattttt catagagatg    5880
gggtttcacc atgttagcca ggctggtggt ctccaactcc tgacctcaag tgatccaccc    5940
acctcggcct ccctaagtgc tgagattaca ggcgtgagcc actgcgcctg gttcgtttat    6000
tgagtgaagg ttattcattg ttaataactg aaagaaagta gaaaatacac ctaatcagtt    6060
gcttattcta attgtagagt tgagatactt gggaatcagt aggcttaagc tggcagcata    6120
gctctatgaa gactcatact cggttaacta aagtgtattg gggctaccta cctgggggag    6180
caaaacgcct tagtgtctta gaagatgtgt gtttttttat tgcattttat tttattatta    6240
tttatttttg agacagagtc tcgcttttgt cacccaggct ggagtgcagt ggcgtgatct    6300
tggctcactg caaccttcgc ctcctgggtt caagcgattc tcctgcctca gtctcctaag    6360
tagctgggac tataggcacc cgccaccatg cccggctaat tttgtatttt tagtagagac    6420
ggggtttcac cgtgttggcc aggttggtct caaactcctg acctcaggtg atctgcccgc    6480
cttggcctcc gaaagtgctg ggccaccgca cccagccaag gatgtgtgta tcctgtaaaa    6540
attgtgtggg tacgtcatcg gaagaggtga aggtattgtc ttgataattc ttcattctcc    6600
attcttgccc tgtcgtcctt tactgttgtc cttttgttct ggaactctcc ctgctgtctt    6660
cctgtttgtt ttctcctctg taaaattctt gttttggtat tccatgcctg tttctggcag    6720
tactcatttg cttttacca ctttggccta ctgagaaagt aagagaaagt tcagtatagc    6780
caggaactgt cagagttgtt ggaggattga ctcattctcc tttggttgta acttgtttct    6840 gttttttgttt ttttgagaag gagtctccct ctgtcgcaca ggctaaagtg caatggcgcg    6900
atctcggctc actgcaactc tcgcctccca ggttcaagcg attctcctgc tcagtctcc    6960 tgagtagctg ggattacagg tgtgtgccac catgcccggc taattttgt attttttagta    7020 gatacaggtt tcaccatgtt ggccaggctg gtctcaaact gctgacctca atgatccac    7080 ctgcctcagc ctcccaaagt gctgggatta caggcatgag ccaccacgcc tggccaacac    7140
tctatgtagg attttaaag aactagttac ttaaaaaata tatcatgaga gggaagacaa    7200
atttataaat tgagagaggg tttatagctt atggctagcg acacaagttt gaagtctgac    7260
tgcctggatt ccagtcctgg cccttgccgt ttcctgcctg tgcgaccttg gcatttcac    7320 ttcatctttg tatgtttccc tattttttgt tttttttttt tgagacagag ttttgctctt    7380
gttgcccagg ctggagtgta gtggcgcgcc tggctcaccg caatctccgc ctactgggtt    7440
caagcgattt tcctgcctca gcctcctgag tagctgggat tacaggtatg tgccaccacc    7500
acgcctggct aattttgtat ttttagtaga cggggttt ctccatttg gtcaggctgg     7560 tctcgaactc ctgacctcag gtgatccacc cgcctcggcc tcccaaagtg ctgggattac    7620
aggtgtgagc caacagtgcc cggcctattt tttattttta tttttattt ttgagacagt    7680 gtcttgctct gttacccagg ctggaatgca gtggcatgat ctcagctcac tacaaccct    7740 gcctctcggg ttcgagtgat tcttgtgcct cagcctcccg agtagctgga attataggca    7800
```

```
tgcgccacca cacctggcta attttgtat tttagcaga gacagggttt caccatgttg   7860
gccaggctgg tctccaactc ttgacctcag atggtccgcc cacctcagcc tctcaaaggc   7920
tgggattaca ggcctgagcc accacgcctg gcccctattt ttaaaaatgg agttgataat   7980
agaacatgtt tcgcttctaa gagctgttgc aaggatagga tttaagtgct taggttgctg   8040
tctggcatgt agtagacact caagaaatat tagtcataaa agtactatta taaagactt   8100 tgggaaattg aggaagcgaa aattttacta gtaatatcga ctatgacgtt aatctccaag   8160
aactctggag aatatgaatt gcaagggcaa ggacttattc ctctgtggga ttttcccctg   8220
tgactgttac attgttttta tgtttgttt tgttgagatg gagtctccct ctgtcaccca   8280
ggctggagtg cagtggcggg atcccagctc attgcaacct tcacctctgc ctcccgggtt   8340
caagtgattc tcctgtctta gcttcccaag tagctgggac tacaggcgtg cgccaccatg   8400
cccagctaat ttttgtattt tttagtagag aaggggtttt actatatgtt ggccaggctg   8460
gtctggaacc cctgacctca ggtgatctgc ccatctcagc ctcccaaagt gctgggatta   8520
cagacgtgat ccaccgcgcc tggccagagc ttgacagttg gattgatgaa acctgagaat   8580
gtatgcttta tatgttgttc attttaattt gttatatcta gaaatttagc tcttactgtt   8640
gactataaca catacatgac gtgagtagaa ttttatctag attgagtttt cagaccgtaa   8700
ttggtttcaa gaaataaat aaggtattgg aagtgaacta aaattagtaa ctggctttgg   8760
cattagactt taatgcactt aaattacatg atctcatctg tgagataatt tgacagagga   8820
ggacgatggc atgtattatg tccatatgag gaaagggcag agaaatagac cctgcaagat   8880
tcattagtgt tactccttcc tcctgttcgt tttctttctt cgttttcccc ccctggtaag   8940
cattaaaaaa aatttttttt ggctgggtgt ggtggctcac tcctgtactc ccagcacttt   9000
gggaggccat gactcacttg aggtcaggag tttgagacca gcctggccaa catggtgaaa   9060
ccccgtctct actaaaaata caaaaaattg gccgggcacg gtggctcaca cctgtaatcc   9120
cagcactttg ggagtccaag gcgggtggat cacgaggtca ggagatcgag accatcatgg   9180
ctaacatggt gaaaccctgt ctctactaaa aatacaaaaa aaaaaaaaa aaattagcca   9240 ggcgtgatgg cgggtgcctg tagtcccagc tactcaggag gctgaggcag gagaatggtg   9300
tgaaaccggc aggcggagct tgcagtgagc tgagatcgca ccactgcact ccagcctggg   9360
tgacagtgtg acactctgtc tcaaaaaaca aaaacaaatt agctaggcgt ggtggtgcgc   9420
acctgtaatc ccagacactc gggaggctga ggcaggagaa tcacttgaac cctggagtcg   9480
gaggttgcag tgagccaaga tcacgccatt ccactccagc ctgggccata aacaagact   9540 atgtctcaag gaaacaaac aaacaaaaaa acacatctct actgaaaata cagaagttag   9600
ctgggagtgg tgacaggtgc ctgtaatgcc agctgcttga gtggctgagg catgagaatc   9660
acttgaaccc gggaggtgga ggttacagtg taccgagatc ttgccactgc tctccagcct   9720
aggcgacaga gcaagacacc atctcaaaaa aagaaaatc ctgtaagatg aatttgttcc   9780
tttatgaaga ataaatttgt gtctgccatt tacaccgtga atgcctttct ttggagtggt   9840
tccttgtagt gtttttttgtt gttgtcgttg ttgttaaatt gtggtaacat atacttaaca   9900
caaaaattac cattttaacc tttttttgtg ggggagggga cgggatgtca ctctgttgcc   9960
caggctggag tgcagtggta tgcttttggc tcactgtaac cttcgtgtcc tagggtcaag  10020
acatcctccc acctcagtct cccgagtagc tgggactaca ggtgcatgcc accacgtctg  10080
gcttgatttt tttattttt gtggagatgg gggtctcact atgttgccca ggctggtctc  10140
```

```
caactcctga gctcaaacaa tctgcctgca tctgcctccc aaagtgctgg gattagagac    10200
atgagctacc acacccagcc tgattttacc aaaagaaact ttttttttt ttttgagac     10260 agagtcttgc tttgttgtca ggctggagtt caggggcatg atctcggctc atggcaacct   10320
ccatctcccg ggttcaagtg attcttctgc ctcagcctct caagtagctg ggactacagg   10380
tgcgcaccac cacgcccagc taattttgt attttagta gagatggggt ttcaccatgt     10440
tagccaggat ggtctcaatc tcctgacctc atgatccact tgcctcggcc tcccaaagtg   10500
ctgggattac aggcgtgagc caccgcgccc agtcttaacc atttttaagt gtatgtatag   10560
ttcagtggtg cagaactttt ttttttttt tttttttttt gagacagggt cttgctctgt    10620
tgcccaggct ggaatgtagg atattatcaa gttcatctgt gtgttagaat ctccttctta   10680
tttaatcctt cttgtggttt ttggagtctt tgttttgtag catggcaaag cccattgtgt   10740
gtgtgtgtgt gtgtatgtaa gaagtatata taattatatt atggtgtact tggagaagtg   10800
gagcatgatg aagagtttga tccataatat aactggttat atagaaccct gtttagcaga   10860
cagagcctag gaagttttct gattgtatag gttctatgct tttgagaatt cctgcttgtg   10920
ttttgatctc atttccatac acagtcctta aagatcatat ttatttattt atttatttat   10980
ttatttatcg agatggagtc tcactctgtc acccaggctg gagtgcagtg gcatgatctt   11040
ggctcactgc aacctccact tcctgggttc aagcaattct cctgcctcag cccctgagt    11100 agctgggatt acaggagccg ccaccacgc ctggctaatt tttgtatttt tagaaaagat    11160
ggggtttcac catgttggcc aggctggtct tgaactcctg acctcgtgat ccacctgcct   11220
tggcctccca gagtgctgaa attacatatg tgagccaccg tgcctggcta agaagggatc   11280
gtttaaattt ttaaaaatac cttaatttat ttttatagag acaggatctc gctgtgttgc   11340
ccaggctggt ctcaaactcc tgggctcaag tgatcctccc acctcagtct cccaaagtgc   11400
tgggattcag gtgtaagcca ccacgcccgg cccaaaagaa gggatctttt atcatgtcgg   11460
gaacagtaac tattcattta ttcaacatac tgatgggctc atcctatgag gcctcagaac   11520
acagcatgtt tcttggaaaa tactggcatg gcaaatgac attgttgaga gcttcaggat    11580
aaagaatctt ttagtttagt ttgtatatcc agactagttt agttttttt tttttttttt    11640 ttttgagaca gtctcgctct gtctcccagg ctggagtgca atggcacaat ctcagctcag   11700
tacaacctcc acttcctggg ttcaagcgat tctggtgcct cagcctcctg agtagctggg   11760
attacaggcg tgcaccacaa tgtctggcta atctttgtgt ttttggtag agaacgaggt    11820 ttcatcatgt tggccaggct ggtctcaaac tcctgacctg aagtgatccg cccgcctagg   11880
cctcccaaac tgttgggatt acaggcgtga accatcgctc ccagctggaa ggtgacttt    11940 ttttttttg agacagtgtc tccctctgtt gcccaggctg gagtgcagtg gcacgatctc    12000
ggctcactga aacctccgcc tcctgttcaa gctcttctcg tgcctcagct tcctgagtag   12060 ctggactac aggtgcacgc caccatgccc agcaatttt gtattattag tagagacggg     12120
gtttcaccat attggccagg ctggtctcaa attcctgact ttgtgatcca ctcacttcga   12180
cctcccaaag tgcggggatt acaggtgtga gccaccgtgt ccggccaagg tgacttttta   12240
aagttaaatt ttaaaacgat ctttgaggag taaatttgac ataagcaggt gttcatgcac   12300
aaatgcctta aaaggtacac atacttcatt tcaaagcagt tatttatttt gacacttgtc   12360
tcattaattt tcctgctctc tcagaaaata ggttatttta tttagccgtg ataattaatg   12420
cagtttgttg ggaaataagc tattttcaat ttaccaggct tggatttggt gagttttat    12480 gtaaattaat agatatatgt acatatattt ttaaaataac tattttagtg aagtttaaat   12540
```

```
tataaatgct tgctcattca ctgaatgctt ttgtgatgca ctttattaag aattgacatg    12600
cattctgata acaactttgt aaggtaagta tgcagactgt tgtcattttc cagactagta    12660
aatttgggat taaagaatcc cagggtcacc tgtaagattt gagacaggac ttgaattcag    12720
aacttttgcc tgattgcaaa gctcaccttc ctaatagctt tgctctgttg cctgccttct    12780
gtgaacagtg cttttaaaaa agtaaagatt gtcgggtgtg gtggctcac gcctgtaatc     12840 ccagcacttt gggaggccga ggtggtgga tcatctgagg tcaggagttt gagaccatcc     12900
tggccaacat ggtaaaaccc cgtctctact aaaaatacaa aaattagcc aggtgtggtg     12960 gcatctacct gtagtcccag gtactcgagg caggagaatt gcttgaacct gggagacgga    13020
ggttgcagtg agctgagact acgccactgc attctagcct gaacgacaga gtcagactct    13080
ttctcaaaaa aaacaaaaa aaaacaaaa aaaaaaaca cctcaagaac aaagtaaaga       13140 tggacccttta gataatagct acttgatttt cattttctct tccaaatggt ttttccaaaa  13200
tccaactgag ttttaaattt ggagtcatgt caaagggaca cattctttgt gtattggcag   13260
agtaagctgc tgctgtttaa aaatctggac tatcaattta aaagtataat taatacatat   13320
gcaaaaatgg tgtcttaaac tgtggtgcaa ggaaaatagg tctttccgaa tagctggtaa   13380 gattttcct tgtttgtttt ttaaggatgt tgttttggct actgtgaaac tcagaactca    13440
gagctgaact tgtgatccac tgattgggca gatccttttt tttttttttt tttttttttg   13500
agacagagtc tcactctgtt gcccagggtg gagtgcagtg gcgtgatctc agctcactgc   13560
aacctcagcc tcctaggttc aagtgattct cttgcctcag cctcccgagt agctgagatt   13620
acaggcgtgc accaccacac ccggctaatt tttgtatttt tggtagagac agaatttcac   13680
catgatgtcc aggctggtct tgaactcctg acctcaggtg atttgcccac cctggcctcc   13740
caaagtgctg ggattatagg catgagccac tgcacctggc tagatctttt ctttattatt   13800
ttgtcattct ttccttcacc tggcttttt aaaaagttaa atttagctat tagctgtctg    13860
aagtgtcttg tttttttttt ttcttaatg gggtcaccat actataaagc tttaagtacg    13920
aatacaacac agttgtaaat cgtttcaaat cttaaccctt caaatttatt ttatttttc    13980 ttgagggata tttgttattt attgatgtaa gtgccagctt tatttcagca gatagaaatt   14040
aacaattttg tatcttaaaa tgtcagcata cgcccctaga aaaatttcac agccggctgg   14100
ccatggtgtc tcacgcctgt aatctgagta ctttgaaagg ccacggtggg aggactgctt   14160
gagcacggga gtttgacacc agcctgggca acatagtgag accctgtctc taccaaaaaa   14220
tcaaaaaaat tagccgggtg tggtggtgca ttcctgtagt ctcagctact aagaaggatg   14280
aggtgggagg attgcttgag cccaggaggt tgaggctgca atgagccatg tccctgccac   14340
tgcattccag cctgggtgac agagcaagac cctgtctcaa aaaaaaaat tcaaacccctt  14400 gatttaaaaa tcaatcctga tcaaagattt ggcctaggga tttcttattt tatttggaag   14460
tacttgccat tcatatatat gtatgagtta tatatattca tatatatg agttaaaaat     14520 taaagtcaaa tgaactaaaa tgagttcttt ggctctattt cttgtctgct gaagtgtata   14580
tgttaatata cattaatata aatcgtgata gtttatatcc tgttattaaa tatttgtaaa   14640
acagaacctc tggccgggca cgatggctct cgccagtaat cccagcactt cgggaggctg   14700
aggcgtgcag atattgcctg ggctcaggag tttgagacca gcctgggcaa catggtgaaa   14760
ccccgtctct actaaaatta caaaaattag ccaggagtga tggtgcaccc ctgtaatccc   14820
agctactcgg gagctgaggc agcagaatca cttggacccg gaaagcagag tttccagtga   14880
```

```
gccaggatcg tgccactgta ctccggcctg ggcaacagag tgagactctg tctcaagaaa    14940
aacaaacaaa caaacaaaaa aaaacacaga gcctgtgaat tgctgaccta atttattttc    15000
cttgggaaaa tacctagtaa gcctatggag ataaactctt agaattgaag tattgttcat    15060
tataagcaag gcatacagaa gtcctgccta ttccaggtct agtgtagtct ctggagaact    15120
tatcttttct aagatactat gtacagtaaa caggaagctc tctgttggag gatatgtcag    15180
agctggagat tggactagaa tactgaagac aatatcgaca acaatgacat tttttgagag    15240
tttatgagtt tactgttttg ttttttttct tttgagacag agtctcattc tgctgcccag    15300
gctggagtgc agtggcacga tctcggctca ctgcaacctc tgcctcctgg gttcaagcga    15360
ttctcctgcc tcagcctccc tagtagctgg gactacaggc gcgtgccacc acgcccggct    15420
aattttttgt attttttagta aagatggggt atcaccgtgt tagccaggat ggtctccatt    15480
tcctgacctc atgatctgcc cgccttggcc tcccaaagtg ctgggattac aggcccgagc    15540
cactgccccg agctgagttt actgttttaa gtgctacctg cattaacatc tttaatcctc    15600
atagcaatcc tgagatgtga ggtaggcact attatgatcc cattttaaag ttgagaaaaa    15660
tgaggttaac taatctgaaa aatatagtaa gggacagtgt taatataaaa ctaggcagcc    15720
agacaactcc tgctcttaac tgctatgtgg ttttttggatt tgtttgtttg tttgttttttg   15780 ttttgtctga gatggagttt ctctcttgtt gcccaggcta gagtgcaatg gtgtgatctg    15840
acctcagctc actgcaacct ctgcccctca ggttcaagca attctcctgt ctcagcctcc    15900
cgagtagctg gaattacagg catgcgcagc catgcctggc taattttgta tttttagtag    15960
agacaaggtt tctctgttag tcaggctggt ctcgaactcc tgacctcagg tgattgcctc    16020
acctcgccct cccaaagtgt tgagattaca gggatgagcc accacgcccg gcctctttttt   16080 tttttttttt tttttgaga ccagtcttgc tctgtcgcca atctaaagtg cagtggtgtg    16140
atctcagctc actgcaacct ccacctccca ggttcaagcg attctcccgc tcagcctcc    16200 cgagtagctg ggattacagg cacccaccac cacacccagc taattttgt agttttagta    16260 gagacagggt ttcaccgagt tggccaggat ggtctagatc tcttgacctc gtgatctgcc    16320
cacctcggcc tcccaaagtg ctgggattac aagcgtgagc caccgcgcct ggcataaaac    16380 tattttaaa agaagaaaaa tagctacaaa atttaaaaag caggtaaaat gtacaactaa    16440
tataaaccag ctagtgatct atgacttttt tttttttttt ttttaacagg gtcttgttct    16500
gtctcccaag ctggagtgca gtggtgtggt cataggtcac tgcagcgtcg aactcctagg    16560
ctcaagtgat cctcttgcct caggctcctg agtagctggg acaacaggcg tgtaccacac    16620
ctggatactt tttaaattt tggtagagaa gggatctcac tctattgcca agctggtgtc    16680
gaactcttgg tcttaagcag ccctcccacg tcagcatccc aaagtgttgg gatttcagag    16740
gtgagccacg gcgcccagtc tgagtcactt ttaaacttag aaaatagttg caagaacagc    16800
aaataaacaa aacttgctca catatctttc acgtagagac ttgcattcaa gttctgccca    16860
tcgttttggt gatggatgtc ctttattgca agactgtaat ccaggatcac atttccaccc    16920
agtttccttg cctctctaat atactttttt gagatggagt ttcgctcttg ttgctcagac    16980
tggagtgcag tcgtgcaatc tcagctcact gtaacctctg cctcccggtt tcaagcaatt    17040
ctcctgcctc agcctcccgg gtagctggga ttacaggcat gagccaccac gctcaactaa    17100
ttttgcattt ttttttttt tagtggagac ggggtttctc catgttggtc aggctggtct    17160
tgaactccca acctcaggtg atccgcccac ctcggcctcc caaagtgctg ggatgatggg    17220
catgagccac tatgcccagc cctctaatat atatatatat attttgaga cggagtttca    17280
```

```
ctctttcacc caggctggag tgcagtggca ccatctcagc tcactgcaac ttcttcctcc    17340
tggttcaagc gattctcctg cctcagtctc ccaagtagct gggattacag gcacctgcca    17400
ccacacccag ccaattttt g tattttagt agagatgggg ttttgccatg ttggccaggc    17460
tggtgtcgaa ctcctgacct caggtgatcc acccacctcg gcctcccaaa gtgctgggat    17520
tacaggtgtg agccatccat cccggcctaa tatactttat tttagaacag ttttcagtg    17580 ttttgagttt cattcatgcc cttgaccttt ttgaagacta gaggcatttt tatagactgt    17640
ctcttaactc aggtttgtcc agtgcttcct catgcttata ttgaggttaa gcattttgag    17700
caggaatatc catgttttcc ttgcattttg ttgggtggga cgtggtgttt gtctgtctgg    17760
agactagtgt taactttgat gacttggtta cgatgggatg tgccatgttc tccttttttt    17820
taaaagaatg aatattttta aagaagaaa agtagctatg aactagtatt ttgtggtaca    17880
atactttggg aaaatgaaaa tatctccttt tagtattgag gaatcctatt tctttgagag    17940
gctgtttttt tggggggggg cagaaggtca gttcatagac ttaaatacca ttatagttgt    18000
tgtctaagcc cttgaaaact taatgttttt ctaaagttta aatttgtaga taatggaatt    18060
tgaaaaatat ttaaaatcgg attaaatttt acagtgtata gtgtggtttg aaagagaatg    18120
gggggctggg cgcagtggct cacacctgta atcccagcac ttgggaggcc gaggtgggca    18180
gatcactaga ggtcaggagt tggagaccag cctagcaaac atggcaaaac cccgtctcta    18240
ctaaaaatac aaaaattagc tgggcatggt gatgggcgcc tatagtccca gctacgcagg    18300
aggctgaggc aggagaatcg cttgaacccg ggaggcagag gttgcagtga gccaagatca    18360
tgccactgca ctgcagcctg ggtgacagag caagactcca tctaaaacaa acaaacaaac    18420
aaacaaacca aataaaaaga cagagaatgg ggaattgagg acatctagtc agttggatag    18480
atctggattc tattcttagc aattctgtga tcttgggcaa tttacattgt cttttaagtt    18540
atcagctgtt cttaggttat aaaaagatcc attttgtaaa ttgtgtcaag cagatgtcga    18600
ccatttataa taaacttatc aagatatgaa gttaatttct ttgctgtcat tcgaaagaca    18660
aactgatagg gtcagcaaac taccttaaac atgttctcat taaaacaaaa attaaaaaca    18720
cagctcctat agccagacgt ggtggcagat gcctgtagtc ccagctaatt gggagactga    18780
ggtaggagga tccttttgagc ccaggagttt gcagccatct tgggcaacat agtgagaccc    18840
ttatctgaaa acaaacaaa caaacaaacc aaaaccctag caaagcacat ttctataga    18900 agctactcag tggacataat taaacaaat ggtagtatct tgaaaaaatt aagacattta    18960
gtgtgaacca catgtctaga aaaaaaatt aaatagaaaa cattaagata tttacaaagt    19020
ctgtgtttac aatctgaact gattatatta aatgtatact gacattttag ggatgaataa    19080
atttccttct gaaaacaga ttttagtttt ggcttttagt acttaataat tataggaga    19140 acatggaaat attaaatacc aacaatttgg ctgggcatga tggctcatgc ctgtaatccc    19200
agcactttag gaggctgagg cgggcaaatc acttgaggtc aggagttcaa gaccagcctg    19260
gccaacatgg ggaaaccctg tctctactaa aaatacaaaa aaagctagct gggtgtggtg    19320
tcaggtgcct gtaatcccag ctactccgga gatccagcca ggagaattgc ttgaacccaa    19380
gaggtggagg ttgcagtgag ccgagattac gcccctgcac tccagcctgg gcgacagagt    19440
gagactctgt ctccaaaaca aaacaaaaac aaaacaaaaa accgaaaaaa ccccaacagt    19500 ttcgagagatg aaaagattta ggcggcctaa aagattgcca aaatgtagta ttacatgata    19560
atctaaacta gttttaatgc agctgaatcc tggtttagac taaagtcagc tgattgaact    19620
```

```
actagtatta gatcttttgg atttatttta agcactattt taggacaaaa tatctaacat    19680
tttacttgat gaattttaac tttttcttac cactcattgt tttgaagaaa ttactttgta    19740
aaagtttgag atgtcactaa ttttttcctt ggcattaagc gatacatgaa ttcattttat    19800
tcttctgact gaggatgttt ctgttagtgt atacattcaa gaatatgatg atgccattag    19860
tcatttaatt ttgttgaaac ttggctttag tggctgttaa taaaatgaat tggttggcca    19920
ggtgtggcac tttgggaggc tgaggcgggc agatcacctg aggtcaggag ttccaagacc    19980
agcctggcca acatgctgaa accccatctc tactaaaaaa agaaaatta gccgggcgtg     20040 gtgacataca cctgtaatcc tagctactcg ggaggctgag gcaggagaat tgcttgaacc    20100
caggaggcgg aggttgcagt gagccaagat cacgccactg cactccagcc tgggcgacag    20160
agtgagattc tgtctcaaaa aaaaaaaaa aaaaaaaaa gtaaatttgg gttttacagt      20220
ttttcctctt atacaaaaga taactggaga ctagatctca aagaatgaag acagctggaa    20280
agctggaaga caccagaaaa ccaagaaaga gagaacttcc ctgaaatact ggccaaggca    20340
gaagtgcatc caccagtact gcagactcac cgctgtagtc catttttttgg aatagggga   20400 caaaaactta ggtttggacg gaaaattttct ctggtaaaag tattatttct gtctgtctct   20460
ctctctctct ctttaatgga cacgggctta ctctgtcacc caggctggag tgcagtggtg    20520
ccatcatggc tcactgcagc cttcacctcc tgggctcaag ccatcctcct gtctcggcct    20580
cccagagcgc tgggattaca ggtgtgagct actgagcccg gctttttttt tttttttttt    20640
tttaactcaa gcctgttgaa taattacaga attgaatacc attacctgtc ttaaatactg    20700
tcttccaggg acaatatcct agtggcaatt attttagcta attttgaagg ttttttctcag   20760 tttttattca tctaagcatc taggggttta gtgattattg tctgaatgca aaacattgag    20820
ttaagaaaga tactgatttt tgcagtcttg agtttatctc gccttcctta agtaaaggtg    20880
cagtgtagat cttcattgct tattacaagt aaaaatagta gcctgtagaa atttgtgcag    20940
aagaaaataa aataatgggc ctggtgtttc tcatcagttt aaatccattt caccttcgtt    21000
gagactgagt cttcagtctt ttaggtggcg agtcaaggtt ttactaattt aaactattgt    21060
ctaaattcag ggctgtctttt cattgttaaa ggagatagtt tgcctgacag tacctggaag    21120
cagtgttttg tgacataagt aatgtgttca cctagataat cggtctgtaa cctactcata    21180
tatatatatt ttttgagaca gagtctcgct ctgtcaccca ggctggagtg cagtggcgcg    21240
atctcggctc actgcaacct ccgcctcccg ggttcaagca attctcctgc gtcagcctcc    21300
tgagtagctg ggaatccagg tgtgcgccac catgcctggc taattttttgt attttttaata   21360 gagatggggt tttagcatgt tggccaggct ggtctcgaac tcctgaccttt gtgatttgcc    21420 cacctcagcc tcccaaaatg ctgggattac aggcatgagc caccgcgccc agctatattt    21480 ttaaaattt tttaattttt tgagatggag tctcactctg ttgctcaggc tggagtgcag    21540
tggcgtgaac ttggatcact gcaacctccg cctcccgggt tcaagggatt ctcctgcctc    21600
agcctcctga gtagctggga ttacaggcgc ccaccacacc cagcttattt ttgtattttt    21660
agtagagatg gggtttcacc atgttggcca ggctggtctc gaattcctga cctcaagtga    21720
tccacctgac ttgacctccc aaaatgctgg gattacaggc gtgagccgct gccatatttt    21780
ccatttattt ttttttttaac caaatgcctt attttcttag aatgtgactg atgctgatac    21840
agaaagttca gtgtccacta tcatctttgc tttctaatga aaaggatatt atactttgct    21900
tcagtcagtt cgtttatgat gagtggcagt taattctctg ctgaaagact gtgtagtatt    21960
atagttgcaa tcactgtcta attatttacc ttgtgttgat tatgttttta aaacctgcca    22020
```

```
ttctttgatt gttattatgc attaaaaagg cagtttggtc ttgaactcta gacctcaagc   22080
gatcctccta ccttggcctc ccaaaatgct gagattacag gtgtgagcca ccacacctgg   22140
ctgtaaagag gcaatttgga atttagagag ggattctagt cccttgttaa agaactaact   22200
ctaggctgtg cacagtggct ctcgcctgta atcccagccc tttcggaggc cgaggcaggc   22260
agatttcctg aggtcaggag ttcaagacca gcctggccaa cgtggtgaaa ccccattttt   22320
actaaaaata gaaaaattat ctgggtggtg gcggacacct gtaatcccag ctactcagga   22380
gtctgaggca ggagaatcgc ttgaacccgg gaggcagagg ttgcaatgag ctgagatcac   22440
accattgtac tccagcctgg gtgacaagag ccagagtcca tctcaaaaaa aaaaaaaaa   22500
aaaaaaata tatatatata tatatatgta tgtatgtata tacacatata tatatgtatg   22560
tatatacaca catatatata attttatata tttatttata tatatttgtg tatatatatt   22620
ataacatgaa aaagaaatag ggcatgaatg taatttaaat aaaagagtgt tctagcacct   22680
gcccacttgc cagtctgact ggaaccttgt tttgaagcag aaatgtattg aaagttcaga   22740
agtatctcag agaacagcat cataaaaaat attaagaacc tcagttttta ttagggtaat   22800
gataaggttt gtaaaaatct tcaagcgcgt tcttcctttc actcactata aaatattttt   22860
ttttgtctgg gtgcagtggc ttatgctttt aatcctagca ctttggtaga ctgaggcggg   22920
aggatcattt gatctcagga gttcgagacc agcctgcgca acatagtgag acccgatctc   22980
tactaaaaat acaaaaaatt agccgggcgt ggtgctgcaa gtctgtagtc ccagctagta   23040
gggatgctga ggtgggaaga tcgcttgaac acaggaggtg gaggcttcag ttagcagtga   23100
tggtgccact gtactcgtcc aggcaacaga gtgagacttt gtctcataaa acccaaaacc   23160
aaatgttgtt gtgtgctgtt tggtattaac agcaaggaat cagataatta aagcagaagt   23220
acagacaaaa agaaaatttt atggaattag ttattggctt attttgagga agaatggatc   23280
agaacagcaa ggacacggat aaatctaata cctgaaatgg atctccaaca ggaaactcga   23340
ggatttcaaa caatggctag agtcttgttt tcagagataa agaaggcatc acatatacag   23400
tagccaacca gaatcggaga taaacaatga aatagcaaca ggccaattga gttcaacttt   23460
gaaactcatg aaggagaatt aaaatcaaat cagggaaacg aaaggtgaag tcaaaaaacg   23520
ttgagaatag aagaactgag gagattaaaa aatgggagg ctgggcgcag tggcttatgc   23580
ctgtaatccc agcacttggg gaggccaagg cgggcagatc acctgacgtc agtagttcaa   23640
gatcagcctg accaacatga cgaaacccca tctctaaaaa aaatacaaaa attagctggg   23700
tttggtggca ggcacctgta atccgaacta cttgggaggc tgaggcagga gaattgcttg   23760
aacctgggag gcagaggttg cagtgagccg agatcgtgcc attgcactct agcctgggcg   23820
atagagcaag actctgtctc aaaaataaaa aaaagaaaa aaagaaaaaa aatgggaaa   23880
gaaggcatac caggctcaca tagctgttat ttttttgtgtg tctgtttaat cacagtatat   23940
cccgtgtcat cttgttctga ccagcccaca gtaattgggt ttgggtaggc tcatgacaca   24000
tatgcccaga tcttttacac aaaatgtaat gggaaggctg gcatagtgg cttacgcctg   24060
taatcctagc attttgggag cccaaagcag acggatcaac tgagatcaga agttcgagac   24120
cagcctggcc aacatggcaa aatcctgtct ctactaaaaa tacaaaaatt agtcagacgt   24180
ggtggtgcac gcctgtaatc ccggctactc gggaggctga ggcaggagaa tcacttgaac   24240
ccaggaggtg gaggttgcag tgagttgaga ttgtgttact gcactccaac ctgggcgata   24300
agtgagactc cgtctcaaaa aaaaaaaaaa agtaatggga ggatgtgata gttctctgcc   24360
```

```
tctgggatca caggacagga atgtggtacg catgaaggtg catgtggctg tcaggtctgc    24420
cttagggaga acacccttct gcttaagctg agagaattct aatgacttat tttgtggttt    24480
tggatctagc tatatgtgga gccagtataa cctttagact taattaatta aatgaagcaa    24540
taaaagttct cttttgtact tgatcttgtt tgaattggga attggtaacc tcgcaatcta    24600
aagtagttct ggctaattca taaattgttc ttgagaataa aggatatgga aggtatggtt    24660
cccagagttg gtgaggttag ttattcttac tgaaaacaac caacactgtt gtaaaattat    24720
aaaacaaaac ttttgtgaaa acaccagaaa gttgaaaagt agagaaaatt tgaagggctg    24780
ggttatggga actcaattga cagaagtgag aattactctt gtcctgaagg caaacatttc    24840
accacttgac cttgagtttt aaaagctttg tggggtgaga gactcagaat agtctgcatc    24900
cttacttgtg gcctgggtta acttctactg ggtgggccaa ggaaccaagt ctcgaacttg    24960
gattagagtg attctaggca ggtgttgtct cttgacacct ggaggaagct gccttcaccc    25020
taggcttaag attataagta attttttcac gtaaaataac taactcacta agataattag    25080
gcatagaagg gaataagaac catgcataag ggtaagaacc actgggaaca acagaaatag    25140
tcctgcaaaa acttgagatt tggaattatc agagactata aaataactgc cccattacca    25200
aagaaatatg acaatcttga aattccttag agagtaggaa actataaaat atgacttagc    25260
agtaactaga aatcatagaa atgaaaatta caaacaaaat taaaaaccgg ataggtgttt    25320
taacaacaga ataaaaagat gaagaaggag ttagtgaaat ggaaggtaag ccagaagaaa    25380
taattgttta gtatggagaa gaaaacgtaa aaaaaggtaa aagctaaaa ggataagtga    25440 tgactaacat acattaatgt gagtcccagt aggataggag atagagaatg gggcagaatc    25500
taaagagaca atagcttaga gttttccaca tcgaaggata ccatttcata gttaagccta    25560 tgaatgcacag acatatgttt aataaaaata aaatctacac ctagaataca cagtgaaact    25620
gtagaaaaca tcttagacaa agaaaacctc ttaaaaacag caggagtagg aatgggaatc    25680
acctaaaaag agaccgtaga ttacttctca atagcgacag tggaagccaa aatataatga    25740
caccaacaga taatgaaata accttagtgt gctgaaagaa tataattgtc aacctaggtt    25800
tctattccag cgaaaatacc tttcaagaaa aattttttag caaacaaaaa cagtttgtca    25860
ccagaggaca gcaggaacac aaaagaatga gcaaattatg tcataaatac gtggttacat    25920
ctaaaggaaa attaaattaa gcaaaatag tgttgcatct aaaaatacag aattaggccg    25980
ggtgcggtgg ctcacgcctg taatctcagc actttgggag gctgaagcgg gcagatcacc    26040
tgaggtcagg agctcaagac cagcctgccc aatgtggtga acccccatct ctactaaaaa    26100
tacaaaaatt acccgggtgt ggtggcaggc gcctgtcatc ccagctactc gggaggcaga    26160
ggcaggagaa ttactcgcac ccaggagctg gagatttcag tgagccagga tcgtgccact    26220
gcactccagc cggggcaaca gagcgagact ccttccccccc accaaagaaa aaaaaaactt    26280
aaaaactcgt acctagttgc attccttatg agcacagagc aaaatgtcct catttttacct    26340 ggtttaattt ttttttttctt ccacggcctc ttttactggg agacctctga gttttgatgt    26400
gtcatgacag ataggagagg tcatatcctt gtgatttgtg gttcattgct ggtgacatca    26460
gaaagtaaag tcaaccagga aaagactcca tgggcctggc tcaggtggct tctggagcac    26520
cacctccatc aaggagcttt tcctggggtc catgtgtagt ccatgttgcc tgctctccca    26580 cccaggggttg ctgtgcttat tatacaagat ggccaataaa gcatgacata tattcaataa    26640
atgttcattt cttttttccaa cccttcttat tttaagttga gggtattcat aaaagggatt    26700
gagcatttcc atttatggac gaggcaactg agtacagccc ccaggggcac gcagcgagat    26760
```

```
ggctgtctgc tgaacccata caccagctct ctaggcgttt ggtcctgtgg ggaccggtgc   26820
atcagatgct tcctaagctg gcgtcacctg cctggcccga tgcctcctct ggtgttcatt   26880
gtttaattaa tgccacctcc tgatggcagt ttctttctgg gaagaggaga aagagagcc   26940 gtccccaagt gaagggtgca gggaagcctc cacgaatagt ttcaactaag gactgtccca   27000
ggaaggaaac tcttgggatg gcaaagaac agcgaacttc cggtgtgacc cggatgcacc   27060
catttccaga gagcaggaag cacagagaag gcccgtgggt cgcccttggg gtgctttcca   27120
tcctgcaggg ctcgctgcct gccctgaaag ttctgataaa gacataggac cttcatcacc   27180
aggggcgccc cgtgggctgt tgctgtagcg tctgtccccc atttcttaca cacattgagt   27240
gtgattgtta ccagtggagg gtgtccaatg gaagaagcac caaaagccga gatttattga   27300
aagtggaagg tacagtccac aaagagggg cgggccgagc ctgggggctg aagagcccct   27360
ttacagaatt ttctggggtt taactacctt ctggggttta actttctggg gtttaatttt   27420
ctagaggttt cccattggtt acctggtgta catcctttgt aaatacagta gtggcctgca   27480
agcagtctga ttggttgtga aaagcaacca attagaggct gacttgaagt tacaaaggtt   27540
acaccctatg caagcatctg tggaaagcaa ccaatcagag actaaagtga agttacaaag   27600
ttacacttgt atgcaaatga cgacttgccc tgccgggctc cagtaatccc agtactttgg   27660
gaggccaaga tgggtggatt acttgaggtc acgagttcca gaccagcctg accaatatgg   27720
tgaaaccccc tctctactaa aaatacaaaa aattagccag gtgtggtggc agttacctgt   27780
aatctcagct actcgggagg ctgaggcagg agaatcgctt gaacccggga ggcagaggtt   27840
gcagtgagct gagatagcgc cattgcactt cagcctgggc aacaaagcaa gaccctctct   27900
caaaacaaaa acaaaaggcc gggcgtggtg ggaggccaag gtaggtggat aacctgaagt   27960
cagaagttcc agaccagcct ggccaacatg gcgaaactcc atctctacta aaaatacaaa   28020
aattagttgg gcgtggtggc gggcacctgt agtcccaggt actcgcgagg ctgaagcagg   28080
agaatcgttt gaacccggaa ggccgaggtt gcagggaacc cagaacgtgc cactgcactc   28140
cagcctcggc gatagagcta gactccgtct aaaaaaaga aaaaaaaag tccggggcg   28200 atggctcacg ccggtaatcc ggccgaggcg ggcggatcat gaggtcagga gatcgatacc   28260
atcctggcta acatggtgaa acccgtctc tactaaaaaa cacaaaaatt agctgggcgt   28320
ggtggcgggc gcctgtagtc ccagctactc tggaggctga ggtgggagaa tggcgtgaac   28380
ccgggaggcg gagcttgcag tgagccgaga tcgtgccact gcactaaaga aaaggaaag   28440 gaaaaagac ttggtcgcag tcagtctggg attcgttgca ggaagcaacc aatcagaggc   28500
tgaagtgaag ttacaatgtt acactcctgt gcaaacgtct gattggttgc agaaagcaac   28560
caatcagaga tactttgaat tttccatctg ggacacagaa aaagtggggg tggtggtttg   28620
caaactgagt agcctcccat cctttgtta cttaggtgtg aaaagttggg gttttccttt   28680
tgatttagtt ctaggaagtc agcatgaatt ggccttaggt tccctgcctc cagacccta   28740 tctccggcct catgatgact tgatggcaga tttatggcga ttaaagatga gaaaaagtgg   28800
taacagcagt aggcagaaaa ttgccctagt ttcatgttct gactgtgata gtggcaatat   28860
gaccttgaca aatcactgca tttgtaaaat gagaacacat ctctgttttc tttcgctggg   28920
gaattaaagg aaagtgaga ttatgaagaa atactatgaa ttttcagaaa taatgaaagt   28980
gtacgctaag tgaatgtcta attatagaaa catatatgcc tttgttgtcc atttcgccta   29040
agccacattt taatggaaat ttacttagac ttgggggaga gggagaggga aagaaaacca   29100
```

```
gacaaattca cttagtttta tccaagagaa aaagaatggg acctaagctg ttaggccaaa   29160
taatttctat aatttaccta ttcacttgct tgatacggcc tttacttccg tctctagtca   29220
gggacccttg tgttgggaat cagatttgct tctgtttgtt caaatatatg gggataagtg   29280
ttttgtttgt tttgtttttg tttttttttt ttgagataga gtcttgcttt gttgtttggg   29340
ttggagtgct gtggcgtgat tttggctcac tgcaacctcc acctactgga ttcaattgat   29400
tctcgtgcct cagcctcctg agtgactgga attacagatg gtacaccacc atgcctggct   29460 aattttgta ttttagtag agacagtgtt tcgccacatt gcccaggatg gtctcgaact   29520
cctggcctca tgagagtcac ctgccacggc ctcccaaagt gctgggatta caggtttgag   29580
ccactgggcc cagccaagtg tcaattattt tttattatgg tttgtattta tttattttat   29640 ttttttgag gcggagtctc actctgtcgc ccaggctgga gtgcagcagc gcaatcttgg   29700
ctcactgcaa cctccgcctc ctgggctcaa gcgattctcc tgcctcagcc tcccaagtag   29760
ctgggattac aggtgcgtgc caccatgccc ggctatttgg aattttaat agagacaggg   29820 tttcaccatg ttgccatgc tgatctcgaa ctcctgacct caagagatcc acccgcctcg   29880
gccttccaaa gggctgggat tacaggcgtg agccaccacg cccagtggat tatggttttt   29940
attataaagc gcaacttcct aagtatgtat gcttcgttat ttgttgatgg gtaatctggg   30000
ctagcagtta attcacatgg taacagataa agctagatca cagtctttaa taatagggaa   30060
atagagcatc ctctttaata atagggaaaa gatttactga cattttttagg cataacagtt   30120 ttctgctgac agctcctcag ctgcttgtcc acgttctcca gaaccctggg gctttagtta   30180
aggaatactc gggtgttgtc agtaaaattaa tttgttttta cagttactat tcttgtttcc   30240
agtgtttaat ttttaaattt ttcagttatc tttccatatt aagtttattt aattattcaa   30300
tagctcccta aaagtagaat taattcaact aaattaaaag ggacaatttt taataggcat   30360
ctaatttgca tgctatttac agaaaacctt tttagtgttt cagttttaga aatttgctttt   30420 agattttgcc atgttagtat gtctttatat ggtgtattgt tttggtttta ttttggtaaa   30480
atatacataa tttttttgtg tgtgtgacag gctcactctg tcaccaaggc tccagtgagg   30540
tggcgtgatc tcggctcact gcaacctccg tctcccaggt tcaagcgatt ccctgtctc   30600 agactcttga gtagccggga ttacaggcgc ccaccaccct gcctggctca ttttttgtatt   30660 tttagtagag gcagagtttt gccatgttgg ccaggctaat ctcgaactcc cgacctcagg   30720
tgatccacct gcctcggcct cccaaagagc tgggattaga gacatgagcc accacgcctg   30780
gccagtatgt ttttatatgg tgtgttgttt tcattttatt ttggtaaaat atacttaaca   30840
taaaatttac acttctaacc attttgtttt gttttttttga gacggagttt tgctcttgtc   30900
acccagactg gagtgcagtg ctgcgatctc cgctcactgc agcctccgcc tcctgggttc   30960
aagcaattct cctgcctcag cctcccaaag tgctgggatg ataggcatga ccaacgtgc   31020 ctggccagaa tatgctgtat tataaagaat cttacatgtt acttgatgcc tgtgatctat   31080
tttcttagta agaagagaaa cttctctcca ctcagcctca gtccactgta cccactcttt   31140
tgtgtgtcag gatgttcagg ggagaagagg gcttagcatc tctgtcctgt gttgagttgt   31200
ggttgcccgt cactgggctg taaagtgcct tgcctcgtct tgttcttact tgggagaaat   31260
ttcactgatt ctgggtgcca cctggattta tttggggtgt gatattgacc caattttctg   31320
gaaataacaa tatatagaaa attaggggat agattcttta tcttatgagg gtttgggcaa   31380
gtcaaatact tagtttctga gccttatttt gtctctagag caagaaaact gtaaattagg   31440
cagccggtga ggggcccctca cagctttggc tgtgggttca ggacaccaga tttctaccac   31500
```

```
tcactttctt cttacttctc ctgcacaggg atcatggccc aagttgcaat gtccaccctc   31560
cccgttgaag atgaggagtc ctcggagagc aggatggtgg tgacattcct catgtcagct   31620
ctcgagtcca tggtgaggcc ttctgttcca tcattccata gttgggtagg cctgcactgt   31680
agataaggtt gatttgtttt tgtggaagat agaattttat ggttttagt tttaatgagt   31740 acttttctt tacttttttt ttttttttt ttttttgag acggagtctt gctctgttgc   31800
ccaggctaga gtgcagtggc gagatcttgg ctcactgcaa cctttacctc ccgggttcga   31860
gcgattctcc tgccttagcc ttccgagtag ctgggattac aggcgcctgc caccacacct   31920
ggctaatttt ttgtatttt agtaaagaca gggtttgacc atcttggcca ggccggtctc   31980
gaactcctga cctcttgatc cacctgcctc agccgcccaa agtgctggga ttacaggtgt   32040
gaaccactgc cccaaccaat gagtagtttt tcttcttgaa tagttatggg tttaagcctt   32100
tcacatcaca gtcattcatt cattcattca tttatttgag acagagtttc gctcttgttg   32160
cccaggctgg ggtgcaatgg catgatatag gctccctgca acctctgccc ctgggttca   32220 agtgattctc atgcctcaga ctcccgagta gctgggattg caggtgtgcg ccaccacgct   32280
cgggtaattt tttgtatttt tagtagagac agggtttcac catgttggtc acgcgggtct   32340
cgaactcccg acctcaggtg atccacccac cttggcctcc caaagtgctg ggattatagg   32400
ctgaggtcag gagttcaaga ctagcctggc caacattgtg aaaccctatc tctactaaaa   32460
atacaaaaaa attagccagc gtggcagcgt gtgcctgtag tcccagtaac ccgggaggct   32520
gagacaggag aattgcttga acccgtgagg tggaggttgc agtgagccga gatcgcgcca   32580
ccacactcca gcctgggcga cagagtggaa ctctgtctta aaaaaaaaaa gaaaaagatg   32640
cccataaata ttttgttccc aggttgttat ggtggtatta tttttagggg ggaaaattgg   32700
aatcaccaac cttttaaata atgttatcag taaatcattc aaggtatatt cattaaatgg   32760
aatactatat actctgtaac attttaaaag aatatttaat ctcgtagaaa tatgcttagt   32820
aaaagtcagt aaatactctg cccacctaaa agtgattctg gctgtgtgta cacaggggaa   32880
tacttctgga ggtggggatt atgtaatgaa tgctgtagtg tgggtttcag acccccaccc   32940
tccttttgta ctgagggcac taattgccca ggtgccatgg ctgttcgagc accttgtaca   33000
agattccacc cttttcccagg ggagggccat gccagctccc agctctgggt gcagctacat   33060
cagtgttcag tgcttcgtct gtccggccct gcctgccttc cgcctcccaa gtgctgtaat   33120
tgacagtgcc ccccagcaag cctgtgtaaa ctctcagtct actacttgga gaatctgacc   33180
tataagagat tacaagggaa ttgtgttttt tttttcctta taaattctgt gttgtctttt   33240
gtttaaaatc aggccaaaaa ctatctcgaa agagaagtac cttaaaaaa tgttgttagt   33300 ttttttaatt catcgagcag aaatgatgct cttaaacgtc cgcctgtaac atgatgtttg   33360
ctgtttgtat tgtagtgtaa agaactggcc aagtccaaag ccgaagtggc ctgcattgca   33420
gtgtatgaaa cagacgtgtt tgtcgtcgga actgaaagag gacgtgcttt tgtcaatacc   33480
agaaaggatt ttcaaaaaga ttttgtaaaa tattgtaagc attgtatttt tatcttttgc   33540
atttcattaa ttttaagcct aaatatttgt aggtaagaca agttatatta ttttctttct   33600
ttctttcttt cttttttttt ttttttgaga tggagtttg ctcatgttgc ctaggctgga   33660
gtgcagtggc acactcttgg ctcaccacaa ccccgctgc gtgagttcaa gtgattctcc   33720
tgcctcagcc tcccaagtag ctgggattac aggcacgcgc cagcacgcct ggctaatttt   33780
gtatttttag tagagacggg gtttctccat gttggtcagg ctggtctcaa actcccgacc   33840
```

```
tcaggtgatc tgcccacctt ggcctcccaa agtgcagagg gattataggc gtgggccact    33900
gcgcctggcc aagttatatt ttcttctaaa acagaatgag gtttaaacta aaaaagattt    33960
tctgaaatgt ttatggagac atttcaaaat gctcaaaagg aatcactgaa atatgtcagg    34020
atagatactg aagagttaag aaaaatggta gtgtttgttg tacggtgttc cttgcttggc    34080
tttactctgg gttaatgaga tgcattagag agaaggtaat gaaggtagag aaattttgaa    34140
taggttaaaa cttttactca gataaggagt tattttcttt ttcttttttt tttttgagac    34200
agagtttcac tcttggcccc ctgggctgga gtgcaatggc acgatctcgg ctcattgcaa    34260
cctccacctc ccatgttcaa gcaattcttc tacctcatcc tcccgagtag ctgggattac    34320
aggtgcccac caccatgcct ggctaatttt tgtaatttta gtaaagacag ggttttgcca    34380
tgttggccaa gttggtctca aactcctgac ctcaggtgat ctgcttgcct tggcctccca    34440
aagtgctagg atttcaggca tgagccacca ctctcggctt tttttttttt tttaagagat    34500
ggggtctcgc tccgtcacca ggctggagtg cagtggcgcg atctccgctc actgcaactt    34560
ccacctcctg tattcaagca attcttctac ctcagcctct ggagtagctg ggattacagg    34620
tgcacaccac catacctaga taatttttg tatttttagt acagacaggg tttctccatg    34680
ttggccaggc tggtcttgag ctcctgaccc gaggagccca cctcggcctc ccaaagtgct    34740
gggattacag gcgtgagcca ccacatccgg ccgggagttc ttttctagat aaaaagttgg    34800
tgtgttgaaa accagtgatt cactgtgcaa gtttgtttaa gcatattgca aaattaaaca    34860
gttctcctcc actccctcac agatacgagt caccttatca cagtcttcag tgagttttgt    34920
aatctgcatt tagagcagtg gtgagcttat ttgacattgg aacagtgttg aaatttacta    34980
tagggtttta atacccacag cctttcacag tatgaccatt ttcatatctg tgtttaacct    35040
aacactgtag gttttatgtt aactgattga tacagcattt tcttaaaaac atggaaaggg    35100
aacaaaaaaa gctagggtat ctataggcac atattatata tgggcatacc tcattttttg    35160
ttgttgtcat ttttgttttt ttgagacgga gttttgctct tgttgcccag gctagagtgc    35220
aatggtgcga tctcggctca ccgcaacctc tgcctcttgg gttcaagtga ttctcctgcc    35280
tcagcctccc gagtagctgg gattacaggc atgcaccacc acacccagct agttttgtat    35340
ttttagtaga gatgggtttt ctccatgttg gtcaggctgg tctcgtactc ctgacctcag    35400
gttatctgcc cgcctcggcc tcccaaagtg ctgggattac aggcgtgagc cactgtgccc    35460
gaccgggcat atctcatttt tttttttgt gccttgcaga cactgcagtt ttcacacatt    35520
gaagatttgt ggcaaccttg tgtcaagtct attggtgcca ttttttcctgc agcatgtgct    35580 tacttggttc tctgtgttgc attttggtaa ctcttggcat agcattattt gagactttt    35640 catgattatt gtatccgctg tagtggaatt tttttttttt tttttttttt ttttttgaga    35700
tggaggtttg ctccgtcacc ctggctggag tgcagtggtg cgatctcggc tcactgcatc    35760
ccctgcctcc ttggttcaag gtattgagat cagtgatctt tgatgttact attgtaattg    35820
tactgggagt cctcgaacgc acacatataa tatggcaaac ctaataggta aatatgtgtt    35880
ctgactgctt caccaatcgc ctggtccccc atcattccct ttcctcaggc ctccctggtc    35940
cctgagacac aatattgaaa ttaggccggc caggcacggt ggctcatgcc tgtcatccta    36000
gcactttggg aggccgagat gtgtggacca cgaggtcaag agatcgagac catcctggcc    36060
aacatggtga aacaccatct ctactaaaaa tacaaaaaat tagctgggtg tggtggcgcg    36120
tgcttgtagt cccagctatt tgggaggctg aggcaggtga attacttgaa cctgggaggt    36180
ggaggttgca gtgagccaag atcgtgccac tgcactccag cctggcgaaa gagcaagact    36240
```

```
ccgtctcaac gaaaaaaaaa ggaaattagg ccaattaata gacctatagt ggcctctgag   36300
tgttcaagtg aaaggaagag ttgcaggctg ctcactttac atcaaaagca gaaatgatga   36360
agcttagtga ggaaggcatg tcagcagctg aggtaggctg aaagctaggc tgaacaggta   36420
gccaggtgga gaatgcgtag gaaaagttct cgaaggaaat gaaaactgct gctccagtga   36480
acacgcaaat gataaagcaa aacagcttat tgctgatagg aagaaagttt gaatggtgtg   36540
gatagaagat caaaccagcc acagcattcc cttaagccac agcgtaatcc agagtgaggc   36600
cctaactctc ttcaattctg tgaaggctga gatgggtgag gaagctgcag aagaaaaatt   36660
ggaagctagc agaggttggc tcatgaggtt aaggaaaga cacagtcagc tgggggcggt    36720
ggctcacgcc tgtaatccca gcactttggg aggctgaggt gggcagatcg tctgagctca   36780
ggagttcaag accaccctag gcaccctggt gaaacccgt ctcttctaaa atacaaaaaa    36840
ttagccaggc ctggtggcgt gcacctgtag tcccagctgc tctggaggct gaggtacgag   36900
aatcgcttga gcccaggagg cggaggttgc agtgagctga gatctcgcca ttgcactcca   36960
gcctggactc ttgagatctg tctcaaaaga aaaaaaagg aaagacagag tctctataac    37020
ataaaagtgc aaggtaaagc agcaagtgtt tgatgtagaa actgcagcaa gttctttaga   37080
agatctagct gaggtaattc atgaagatgg ctacactcac aaaacccgat tttcaacgta   37140
gacaaaacag cctttatattg gaagatactc tctaggactt tgctagctag agagaagttc   37200
attcctggct tcaaagcttc aaaggacaag ctgaattcct tgtgaggggt taacgccgct   37260
ggttactttg aagccatgtt catttaccat tctgaaaatc ctggggtcct gaagagttac   37320
actaaatctg ctctgcctgt gctctattga tagaacaata aagcctggat gacagcacat   37380
ctcttgatag tgttgttcac cgaatatttt aagcccactt ttgagaccta ctgctcagaa   37440
aaaaagattg ctttcaaaat atgactgctc acagtcactc acagagtcct gatggaggtg   37500
tataaggaga tgcttgccat tttatttta tttttttattt agtttttttt gagacagagt   37560
tttgctcttg ttgcccatgc tggagtgcaa tggcgcgatc tcagctcact gcaacctcca   37620
tgaacactgt tgaaatgata acaaaggatt tagagtatga cataaactta gttcataaag   37680
caatggcagg gttttggagg attgactcca attttgaaac aagttctacc gtgggtgaaa   37740
tgctaccaaa tagcctcaca ctacagagag acctttcatg aaagcaagag tcaatgtaac   37800
ttttatatgc attgggaaac caaaacatct gtgtgacttt actttatact tgtattattg   37860
tggtgatttg gaaatgaacc tgcagatgct tgtatgccac taaggtctaa agttaaactt   37920
ctgatgtcag tttagattaa attggtgata cattcagcaa cttattagtg aacaaaaagt   37980
tttgttaatt cacgaatttt aattcccaat tgtatttta gtttgtttta aaaactatcc   38040
cctgccactg tattcctccc cctgtccctt acccccatgc tgtaatcttc taagctttat   38100
gttagtaact tattttaaa atgttgacat tattataatg ttgagaaatg ttcaagcatt   38160
gattatgttt ctgtgtttct ttatactaat aatgctgttt tgattgtgtg tgtatcagct   38220
gctgtctgcc ccaccaatac cataagcccg cctgcagctg tacttattct cccttccct    38280 gtcctgcctg gctatgtggg ttctccactg gttagaacta agcattaagg gcgctgtcct   38340
cagctgcaag ctgtagtcac tgtccatcag tattcatact ttgtttttat tgctaataat   38400
tttttttttt ttttttaagga gtctcgccct gtcacccagg ctggagtgca gtggcgtgat   38460
cttggctcac tgcaacctca gcctcccagg ttcaagcgat tcttctgtct cagcctcccg   38520
agtagctggg attacaggca cacctggcta atttttgtat ttttagtaga gatggggttt   38580
```

```
tgccctgttg gcctggctgg tctcgaactc cttacctcaa gtgatccacc caccttggcc    38640
tcccaaagtg ctaggattac cggcgtgagc caccgtgact ggcctcattg ttaataattt    38700
gatccatgga gaatggtttc tgtatctaat tctccttctt ctctttttt ttgagacaga    38760
gtctcactat cgcccatgga gtgcagtggt gcgatcttgg ctcactgcaa cttctgcctc    38820
ccaggttcaa gcaagtctcc tgcctcagcc tttctagtag ctgggattac aggcgtgtgt    38880
cactacactc ggctaatttt ttttttttt ttcgagacgg agtctcgctc tgtcgcccag    38940
gctagagtgc agtggcacga tctcagctca ctgcaagctt cacctcccgg gttcacgcca    39000
ttcttctgcc tccgcctccc aagtagctgg gactacaggc gcccaccacc atgcctggct    39060
aattttttgt atttttagt agaggtgggg tttcaccatg ttggccagac tgatcttaaa    39120
ctcctgacct caggcgatct gcccttcctg gcctcccaaa gtgctgggat tacaggcatg    39180
agccactgca cccggcctaa ttctcaagta cctcttactt gtttgtgtaa agtactttgc    39240
agataaggag caataatggt cttctggaag gtaatcaata ggtttatgag gcaatcatag    39300
aaattcttca ggagaattct gagcgctttt ctgggattta gaaaagcgtt gttcagcaga    39360
aaaaagtatc atgtgagtct ctcacataat ttaaaacttt ctagttagaa cattaaagaa    39420
aaataaagaa aaacaagtga aattcatttt actggtaata ctttaactta ttatatctaa    39480
aatatttcaa catgtaatca atttaaaaat tattaatggg ccgggtgtgg tggctcatgc    39540
ctgtaatccc agcactttgg gaggcagagg caggcggatc acgaggtcag gagatcgaga    39600
ccatgtggcc aacatggtga aaccctgtct ctactaaaaa tacaaaaatt agctgggagt    39660
ggtggcgcgc acctgtaatc ccagctactc gggaggctga ggcagaagaa tcgtttgaac    39720
ctgggaggtg gagattgcag tgagccacga tcgtgccact gcactccagc ctggtgacag    39780
agcaagactc cgtctccaga aaaaaaaaat tattaatggg atatttgtca tactttttt    39840
gtaccaagtc ttcaaaatcc agtgtgtatt gtacactcat gaaacatctg aatttggacc    39900
agccaagttc caagtgccac atgtatctat ttgttatcgt gctagacttt gcaagcctag    39960
aatttttttg tgtcgataat cttctcatat ttaaatttgt aaccaataca aattttcttt    40020
tttaaagtag tacaagggta ctggtatgta gtatttttag ctatagctac acttatttca    40080
gagatggtca ccatttcata ttactttcat tcatctaagt attttagatt tttatttgaa    40140
aagttccctt ttaaatctcc atctcccctgc cttttatttt ttatttttt gagacggagt    40200
cttgctctgt cgccaggctg gagtgcagtg gtgcaatctt ggctcactgc accctccacc    40260
tcccgggttc aagcaattct cctgcctcag cctcccaagt agctgagact acaggtgtgt    40320
gccaccatgc ccagctaatt tttgtatttt tgtttgtttg tttgtttgtt tgtttgagac    40380
ggagtctcac tctgtcgccc aggctggagt gcagtggcgc aatttccgct cgctgcaagc    40440
tccacctccc gggctcacgc cattctcttg ccccagcctc ctgagtagct gggaccacag    40500
gcgcccgcca ccacgcccgg agaatttttt gtatttttag tagagacgga gtttcactgt    40560
gttagccagg atggtctcga tctcctgacc tcgtgatcca cccgcctcgg cctcccaaag    40620
tgcagggatt acaggcgtga gccaccgcgc ccggcctaat ttttgtattt ttagtagaga    40680
cggtggtttc atcatgttga ccaggacgct ctcaatctct tgaccttgtc atctgccagc    40740
ctcagcctcc caaagtgctg ggattacagg tgtgagccac cgcacctggc cttttttttt    40800
ttttttttt tttttttaat ttaagagaca cagtctctat ccatcaccca ggctggagtg    40860
ctgtggtatg ttctcggccc catcatagct cactgcagcc ttaaacttct agactcaagc    40920
agccctcact tcagccccca gacagctagg actgcagaca tacaacacta tacctggcta    40980
```

```
ttttcatttt tttgcagaga tgtgtccttg ttatgttgcc aaagctggtc ttgaactcct    41040
gggctcaagc aatcctcctg cttcagcctc acaaggtggt ggaattacag gcgtgagccc    41100
ttgggcttgt cctctttttt gcttttataa caaatcacaa atgacttgct attttgttac    41160
aaaataacaa atcattggtt acaatgatta ataaatgtta aagaatggtt aggaaatagt    41220
tttttcctgt tagaatacat gataaaagta gttttccctg ttaggataca ggaaaacgat    41280
ttttactaaa aaccaaatat taaggtaatg gatatggacc ttattattat tttttttattt   41340 tattttttat tttttttaca ggtgttgaag aagaagaaaa agctgcagag atgcataaaa    41400
tgaaatctac aacccaggca aatcggatga gtgtagatgc tgtagaaatt gaaacactca    41460
gaaaaacagt tgaggactat ttctgctttt gctatggtaa aaacaataga tttaattttt    41520
ctaaaagata cattatataa ttgaattttc taaagggaag cttatgtaat tgattcgaaa    41580
atcatataac acacattttc agtgactgaa tggattagca ataaccttac tttcttccac    41640
ttccattttg aaggaaccca ggaggaagtg tggccagtag agctgtttct ttctttctgt    41700
tttttttttt tgagatggag tctcgctctg tcgcccaggc tggagtgcag tggcacgatc    41760
tcagctcact gcaatctccg cctcccggtt caagtgatt ctcctgcctc agcccctga     41820 gtaactagga ttacaggtgt ccgccaccat gcccggctaa ttttttgtgtt aaattttagt   41880 agagatgggg tttcaccaca ttcgccaggc tggtctcgaa ctcctgatct caggtgatcc    41940
acccaccttg gcctcccaaa gtgctgggat tacaggcgtg agccaccatg cctggcctag    42000
ctgtttcttt ctaataagca tgctcatctc tctaattcca tgcaaagcca ccttttctta    42060
ctcttgtcac atcataaaac aaagctctta caagaaaaca gtcaaaggag gagattgagg    42120
ttttactgca gggtcatagg tgaaaatcaa ttctctggaa tgggattttc agtatgtgtg    42180
aggctcgctg cccaataggt tgacagtata tactcatttg taaatgggaa gtttgtatt    42240 acctgataag ttttcaatga gaatattagc caaaacattc ctggtatttt atggtaatag   42300
ttggatgtgc tgggcttctg tattctgagg ccaaattgta cctgagaata tgccaggatg    42360
ggaccatctt caagaaagac aatagtgcaa gaaaccaacc attgctctct ctatgtgttt    42420
tttaaagtaa aatattttat ctacttttca ttttggccct tcggatcagt ttcaggttta    42480
gaccttctgc tgacatgggg agatagaatg ctgtagtatt aattaatttt gaaatcatat    42540
attataaaaa atcatggatg cccttattaa gccacaataa gctagcgatg atttcatttt    42600
gtaatcttac cattgaatga tgttcatccg cttttcatct gccccaggga aagctttagg    42660
caaatccaca gtggtacctg taccatatga gaagatgctg cgagaccagt cggctgtggt    42720
agtgcagggg cttccggaag gtgttgcctt taaacacccc gagaactatg atcttgcaac    42780
cctgaaatgg attttggaga acaaagcagg gatttcattc atcattaaga ggtgaagtgc    42840 tttctcccctt tgtacccatc aacagttgat tcgtataaat ttgaatattt agcttacgtt    42900
aatgtatttt taaaatttat atttaacaca gaagtcattt aaatgtatgc tttcaaataa    42960
ttttgcgtat tcatacgaag ttttgttttg ttttgtttta atgcagacct ttttagagc    43020 caaagaagca tgtaggtaag taagtgcttt gcttccttga tagctggctg gcctccgttt    43080
tgctagattt tcatacactt taatggtttc tgttttattg tctttgagaa tatgatgtca    43140
gacattttcg gatgggctgt ttagatgttt atataatcca caaaggttc attgagctaa     43200 aaaagtggag acttgttttt ttgttttcag cttcgctgct tgttttctat agaagatcat    43260
acatctgccc tcacttacca gaattatgag taggatttaa ttgacctaat gtcatcgact    43320
```

```
cggcaagatg ttgttgggca cagcattggg tggggagggg atacgcagct gtgtatcagc    43380
attaccactt ttgagagctg tgagtctcat ggaagagaga aaattctgta aaatgaacat    43440
ggcaagaaca ttgcatccct acggcaagaa tggctctgag aaagtgctgt ggatgttatt    43500
ggaggttgga ttcctttata gttcaggaaa gagttcatga ggaagagagc atttccagga    43560
agggcgtttg aagaatgatg cggatttcag cttcctttag ggaagtctag ccatttcatt    43620
tgaagggaaa acaggataaa gagtaatacc ctttagagcc aggtttattt gagactttcg    43680
gaagtaaata accagtatca ttggaatact tttaaacatg taactatgaa aggaaaaaat    43740
tatatataca taaacataca cattgtgttt tctgttaacc tttgtcttat tctcattgtg    43800
gtgaaaagat taatttttta gcagctttat tgaggtataa ttgatacacc ataaaattca    43860
cctgcctttt tttttttatta ttattttttg agacggagtc ttgctctgtc gccaaggctg    43920
gagtgcagtg gcgcgatctt ggctcactgc agcctctgct tcccaggttc aagtgattct    43980
gcctcagcct cccgagtagc tgggattaca ggcacatgct gccacgcccg gctaattttt    44040
tgtattttta gtagagatgg ggtttcacca tgttaggatg atctcgaact cctgacctca    44100
aatgatccac cgcccccggc ctcccaaagt gctgggatta caggcgtgag ccactgtgcc    44160
cagccaaatt cacctgtctt aagtatataa ttcactaata gtagatttac aatcttaaaa    44220
tgtttttaag gggtttttac ccatcatcac agtcttaatt tgggatgct ttcatcgtcc    44280 ctgtctctgt tatttcatga atgttgtaga aatgaatat gtagtatgta tcctattgaa    44340
atgagctttt ttcactgagc atcactcact cgaggctcat cgagcttggt aggtgtagcc    44400
gtagcttctt tttattgctg agcactaact attctgtgac atgaacatac tgtctgttga    44460
tccagtcatc agtttataga tattttggtt gtttccacct ttgggtattg gaataatgt    44520 tacagtgaac atacttgagc aaggttttgt ctggacatat tccttgatat ctcttggata    44580
tttacgtagg agtgcaatta ctaggaatag ggtaaattta cactgaactt ttttttttttt    44640 ttaattgaga cggagtctcg ttctgtcacc aagttggagt gcagtggcat gatcttggct    44700
cactgcaacc tccgcctcgt ggattcaaga gattcacctg cctcagcctc ctgagtagct    44760
gggattacag gcacgcgcca ccacacccgg ctaattttg tattttagt agagacgagg    44820 tttcaccatg ttggccagga tggtctcaat ctcttgacct catgatcaag ggaggcctct    44880
caaagtgctg agattacagg cgtgagccat cgcgccctgc tacactgaac tttgaagaaa    44940
ctgacaagct gttttccaag gtggctatac catgttatat tctcacagca ggataggagg    45000
gttaccccca cattgctgcc aacttacttc ttgattttag ccattgtaat agatgtgaag    45060
tggtatctaa ttttttttga tttttaaaaa tttctctagt gattgttgat gtgttttac    45120 ttttctttct ttctttcttt tttttttttt tgagacaggg tctcaccctg tcgcccaggc    45180
tggagtgtag tggcgccatc tcagcttagt gcagcctcaa cctcccaggc tcaagcaatc    45240
ctgctgcctc agcttctcag tagctaggac tacaggcgtg tgccaccata cccagctcat    45300
ttctgaacct ttttttggta gagacaagct cttgccgtgt tggccaggct ggtctggaac    45360
tcctgagctc aagtgatccg cctgtgtcag cctcccaaag tgctgggatt acaggcttgt    45420
gttatcttca attgtgctta ttggtcatcc atacatattt tttggagaaa tatctcattta    45480 ggtccttttc ccatttaaaa attgggtttg tttgtctttt tattattgag tcttgttttt    45540
tatatagtct tgatataagt ctctaattga tgatttgtta aaaaaaaatt ttttttttct    45600
ttttgcaatg gtgtcactct gttatccagg ctggagtaca ggatttggga atattttctc    45660
caattctaat aaatctacat tatccttatt gtataacttg tcttcttccc ttacttggta    45720
```

```
gtatcctttg aggcacaaac gttttaaatt ttgataaaaa taagtttatt cttttgttaa  45780
cttgtgcttt tttttttgag acagagtctc gctgtgtcac ccaggctgga gtgcggtggc  45840
atgatctcag ctcactgcaa tctgcctccc gggttcaagc aattctcctg tctcagcctc  45900
ccgagtagct gggactacag gtgcccgcca ccatgcccgg ataactttag tattttagt   45960
ggagacgggg tttcaccata ttggtcaggc tggtctcaaa ctccagacct caggtgatcc  46020
acctgcctca gcctcccaga gtgctgggat tataggcgtg agccactgcg cctggccctc  46080
acttaagctt ttgacttcat attcaagaaa ccattgcgta aacccaaagg catgaagata  46140
tgacttctgt gttttcttcc acaagtctta tagcttcaac tctcacattt agatctatgg  46200
ttcattttga ggtcattttt gtatattata caaggtaaag gtataaattc atcttttgc   46260
acgtggatat ccaatgattc caggacaatt gcagaaaag accgtccttt ccctcaagat   46320
atccttgtca tctttgttga aagtcttttg actctttgtt tatttctggg ctttctatgt  46380
aggagatcat gttgtgtgag aatcaagaca atttaccccct ttctttgcaa tctaagtgcc 46440
tcttatttct tcttcttgtt gctctgacta gaatataaat gtcacacagc attggtgata  46500
gcagacatca ccttgtgata ttagtaggaa agcattctgt cttgaccat gaagtatgat   46560
gttagtggta ggattttgt gtaaatctct tttaagatgg agaaatattt atcatgttta  46620
tgttaaattt cagacttaaa agtttttttt aaacttaatt attattttta tttatttatt  46680
tatttattta tttatttatt tttttattta ttttgagatg gagtcttgct ctgtcgccca  46740
ggctggagtg cagtggcatg atcttggctc actacaacat ctgcctccca ggctcaagca  46800
aatctcctgc ctcagccttc tgagtaactg ggattacagg cgcccgccac cacacctggc  46860
taattttat attttttag cagagacggg ggttcaccat gttggccagg ctggtctcaa   46920
accctgacc tcaagcaatc tacccatctc agcctcccaa agtgctggga ttacaggtgt   46980
gagcctccac gcccagccta atctcagcat tttgggagac cagagtggga gtctcccttg  47040
aggccaggag ttcgagataa gcctgggcaa catagcaaga tccaatttct acaaaaaata  47100
gaaacaatt agctgggagt ggtaatgcat gcttctgtag tcccagctac tcaggaggct   47160
gaggtaggag gattgcttga tcctcgagag ttggaggctg cagtgagcta tgatcatgcc  47220
actgcacacc aacctgggca acagagtaaa accctgtttc taaaaaaaaa aaaaaaaaaa  47280
aaaaaaaatc tgtttcatca tttatatgtc agcagagtca tattctccat attccatctt  47340
actagacaaa tggtatgttt ctgcatttct ctcactgatg aaaataagag cttttcatt   47400
caaggaggtt gtggttgggt gaagggatga aaagcagtgt ttattctggt gtgatccaga  47460
gctgcaaagc ctagttctac cccactaatt ctatatttaa agcctttaga catattatat  47520
ttgaaatgtt gaaaaactaa ctccaatttt tttttttgt atgtaggtgg tcgtgtgatg  47580
gtaacagatg ctgacaggtc aatactatct ccaggtggaa ggtaaaacct aatttcatta  47640
ctgctgttta actcccacac ctcaaaaagt tttagttgtt agataattga gatatcagaa  47700
tattaaaaag gcctcatgtc acacatctta aagtttaata ggcaaggata tcatttgggg  47760
atcttgtgaa catgccctct ttgacttggt atttctgaat agtagagttc ctgggaaaag  47820
ccagaggcat tggtcacact gtgaattggc cttagagtgg tatttggaag ttaatatgct  47880
attctgtagt attttattat actgttttcc ccaaaagata gatagaaatt aaagtactaa  47940
gttcagttgg taactctttt tttttttttt attttgaga tggagttttg ctcttttgc   48000
ccatgctaga gtgaagtggc gcgatctcgg ctcactgcaa cctctgaccc cctgctgggt  48060
```

```
tcaagcgatt ctcctgcctc agcctcccaa atagcaggga ctacaagcat gtgccaccat    48120
gcccagctaa ttttttttgta ttttttagtag agacggggtt tcaccgtgtt ggccaggctg   48180
gtctcgaact cctgacctcg ggtgatccac ctgcctcggc ctcccaaagt actgggatta    48240
caggcatgag ccaccacgcc tggcccgata agtcttaata tgctactctg tagtatttta    48300
ttgtactttt ttccccaaaa gatagataga aattgaagta ctaagttcag ttgataactc    48360
tttttttttg tggagacaga gtctccctct gtggctcagg ctggagttca gtggcatgat    48420
ctcagctcac tgcaacctcc gcctcccgga ttcaagtgat tcaggtgagc gccaccacgc    48480
ctggctaatt tttgtatttt tagtagagat gaggtttcac catattggcc aggctggtct    48540
tgaactcctg acctcgtgat ctgcccgcct cggcctccca atgtgttggg attacaggcg    48600
tgagccactg tgcccggccc aataactctt atttatgcaa taaataaata tgtcagtttt    48660
aagctgagtc aggtttgcac ccaccttggt caagggaggg atcttaacac tttgagaccc    48720
agagactttg aatgctgtgg gaatggctgt caccagcacg tggcttgatc agggctttct    48780
tctccttgca gttgtggccc catcaaagtg aaaactgaac ccacagaaga ttctggtatg    48840
tactagcact tttagaatca atggtgaaat taaggaagac ttttccttag tgtagaagtt    48900
tatagtttga ctcaattatt gttttgtttt gataagaaag aggcagtcac tactaatgta    48960
ttccaactgt gacactattt gttaatgtta tcacattaag acccagaaag gtaatttgct    49020
cagtaagtgg taggcagagt tctttgccag ttacatatgt ttgtagataa aatgtatttt    49080
tttttcccgt tgtacagaca tataatgtaa gaggtcagct gttctatagt gcttttttaca   49140
aaaatcaata gaatgccccc ttcgtctcca ccttccttct ctgcactcct gttttccact    49200
ctccaaggag accatttttca attctcaaat aaaattgcta tttaattcct tatttattta   49260
tttatttttt gagatggagt cttgctttgt cacccagact gaagtgcagt ggcacgacct    49320
cggctcactg caacctctgc ctctgggttc aagcgattct cccacctcag cctcccgagt    49380
agctgggatt acaggcatac gccatcacgc acgactaatt tttgtatttt tagtagcgac    49440
ggggtttcgc caggttggcc tggctggtct tgaactcctg acctcaagtg atcctcctgc    49500
ctcagccttc caaagtccta ggattacagg cataagccac cgtgcccggc cccgtttat    49560
aattctgttc tgtcctagaa ccgtggcacc cagatgttct cagcatatgt atttatttca    49620
tcatttccca gtgttatcct gtgtcctagt gccactgtca agcctcccgc tgctcggccc    49680
tgtgcccctt attcacacgg gacactcctt agtgggctgt caccgccctg cctgcccct    49740
catctccctc tgtctgacca ggccctcggc agcttcccca gccccttccc cggccctttg    49800
tcagccttct cattctgcca tgcttcctgg gcagccacct gccccgcttc accccatcta    49860
agggcatctc gaatgagttg ttggggagga gggtagggcc gcgttaacgt gtgtgtgcgt    49920
gcatgtgaat gagagctttt atgtatgtaa gtgtattttg ggagagctgc aagaaagtgt    49980
tgaattatcc ttttttggaa aaggtatttg agtcttttac actgtttgct ggttttacag    50040
aaggttttc ttttttcttt atttttcactc cataggaaat ctcaaatttt tgtgtggttt    50100
tcagtagatt gtgccaaaaa aaatcatcat tttgcaaatg tttccccta attcatatat    50160
tcatctcctg aatatttagt ttgcttctaa aagaaacat gctgaattca gaaaccccat    50220
gtgtttaatt gaattctttc aactgtcttt atgtacacat cagcatcatt ataggttttt    50280
tttttttctct tttacacttt gcatctttgt attcttaatt tatcctgcaa ataagatgta    50340
catttatagc cagggtgcag ccaggagaca gaaaccatat cagttattgg aacagagaaa    50400
atttaatgta aagattgttg gccgggtgca gtggctcaca cctgtaatcc cagcactttg    50460
```

```
ggaggctgag gcgagtggat cacctgaggt caggagttgg agaccggcct ggccaacatg   50520
gtgaaaccca gtctctacta aaaatacaaa aaaaattagc agggcatggt ggtgggcgcc   50580
tgtaatccca gctactcaag aggctgaggg aggagaatcg tttgaactca ggaggtagag   50640
gttacattga gtcaagatcg tgccattgca ctccagcctg gcaacaaga gtgaaactcc   50700 atctcaaaac aaaacaaaca aaaacagatt gttaactggt tataaaattg ttaactttgt   50760
aaccttaagg agaatactaa gttttttttt aaggaacaat tctaggcagt ggctgccacc   50820
ccatcagctt tccatctgac ttctgaggtg gggtagtgtt tggctggtgc tggtggctga   50880
ggggcatggt gaggctgctt ctggtagtgt tggagacatt gccaaccagg cacagctgtt   50940
gtgatgggag ggcctgcttt ggccaggctg aacgagggta ccaaggagtg acctttttgg   51000
gatgagaatg cagacaagaa gccaaaagga aggcccagat ctcttctcct cctctagcct   51060
ttctctctgt agtgtatctt tgtggcagag actcacatgg agccagctgc tatgcagagc   51120
tcaaacttca gcagaaaccc agaggatggg tttgcaactg agagacatca gttttgtggg   51180
tggcccaggc tgttctcttt ggctgctcag catatataca cacccttccc tgcacatttg   51240
accttctgta caacaacgag acaactgttc catctaaaga gatgcaactt tacttcctac   51300
aaagaaatcc attttactc tctcctcaaa atgggggac acagtgttcc agcagtcaca   51360
cccatcgctg ggagactgac tgaaaatcca gtcgcgagct atgttacctg ctctttaaat   51420
gcagtgcaaa cctatttgag taatctctag tctaatggac aaatggaaag gaaacttcca   51480
gccaaactat tgtgaaatac taccacacag aagagaatag ttagtatatg caagcatata   51540
atcttcacac aaacacattt gtaacagaca aggaagacaa taggcatagt cgccacagtc   51600
tacgtttctg cagcttacca gactttttt tggatttacc tttttatttt tatttattta   51660
tattttttga gacaaggtct cactctgtcg tccagactgg agtgcagtcg tgcgatctcg   51720
gctcaccaca acctccgtgt ctcagattca agcgattctc ccacctcagc ctcccgagca   51780
gctgggatta cagacgtgtg ccacccagcc aattttttgta ttattcattt atttatttta   51840
gtagagacgg ggtttaacca tgttgaccag gctggtcttg aactcctgac ctcaggtaat   51900
catccgcctc agcctcccaa agtgctggga ttataggcat tagcctctgc acccagccag   51960
tatgtgtaag gttctttagc caattggagt gacccaaatt tttattcctg aagggtctga   52020
atccccagtg gatctgcctt ttttgttagc tgtaatgctg tgattttctt tctttcttta   52080 ttttttttt ttgagacgga gtcttgctgt gtcgcccagg ctggagtgta gtggtaccat   52140
ctccgctcac tgcaacctcc acctcttggg ttcaggtgat ctttgtgcct cagcctctcg   52200
ggtagctggg actacaggtg cgtgccacca ctcccggcta attttttgtat ttttagtaga   52260 gacgaggttt caccatgttg gccaggctgg tctcgaactc ctgacctcag gtgattcgcc   52320
cgcctggacc tcccaaagtg ctgggattac aggcacgagc caccgcacct ggctgttagc   52380
tgtaattttc tattaacttt tactgatgga catgaaagtg ctaagttagc ccagagagtt   52440
gcaaaggtct cagatgcagt gttctctgcc accactgtgt agcagcaaaa cactttcccc   52500
ttggtgattg aaggcaatgg agtaactcct ttttttgctt gttgcttcag ggatgcatac   52560
cctttgtata tcaatttaac tctctttgag ctctttctct agagttgaaa atattcttta   52620
caaagttgcc caagtcagag ctcacgattt cgtttgtgtt agggttggta tgactgtggt   52680
tgaatatctc agtctgaaat gtgtatgtgc acccatgcat tgttcatttc tttttctttt   52740 ttttgagag ggagtctcgc cgtgtcaccc aggctggagt gcagtggcac aattttggcc   52800
```

```
cttcccaaag tcaactttttt aataacatcg attgcttttg cctatttttga ccttcatatg    52860 agtggaatta cacaacatgt actcttttgt atctggccac aaaggtctgc ttcaaatcat    52920
ctgtcctaat tgtgggcaaa gctttatgca gaaaggtgtg ctttgtaccc ttacacaaat    52980
ccctgtaata aaagggatgt attaggcaga aaaaaaccaa tgtatctcat tattgaaatt    53040
gttgaccatt atgctatctc tcctttggaa tactgagtta ttaaaactga tgtttataag    53100
tgtgtttcaa tggtttataa aagtattttt aatattaagt gaaaagggag tgtggtaaaa    53160
ttttctttga ttctaaagat aagaatttgc tggagaaaag agcagcacat aattgcagaa    53220
tattaataaa tggttaaaac tttgcattgg ctgggattat agtgattttt taccttctgc    53280
tacctagcaa acttttgtct tttcaaagac gtaaagtctt tacttaaaat aaatatgcat    53340
tgctgtattt ataggaggg cagagaggat ttccctacac aatctagctg aaagttctca    53400
catgcaatca tatcattgca tttgcttttc taggcatttc cctggaaatg gcagctgtga    53460
cagtaaagga agaatcagaa gatcctgatt attatcaata taacattcaa ggtaatttga    53520
attaatgcaa ttttctttc taaaaattat tcgtggttaa aattaaaatt tgctcatcaa    53580 ttgcttttaat ttcttaaata atattttatt gatcagttct tgattgacat atatattgta    53640
attcagtccc ggggataaaa catttaaaaa tggggctaaa agatcaactc agacaatcca    53700
gaggggatat gtaaaatagc catttgtgtt cttaaaagga tgagcaaaag ttgtggcaca    53760
atttagaatt caatcccagg ttctagtgtt gcaaataaaa acaaacctat taggcaaatg    53820
cagataatgt cagcttaatt ttttctcact gcataattat agtatattaa acacttaaag    53880
taaaaaatct ggttagcttt gccatctaca tatctaatac accatcttca ttgcatccaa    53940
gataatgaaa tatctataac cccaaaagtt tcctgtgtcc ccttgttatt cattgccctg    54000
cccagtattc aggcaacacg gatctgtttt ctgttttagg ttagtttgca ttttctataa    54060
agtcttatga atgaaataat aaaatgtgga ctattttcat gggccgggga gcagtgtggc    54120
ttctttcatt tcaaatgatt gttttgaaat tcatccacag cgttgcacgt atcagtagta    54180
gattccattt gattgttgat ttgtattcta ttgtatgcct gagtcaaaat ttattcatct    54240
ctttgtctgt tgatagccat ttgggttctt ccagtttggg gccattacaa atagaggtac    54300
tatgaacatt gtgtagaggc ttttgtgtgg acataggcct tcatttctct cttttttttt    54360
tttttttttg agacagagtc tcactctgtt gcccaggctg gagtgcagtg gcgcgatctt    54420
ggctcactgc aacctccacc tcccaggttg aggtgattct tctgcctcag cctcccgaat    54480
agctgggata gcaggtgtgt gccaacacac ctggctaatt tttgtgtttt ttagtagaca    54540
cagggtttca ccatgttggc caggctggtc tcgagctcct gacctcaggt gatccacccg    54600
ccttggcctc ccaaagtact gggattacag ggctaacac gctttttaa aatgaaatat    54660 ttaaaaccta aaagcatagt atcagtctgc ccaggtttag tgaaccatag tatttgtctc    54720
ttctctcctc cctccaagaa acaacgtgta actatttcat tgaagccttt ctttgggctc    54780
ccccaaatcc ccactttttct ctctattctt aagttaacca tgatcttgaa aactgagaat    54840
tgtccttcct gatggtgatg tgctttacta cgtaaatatt ctcccgggag tgtgtgtgtg    54900
tgtgtgtgtg tgtgtgtgtg tgtgtgtcat gtcatattta ttgttttata tatgccactt    54960
cctgagtgaa gcttacacag tggtacactg tatgtgttgt tgagtatagt ctgtcactca    55020
atttaagttt tcaagattta tcttttttt tttttttttt ggcgtggggg tggggatgga    55080
tttttgctct gtcgcccaag ctggagtgca gtggtgagat ctcggctcat tgcaacctcc    55140
gcttgccggg ttcaagcaat tctctgcctc agctgggatt tatctgtttt gtcacaagta    55200
```

```
gatttaatca tgtcatcatg gtagttacac tgtgtgatta aatacagtt cgttttttcg    55260 ttcttctaca taaagacatt gatgttttct tctaaaactt ttgtattcca aaataggctt    55320
ggatatattt ctctgtgcac ctcagtgctc ctgtaaaata gtgacattca aatgtgagtg    55380
ttgggaatgt gttgattttc tcaatgagtg gtaggcacct caagcatttg agaggtggag    55440
gttaagtatg ttttagggtg aataaaatca agtaccattt ttagggtgaa taaaattcaa    55500
atatgggaca ttaaaataat ttgaaagtat agtgatacgt gaaggtattt tgagtaaata    55560
ccaactaaaa aaatatagt ttagcaatat tggaagccaa aaacagtagt agcaggatag    55620
aataagacta tgtcgtattt aaaggaattg gtcactaagt tgatataaca accattagtt    55680
tgtatgtgcc taactatgta tcctcacagt aaaagtaaaa attatttaca aattataagt    55740
ctctatagat atgtacagtc atgtgggaga ttttaaccaa tgatatacgt ctagctgatg    55800
aatactcttt taacatttat atgctaaata gaatattttc actacagtta atatatgtaa    55860
gctaactata gaaaactgtg tacccaagaa ataagtttat ttacaaagca tgaatcattt    55920
ataaaaattg actgtatact tgttcacagt cttaataaat tctctgaaca tactgaaatt    55980
aaattattaa tagaaaacat acacagtggg aatcctagga aacatgcttg taattgactt    56040
aatgagggcc tcattaaaaa tatttagacc agaatattga gaatgccaca tagttaaact    56100
tgtgaagagc aactaaagca gtacttagag gtcaattagt agccttcact aaggttgcat    56160
ttttaaatcc tgtaaatagc acatcttcct tttcttgagc tctgtatatt ttactcagag    56220
tcagaagact aggaagcagt ggatctagca tttgaattta ggagtctaca ttccaagact    56280
tgctcttctt tgagattcca aatagaaact atttctttat ttctcatgca attgattttt    56340
ttctctgatg tgtcctttgc ctgtaatgtg tagtgtggtg catctttgtg aaatttctta    56400
ggctttagag aatgaagcct ttcaaacaac ttcggatgtt ttcccaattc tcttcagaga    56460
tagttaactg aactgtggtc atattaatgc caaaatgtgt tttatattaa atagccattg    56520
aaaacacaat gttttgtttt ctattttaaa actattatta ttttaatcat taaaaagttt    56580
gatgataaca tgtaaatgtg ttgtcaaaat atagcagttt gtgaagttga atttaactca    56640
gagtactttc tgtgttttgg aaagaacctt attagaaaaa gtgcccgctg tgctggaaga    56700
aagggagaat gaattaatag ctgttagttt gtcacatttc tatttcagta gagattcaag    56760
gagatggttt acgttatttt agagattcta aggaaggtat ataacatttg gttctgcatt    56820
tttcttcagt atgacaaaag agtaagcaaa tatttgccaa agaagaaaca aataaacctg    56880
tgagataaac ctgcatttgt aatctgtatg aagtaaaagt tacagtttac tgttatgaac    56940
attgtactgt tttaaaaaac ccacatcttc cattttagac ataccattcc cattcaatcc    57000
atatgtccag tcatcttcaa aatttctttt gactgtttac atatgaattc acctgattac    57060
atttttccat tcaccaagac cataaattga cattgctcat cttgtcagtc tttttttttt    57120
ttaatttttt tctttttatt tataaaaagg ccattccatg tatctcaccc aaatttgttg    57180
actaaagtca ccccacattt tttttgggg gggattactt ttgaagtatt atctttgtat    57240
cccaaagcag gcccttctga aactgatgat gttgatgaaa acagcccct atcgaagcct    57300 ttgcaaggta taatctttc acttccattc tcccacatac tgcttgtgtt taatgtttcc    57360
ttatattgca cagactgtgt tttaatattt ataagtacag tattacttt ctaaatggaa    57420 aaggaaaaaa atgtattggc ctttttttaa catataaatg aacttcacaa gcaacaattt    57480
ttcaaaaatc aattttccct tttgtgaatc tagtaatgaa tctcgaaatg ggtacatgac    57540
```

```
acactttcct attgaaggta aagtacacat ttatacctta tctcagaaca gtcagaagcc    57600
aggttactgt tttattggtt agtgatgcaa atattgataa ggtcaggttg atacttagta    57660
tttagaagaa ttctgaaata gcacttgtta atctgtaagt ttcgaattga ttgccttttt    57720
ggcaattttt tacagtgttc ccaaacttga tactcatagg ctattagtaa tggcatttac    57780
ttctatctat tctggctttg agtgcataag atgtattttc tttaggctta gcatataatg    57840
taaatgtaat tgtttatttc agattttaaa agacatacag aattattgct tacacgaaca    57900
atcatcttaa ctgttattct ttgctgaaat tttacttttt acctactggc ctcatcattt    57960
cactctcatt cctttgacct cacatctctt tttctttga cttttacagt caaataactt    58020
aatgctccat aaattcaaat attaagatta aaaaagaga aggaagtgt gtagagaaag    58080 catattttaa aaatgaatta aagagtgact cataggtata ggtttgtaga tttacctaga    58140
gtttgagttc aggtgagttt tcacaatata aagtaagtgg aaaagaatcc ccagataatt    58200
gtgacatgct aaagctagat actgagaacc aaaaagatgt gacctcagta tgggactttt    58260
aattcaagga tattagctac caaatgacag ttttcagac cgtaagcatt gcttttaaa    58320 aatcaagata aaatacattt ataacatatc ttacttttag tatagcttct gaatttagtt    58380
ctcaatagat aagacaaaag agatgaacat ctgcttcctt tcccctcaag cgatgtattc    58440
ttactaatag gtaatatgtt ttttttggt acttaaaggc agtgttttc aatcttttcc    58500 atgttagtag ctcagatctt taaggacaga ggatacaaat taggggggcag cttgcgttct    58560 taatcctaag tggctctctg atgtcttaga ttcttccttt ccttttgtg agtaaaactt    58620 ctgctctagt aggatgagcc tgttcacctt gtgactgcct aactgatcat tgctttatgt    58680
tccagttttt agaagcaggc agattatatt acctgactta aaatgctttt gagactaaag    58740
gtagtatctt aaattttaac ttacgagttt ccttaagta caactttgat gaaattatgg    58800
ggattgagtt tccatggctt tcaccatagt gaaaatggaa agcatgaaac attccacagc    58860
aaaccctgaa cttatttata gggagttaat taagtgtctg atcacagcaa gcatttactc    58920
tgatctgttt gtgtatgtgt gtctttgaca gatgagcatg gtacttgaag cataattctg    58980
cttcctcaga ttccaatatc tagtaatttt atcatgtagt tatagtaact aatattaaat    59040
ccccaaacct acttaggtct actctgtatt tgtgttttca ataattttt ttagcttcca    59100 aatagaagcg ttgtattctt ttctgaatta gaaaacattg ttcgacttaa ctgctaaaga    59160
gttagacaat cattttgcat atgtttatta tgtcttagat tgtttgcatt gttacctaga    59220
ttctctttca tctttcaatg tcagtttttta ttggttatt atatgttgtt tattttcttt    59280
ttaggaagcc accattcttc agagggcaat gaaggcacag aaatggaagt accagcagaa    59340
ggttaggaga aaaagagatt gcatattttc cactatttgt tgtatgttta ttctatttta    59400
tagattctat tatccttaaa acaccttatt tggaaataaa aggtgattcc cttggtatgc    59460
cttcctagcc aacaggttat tattttttta aaaattctaa gatgtaatat acttctttga    59520
ccatactgat taataaagcc tatgggaatg aaactaagtg gtaagtaaag ctcttacatg    59580
atgcaaaatg ctactttttt ttttgtcctg gttttcttgt gccatattaa atatctttta    59640
aggaagaata gcttcagtgt ttcagaatta aaattactag ctccattcat attttatttt    59700
caaatgtatt ttttaatact ttagtctctt agtagggtag gaatttagtc tacataaaat    59760
ttatacagga gagagtttct ccctttattt tgtactcaca actactccat aaatgacttt    59820
gtcagtttac cagctctaca gctttggttt tagaattgaa cgcctgactg aggtacagtt    59880 cttttttgttt agaatcctga gttcaactta tcatgtaggg tggcttctta tttccaaggt    59940
```

```
gtttaaacgg ttccacacaa attttttgtag atttctccca aggaaaatga ctggtaaggt   60000
aactgaatct tgttttagaa ttatttctct cataaattgg tcatgttatc ccttatttt    60060 ctagaatgaa aagaggagtc tgttatgtaa ctgcttatat tccattgtat ttacatttt    60120 attttaatta aaaaaaaaca tttgtttgat cttttacctt ctttgaggga aaggcaatct   60180
taaaagttcc ccagtatagg ctggtttctc caaattcaat tatagaatta gggtttctcc   60240
ctggaataca tttctctcaa aaatactgat atgctcattg taaaccgttg gttacatttc   60300
cctgtcagcc cttttatag aagattgtgt gggtgaatgt tgtatgcttt actgtgtgga    60360
ggtgggtatc ttctgtgtga cagagttttc agctttgaat aggcgggatt tagaacaaca   60420
agacctaggt aatagatcat gtgcagtacg agggctcatt gggcagtacc gatggctcac   60480
cgccttgcag ccccgccggc aggtactgca ccttgaagac tgcgttttta ggacatttt    60540 actgtcatat tccagtgtta acaaagttga atcgaatctg ggttctggcc tttattcctt   60600
tactaacaag taaacataat ctttggcaaa tcaattaatc tctcaacctt tgcacaatga   60660
aagagaacta atgaaaatac tctataagct tctagcacta acactctgat gtacatttgt   60720
cttgtgtagg aacaaatatg aatgaacttt gtaattttg aaatatgttg catacaaagc   60780
cagaggatat agtcttgtgt gcacttgtga cactcagtct cttgatagga aagtctccat   60840
tgtaaagcct gggttgtggt tttattgaac agtagaaacc actcctcaca tttctgaaag   60900
gagagaagaa attctaacca aagtagaaag catttgtttc tatccgagca tcttctagct   60960
gtggcaggaa attcattgtg actttgtcat atcctcattc ctccaagact atgggatttt   61020
tttgagtcaa tttctgcagg taacatgtta tcatctaaat ttttccagag tttttctaat   61080
ttttgttttc ttttatccct atttataatg acaagggtca atttttaatt tcattaatat   61140
gaaatgaatg aaaatgccag tggattttta tagtaggctg cttttggagt atcaaatcag   61200
taaaatgttg gaacatatgg aaacatgctt aataatgaat gtcattttag aatttattt    61260 ttttcaagat tctactcaac atgtcccttc agaaacaagt gaggaccctg aagttgaggt   61320
gactattgaa ggttagttat ctaaaagcct tgattccaaa gtttacttct ggtcataaaa   61380
atacttgtca cattcacatt gctaaatatg catttcattc attttaaag gagacttgtg    61440 ggacgaatac atgtgtctgt gtggccaaag cagcccactc cccagtgctt tgggagtttt   61500
agatgacaga atgaggccgt gagaattagc attgggcccac gggtggccca agctatcctt   61560
gctatcagtg ggagttgaaa agagaaaaag aaaattatga ccagacttga tacacacaaa   61620
aacagattct ataatctatt gggttgtgat agaagaagac ttatttggag ctggaatccc   61680
taatttctaa ttaagtaaag tggaggagaa agtgttgata gtttagtgag taattttaa    61740 agcaagtccc tgcccccttc aacgacccgc aaatactact tagaggctga catacaattt   61800
atctttcaaa actgttttga agcaatagct acaaatatat tctacaatac tctctatagc   61860
taagattgct tcaaacctgt tttttctcc aagataagc ttgaactcag ctgagccagt     61920
ttatcctgaa ttatttgaaa attcagctaa tagaattatt aactatcact tcatattaat   61980
agttattaaa tgagcattgt gttttttcctt ttaaattaat gtctcacagc tgggcacggt   62040
ggctcacacc tgtaatccca gcactttggg aggccaaggt aggcagatca cctgaggtcg   62100
ggagctcaag accagcctga ccagcatggt gaaacgccca tctctactaa aaatacaaaa   62160
ctagctgggt gtggtggtgc atgcctgtaa tcccagccac ttgggaggct gaggcaggag   62220
aatcgcttga accctggagg cagaggttgt agtgtgctga gttcacgcca ttgcactaca   62280
```

```
gcctgggcga cagagtgaaa ctccatctca aaaaaaaaat taaaattaaa attaatgtgt    62340
cacaatactt gtgtaagttt cttcccctga aagtacttct ttcttgtggt aaaatgtgaa    62400
aatggtacag taaattgtac agtggaaagt tttcttcacc ctcactctgc tcccaagtcc    62460
caatactgag ggatgtatgc cagcttattg tgtctactta gagaaataat tgcagtacat    62520
atcttgatgc gaaaatacac agatgctttc agcatacatt acaatgcaca ttttaaaata    62580
ttacatattc cataggcctc cccctcccat aactgcacat cttggtactt tattagtttt    62640
tttttctagc tgctgcgtaa cctttcttgg tttgctgtct gtctctcttt ctctcttaat    62700
aacctgtcac ctactgatgt cacttggtta tttctagtgt ttgactactc caaactactc    62760
aacgtgtctg tcttcattgc ttctaaaata taagtcaatt agtagcttcc acttaataca    62820
agaaatcttt tcatacttca tgtgttaact taatatacag atttctttt tcataaatat    62880 aatttttcta atctaaaaca ttttgcattg tttacagtct agcattaaat ggttgaaatt    62940
taattcgttt ttagtgagaa acctcattaa caggaaaaaa atttaagaac atacaaatat    63000
tacaactact cagctgtgcc ctttctatgg agatattaat aggaggttat taaaattata    63060
aaaataaagc ttttagggta ggactaataa ccattttgat ttgtcaaatc ttaaagcaga    63120
tagaagctgt atttttttt tttttttttt tgagacagag tctggctctg tcgcccaggc    63180
tggagtgcag tggtgcgatc tcggctcact gcaagctctg ccttcctggt tcacgccatt    63240
ctcctgtaga ggctgtatta aaatggttta gaatgtaaat acttgctttt atagtataag    63300
acttttaaag aaaggttacg aaaatccaga ataaatggc tcatgaacct gaagcttatg    63360
tcagcctttt gaacttttaac tgttttggat ggagtaataa atctcttttc ttttcattta    63420
tttgtttatt tatttattta tttgtttttg agatggagtt tcactcttgt tgcctaggct    63480
ggagtgcatt ggcgctatct cggctcaccg caacctccgc ctcgcaggtt caagcgattc    63540
tcctgcctca gcctcctgag tagctgggat tacaggcatg cgccgccatg ctcggctaat    63600
tttgtatttt taatagagac agggtttctc catcttggtc aggctggtct cgaactcctg    63660
acctcaggtg atctgcccac ctcggcttcc caaagtgctg ggattacagg catgagccac    63720
cgcacctggc cattcatttc tttttaaacta agacattgtg ccataagcct gatttaatgt    63780
tcacatttgt gattaagtag tagaattttg ctagtagacc tctttctttt cagaagacca    63840
gtgaaatacc aggtctgagt aaagtaatcc ttttaaaagg tagcatttc catgtcatat    63900 gtgcatatac acacacacat tttatgtatt atatataaaa aatatgtata ttatatagaa    63960
attacatcaa caattaaatt cctcattttt ttaagaagat aaaaaactgt ctcaatatta    64020
acaaggaagg tcaagtgaga acttacatgc acacctctgg ttaataatgt gtatcatata    64080
ttctttctgg aaagattact tccaaatggt aggagctatt tagatacccg tagttaggaa    64140
ataaaatttt ggtatatctt cataacagaa aaatatatag ccattgaaat cctgataatg    64200
ttttccaata atctgaaaaa agatctctaa tataaaatgt tcagtggaaa aaaaaaaaat    64260
cctgccttga gaacaaggca acttgaaaag caaaagtgca tctagaggat aatcttagtt    64320
ttgttttgga aaatactcat gcttggtagg aagacggaca aaaataaact gagatattcc    64380
tgcttgcttg gagacgactt aatttttctcc tttttatatct tttcacattt cccaaatcat    64440
tggtagaaaa aaaaacagaa ctttgttatc aaataagtct gtccgatttt tcacagtgtt    64500
ttcacctcga tatcttcatt tgcaattatg tggagttctg aagtggctaa tttgacaccg    64560
acgcggacgt gtttgtggat acagggtcat tacttaccca ctgccggtgc gctctgagct    64620
gtgcacttcc atttgtggcg ttttatttgt acttggagtc ggtggtaaac atttaaaaca    64680
```

```
tacgtgactt aggtttggga aatcggcctt ggactaatag gaccgcatgc ctcagttttc   64740
gtaaacaccg tgactacatt tctgggttaa ggtgaattgc cgtcaggtat gttatctcta   64800
atgtgtgcag agaaaacctt atcagacttg tttcaggtct agctgtcatg ggagtgctaa   64860
gaaccgtgta aaggaggttt cttcttgcg cagttctctc ttagggccta gcttcccaaa   64920
cctgagtcac ttacctgtta cctgtgttcc ttctgctgtg gcctaactct ctgttcatta   64980
cttaacctga ttttttccc ttaaattgat tttaagtaaa ttcattttgt gatgaatttt   65040
acgtcttcct aagtcaaact ctggctttt tatttctcat attttgaaag gtatatgtaa   65100
ataatttcaa atataattga ctcacatgac cacacgtggc acacttactg cagctggtac   65160
tgtaggtttt ttaggatctc tgtaattgag gaggttagcg ttggaaaact tctgtgtttt   65220 ttattttat agctgccaat cagacactta atgaatacac aattatatat gtaaaaaaag   65280
gagtctcaga ggaattatgt actaagattt gaataatacg tttttagagt ttcagtattt   65340
tagtagggtt tatgatgggc agttggacta cctaccatcc cttcttgtg gaatttatgt   65400 ttaagatagt gccagatact tgactgcagc atataattag ggactaaact attcatatgt   65460
tcatttaatc cctccacaaa tactgagcac attgtatgta ccaggtgcta agagtttttt   65520 ttttttttt ttgagacgga gtttcgctct gtcgcccagg ctggagtgca gtggcgcaat   65580
ctcggctcac tgcatcccct gcctcccagg tttaagcagt tctctgcctc agccttcctc   65640
cgagtagctg ggattatagg cgcccgccac catgcctggc taatttttt tgtattttta   65700 gtagagacgg ggtttcacca ttttggccag ggtgatcttg aactcctgac ctcgtgatcc   65760
gcccacctca ccctcccaaa gagctgggat tacaggcata agccaccgct cccggcctct   65820
tttttttttt tttttttttt tttttttttt ttaagacgga gtcttgctct gttgcccagg   65880
ctggagtaca gtgacctgat ctcggttctc cgcagcctcc gcctcctggg ttcaagtgat   65940
tctcctgcct cagcctctgg agtagctgga actacaggca cacgccacca tgtccagcca   66000 atatttact tttagtacag acaggggttt caccatgttg gccaggctgg tcttgaactc   66060
cttacctcag gtgatccacc cgcctcggcc tcccaaagtg ctaggattac aggcatgaac   66120
caccgcgcct ggccacggtg ctaagaattt agtagtgaat aattcagtgg caaatcctcg   66180
ggagtgtttt gaaataaga gtgacacttt ttgtccttca cttctaggaa acgtggtgac   66240
tatgttgaga aaggggaa aaaaaaaaa agagaagacc tagagcagtc aatagttttt   66300
tgacagaaaa ctagcttggg agcctcttgg aactacctag ggcacagaga agagtgcttt   66360
agagcaggtt ggtggcaggg gagataagaa gttgttgatt ctggggagat tttgaagaca   66420
aagccaccag gctttgctgt ttattgttta attcttgtat tttcttaaat gtctctgcag   66480
cacttttaaa atggacataa ttgcttaggt tagcacttga acactttgtt ttaaatttt   66540 tttattgctg ccaaatagtc atttaataaa tacccaattg tttatgtaaa gagttttaga   66600
ggagctataa gtggtatcca tgggtgaaag aatgaatcca tttatttgaa atgtataggg   66660
taattaatgg ctctagtttt gaaatagata tattacctgg tgttgattgt ttttttaact   66720
ttgaatagat gtcagattgt atgataacac attcccagtc tgattatgtt gaagctaaga   66780
gtatcagaac atattgtaac atagtctatt tattgattca ccggccagaa tgcagtgata   66840
aacagcttta gctctgaagc ctgtattatc tttaggtgta ttcgttaata tgttgcaaaa   66900
aggaagttgg tgttttctaa acacaaattt tgagttaggg acggtgttgc caacttgaag   66960
gtattggcgg agtgcttttg ttagtgtggg tagcataact attgtaaatt gatgaatagc   67020
```

```
accttttgca tattaaaata tcttaaaatg ggccaggtgt ggtggtgtaa tcccagcact   67080
ttggaagacc gaggtgggtg gatcacctga ggtcaggagt ttgagaccag cctgaccaac   67140
atggtgaaat tccatctcta ctaaaaatat aaaaattagc tgggcgtggt ggtgggcgcc   67200
tgtaatccca gctactctgg aggctgaggc aggagaattg cttgaaccca ggaagtggag   67260
attgcagtga gccaagatcg tgccactgcc cactgcactc ccagcctggg tgacagagca   67320
agactccatc tcaaaaaata aaataaaata tcttaaaatg tattttaaaa gctttacatt   67380
ttgattatgg aaacagagtt tgggcttgaa tttgaagcat gctgaaacgt gtgtcttgtt   67440
aaacaaaaat ggttgtttat actttggaaa cggcagataa ttggaagagc aatgcccagt   67500
atgtgagggc aggccctaga gctttagttg atgttttatg cttcagagta aaaagtaatt   67560
ttgatccttt gtggaaagga ttttaggtcg agaaacccat ttttttttctt actttctcaa   67620 aaccaattaa ttgcaacaaa gagttaattg cagaaaaaat tgaggatgtg gtgaagttta   67680
tagctgttct gatgcctgaa tgccatgttc catatgactt aaaacaccca agattaatt   67740 aataagttta tgaaacaggg ttttttaaaat agaatatatg gtgtgatatt ttatcaataa   67800
ctacatccag ctgggtgcgg tggctcacac ctataatccc agcactttag gaggccaagg   67860
caggaggatc acttgaggcc aggagttcaa gaccaacctg gcaacatag ggggacccct    67920 atctctacaa aagttaaaaa aaaaaaaaat tagctgggcg tggtggtgca ggcctgtagt   67980
cccagctatt gggaggctg aggtgggagg atcacctgag cctgggaagt cgaggctgca    68040
gtgagtggtg ctccagcctg ggtgaaggag ggagaccctg tcttaaaaaa taaagtaact   68100
acattcatct ctatatatgt tcacatttaa cagattgaac tttattattt gtcagtgaag   68160
aggaaaatgt gatatccctg atattttcaa tattttacag tctttgttgt attaaaaaag   68220
cactctagta gatttgcctt tttctcttttc tttttttttt tttggtttat gatcgattgg   68280
gttaccttca taaatatat ttatgctatt aaatctattg tggtctaaaa tgtttgtgtg    68340
actgaaaaag tgaagtcttt tcagtaagga aaacctgtct tcccttcccc tgggcctcag   68400
ctgtgaagtt tggatttgga ctgagatcca tgggatggag ctccacaggt gtcccttcca   68460
ttccatctac agctgtgttt cctttctcat gtcattctac tctagcagct ttcagtttat   68520
gtcactcaat gaatagtcag cttaaatgat gatctataag gatacttagg agaccttaac   68580 ctataggggaa aatacttta ttttagaagt tactgcttaa tgtttgtaaa aaatatata    68640 gtaatattaa gcatttataa tgctttgaca gtattcatag gtgaaatgag tgtattttgt   68700 tttaacccttt ggaagccagc ataaaaatac tcttaaggtt tctaaaatct gtttgggagt   68760
tggaaaatcg ggtttttttta aaagtatatt ttcagaattg aggtccaaac ttacacactt   68820
ctgttttcca gattgtttct acttaggttg gaaccttaat ctatttatag ggtgtcttga   68880 ccattttttaa tccttacagt catacaaacc caggtgccag tcaagttta tttcacaggg   68940 aggttgtcat tttaaaattg ttttctgtcc tggtcccgtg gctcatgcct ataatgtccg   69000
cactttggga ggctgaggca gaaggatcac ttgaggccag gagtttcaga ccagcctggg   69060
caacataatg agaccctgtc cctacaaaaa attaaaagaa aaatagccag gtgtgttggt   69120
cccagctatt gggaggctg aagcaggaga tcatttgag gccaggagct cgaggttgca    69180
gtgagctata atcatgccac tgccctccag cctgggcgat agaatgagac cctcctgaca   69240
gatagataga tagatagata gatagatag tagatagata gatagataga tagaatgaga   69300
ccctgccaat agatagatag atagatagat agatagatag atagatagat agaaagaatg   69360
agaccctgcc gatagataga tagttttcta tcaaattttt tcctagattt gaacatgttt   69420
```

```
ttctaaagta gcattcaaca catcagcatt ttatagcgtc attagttgtt actatgatta   69480 tgttttctg aaatagtatc ctttacaaaa gcacttctgt ctttctaagc acatacatag    69540
gtcctaaaat gaatttgtct gatgttggtg acctcggaac cattttctcc agttgattag   69600
cacggccagc cagtcaataa tttcaggtca ctgttggcct tagaggaaga gcccaaaggc   69660
agcaagcaag ggtgctggtg tccagtcgcc ttctagaagc attttcacct tcccttaaga   69720
tttcccttga ttaacacaga agtgtctata gaagtgaccc agtgctgccc cgggcaacat   69780
cgtatattag gccaaatttg catttcttac ctttatgaga agcaccctcg tagtctagtg   69840
gagttacaca cacacagtct gatctcagct gtgctctcca gagatacaac atagtccaat   69900
caaataacat cctctgagcc tgtttcttta gctgtaaaat aagaataaca attatacccca  69960 tctaaaaaga tagtgtcttg tacttgagtg atctttttttc tatgatactg tctttaacac  70020
aataattatt ttcttcacca taccacattt gtttttaaat aagaatttct taaaatgatg   70080
ttttcagtat tttatagatg atgtttgagc agcaatatta atagcatgtt acctgacact   70140
ttgagggact agaagatgac agtggcagct gatatgaccc agatgtctct aatcctaaca   70200
tgaggtgtac tgaagggtca cagcagagtg agttcctggt gtatccacaa ggaaatgagc   70260
acggaactct cacaacagcg tgtgtgctgt gcgctgtgct tgaatagctg actgctcctt   70320
tatacacagc ctctgtgctg actgaatcaa cagtatctgt ttcatcataa tgcagcccta   70380
tttctttaag cccatacatt ttgcacttgt taaaagtatt tgaacaggcc aggcgcggtg   70440
gctcacacct gtaatcccag cactctgggt ggccgaggtg ggtggatcac ttgaggccag   70500
gagtttgaga ccagcctggc caacatggcg aaaccccatc tctatcaaaa aaatacaaaa   70560
attagccggg cgcggtggcg ggtgcctgta atcccagcta cttcggaggc tgaggcatga   70620
gaatcgcttg agcccaggag gtggaggttg cagtgagcca agattgcatc actgaactcc   70680
agcctgggca acagaacaat tctctgtctc aaaaacaaaa acaaaaacaa aaacaaaaaa   70740
aaactattta cccaatttcc cttgcttatg catgcttaaa ttttgtataa gcttaaatat   70800
cttttccatc taagctgtac tctatccccct tttataactt taggtggctg tctttattaa   70860 aagtttttttc ttgaaagtct taaaacaata tagttcttgg caatttgaaa gttatttgag   70920
aaggggaaat ttataatgac aattcaaatg aagcaaacta aaaaataatg aagaaagaca   70980
gaggaaaaag cagtattcac ttgaacacat cccaaacaaa gaaaatttca aatgtaacaa   71040
ggaaaaagcc tgctaaagct cacaatacag aaataactat tgatactcaa aatagcttta   71100
aagccctgct caccttttga atgttgggaa ttgaccagga ggtgactgta actgtaagat   71160
ggttcttcca gtaatgacca ttttctttttt caagatgatg attattctcc accgtctaag   71220
agaccaaagg ccaatgagct accgcagcca ccagtcccgg aacccgccaa tgctgggaag   71280
cggaaagtga gggagttcaa cttcggtaag ttctcagcga acgacgtgac cttttccttc   71340
atcttctgga ttctcagtgt gactgataaa tgttgcaaca tgctctgcag ggggaaaatg   71400
ctttagcgtc tattactgca tcataatctc atctttggaa agccaggagc attttgaaaa   71460
ttacattaca gacattgttt aaacatagtt tggatttacc aaagcatagg acattgtctt   71520
gtctgatgtt aattagtcag ctcaagatta gtgctaaaga cttagtaatt tagttatttc   71580
tcttagcttt aaaatcttta tttcagaact atttcacctc ttggttttct tttttttttt   71640
ttttgctctg tgttactgca gctgctaatc tgtgagctct caatgatgga tgtatcctag   71700
caagggactg aatgagatat tagcggcaaa ttatgttgat gattcatatt ttgaataaat   71760
```

```
ggaatattaa gcttgtatac atcttgaaaa tagtacttta atattctact gtgtcgtagt   71820
cacaatgatt ggatatgaat tgaattttg  tacttttaa  atatgttttt gttctttatt   71880 tttaatttt  attattattt ttttgagaca gagtcttgct ctgtcaccca ggttggagtg   71940
cagaggcacg atctcagctc acagcaacct ccgcctcccg ggttcaagtg attcttctgc   72000
ctcagcctcc tgagtagctg ggattacagg cgccaccac  catgcccagc taattgttgt   72060 attttagta  gagatgggat ttcaccatgt tggccaggct ggaatcgaac tcctgacctc   72120
aggtgatccg catgcctcag cctcccaaag tgctgggatt acaggcatga gccactgcac   72180
ttggcctgtt ctttagcatt ttaagttgca actatatatc cgtaaagtct tatttccaca   72240
caactgagac atgttttagg aagtttgcta aaagacccct ggagaccttt atcgtggtct   72300 ccctttgtc  gtgtttcatt tgcttgatct tttctgccct cctgcttttc agaaattaaa   72360
aggctaaaaa gaggtgctaa atgttaaaac ttctcgtgta gtctcccatg agactattaa   72420
aagtaatggc aaaagccaca gttacttttg caccaaccta ctaattctaa gaaccaccaa   72480
aaaggggaaa gttcttggaa agcagtaaaa tgatatggac agttgggatg taaaaatgta   72540
gaaaatatgt cattgtatgt tcagtcatcc caagaccta  gtgctgcccc gatggtaggg   72600
acttcttaat gagaattaac ttttgctcaa ttttcagaga aatggaatgc tcgcatcact   72660
gatctacgta aacaagttga agaattgttt gaaaggaaat atggtatgtc taaataggaa   72720
aattcctgta atactttgtt catgagcatt tacacaatgg cgttactgtt catcatgggg   72780
gtgatgtgga caagcccagc ccagggctgc cagtgaaccg tgccacactt tcttacacgt   72840
ctctcattgt aaggtcctta gtagtgtctg tctaaatatt agaaacagtc tttgtttcta   72900
gattacagta aagctaagga aaagttgtat ttctatagtt atcagctaac atttctttta   72960
aacttccagc atggatattt gggaatttat ttacatattt attacaaagc tctggatctt   73020
gggggtttca ttaaaaatta tttttttaac tgacagtttc tgttaatcta ctttgttaaa   73080
tccagtattt gctgagatcc ccctattgtc tctactttta tctttttttt tttttttttt   73140 ttttttttg  agacggagtc tctgcattgc agtagtacaa tctcggctca ttgcaaccctc  73200 cgcctcccgg gttcaagcaa ttctcctggc tcagtctccc aagcagctgg gactacaggt   73260
gcccgccacc atgccctgct aattttgta  tttttagtag agacagggtt tcaccatgtt   73320
ggccaggctt gtctcaaact cctgacctca agtgatcctc ccgccttggc ctcccaaagt   73380
gctggcatta caggcgtgag ccacccttcc cggccactgc ttttatcttg atgtataact   73440
gagttgatgc tagatttcaa ttccttcttt gtccttttac tattctgtcc tatagccacc   73500
tttatataat gatcaaagaa attcgcaatt tgttattatc atttttattt tttataaaat   73560
atttaaaatg atttaaaata aaatcattt  tattttatc  atatttatta tcatctgtta   73620 tcattttat  ttggatgact atttactttg ccattaacta gcaagcggta aaattgtatg   73680
atatgcagtt ttaactgaat tgctataagt gaaaatttaa atgcaataaa ccatattgat   73740
ggtatttgtg ttaacaaact taaaatgagc attttttctt catcatgagt aatataacct   73800 accctcaat  gaaaatctac aattagagta aatttgctaa tgaattcagt aacttttcca   73860 tattttagt  ggtttactta aggttctctt agtgttctc  ccagttttta atagcttaca   73920
ccttttttgc ccgtggtttt tgtttttg   ttttgttgtt gttttttttt ttttgagata   73980
gagttttgct cttgttgcct agtctggagt ggcacgatct tggctcactg taacctctgc   74040
ctcccaggtt caagcaattc tcctgtctga gcctcctgag tagttaagat tacaggtgcc   74100
cgccaccatg cccagctaat ttttgtattt ttagtagaga caaggtttca ccatgttggc   74160
```

```
caggctggtc ttgaactcct aacctcaggt gatccaccca cctcggcctc ccagagtgct   74220
gggattacag gcgtgagccg ctgcgcccgg cctcatgttt tctattggtt cattatgaag   74280
caaaaacttc atagcatgtg ctacctggaa gcactgtaac ctagtggtaa gatcataggc   74340
tctggggaca cagtgccttg ccacgtctct tctcctgtct gagtcttagt atcctctttt   74400
gtggtcatga gaactgaaga tctatcctgg agattgataa gatagtaaag tgcttcacgt   74460
aatacctggc atacatgtaa taaatgcttc ctgtgtgtat atatatacac acatatacat   74520
atatatgtat atatacatat acacatatac atatatatat atatatatat acataaacac   74580
atatacatat atatataaca cagtgaaacc cccgtctcta ctaaaaatac aaaaaattag   74640
ctgggcgtgg tggcgggcac ctgtagtccc agctactcgg gaggctgagg caggagaatg   74700
gcgtgagccc gggaggcaga gcttgcagtg aaccgagatc acaccactgc actgcagcct   74760
gggagacaca gcaagactcc atctcaaaaa aataaaaaaa aagttaaaga gcactacaga   74820
ttcaatgatt tattattctt ttctacaaat tgtgtttaaa tgatatctct ttctcttttt   74880
gtccttatag ctcaagccat aaaagccaaa ggtccggtga cgatcccgta ccctcttttc   74940
cagtctcatg ttgaagatct ttatgtgaaa ggacttcctg aaggaattcc ttttagaagg   75000
ccatctactt acggaattcc tcgcctggag aggatattac ttgcaaagga aaggattcgt   75060
tttgtgatta agaagtaaga ctcttggatt cctgttgaac tcttgtctct tttctgagta   75120
atacgtcttt tttattgttg accaatattc attcaccact aggttctatg tgatgaagtt   75180
tgagttattt tatgtatttt tatcttgcac tttttaattt atctgggtcc agcattgcat   75240
cagtcatgca gtgttggcat tcgaagcatg aacagtgccc gcactggatt ggcatgcaac   75300
tcacattttc tttcacaatt ttctgctact tttgctaaag aacatagaat ccacgccttg   75360
tttttaggcc tgatatatat atatattttt tttttcgaga tggagtctca cactggaacc   75420
caggcttgag tgcagtgtcg caatctcagc tcactgcaac ctctgccttc caggttcaag   75480
cgattctcat gcctcagact cccgagtagc tgagattaca ggcgtgcgcc accatgcctg   75540
gctaattttt gtattttttag tagagacggt gattcaccat gttggccagg ctggtcttga   75600
actcctgacc tcagatgatc tgccaacctc gccctcatag gcctgagatt tttaaagcat   75660
gcgtgggaat atatgattgt ttttatagat gtgcagagga agatagtctt gaatgcaata   75720
tgacattaaa ggatcccatt taagatttt gtaaatgct tcaaagacct gtgggttgca    75780
aagttacctc tttacttgtg aggatacatg ctccatgaag caccttatga gacaacttgc   75840
aattattagt ttgctttta ctctgtagaa acctcaaatt aagatttagt tgtgggctgg    75900
gtgtagtggc tcacacctat aatcccagca ctttgggagg ccaaggcggc tggatcaccc   75960
gaggtcagga gttcgagaca agccaggcca acaatggtga aacactgtct ctactaaaaa   76020
tacaaaaatt gaccaggtgt ggtggtgggc gcctggaatc ccagctactt gggaggctga   76080
ggcaggagga ttgcttgaac ccgggaggtg gaggttgcag tgagtcgaga ctgcgccatt   76140
gcactccagc ctgggaacaa gagcaaaact ccgtctcagg aaaaaaaaa aaaaagattt    76200 agttgtgctc aagcatccag attatctttt cttttcaaaa ccagccttac tgactaaatg   76260
ttaaatatgt actagtcgtt attagtttgc tgaatattac ctagtgatta ttgagtattt   76320
attctcacct ttcagacatg agcttctgaa ttcaacacgt gaagatttac agcttgataa   76380
gccagcttca ggaggtaggt cttcaatctc gaggcagatc agaagattat gtgcaataat   76440
tatttcacgc ttaacattga tttcttcttt atgttacctt ccacatgaaa taatatgtct   76500
```

```
ctaactatta attatgtgcc attacaggag aattcatgtt gtcaaaattc taataatttc    76560
tagaagaata aacgcatctt cttttttatta acccattgta aatacttata aatattgcat    76620
ttatgggtag acagaagtaa aagaacaata tttgttctac ttttgatgca agatttatct    76680
ggcataatgc attgaacagt ttattattga agtctacacg agtcaatgga acaagcattc    76740
attgaatgtc catgatatgc aggacataag aaggtttcct tttagagcat ggagccattt    76800
atatcatctc ttaattgtta gatgtatttt gttttgtttt gttttgtttt ttgagaggga    76860
atcttgctct gttgcccagg ctggagtgca gtggtgcgat ctccgctcac tgcaacctcc    76920
cgcctcctgg gttcaagcag ttctcctgcc tcagcctccc tgtagctggg attacaggtg    76980
cctgccacca tgcccagcta atttttgtat ttttcgtaga cagggtttt cactatgttg    77040 gccaggctga tctcaaactg ctgacctcag gtgatctgcc cacctcggcc tcccagagtg    77100
ctaggattac aggcatgagc caccgcgccc agcctgttag atgtgttttta aaataaatag    77160 aaatataatt gattttcttg cttgcttttg ctctggagtg gagtggagtg aggataaaac    77220
agaatggaat caccctgttg atatttacta agatagaagg actgcagcaa gatcatagcc    77280
ctaatcttcc tgtagcaagt gttacctgct agctgttcct gaatacactg agttttgctt    77340
tttcctagct ctaatgaatg tttcgttctt cctcttttg tacagtgtca gcattgtttt    77400
agaaataaat acattctaga atcttaggaa taattttatt attgtctttt ttttttttttg    77460 agacggaatc tcattctgtt gcccaggctg gagtgcaatg gcgcaatctc agctcactgc    77520
aaccgctgcc tcctgggttc aagcgattct cctgcctcag cctcatgagt agctgggact    77580
acaggcgtgc gccatcacgc ctggctaatt tttgtatttt tagtagagat ggggtttcac    77640
catgttggcc aggctggtct caaactcctg acctcaagtg acccgcctgc ctcggcttcc    77700
caaagtgttg ggattacagg tgtgagccat gcacctggc cacgaatctt agaaataatt    77760
ttggccatag gaaaaggaaa agttatacct cttattttat agtaataatg tttaataatc    77820
aagttattaa acccattaaa ttgagaacac ttgtattact gttattttga cagtaaagga    77880
agaatggtat gccagaatca ctaaattaag aaagatggtg gatcagcttt tctgcaaaaa    77940
atttggtaag tctgttttttt ttaattaccc cttcaactaa aatgtattac tgagtaacat    78000
ttttttaaat gttgttttat tttaggaaag taaatacagt gaataggact cagctttagt    78060
tttccctgtt tttttttttt gggttttttt ttttttcttg agaaggagtc ttgctctgtt    78120
gcccaggctg gagtgcagtg gtacgatctc agctcactgc aacctcctcc tcccgggttc    78180
aagcaattct cctgcctcag cgtcccaagt agctgggatt acaggtgccc gccaccacgc    78240
ctggctaact tttgtatttt tagtagagat ggggtttcgc catgttggcc aggctggtct    78300
caaactcctg aattcaggtg atccacccgc ctcagcctcc taaagtgctg ggattatagg    78360
cgtgagccac cgcgcccggc ccccattcta tgaattatct gtggaaagtt atttccttta    78420
aaatggcatg ctcgtgaggt tgaaggggta aagaacattg atctggttgc cacgcagatg    78480
aaagtgtagt cggaaatgtg ttaccagttt gccatagccg atggaggagg gtaattacgg    78540
tcctgaacag ttagtagcaa aaggctgctt ccagatagta tttaggttgt gtcctctatt    78600
gtccatgatg attttcttc tctcttttct tcctaaggat attgaaaaac aaactttaat    78660
cttttaaaga tctcagagct attaagattg tcttaggacc aggacactta aatctgccca    78720
aatctggctg ttgatgatcg gtcatctcta cttgtctttg ctgtattaag tctattcaat    78780
agttaataaa tatgtttcta gaaagagttt ttttcaagta aaacaaaatt gacctgtgcc    78840
tttctttgga ttgtactaaa atctgatttc aatacaaatg tagtctcccg aattgctttg    78900
```

```
atttttgtcc agcggaagcc ttggggagca ctgaagccaa ggctgtaccg taccaaaaat  78960
ttgaggcaca cccgaatgat ctgtacgtgg aaggactgcc agaaaacatt cctttccgaa  79020
gtccctcatg gtatggaatc ccaaggctgg aaaaaatcat tcaagtgggc aatcgaatta  79080
aatttgttat taaaaggtaa gatgataatc tgtagaaata gtttcagtgt cttccctgag  79140
aagaggttaa tttgatgaag aagggccttt tgtttacctt atgacttatt tctattgaca  79200
atgaaggcat taatatttag attcacttag tgaacaaata ttagtataag catcagatgt  79260
gcaaaattgg gtctaacaag aacactgtcc ttggggcctt catacaaaga aaaatgcact  79320
gaaggccagg cgcggcagct cacgcctgta atcgcagcac tttgggaggc caaggcaggt  79380
ggatcacttg aggtcaggag ttcaagacta gcctggccaa catgatgaag ccccatctct  79440
agtaaaaata caaaaattag ctggaagcgg tggtgcaagc ctgtagtccc agctactcgg  79500
gaggctgagg ttgagaatc acttgaaccc tagaggcgga ggttgcagtg agccgagatc  79560
gtgccactgc actccagcct gggcaacaga gcgagactcc atctcaaaat aattaaaaaa  79620
aaaaaataga aaatgcaat gaagtgttat tgagcgtttt taagggagaa ggcaaggatg  79680
gcacacccag ctcggtcact tgtgcatcca aagagatgg aaggtgtttc aagtgaagga  79740
aatcatatga gtaggggag gaggtggcaa atatgcctgc gtatccacag aactcaccca  79800
ccgtgtgtgg agtgaggact gccacgtggg cgtggtgggg ttgcatggat cgacttgggt  79860
gggcaagtgg aggaaggcct gagatcctac gaacacagag gcagtcacga agtggtctcg  79920
aggcagatgc ctctgaaaat aatgtggatc cgccctttag aaaggtaatt ctggcttgat  79980
tttgaaggat aacacaatgg ttagtttggg tgcagggtta ggaacagaag gcctctctcc  80040
actcattgac gggatgtgga agggtaaacc ttccttactg attggggtca tgcctctgtg  80100
tgtttgttgg gactgagtta taagggatag gaaacgttta agatgctaca gcgagctgct  80160
tctggctgtg ctgtgggaca gttcatgtaa gattcagaaa cagaattgag ctggtttggg  80220
ggaaaagtga ctttcgcctg tttatcttaa atataggatg attttgaagg tctcacccga  80280
atatctgaaa attgccattt tcaaaataaa ctcgtcacca aaatgatttt ttttcacta  80340
taaaatgaag gcaggatgaa ccatatttat aactaattgg caatgaacag ctgtgtgaga  80400
aaggcctgtg agttgcttct aaatgctttt ttactaatat caactctgtt tctacagacc  80460
agaacttctg actcacagta ccactgaagt tactcagcca agaacgaata caccaggtaa  80520
actagttgtg aaatcctttt ttaaaaacac agatcagcca ggctcggtgg ctcacacctg  80580
taatcccagc actttaggag gctgaggcgg gcagatcaca aggtcaggag atcaagacca  80640
tcctggctaa catggtgaaa ccccatgtct actaaaatac aaaaaaatta gccgggcctg  80700
gtggcgggca cctgtagtcc cagctactcg ggaggctgag gcaggagaat ggcatgaacc  80760
caggaggcgg agcttgcagt gagccgagat cacgccattg tactccagcc tgggcaacag  80820
agcaagactc tctcagaaaa aaaaaaaaaa aaaagcacag atcaatactt tttaagcttt  80880
taaaagttaa tcttttaaaa ttatggaagt ccccttccc ctgcctcccc aaaaaatcat  80940
ttgcagaagc tcaatccagc cactccttga tttatcaatg tgaacacctg cagtgcacag  81000
ataactcaag ctttgaccgt agaccactgc tatccatgag aaaggcagtg tgccccacaa  81060
atgcaagcca catgtgtaat cgtccacgtt ctagttcagc ctgtaatcat tataaagaaa  81120
tacacaggga agtatttcac ggtctttatc ccatgttctt tatttgacag ttggcgcgtc  81180
tttcatactc acagcatatt tcagttccaa gtagccacat ttcaaacatt tcaactgctc  81240
```

-continued

| | | | | | |
|---|---|---|---|---|---|
| ggggatagta | cctgctatat | gcatttagac | cttaatgttt | attcatatgt | atcgtgttcc | 81300 |
| taaaatggca | gactgtaact | ctgacctgca | cacaaatatc | acagcctaat | agggaagatc | 81360 |
| taagaagtct | ctgttcaatg | aatgatgtta | ttttctttat | tagagctcta | agtgtgcctt | 81420 |
| tatttctttc | ctatcttttt | tttttttttt | ttttgagacg | gagcctcact | ctgtcatcca | 81480 |
| ggctggagtg | cagtggtgca | atctcggctc | actggggcct | ccgcctcccg | ggttcaagca | 81540 |
| gctctcccgc | ctcagcctcc | cgagtagatg | ggactacagc | tgcacgccac | cacacctggg | 81600 |
| ctaattttg | tattttagt | agagatgggg | tttcaccatg | tcagtctggc | tggtcttgaa | 81660 |
| ctcctgacct | caggtgatcc | acctgccctg | gcctcccaaa | gtgttgggat | tataggcatg | 81720 |
| agccactgca | cctgacctct | ttcttttgt | ttgccgttgt | gtaatgtcag | aggaagtgac | 81780 |
| cacactctgt | agatcatcag | ccaccttagg | aacttctgtt | gccaagaacc | aataaatgcc | 81840 |
| catccctgt | agtgtgtaaa | tgcccatacc | ctgtagtgtg | aagttttctg | ttgttagaaa | 81900 |
| taagtgttag | gaatcaagta | tgaaatttgt | gtgtgtacta | ggtgtataca | gattggtgca | 81960 |
| gttaatcatg | ctcacgacta | ctaaggtgaa | caaatgtttc | aagttgggtt | cctgggtgtg | 82020 |
| ccctaaaata | cttctccttc | agctctcaca | gcaccttgtg | gacatgagtg | aaggtcagtc | 82080 |
| agtgtgccaa | atagatttg | tgtggattat | ggcatggaaa | gtggctgaga | aattctgtag | 82140 |
| cagggtaaca | aaattatctt | ggtccaggag | tcctgtagtg | gagaagataa | aagtcaatgc | 82200 |
| ttaactcata | ggttaacctc | agcatgcttt | tgatttggtc | aagcaatcaa | agtactggtg | 82260 |
| aagaattgaa | gattggaagt | gacacatttt | ttgctcaggg | aagtaatgga | gaaagaaaaa | 82320 |
| tcttcctgga | ggtagatctt | cagtttggat | tagtctgaac | atgatgaaac | ctgtagaaac | 82380 |
| cttcatttct | caagacaaag | ctcaaattca | aggttgtgag | gaatgcagtc | accacttttg | 82440 |
| ttaggggcag | ttgtgacagt | gagtgactgc | aaaaactgag | aatgcgaagc | ctctattgta | 82500 |
| aaaagaatgt | gcaagtgcca | tagaagtcac | tgcaaggatt | gggtgctgga | gcagtgccgg | 82560 |
| acctgccatc | gtcaccagag | tgcagcagat | tcaccagaag | gagaatctcc | actcttgtcg | 82620 |
| tcactaacag | cacttgactt | tgtcccattc | ataaagatc | ttggaaggaa | ttaaaggtgc | 82680 |
| ttggtggttc | ctcattccaa | caacacctta | cttggcctgc | ccgtggaaca | tgcgttagtc | 82740 |
| tttggacagg | acaactcgag | tcacagacca | caagagaaaa | gaattttgtg | gccatcagaa | 82800 |
| ttgtctgctt | aaaacacacca | cggggtgcaca | gtgtcctcag | cttggtgaaa | gggagatgtc | 82860 |
| acacgcgaga | aggcagcgga | gccaggcatg | tgatggagtg | ggaggtggca | cctggctctg | 82920 |
| tgaggaggct | gtgaagtcct | gcatgggagg | agcaaggtgg | gggaggaggg | ggtgggggtg | 82980 |
| gggcagaaga | ggaggctgag | cagttaatag | aggcgctcga | ccttagagga | ggagagtccg | 83040 |
| aggtctttat | tggtagtatt | caaatgtggt | tcatccagag | ttatttctg | tggctgaatg | 83100 |
| gcctactctg | aaatccacag | ggaaaaaaca | actcacattc | aacccttgag | atgctaagtt | 83160 |
| ttctttaaa | gtaaaggaaa | tgttataaga | ttttctgaaa | ccaccaacct | ttagcgatat | 83220 |
| tgtcagacct | tctccaacat | tttccactgc | atttgtcagc | aatcagagat | gacctccaca | 83280 |
| ccgaggcgaa | ccctccaccc | cccgacccgt | ttcctctttc | tctctttccc | tcctttgctc | 83340 |
| atccagaaac | acttcagtca | tcctgcattg | tctccaagtt | gacctccatc | ctcatccgca | 83400 |
| cctcgtccac | acctgaatac | tctgtccaca | tcagtgatat | tctacatgtc | tttataatag | 83460 |
| cttttttgtt | tgtttgtttg | tttgttttt | aaattttgat | gcttaaaagg | caatggttgt | 83520 |
| cttagggata | ggaaaacaca | ccccactgtc | actgtgagtg | aagctgaata | acgtctctag | 83580 |
| gtcttttacc | attgctttct | ttttttctg | aagtgatttt | tccttttatg | tccattgctt | 83640 |

```
taagccattc gtgaaattgc acagtgattt ctggagtggg gacagaagga aggcggtagt    83700
aaaagtcatt ggtgctgtgg cccagttggc tggaggaggt gcagggcagg gcggcctgcg    83760
ctggggcagc tggaggagca cagatgtccc cacgggcagg tggatgagtt ctgagagctg    83820
gagggccggt acagtgtcct ccatggttcc agcttgtggg cttgatcagg ccgtcacctg    83880
cggtggccac tgagctggcg atgaactccg tggccttgga gtcgccctcg gcagagatga    83940
tggccgccgt cttctgctgc tcagcccttg ccaccacaga tctggccctc tcttcttcct    84000
gctgagccac ctctttggtt ccactgcttc tgcaaattcc ttcccgaagg tcagatccaa    84060
ggtcacagca tccaggagga gcccaaaggt tgctgcttgc tccgaagtta attgctcacc    84120
tgtctggagc ccagctctcc ctgcgtgatc agttctccag cgtcagcctg agccgccccc    84180
agcttgagga gctccgcagt gatggatggc agcacattct tcattggctt ctccagtaat    84240
tggaagatgc aaggacctgg ccagcaacaa ggtgggaaga ggacgcccag tgtgatggtg    84300
acaatctttg ctcacagtga tgattggtgc ataatgtggt caagagcagc agtcaaaaat    84360
aattggtttc ttttcccatg ggatgagaaa gtgcgttcct tccctatca cagtgtcctg    84420 aatgccatgg aattggtcga agatgacaga cagctctctg tgcagcatca cattgtagaa    84480
ggcagagttc cccacacctc ctgcagaagc taaggacagg gcagacttgg cagctgtgtt    84540
tccatctgct ggacccactc acgcctgcgt ccactccaac cccccacatg aattccgtcc    84600
ctttatcatt gatttctgat gcgaaaagtc actttgatta gtgaagtgtt gctttatgta    84660
gattttaggg cacacatctg ttagataaaa tgaggattgc ctgtagagaa agcaaataaa    84720
agcaaagtcc ctcttgttga aactggtgtg ggagcccttg aacctcatgc agctggcctc    84780
cctgctctga ccgagttccc tgagggactt ctccaaggag gaatgtgtga gaagcactga    84840
ttttgagcac tctttcatgt ggacaaattt cactttattt acaatgtaaa cttaaattta    84900
aattctgtct ttctaggctg gcacggtgg ctcacgcctg taatcccaac actttgggag    84960
gccgaggcgg gcagatcact tgaggtcagg cattcaagac cagcttggcc aacatggtga    85020
aaccctgtct ctactaaaaa tataaaaatt agccgggcgt ggtggcggct acctgtaatc    85080
ccagctactc gggaggctga ggcaggagaa tcgcttgaac ccaggaggcg gaggttgctg    85140
tgagctgaga tcacgccact gcactccagc ctgggcgtca tagcaagact ctttctctaa    85200
ataaataaat taattctgtc tttctgcagt ttttctgata tttggcaagt actggaaatt    85260
attattttcc ttaagacccc aaattttcac accaacatgg cacatgtata catatgtaac    85320
aaacctgcac gttgtgcaca tgtaccctag aacttaaagt atgataaaaa ataaataaat    85380
taattaattt aaaaaaaaag accccaaatg tttgctttta acaaaactga attaagagaa    85440
tcactgcagg ccgggcgtgg tggctcacgc ctgtaatccc agcactttgg gaggccgagg    85500
cgggcagatc acgaggtcag gagatcaaga ccttcctggc taacaccgtg aaacccccatc    85560 tctactaaaa atacaaaaag aaattagctg ggcatggtgg cgggtgcctg tagtcccagc    85620
tactcaggag gctgaggcag gagaatggcg tgaacctggg aggcgaagct tgcagtgagc    85680
cgagatcgcg ccactgcgct ccagcctggg cgacagagca agactctgtc tcaaaaaaat    85740 aaacaaaac aaacaaaaaa gaatcactgc aaacaagagt actttctagc aaaatccatt    85800
ctgatttgca acagcactga taaataacat ggttattggg tttcttttttg ttttccagtc    85860 aaagaagatt ggaatgtcag aattaccaag ctacggaagc aagtggaaga gatttttaat    85920
ttgaaatttg gtaagtaaaa gccagtattt atgtctttaa taacatatca acaagggcc     85980
```

```
atgtctgaat gaagtataga agttcgggac cagccgggtg cagtggctca cgcctgtaat    86040
cgcagcactt tgggaggcca aggcgggcgg atcaggaggt caggagatcg agaccatcct    86100
ggctaacacg atgaaacccc atctctacta aaaatacagg aaaattagcc gggcgtggtg    86160
gcgggcgcct gtagtcccag ctactcggga ggctgaggca ggggaatggc ttgaacccca    86220
gaggcggagc ttgcagtgag ccaaaatcgc accactgcac tccagcctgg gcgacagagt    86280
gagactctgt ctcaaaaaaa aaaaaaaaag aaggaaaaaa agttcaggac ctaaagaagg    86340
aaggtcccag aaactgggtt tctgtttctt tctaccacta cacttgctac tgaaaccaag    86400
cagatgactt catttctctt ggattccact ttctcacgtg tcagaatggg agaggaaggg    86460
aggtgttggg ataagtttca gttccactgt ttgtacttct cgtctggcta acacccatgt    86520
ggcaaatagg tttcatcatt tgtttcagct tagatttgtt gacagcggtt tcctggagtg    86580
ctgtcttgag aacgattctg aggaggctca gcaagaaaga gtgtttcagt tgattgggtg    86640
tgtctgtcat ggagaaggaa gtaaggagtg ggcagtgcta gcaaaattcc cggggcactt    86700
ctgtccatta tctcaatacc tggggttgac atttcctgtc tcagatcagg agtcctgact    86760
accctgcctc tgaccactcg aactgagtgc tgcttagctg tatcgtagac accgcctgtt    86820
tgtgaacaga caccctgctt cttgatgata acacaaaggc cagcagggtc cactgctgtg    86880
tggaatggcc ttcggtcatt tctgcccaga gcatagaggt cattttcact aataacataa    86940
ctctcctttt gattgaaagt gttaaaatgt tcctcctaaa agcacttatt ttttaggctc    87000
gttcttcaga tttgccccat atcctaagca aaatgccttc aatatgaagt ggatattgct    87060
tgaccgtagg gagcttgtcc atactgtact cgagaatgta gacacaaaga aagaatgtct    87120
gtgtcaaatg ttatcctccg caacttaacg ttctcttgca ctttcagctc aagctcttgg    87180
actcaccgag gcagtaaaag taccatatcc tgtgtttgaa tcaaacccgg agttcttgta    87240
tgtggaaggc ttgccagagg ggattccctt ccgaagccct acctggtttg gaattccacg    87300
acttgaaagg atcgtccgcg ggagtaataa aatcaagttc gttgttaaaa agtaagttct    87360
ttttgccact gtagtcgttt ctggaatcaa acaataaaaa tgacatttct gttaagatgt    87420
ttttcaagct agaggtgaca ggcgtggctg taagtccttg atggcaaagc ctggctgtga    87480
gctgcagtcc gggtactgtc cattgcccct gcccatactc aatcatcttc atccgtgcaa    87540
ggaaaatagt gacaatcgcc tccgcggagt caccgtgagg ccccgtggtg actcgcagca    87600
tgcctgagta cttgaatgga agtttaattt gctggttttt atctgctctg ttattcctgg    87660
tcaatcttga gagcgactaa atattgatga ttgagtttct ttcttttttt tgagacggac    87720
tcttgctctg tcgcccaggc ttgagtgcgg tggcgcaatc tcagctcact gcaacctccg    87780
cctcctgggt tcgagcaatt ctcgtgcctc agcctcccga gtagctggga ttacagactt    87840
gcaccgccac gcctggctaa ttttttgtatt tttagaatag atggagcttc accgtgttgg    87900
ctaggctggt ctggaattcc tgacctcagg tgatccaccc gcctcagcct cccagaatgc    87960
tgggattaca ggcatgagcc accgtgcacg gcctaatgat tgattttctt atctacattt    88020
ctgcagaatt ttagtggcta agaaagtac actagtgttt ttttttttctt ttttaatgaa    88080 aatagtcact tatttactct tcataaaatg gcttaccagt catgggaagg aaaagtcagg    88140
gtcttttgtc cacaacacta ggaattattg tgttacagga tgattctgtg aatgccttta    88200
gaaaaaaaac cctgatcaca tcacgaccgt tttactagct gtgaggccac cactgtgctg    88260
gctactgtaa cacttcttgg ttttctttct agacctgaac tagttatttc ctacttgcct    88320
cctgggatgg ctagtaaaat aaacactaaa ggtaagagac gacgtgtact ccgtatccta    88380
```

```
tttgagcgca ttaagacact ctttatccgc attccttaaa tcatacggaa tcggccaata   88440
tctctgtggg gcttggagtt gtttactttg ctttctaagg tattttattt aatggaacta   88500
tttttctttt tttttttaaa aaaaacaaaa catttcattg gaaatgtcac atttgcaatc   88560
ccagttcatt catgttttca cagctttgtt gagcccctgt ggaggattac actacaagtt   88620
taattctgca ggtttctttg aaaagaacca aactgtatga attttaatac tctgctctta   88680
taaagcatct ccttctgtat ttttttttcc ctacaatata caaaaggaac tctgcttatt   88740 ttacagctttt gcagtccccc aaaagaccac gaagtcctgg gagtaattca aaggttcctg   88800
aaattgaggt caccgtggaa ggtaagggcc agtcctcggt atgtttctgt tcattctcta   88860
gttactaatt atgtcagttc actagctatg tgtttataca ggtttataca gatgacgtta   88920
accaaactag cttttaactg tgaacagctg cctgtgataa agctaaattt ctgaatgctt   88980
ctaattgaaa attttaaat ccttaataga aaacagataa catggatcac atcataaact    89040
tcccccaaga aaagtcctaa aatgcttttc ctttatcata acaaataagg gtgcagagtc   89100
atgtggaatg ttttatcttt ttttttcctct tcattttttt ctattctttt aaggaaagaa   89160
agtttagggt ggtttaaaca gcagtgcctt gaataaaagt attttctttt tcttttttga   89220
gacagagtct ggctctcttg cccagggtgg agtgcagtgg cacaatctcg gctcactgca   89280
gcctccgcct cccgggttca agtgattctc ctgcctcagc ctcccaggta gctgggatta   89340
caggcgtcca ccaccaactc cagctaattt ttatatcttt agtagagacg gggttttacc   89400
acgttggcca ggctggtctc gaaccccctga cctcaagtga gccaccacgc ccagctggtt   89460
cttgtctttt caggctcaca gtgttaaaat actgcataca atactaaaga caatctccaa   89520
ccaactgtca agtatggata tttcttccat ctcttcataa atgcagaagg aaatcactgc   89580
attaggatca ttctctacat cccaggtgtc aagtttttaa ataagagttt gccgtactgg   89640
tgttgagtgg cgcagaagtc cctatttagt catgtggcac actttcagag agcctgcttt   89700
ctcataagat agccaacaag catccatgga caacttacac ctgattaatt atttctgttc   89760
aaaaatgcca agaattaaaa atatattgaa cccttgactt tcctccttcc ggaagagatc   89820
agaggaagat ctctcttata tacaagatgc cagccttttcc taaagggcag agccaagttc   89880
acggggcctg ggaggcctgc tttaagaata caaaattagg gccaggcgtg gaggctcacg   89940
cctgtaatcc cagcactttg ggaggccgag gcaggcggat cacctgaggt tgggagatcg   90000
agaccagcct gaccaacatg gagaaacccc atctctactg aaaatacaaa attatctggg   90060
cctggtggcg catgcctgta atcccagcta ctcaggaggc tgaggcaaga caatcgcttg   90120
aaaccaggag gcagaggttg tggtgagccg agattgcgcc attgcactcc agcctgggca   90180
acaagagcga aactttgtct caaaaaaaaa aaaaaaaga agaagaagaa gaagagaaga   90240
aaaatgggtt tctgtagaaa tagaaaaatg gtttctgtgg aactcgccgg aatgacaaga   90300 atacccatt caatttgaac ctagctttgt tttctggcac aggctggact tgaagattgt    90360
aacctagaga cacttacgtc attaaatgtg tgttgattat cattattttt tctgtctttt   90420
aggccctaat aacaacaatc ctcaaaccctc agctgttcga accccgaccc agactaacgg   90480
ttctaacgtt cccttcaagc cacgagggag agagttttcc tttggtaagt aagcgtttta   90540
tttttctttc tttcatagtt ttaaatagaa tacgttcatt atgtttcatt ttaccaggtg   90600
aattgttcct attggtgagt cagtatatat caaaggttaa aggaatagcc cgtagagcca   90660
ggctgcctga gttcagatct gagttcaaat ccgatgccac ttgggcaggc gaatacaccc   90720
```

```
tgcctcagtt tcccttgtg caaaatggta ataacattac tttctttctc atgaggttat    90780
ggtgaggatt ataaatactg tcatttaaag tacttagaac catacctcgc atgtagtaga    90840
gactataatt tgtgggggca ttttgggggt tttcatttgt tttttcttta ttttagcatt    90900
tgttcactta tttgtagtca acataaaagc aatgtactaa aacagtttgc ttatgtatca    90960
ggatgggagt agttgtcaag tcatatcatg gtaaaagatt atgcatttt tatttcttct    91020 taaagatgca caaataaggc caggcgcagt ggctcacgcc tgtaatccca cactttggg    91080 aggccgaggt gggcggatca cctgaggttg ggagtttgag accagcctga ccaacatgga    91140 gaaacccgt gtctaccaaa aatacaaaat tagccaggca tggtggcgca tgcctgtaat    91200
cccagctact caggaggctg aggcaggaga actgcttgaa ctcaggaggt ggaggttgca    91260
gtgagcagag atcgcaccat tgccctccag cctgggtaac aagagcgaaa ctctgtctca    91320
acaaaaaaaa aataagatgc acaaataaga tgaaacactc ctgcctgtga atgtgtattg    91380
ataagtactg tgataagtat tgcaatttaa ctctcttatg ttttatatgc agaggcctgg    91440
aatgccaaaa tcacggacct aaaacagaaa gttgaaaatc tcttcaatga gaatgtggt    91500 aagtctattt tgaaaccttc ttactgccac gcagggtgcc ttcatgggag taggagggag    91560
cagagtggga tactgagcgt tggagtatcc ctgtcattgg caacgtgtgg ttttttcggg    91620
attgaatggc gtcatttcgc ccatgttctg tttcgtgtac gcggctgttt tgcaggggaa    91680
gctcttggcc ttaaacaagc tgtgaaggtg ccgttcgcgt tatttgagtc tttcccggaa    91740 gactttatg tggaaggctt acctgagggt gtgccattcc gaagaccatc gacttttggc    91800
attccgaggc tggagaagat actcagaaac aaagccaaaa ttaagttcat cattaaaaag    91860
taaggaaact ggatgaagtg ggattagcat gagttgattg tgtttgacac tgggagatgg    91920
gtatgtgggt ttgtgtttgt ggcagggctg aattagctct ggagtcagaa aaactgcttt    91980
ttaagctgca ctcttgtata tgtttaaaac ttctggccag gtgcgatggc tcacacctgt    92040
aatcccagca ctttgggagg ccaaagcagg tggattacct gaggtcagaa gttcaagacc    92100
aacctggcca acatgatgaa acccatctct actaaaagta caaaaattag ctgggcgtgg    92160
tggcacgtgc ctgtaatccc agctacttgg gagactgagg caggagaatc acttgaaccc    92220
agcaggcaga ggttgcaatg agccaagatc gtgccactgc actccagcct gggcagcaag    92280
agcaaaactc catctcaaaa acaaaaaaaa aaaaaaaaaa gaagaagaaa ttttccttat    92340
gctgctggta gagggaagg aggactccac catactagag agataacgac ttttggttgc    92400
taaatctaca cagctatgtt gttactattt gatgctgctg gaatctgagc agctgtttag    92460 ttttcaagt cctttattt ctccaactta atagaatatt ttcaatttct cctgtttgct    92520
tgaacatctg tggattaggc taacataatt gaaatagata ggaatgggcc gggtgcggcc    92580
ataaatccca gcactgtggg aggctaaggc aggcagatca cttgaggtca ggagttcgag    92640
accagcctgg ccaacatggt gaagccccat ctctacttaa aatacaaaaa aaaaaaaaaa    92700
aaatagccag gggtggtagc tggcacctat aatctcagct actcagggag gctgagacag    92760
gagaatcact tgaacccagg aggcggagga gatcgtgcca ttgcactcca gcctggatga    92820
cagagtaaga ctctgtctca aaaaaaatta aaaaagaaa taagaataat tggaatttta    92880
tagtacatgc taatgcacat gaattatttg aaatcaattg aaatgaattt taggtttcat    92940
ttgcttggtg tcaggcttaa ttttgagtca cccagggatg ctctcaagca aagctggcca    93000
cttttttttt tttttttttt ttttttttgt gagacagaat ctcgctctgt acccaagact    93060
ggagtgcagt ggtgtgtgat atcggcttac tgcaaattcc gcctcctggg ttcaagcgat    93120
```

```
tctcctgcct cagcctccaa agtagctggg attacaggca tgtgccacca tgcccagcta   93180 attttttgtat ttttagtaga aagggggttt caccatgttg gtcaggctag tctcaaaccc   93240
ctgacctcat gatccgcctg cctcggcctc ccaaagtgct gggattacag gcgtgagcca   93300
ccgcgcccgg ccgccacctt ttatgctttt ggccaggtct gcagaggttt ggcagcctct   93360
aagccctctg cttctgcttc cggagtgaga gcctcaagtg ctcctgtttt cacagcccat   93420
cttgtgtttc catgctgcgt ttgtggggcg ttttctcttt ccatcctcaa ttctggcgct   93480
gattcttttc aggatacatt ctaaccttgg aaagaagatg ccaataaaac cagtgtaggg   93540
gaagggcagc caatgagagg cagcaatgga tgttaaattt acaattgtgg tttgtctttt   93600
tggctgtggt tctttagata agcatgtgat ttctgttctt catgactaag aattgaattt   93660
agactttaca gagttactgg tttgtaaatc tttgagttgt ttaaatttta atgttagagt   93720
tttactgttt gatcagcaca ttttttttct cttttgtcta taggcccgaa atgtttgaga   93780
cggcgattaa ggagagcacc tcctctaaga gccctcccag tgagtgtatt ttctgtattt   93840
tcattgctat agaacacacg ctcttaggca tgcattgtgc agctgtggtt tacaaacatt   93900
gtttaaagaa tagccattga ggccaggcat ggtggttcac gcctgtaatc ccagcacttt   93960
gggaggctga ggtgggtgga tcacctgagg tcaggagttt gagaccagcc tggccaacac   94020
ggcaaaaccc tgtctctact aaaaatataa aaaattagcc aggcgtggtg gcaggcgcct   94080
ataatcccag ctactcagga ggctgagaca gcagaatcac ttgaacccgg gaggcggaag   94140
ttgcagtgag ccgagatcgc accactgcac tccagcctgg acaacagagc aagactcatc   94200 tcaaaagaa aaagaaaac ccattcaaag ttgtagttca ggctatttca caattttag   94260 ttatttaata attgggtggc tctgtgagtg tgtgatgatc tcctaagtac ccccaggaag   94320
agaaaaacag tgaaaggcag cccttcaggg ggcatcatgt cttcttgaaa tgatctacca   94380 tggaagaaa gaaccttgaa caggactgag ataaaacagt ctcagacagc atgattatta   94440
gagatgttga ccgtgttttc tacaaattct gattttaaat gtatattttc aggaaaaata   94500
aattcatcac ccaatgttaa tactactgca tcaggtgttg aagaccttaa catcattcag   94560
gtgacaattc caggtatgag ttctctgctt ccatcagagt ttttggggt ctcttcaggg   94620 cctcttggac tttcccaact agagaggttt gctcagctca tccggggact cggatacatt   94680
acacgttgcc tggtgctcct cccagactcc tacagcagtt gccttccaaa tacagttgct   94740
ctccaaacag caacggcaag ttttggcact tggcatgagc taaatcctgt taaccaccca   94800
aatggctagt ctgttcctta aaaaaagtct atatgagacc gggcacggtg gctcacgcct   94860
gtaatcccag cactttggga ggctgaggca ggaggatcgc ttgaggtcag gaattcaaaa   94920
ccagcctagc caacgtggtg aaaccctgac tctactaaac atacaagaaa aattagccag   94980
gcctggttgt gtgtggctgt aatcccagct acttgggagg ctgaggcagg agaagtgctt   95040
gaacccggga ggtggaggtc gcagtgagcc gagatgggc cagtgcactc cagccttggt   95100
gacagagcca tactccatct gggaaaaaaa aaaaatctat ataaacagc aggtaaaggt   95160 ctttataaca agaataaatt tgtagcattt ttagttaggc attattttaa acaatttcaa   95220
atttaattag ctcaaagtgc tcaaatactt aaatcattaa aaaatggaaa atgcttgaaa   95280
acattacaca gagctcctaa aaattgggat taaagtgca tcattgagca gcggcttgta   95340
cctgtagtct cggctacttg ggaggcttag gcaggaggat cgcttgagcc caagagttca   95400
aggccagtct gggcaacatc gtgagaaacc atctctttac cataaaaaaa aaaaaagca   95460
```

```
gtatttaagt tttgggtttt ctctgaactg tttcagatga tgataatgaa agactctcga    95520
aagttgaaaa agctagacag ctaagagaac aagtgaatga cctctttagt cggaaatttg    95580
gtaagttttg catttgcaaa gtacagttgc tataagcaaa gagatttgtt ttaataagat    95640
cttttcagca gatgatggtt ggatggttgt aatcctatat aaaaggagtt aaaatttaaa    95700
agtgagttgt ttgtgctaaa tttatttaat aagataccat tagtgttaca ctattgattg    95760
tcagtatgaa agttaatgaa tttaaggttc accatctggc agtgtggctc acacttgtaa    95820
tcccagcact ttgggagccc gaggcaggtg gatcagttga ggccaggagt tcgagaccag    95880
cctggccaac atagtgaaac cctgtctcta ctaaaaaatt caaaaaatta gccgggtatg    95940
gtggtgcaca cctgtaatcc cagctactca ggaggctgtg gcacgagaat tgcttgaacc    96000
tgggaggcag agattgcagt gagctgagat caagccacca cactccaacc tgggtgacag    96060
agcaagactc tgtctcaaaa aaaaaaaaaa tttaaggttc atatttaaat ttgtttgaag    96120
tgtacaaaga ccttagttaa cagcagagac agtcttttaaa ataaatgttg atcttgtgct    96180
tttgacaggc tgtttaaggc ggtgggttaa tctgtgctgt tgtgctgttt gtctcactgt    96240
ccctgtaggt gaagctattg gtatgggttt tcctgtgaaa gttccctaca ggaaaatcac    96300
aattaaccct ggctgtgtgg tggttgatgg catgcccccg ggggtgtcct tcaaagcccc    96360
cagctacctg gaaatcagct ccatgagaag gatcttagac tctgccgagt ttatcaaatt    96420
cacggtcatt aggtaagtga gagttttcctg cttagtcaca ggagcgaatc tggagctcat    96480
gaggctgact cttctaaaat gcagccacag gtagtcatcg aatccggctt cctatgctgt    96540
gcaatcaaca aatcaaaata acttgtgtca tcattagaat gtcagatgtg cttctacgaa    96600
ctaagctgac tcttttaatt ctttggcaaa gggttggcaa actaggactg tttgccaaat    96660
tcaggctgcc tcctattttt agagtcttcc tgaaacacag ctacaccegt attatccatg    96720 gctgctttcc tgtcacagtg agtaagtagc tgggactgag aaggcatggc ctccaaagtc    96780
taaaatattt actctctagc actttgtaga aaaaccttag ctaggcacag tggctaacgc    96840
ctgtaatccc agcattttgg gaggccaagg caggcagatc acctgaggtc aggagttcca    96900
gaccagcctg gccaacatgg tgaaatccca tctctacaaa aataaaacag ttagctgggc    96960
atgatggcgg gtgcctgtaa tcccagctac tcggaggct gaggcaggat agtcgcttga    97020
acccaggagg tggaggttgc aatgagccaa gatcatgcca ctgcactcca gcctggacga    97080
cagagtgaga ctccatcaca agaaaaaaag aactttgtca acctctgtct tagggcgcct    97140
tgtcacaggc ttcgggtcag acggattcaa ccttgcatca gccatttgtt agccaggtca    97200
ctctgttctt tgtctgtaaa tgagattgat cgttgttccc actgagagtg tcagctcctt    97260
cccgtagagc aggcatgatg attgtactca cctctgacac cattgtgagt gccacattcc    97320
ttcccacgtc cttgtcactg taagagatgc ccacctgagc accaaccca ggttatcttc     97380 cccttttgtct tccagccccc cagaaacagc tacgactcaa cctacccaat catttcatca    97440
tcagattgcc actgtctcta gttcaggtct cttgggactg gcactcagaa atctcataat    97500
aaatcctctt gaggcttctc atacactcgt cttcttccaa tcttctttcc ctcaaaatct    97560 catatttttgg ttccacttca cccaccgtca ttctccatat cactcccagg agttaggcaa    97620
aaagcccctt ccgttcttcc gtatgttaaa cttagaatca ctctgttccc tgctctgcgt    97680
ttctattttt tgttttttcct ccatttacta gtagcttaac actttctaac agtgttctta    97740
ttattgatac gtatctatct cttccataag cttataaggt cacggataat acttctcatt    97800
gtagtacgta aatgacgtgg gctagatatg agttgaataa acagttatac ctgtaaattc    97860
```

```
ttacagagtg aaaataaatt gttatacttt acaatttgtt tctctcttta gaccatttcc   97920
aggacttgtg attaataacc gtgagtattt tgtgaagtgt tttgttttg ttttttcctg   97980
gggtctgacg tgtgtgcgtg tgagtgtgta tacatgctta acgtatatca cgttacttca   98040
cctatgtcag taaccaggcc aaatacttgt tttagccctc agtaaaaaca ccaggcactt   98100
cctagttgta aaattattca agcttcttaa cttcctatcc tcgatgcact taatcataaa   98160
atggtaataa tagcaccgat tttgggggag tcgttccagt agatggaaag catctggaac   98220
aggtgtcagc aagctcctgc cgacgtgtat gcataaagtt ttattgaaac caccatcgtg   98280
tccatttgtt tatggcagaa ctgagagatg gcagcagcaa gtgtgtgcct gcaaaaccta   98340
aaatatttac taattggctc tgcaagaaaa gagtttgcat ccccctaacc tagaacagtg   98400
tctagcctct agtatgtgtt tagcctacag tatgtgctca gcgaatacaa tctatattta   98460
ttactgcttt tatgactgtt ataattactg tgcttggatt tcgttacaaa gtaagtcaca   98520
atgtgcctgc ttctgttagt atttcagcac agtgcctggc acacatgggg ctctcaaata   98580
ttgctgagcg agtgaacaaa tgtcctttca attccttaac gttgatgtca ttttcaatag   98640
tattttgagc caaacttaat tttgcgagtg tgttttgttt tcttaacttt attattaaaa   98700
atgtataaaa gtgaggccag gcgtggtggc tcacgcctgt aatcccagca gtttgggagg   98760
ctgaggcagg cggatcagtt gaggttggga gttggagacc agcccgtcca acatggtgaa   98820
agcctgtctc tactaaaaat acaaaaatca gctgggtgtg gtggcgcgtg cctgtaatcc   98880
cagctactca ggaggctgag gcaggagagt tgcttgaatc ctagaggtgg aggttgcagt   98940
gagctgagat cgtgccattg cactccagcc tgggcaacaa gagcaaaact ctgtcccaat   99000
aaataaataa ataaaatgtt ctcttttgtt cctgttcttg tgcggtagtg tggtatagag   99060
ttttatggta attactgtga attagtgatt ctgagggaca tatcagaact ctgaggtttg   99120
tttccttctc atcttgaggg aaacagcaaa tgtatgttaa aatgcttttc caagggaaca   99180
acacatcctt acattattta aaccaatctg cttcattttc agagctggtt gatcagagtg   99240
agtcagaagg ccccgtgata caaggtgagc gaggcagggg agggcccgga gctactcctg   99300
cctgcacagt ggcacacatg gcgtgcctgc gtgtggcttc ggctctcagt cacctgccct   99360
gaggggactc agttacacag cacacacatg cttctctgtg gttttcactc ctgggtttga   99420
cagctgatca aaacataaat tcaagctgtg ggtcctgatt gagaactggg ggctgcagac   99480
catttgcacc ccctatccca gctcaggcct aacatcagga accccaggat taatgggtag   99540
gatgaaatgg cagagcaaga gggccgtcac tttaacctga ctctgccatc catttctaat   99600
gtctgccata agtcagtgag caaaatgttc ttcagtagaa atgtacagat tgtgctctta   99660
aaaaattcct taaaaacaa gtggaatggc ctggtgctgt gtgagtcatt gaaagtaatg   99720
agactgggcg tggtggctca cgcctgttat cccagcactt tggaaggctg agaagggtag   99780
atcacttgag atcaggagtt cgagaccagc ctggccaaca tggtgcaacc ccgtctctac   99840
taagaataca aaaactagcc agacgtggtg gcgtgtgccg gctactcagg aggctgaggc   99900
aggagaaccg cttgagcctg ggaggcgagg tcgcagtga gccaagatcg tgccactgca   99960
ctccagcctg ggcaacagaa aggagattct gtctcaaaaa aacaaacata cgaagaaaaa  100020
caaaaaagt aatgaaaagc ttttattaaa gggagtaaac agaaggataa gggagaaagc  100080
ataactaagg agcttgtttt catggtagag ctatgttaag actctgctct ttcaaacttc  100140
agttgtatat gtgaacttag gaccacattt gaaaaacaga aatttgaaag tacacttgga  100200
```

```
taatcgtgtg ctccatctca agaccgtgag cattgtttca tcatgcacct gtgtttgtac    100260
agagtctaga gggcttttct cctcttcctc ctcctgggtt ctttacatag tataaagcag    100320
ctgttgaaca atgtggaaat cagtctctgt gtttctcttt agaatcagct gaaccaagcc    100380
agttggaagt tccagccaca gaaggtaaaa gggtggggtg gtcctgcaag tccttaagac    100440
ttcttctttc ttcttctttt tttttttttt aaagacagag acttgctctg tcacccaggg    100500
tggagtgagg ttgcgcgatc tctgcaacct ccgcctcccg ggctcaagca gttctcctgc    100560
ctcagcctcc cgagtagctg ggattacagg cctgcaccac catgcttggc taattttttgt    100620
atttttagta gaaacggggt ttcaccatgt tggccaggct agtctcagac ttctgacctc    100680
aagtgatccg ccagccttgg cctccaaagt gctcggatta caggcgcgag ccaccttgcc    100740
cagccaagac tttttatca ggacaaagga ttgtgcattt aaactatttc actagaactg    100800
ggtggtggtt ttgctctctt tcttctgggt gaattggatt tgcaggttat gctgttgagt    100860
gatgacgcat agctgctttt gctccatttc ccccagatga cttggtaaat tctccgtgaa    100920
tgactctgct acataaccta gataacctaa cgtgtgtcct ttaaatgcat gtaagccaga    100980
agatgtatgt tactttgaaa acataagtaa caaaattttg aatgtattgc taaagagatg    101040
tctctctgaa gctcttttga tgtttggtgt cttgtccttc ttattaaacc atatcttagt    101100
aaatagtttg gtacgaatgg atttatcact gagcaggtct gcaaaataat taatcggtac    101160
cgttttgttt ctgttgatag aaataaaaga gactgatgga agctctcaga tcaagcaaga    101220
accagacccc acgtggtaga cctcttccct cctagggtaa atcagcttct gtgtcaggga    101280
tgctgtgtgg tgtccatctg aaccccctgc atacgcgtag ctaatgtgat ctccccactt    101340
tcacataaga tggtggccct gccttcaggg aatgtgggag ccaggtggga gccttcccgg    101400
atatttaagc tagaagattc tacagggaga ttctccttgg atcaatatat gtctctcagt    101460
caaagatgta aaagcacttt tgccttaaaa agaatgttct gtttctaaat agagtcaacg    101520
ttgtcctcct cattggaatt cactatgagt cagaatcatt agactgactt ttttttttcc    101580
atagtaatag tattttgcag agtctcacag agctgcagat cttttgttca tcttgcagag    101640
ttaacaagtc tgatcctgtt agtccagatt tcttaaattt ggccaagtta taataggagc    101700
agtagcttga gacccgaagt caggaaactt tgacaatgga ttttttttt taatccagag    101760
acttgtactg gaatttgcct taccctgtca gctcatggac ttaaggtttc atcccgcttt    101820
atgagtgctt ctgaatccaa gtcattgtta cctgaatttg caaattaagt tgtgatattc    101880
gtgactgtta aattcctgta attagattaa cctctttgct tgcttgtttg ttttctctcc    101940
tattttagct taaagtatca gtggttgaga agagcttttc ggacctgtta ctaccccaag    102000
ctgtgtaata tacttgtata acagaaatac cttctataca aaccttttt tctacttta    102060
gatagaaatg tctactttt cagcagttct gtgaattaaa gagcagagtg actgtgggtc    102120
tggaatggct ggtgtacttg ggaatgtact atcaggattt tacagcaatg ctgggaaatg    102180
acagggaaaa tgacaggaat gaatctcacc agatttttta tgtactcagc agagccttga    102240
gttacggtgt ttattttcca atcaagtgaa gatatctcct acttctccta ctggaacatc    102300
tcagcttctg cagtgaagaa aaattcctgt gatagttcag ttctttagtt tttctatttg    102360
aaaaaaaaaa atcatttaaa tgatcctttg ttcacggctc tccttaatga ctgagtgaac    102420
agttcctatc tgtatatttg actaaaacctt ttcctaagct atctctcatg gttcctatgt    102480
tttttttatca taattaaaag caaaaccatc tggatcacct aacagtcaga ggtcagtatc    102540
tcagcgtgtg aattatagag gaaatacaga gagaacctct tccactttta cttttcgtcc    102600
```

```
aaataaaatg catggtgtac cagaagttga agatcgggtt gaggattggg gctagctcga    102660
tgacactaag gccccaacat cgcgggacct gctgtggcgc ggattcttag gaacgctgtt    102720
ctagccggcc ccctctccag gggtcgccgt ggccggcatt atttcctagt tcttcttgta    102780
accctgaggt gccagcgcgg ggagtgagga ggggtcaggg ggctaaggat gcaacctctg    102840
acgttctgcg ccttcctagg agagtcttac atgtgttgag atttcacaag caatgcgagt    102900
tgtaaaatac cagctctaca agaagctagg ctctgtgacg gcatagtttt cagtagcttt    102960
atcacaatat tcacaatgga gaattatatg acatggtagc agaaataggc cctttttatgt   103020 gttgcttcta ttttacctca aattgtagat ataggggtaat caataaaatc catccatgcc   103080
tttcacacac taagtcattg ctctctcggc tgttttcatg gtcctgtctg gggaagcttg    103140
ggggtggctc ggcgtaggtg ggacgcagac caaggccgag gctggcgctg ggc          103193

<210> SEQ ID NO 2
<211> LENGTH: 184
<212> TYPE: DNA
<213> ORGANISM: Homo sapiens

<400> SEQUENCE: 2
ctcaagccat aaaagccaaa ggtccggtga cgatcccgta ccctcttttc cagtctcatg      60
ttgaagatct ttatgtagaa ggacttcctg aaggaattcc ttttagaagg ccatctactt    120
acggaattcc tcgcctggag aggatattac ttgcaaagga aaggattcgt tttgtgatta    180
agaa                                                                184

<210> SEQ ID NO 3
<211> LENGTH: 2934
<212> TYPE: DNA
<213> ORGANISM: Homo sapiens

<400> SEQUENCE: 3
atggcccaag ttgcaatgtc caccctcccc gttgaagatg aggagtcctc ggagagcagg      60
atggtggtga cattcctcat gtcagctctc gagtccatgt gtaaagaact ggccaagtcc    120
aaagccgaag tggcctgcat tgcagtgtat gaaacagacg tgtttgtcgt cggaactgaa    180
agaggacgtg cttttgtcaa taccagaaag gattttcaaa aagattttgt aaaatattgt    240
gttgaagaag aagaaaaagc tgcagagatg cataaaatga aatctacaac ccaggcaaat    300
cggatgagtg tagatgctgt agaaattgaa acactcagaa aaacagttga ggactatttc    360
tgcttttgct atgggaaagc tttaggcaaa tccacagtgg tacctgtacc atatgagaag    420
atgctgcgag accagtcggc tgtggtagtg caggggcttc cggaaggtgt tgcctttaaa    480
caccccgaga actatgatct tgcaaccctg aaatggattt tggagaacaa agcagggatt    540
tcattcatca ttaagagacc ttttttagag ccaaagaagc atgtaggtgg tcgtgtgatg    600
gtaacagatc tgacaggtc aatactatct ccaggtggaa gttgtgggccc catcaaagtg    660 aaaactgaac ccacagaaga ttctggcatt tccctggaaa tggcagctgt gacagtaaag    720
gaagaatcag aagatcctga ttattatcaa tataacattc aagcaggccc ttctgaaact    780
gatgatgttg atgaaaaaca gccctatcg aagcctttgc aaggaagcca ccattcttca    840
gagggcaatg aaggcacaga aatggaagta ccagcagaag atgatgatta ttctccaccg    900
tctaagagac caaaggccaa tgagctaccg cagccaccag tcccggaacc cgccaatgct    960
gggaagcgga aagtgaggga gttcaacttc gagaaatgga atgctcgcat cactgatcta   1020
```

| | |
|---|---|
| cgtaaacaag ttgaagaatt gtttgaaagg aaatatgctc aagccataaa agccaaaggt | 1080 |
| ccggtgacga tcccgtaccc tcttttccag tctcatgttg aagatcttta tgtagaagga | 1140 |
| cttcctgaag gaattccttt tagaaggcca tctacttacg gaattcctcg cctggagagg | 1200 |
| atattacttg caaaggaaag gattcgtttt gtgattaaga acatgagct tctgaattca | 1260 |
| acacgtgaag atttacagct tgataagcca gcttcaggag taaaggaaga atggtatgcc | 1320 |
| agaatcacta aattaagaaa gatggtggat cagcttttct gcaaaaaatt tgcggaagcc | 1380 |
| ttggggagca ctgaagccaa ggctgtaccg taccaaaaat ttgaggcaca cccgaatgat | 1440 |
| ctgtacgtgg aaggactgcc agaaaacatt cctttccgaa gtccctcatg gtatggaatc | 1500 |
| ccaaggctgg aaaaaatcat tcaagtgggc aatcgaatta aatttgttat taaaagacca | 1560 |
| gaacttctga ctcacagtac cactgaagtt actcagccaa gaacgaatac accagtcaaa | 1620 |
| gaagattgga atgtcagaat taccaagcta cggaagcaag tggaagagat ttttaatttg | 1680 |
| aaatttgctc aagctcttgg actcaccgag gcagtaaaag taccatatcc tgtgtttgaa | 1740 |
| tcaaacccgg agttcttgta tgtggaaggc ttgccagagg ggattccctt ccgaagccct | 1800 |
| acctggtttg gaattccacg acttgaaagg atcgtccgcg ggagtaataa aatcaagttc | 1860 |
| gttgttaaaa aacctgaact agttatttcc tacttgcctc ctgggatggc tagtaaaata | 1920 |
| aacactaaag ctttgcagtc ccccaaaaga ccacgaagtc ctgggagtaa ttcaaaggtt | 1980 |
| cctgaaattg aggtcaccgt ggaaggccct aataacaaca atcctcaaac ctcagctgtt | 2040 |
| cgaaccccga cccagactaa cggttctaac gttcccttca agccacgagg gagagagttt | 2100 |
| tcctttgagg cctggaatgc caaaatcacg gacctaaaac agaaagttga aaatctcttc | 2160 |
| aatgagaaat gtggggaagc tcttggcctt aaacaagctg tgaaggtgcc gttcgcgtta | 2220 |
| tttgagtctt tcccggaaga cttttatgtg aaggcttac ctgagggtgt gccattccga | 2280 |
| agaccatcga cttttggcat tccgaggctg gagaagatac tcagaaacaa agccaaaatt | 2340 |
| aagttcatca ttaaaaagcc cgaaatgttt gagacggcga ttaaggagag cacctcctct | 2400 |
| aagagccctc ccagaaaaat aaattcatca cccaatgtta atactactgc atcaggtgtt | 2460 |
| gaagaccta acatcattca ggtgacaatt ccagatgatg ataatgaaag actctcgaaa | 2520 |
| gttgaaaaag ctagacagct aagagaacaa gtgaatgacc tctttagtcg gaaatttggt | 2580 |
| gaagctattg gtatgggttt tcctgtgaaa gttccctaca ggaaaatcac aattaaccct | 2640 |
| ggctgtgtgg tggttgatgg catgccccg ggggtgtcct tcaaagcccc cagctacctg | 2700 |
| gaaatcagct ccatgagaag gatcttagac tctgccgagt ttatcaaatt cacggtcatt | 2760 |
| agaccatttc caggacttgt gattaataac cagctggttg atcagagtga gtcagaaggc | 2820 |
| cccgtgatac aagaatcagc tgaaccaagc cagttggaag ttccagccac agaagaaata | 2880 |
| aaagagactg atggaagctc tcagatcaag caagaaccag accccacgtg gtag | 2934 |

<210> SEQ ID NO 4
<211> LENGTH: 2937
<212> TYPE: DNA
<213> ORGANISM: Homo sapiens

<400> SEQUENCE: 4

| | |
|---|---|
| atgggcccaag ttgcaatgtc caccctcccc gttgaagatg aggagtcctc ggagagcagg | 60 |
| atggtggtga cattcctcat gtcagctctc gagtccatgt gtaaagaact ggccaagtcc | 120 |
| aaagccgaag tggcctgcat tgcagtgtat gaaacagacg tgtttgtcgt cggaactgaa | 180 |
| agaggacgtg cttttgtcaa taccagaaag gattttcaaa aagattttgt aaaatattgt | 240 |

```
gttgaagaag aagaaaaagc tgcagagatg cataaaatga aatctacaac ccaggcaaat      300
cggatgagtg tagatgctgt agaaattgaa acactcagaa aaacagttga ggactatttc      360
tgcttttgct atgggaaagc tttaggcaaa tccacagtgg tacctgtacc atatgagaag      420
atgctgcgag accagtcggc tgtggtagtg caggggcttc cggaaggtgt tgcctttaaa      480
caccccgaga actatgatct tgcaaccctg aaatggattt tggagaacaa agcagggatt      540
tcattcatca ttaagagacc ttttttagag ccaaagaagc atgtaggtgg tcgtgtgatg      600
gtaacagatg ctgacaggtc aatactatct ccaggtggaa gttgtggccc catcaaagtg      660
aaaactgaac ccacagaaga ttctggcatt tccctggaaa tggcagctgt gacagtaaag      720
gaagaatcag aagatcctga ttattatcaa tataacattc aaggaagcca ccattcttca      780
gagggcaatg aaggcacaga aatggaagta ccagcagaag attctactca acatgtccct      840
tcagaaacaa gtgaggaccc tgaagttgag gtgactattg aagatgatga ttattctcca      900
ccgtctaaga gaccaaaggc caatgagcta ccgcagccac cagtcccgga acccgccaat      960
gctgggaagc ggaaagtgag ggagttcaac ttcgagaaat ggaatgctcg catcactgat     1020
ctacgtaaac aagttgaaga attgtttgaa aggaaatatg ctcaagccat aaaagccaaa     1080
ggtccggtga cgatcccgta ccctcttttc cagtctcatg ttgaagatct ttatgtagaa     1140
ggacttcctg aaggaattcc ttttagaagg ccatctactt acggaattcc tcgcctggag     1200
aggatattac ttgcaaagga aaggattcgt tttgtgatta gaaacatga gcttctgaat     1260 tcaacacgtg aagatttaca gcttgataag ccagcttcag gagtaaagga agaatggtat     1320
gccagaatca ctaaattaag aaagatggtg gatcagcttt tctgcaaaaa atttgcggaa     1380
gccttgggga gcactgaagc caaggctgta ccgtaccaaa aatttgaggc acacccgaat     1440
gatctgtacg tggaaggact gccagaaaac attccttttcc gaagtccctc atggtatgga     1500
atcccaaggc tggaaaaaat cattcaagtg ggcaatcgaa ttaaatttgt tattaaaaga     1560
ccagaacttc tgactcacag taccactgaa gttactcagc aagaacgaa tacaccagtc     1620 aaagaagatt ggaatgtcag aattaccaag ctacggaagc aagtggaaga gatttttaat     1680
ttgaaatttg ctcaagctct tggactcacc gaggcagtaa aagtaccata tcctgtgttt     1740
gaatcaaacc cggagttctt gtatgtggaa ggcttgccag aggggattcc cttccgaagc     1800
cctacctggt ttggaattcc acgacttgaa aggatcgtcc gcgggagtaa taaaatcaag     1860
ttcgttgtta aaaaacctga actagttatt tcctacttgc ctcctgggat ggctagtaaa     1920
ataaacacta aagctttgca gtcccccaaa agaccacgaa gtcctgggag taattcaaag     1980
gttcctgaaa ttgaggtcac cgtggaaggc cctaataaca acaatcctca aacctcagct     2040
gttcgaaccc cgacccagac taacggttct aacgttccct tcaagccacg agggagagag     2100 ttttccttg aggcctggaa tgccaaaatc acggacctaa aacagaaagt tgaaaatctc     2160
ttcaatgaga aatgtgggga agctcttggc cttaaacaag ctgtgaaggt gccgttcgcg     2220
ttatttgagt cttttcccgga agactttat gtggaaggct tacctgaggg tgtgccattc     2280
cgaagaccat cgacttttgg cattccgagg ctggagaaga tactcagaaa caaagccaaa     2340
attaagttca tcattaaaaa gcccgaaatg tttgagacgg cgattaagga gagcacctcc     2400
tctaagagcc ctcccagaaa aataaattca tcacccaatg ttaatactac tgcatcaggt     2460
gttgaagacc ttaacatcat tcaggtgaca attccagatg atgataatga aagactctcg     2520
aaagttgaaa aagctagaca gctaagagaa caagtgaatg acctctttag tcggaaattt     2580
```

| | |
|---|---:|
| ggtgaagcta ttggtatggg ttttcctgtg aaagttccct acaggaaaat cacaattaac | 2640 |
| cctggctgtg tggtggttga tggcatgccc ccgggggtgt ccttcaaagc ccccagctac | 2700 |
| ctggaaatca gctccatgag aaggatctta gactctgccg agtttatcaa attcacggtc | 2760 |
| attagaccat ttccaggact tgtgattaat aaccagctgg ttgatcagag tgagtcagaa | 2820 |
| ggccccgtga tacaagaatc agctgaacca agccagttgg aagttccagc cacagaagaa | 2880 |
| ataaaagaga ctgatggaag ctctcagatc aagcaagaac cagaccccac gtggtag | 2937 |

<210> SEQ ID NO 5
<211> LENGTH: 2997
<212> TYPE: DNA
<213> ORGANISM: Homo sapiens

<400> SEQUENCE: 5

| | |
|---|---:|
| atggcccaag ttgcaatgtc caccctcccc gttgaagatg aggagtcctc ggagagcagg | 60 |
| atggtggtga cattcctcat gtcagctctc gagtccatgt gtaaagaact ggccaagtcc | 120 |
| aaagccgaag tggcctgcat tgcagtgtat gaaacagacg tgtttgtcgt cggaactgaa | 180 |
| agaggacgtg cttttgtcaa taccagaaag gattttcaaa agattttgt aaaatattgt | 240 |
| gttgaagaag aagaaaaagc tgcagagatg cataaaatga atctacaac ccaggcaaat | 300 |
| cggatgagtg tagatgctgt agaaattgaa acactcagaa aaacagttga ggactatttc | 360 |
| tgcttttgct atgggaaagc tttaggcaaa tccacagtgg tacctgtacc atatgagaag | 420 |
| atgctgcgag accagtcggc tgtggtagtg caggggcttc cggaaggtgt tgcctttaaa | 480 |
| caccccgaga actatgatct tgcaaccctg aaatggattt tggagaacaa agcagggatt | 540 |
| tcattcatca ttaagagacc ttttttagag ccaagaagc atgtaggtgg tcgtgtgatg | 600 |
| gtaacagatg ctgacaggtc aatactatct ccaggtggaa gttgtggccc catcaaagtg | 660 |
| aaaactgaac ccacagaaga ttctggcatt tccctggaaa tggcagctgt gacagtaaag | 720 |
| gaagaatcag aagatcctga ttattatcaa tataacattc aagcaggccc ttctgaaact | 780 |
| gatgatgttg atgaaaaaca gccccctatc gaagcctttg caaggaagcca ccattcttca | 840 |
| gagggcaatg aaggcacaga aatggaagta ccagcagaag attctactca acatgtccct | 900 |
| tcagaaacaa gtgaggaccc tgaagttgag gtgactattg aagatgatga ttattctcca | 960 |
| ccgtctaaga gaccaaaggc caatgagcta ccgcagccac cagtcccgga acccgccaat | 1020 |
| gctgggaagc ggaaagtgag ggagttcaac ttcgagaaat ggaatgctcg catcactgat | 1080 |
| ctacgtaaac aagttgaaga attgtttgaa aggaaatatg ctcaagccat aaaagccaaa | 1140 |
| ggtccggtga cgatcccgta ccctcttttc cagtctcatg ttgaagatct ttatgtagaa | 1200 |
| ggacttcctg aaggaattcc ttttagaagg ccatctactt acggaattcc tcgcctggag | 1260 |
| aggatattac ttgcaaagga aaggattcgt tttgtgatta gaaacatga gcttctgaat | 1320 |
| tcaacacgtg aagatttaca gcttgataag ccagcttcag gagtaaagga agaatggtat | 1380 |
| gccagaatca ctaaattaag aaagatggtg gatcagcttt tctgcaaaaa atttgcggaa | 1440 |
| gccttgggga gcactgaagc caaggctgta ccgtaccaaa aatttgaggc acaccgaat | 1500 |
| gatctgtacg tggaaggact gccagaaaac attccttccc gaagtccctc atggtatgga | 1560 |
| atcccaaggc tggaaaaaat cattcaagtg ggcaatcgaa ttaaatttgt tattaaaaga | 1620 |
| ccagaacttc tgactcacag taccactgaa gttactcagc caagaacgaa tacaccagtc | 1680 |
| aaagaagatt ggaatgtcag aattaccaag ctacggaagc aagtggaaga gattttaat | 1740 |
| ttgaaatttg ctcaagctct tggactcacc gaggcagtaa aagtaccata tcctgtgttt | 1800 |

```
gaatcaaacc cggagttctt gtatgtggaa ggcttgccag aggggattcc cttccgaagc    1860
cctacctggt ttggaattcc acgacttgaa aggatcgtcc gcgggagtaa taaaatcaag    1920
ttcgttgtta aaaaacctga actagttatt tcctacttgc ctcctgggat ggctagtaaa    1980
ataaacacta agctttgca gtcccccaaa agaccacgaa gtcctgggag taattcaaag    2040
gttcctgaaa ttgaggtcac cgtggaaggc cctaataaca acaatcctca aacctcagct    2100
gttcgaaccc cgacccagac taacggttct aacgttccct tcaagccacg agggagagag    2160
ttttcctttg aggcctggaa tgccaaaatc acggacctaa aacagaaagt tgaaaatctc    2220
ttcaatgaga atgtgggga agctcttggc cttaaacaag ctgtgaaggt gccgttcgcg    2280
ttatttgagt cttccccgga agacttttat gtggaaggct tacctgaggg tgtgccattc    2340
cgaagaccat cgacttttgg cattccgagg ctggagaaga tactcagaaa caaagccaaa    2400
attaagttca tcattaaaaa gcccgaaatg tttgagacgg cgattaagga gagcacctcc    2460
tctaagagcc ctcccagaaa aataaattca tcacccaatg ttaatactac tgcatcaggt    2520
gttgaagacc ttaacatcat tcaggtgaca attccagatg atgataatga aagactctcg    2580
aaagttgaaa aagctagaca gctaagagaa caagtgaatg acctctttag tcggaaattt    2640
ggtgaagcta ttggtatggg ttttcctgtg aaagttccct acaggaaaat cacaattaac    2700
cctggctgtg tggtggttga tggcatgccc ccgggggtgt ccttcaaagc ccccagctac    2760
ctggaaatca gctccatgag aaggatctta gactctgccg agtttatcaa attcacggtc    2820
attagaccat ttccaggact tgtgattaat aaccagctgg ttgatcagag tgagtcagaa    2880
ggccccgtga tacaagaatc agctgaacca agccagttgg aagttccagc cacagaagaa    2940
ataaaagaga ctgatggaag ctctcagatc aagcaagaac cagaccccac gtggtag      2997
```

<210> SEQ ID NO 6
<211> LENGTH: 2874
<212> TYPE: DNA
<213> ORGANISM: Homo sapiens

<400> SEQUENCE: 6

```
atggcccaag ttgcaatgtc caccctcccc gttgaagatg aggagtcctc ggagagcagg     60
atggtggtga cattcctcat gtcagctctc gagtccatgt gtaaagaact ggccaagtcc    120
aaagccgaag tggcctgcat tgcagtgtat gaaacagacg tgtttgtcgt cggaactgaa    180
agaggacgtg cttttgtcaa taccagaaag gattttcaaa agatttttgt aaaatattgt    240
gttgaagaag aagaaaaagc tgcagagatg cataaaatga atctacaac ccaggcaaat    300 cggatgagtg tagatgctgt agaaattgaa acactcagaa aaacagttga ggactatttc    360
tgcttttgct atgggaaagc tttaggcaaa tccacagtgg tacctgtacc atatgagaag    420
atgctgcgag accagtcggc tgtggtagtg caggggcttc cggaaggtgt tgcctttaaa    480
caccccgaga actatgatct tgcaaccctg aaatggattt tggagaacaa agcagggatt    540
tcattcatca ttaagagacc tttttagag ccaaagaagc atgtaggtgg tcgtgtgatg    600
gtaacagatg ctgacaggtc aatactatct ccaggtggaa gttgtggccc catcaaagtg    660
aaaactgaac ccacagaaga ttctggcatt tccctgaaa tggcagctgt gacagtaaag    720
gaagaatcag aagatcctga ttattatcaa tataacattc aaggaagcca ccattcttca    780
gagggcaatg aaggcacaga aatggaagta ccagcagaag atgatgatta ttctccaccg    840
tctaagagac caaaggccaa tgagctaccg cagccaccag tcccggaacc cgccaatgct    900
```

| | |
|---|---|
| gggaagcgga aagtgaggga gttcaacttc gagaaatgga atgctcgcat cactgatcta | 960 |
| cgtaaacaag ttgaagaatt gtttgaaagg aaatatgctc aagccataaa agccaaaggt | 1020 |
| ccggtgacga tcccgtaccc tcttttccag tctcatgttg aagatcttta tgtagaagga | 1080 |
| cttcctgaag gaattccttt tagaaggcca tctacttacg gaattcctcg cctggagagg | 1140 |
| atattacttg caaaggaaag gattcgtttt gtgattaaga acatgagct tctgaattca | 1200 |
| acacgtgaag atttacagct tgataagcca gcttcaggag taaggaaga atggtatgcc | 1260 |
| agaatcacta aattaagaaa gatggtggat cagcttttct gcaaaaaatt tgcggaagcc | 1320 |
| ttggggagca ctgaagccaa ggctgtaccg taccaaaaat ttgaggcaca cccgaatgat | 1380 |
| ctgtacgtgg aaggactgcc agaaaacatt cctttccgaa gtccctcatg gtatggaatc | 1440 |
| ccaaggctgg aaaaaatcat tcaagtgggc aatcgaatta aatttgttat taaaagacca | 1500 |
| gaacttctga ctcacagtac cactgaagtt actcagccaa gaacgaatac accagtcaaa | 1560 |
| gaagattgga atgtcagaat taccaagcta cggaagcaag tggaagagat ttttaatttg | 1620 |
| aaatttgctc aagctcttgg actcaccgag gcagtaaaag taccatatcc tgtgtttgaa | 1680 |
| tcaaacccgg agttcttgta tgtggaaggc ttgccagagg ggattccctt ccgaagccct | 1740 |
| acctggtttg gaattccacg acttgaaagg atcgtccgcg ggagtaataa aatcaagttc | 1800 |
| gttgttaaaa aacctgaact agttatttcc tacttgcctc ctgggatggc tagtaaaata | 1860 |
| aacactaaag ctttgcagtc ccccaaaaga ccacgaagtc ctgggagtaa ttcaaaggtt | 1920 |
| cctgaaattg aggtcaccgt ggaaggccct aataacaaca atcctcaaac ctcagctgtt | 1980 |
| cgaaccccga cccagactaa cggttctaac gttcccttca agccacgagg gagagagttt | 2040 |
| tcctttgagg cctggaatgc caaaatcacg gacctaaaac agaaagttga aaatctcttc | 2100 |
| aatgagaaat gtggggaagc tcttggcctt aaacaagctg tgaaggtgcc gttcgcgtta | 2160 |
| tttgagtctt tcccggaaga cttttatgtg aaggcttac ctgagggtgt gccattccga | 2220 |
| agaccatcga cttttggcat tccgaggctg agaagatac tcagaaacaa agccaaaatt | 2280 |
| aagttcatca ttaaaaagcc cgaaatgttt gagacggcga ttaaggagag cacctcctct | 2340 |
| aagagccctc ccagaaaaat aaattcatca cccaatgtta atactactgc atcaggtgtt | 2400 |
| gaagaccta acatcattca ggtgacaatt ccagatgatg ataatgaaag actctcgaaa | 2460 |
| gttgaaaaag ctagacagct aagagaacaa gtgaatgacc tctttagtcg gaaatttggt | 2520 |
| gaagctattg gtatgggttt tcctgtgaaa gttccctaca ggaaaatcac aattaaccct | 2580 |
| ggctgtgtgg tggttgatgg catgccccg ggggtgtcct tcaaagcccc cagctacctg | 2640 |
| gaaatcagct ccatgagaag gatcttagac tctgccgagt ttatcaaatt cacggtcatt | 2700 |
| agaccatttc caggacttgt gattaataac cagctggttg atcagagtga gtcagaaggc | 2760 |
| cccgtgatac aagaatcagc tgaaccaagc cagttggaag ttccagccac agaagaaata | 2820 |
| aaagagactg atggaagctc tcagatcaag caagaaccag accccacgtg gtag | 2874 |

<210> SEQ ID NO 7
<211> LENGTH: 2931
<212> TYPE: DNA
<213> ORGANISM: Homo sapiens

<400> SEQUENCE: 7

| | |
|---|---|
| atggcccaag ttgcaatgtc caccctcccc gttgaagatg aggagtcctc ggagagcagg | 60 |
| atggtggtga cattcctcat gtcagctctc gagtccatgt gtaaagaact ggccaagtcc | 120 |
| aaagccgaag tggcctgcat tgcagtgtat gaaacagacg tgtttgtcgt cggaactgaa | 180 |

```
agaggacgtg cttttgtcaa taccagaaag gattttcaaa aagattttgt aaaatattgt    240
gttgaagaag aagaaaaagc tgcagagatg cataaaatga aatctacaac ccaggcaaat    300
cggatgagtg tagatgctgt agaaattgaa acactcagaa aaacagttga ggactatttc    360
tgcttttgct atgggaaagc tttaggcaaa tccacagtgg tacctgtacc atatgagaag    420
atgctgcgag accagtcggc tgtggtagtg caggggcttc cggaaggtgt tgcctttaaa    480
caccccgaga actatgatct tgcaaccctg aaatggattt tggagaacaa agcagggatt    540
tcattcatca ttaagagacc ttttttagag ccaaagaagc atgtaggtgg tcgtgtgatg    600
gtaacagatg ctgacaggtc aatactatct ccaggtggaa gttgtggccc catcaaagtg    660
aaaactgaac ccacagaaga ttctggcatt ccctggaaa tggcagctgt gacagtaaag     720
gaagaatcag aagatcctga ttattatcaa tataacattc aaggcccttc tgaaactgat    780
gatgttgatg aaaaacagcc cctatcgaag cctttgcaag gaagccacca ttcttcagag    840
ggcaatgaag gcacagaaat ggaagtacca gcagaagatg atgattattc tccaccgtct    900
aagagaccaa aggccaatga gctaccgcag ccaccagtcc cggaacccgc caatgctggg    960
aagcggaaag tgagggagtt caacttcgag aaatggaatg ctcgcatcac tgatctacgt   1020
aaacaagttg aagaattgtt tgaaaggaaa tatgctcaag ccataaaagc caaaggtccg   1080
gtgacgatcc cgtaccctct tttccagtct catgttgaag atctttatgt agaaggactt   1140
cctgaaggaa ttccttttag aaggccatct acttacggaa ttcctcgcct ggagaggata   1200
ttacttgcaa aggaaaggat tcgttttgtg attaagaaac atgagcttct gaattcaaca   1260
cgtgaagatt tacagcttga taagccagct tcaggagtaa aggaagaatg gtatgccaga   1320
atcactaaat taagaaagat ggtggatcag cttttctgca aaaaatttgc ggaagccttg   1380
gggagcactg aagccaaggc tgtaccgtac caaaaatttg aggcacaccc gaatgatctg   1440
tacgtggaag gactgccaga aaacattcct ttccgaagtc cctcatggta tggaatccca   1500
aggctggaaa aaatcattca gtgggcaat cgaattaaat ttgttattaa agaccagaa    1560 cttctgactc acagtaccac tgaagttact cagccaagaa cgaatacacc agtcaaagaa   1620
gattggaatg tcagaattac caagctacgg aagcaagtgg aagagatttt taatttgaaa   1680
tttgctcaag ctcttggact caccgaggca gtaaaagtac catatcctgt gtttgaatca   1740
aacccggagt tcttgtatgt ggaaggcttg ccagagggga ttcccttccg aagccctacc   1800
tggtttggaa ttccacgact tgaaaggatc gtccgcggga gtaataaaat caagttcgtt   1860
gttaaaaaac tgaactagt tatttcctac ttgcctcctg ggatggctag taaaataaac    1920
actaaagctt tgcagtcccc caaaagacca cgaagtcctg ggagtaattc aaaggttcct   1980
gaaattgagg tcaccgtgga aggccctaat aacaacaatc ctcaaacctc agctgttcga   2040
accccgaccc agactaacgg ttctaacgtt cccttcaagc cacgagggag agagttttcc   2100
tttgaggcct ggaatgccaa aatcacggac ctaaaacaga agttgaaaaa tctcttcaat   2160
gagaaatgtg gggaagctct tggccttaaa caagctgtga aggtgccgtt cgcgttattt   2220
gagtctttcc cggaagactt ttatgtggaa ggcttacctg agggtgtgcc attccgaaga   2280
ccatcgactt ttggcattcc gaggctggag aagatactca gaaacaaagc caaaattaag   2340
ttcatcatta aaaagcccga aatgtttgag acggcgatta aggagagcac ctcctctaag   2400
agccctccca gaaaaataaa ttcatcaccc aatgttaata ctactgcatc aggtgttgaa   2460
gaccttaaca tcattcaggt gacaattcca gatgatgata atgaaagact ctcgaaagtt   2520
```

| | |
|---|---:|
| gaaaaagcta gacagctaag agaacaagtg aatgacctct ttagtcggaa atttggtgaa | 2580 |
| gctattggta tgggttttcc tgtgaaagtt ccctacagga aaatcacaat taaccctggc | 2640 |
| tgtgtggtgg ttgatggcat gcccccgggg gtgtccttca aagccccag ctacctggaa | 2700 |
| atcagctcca tgagaaggat cttagactct gccgagttta tcaaattcac ggtcattaga | 2760 |
| ccatttccag gacttgtgat taataaccag ctggttgatc agagtgagtc agaaggcccc | 2820 |
| gtgatacaag aatcagctga accaagccag ttggaagttc cagccacaga gaaataaaa | 2880 |
| gagactgatg gaagctctca gatcaagcaa gaaccagacc ccacgtggta g | 2931 |

<210> SEQ ID NO 8
<211> LENGTH: 259
<212> TYPE: DNA
<213> ORGANISM: Homo sapiens

<400> SEQUENCE: 8

| | |
|---|---:|
| ctcaagccat aaaagccaaa ggtccggtga cgatcccgta ccctcttttc cagtctcatg | 60 |
| ttgaagatct ttatgtagaa ggacttcctg aaggaattcc ttttagaagg ccatctactt | 120 |
| acggaattcc tcgcctggag aggatattac atgcaaagga aggattcgt tttgtgatta | 180 |
| agaaacatga gcttctgaat tcaacacgtg aagatttaca gcttgataag ccagcttcag | 240 |
| gagtaaagga agaatggta | 259 |

<210> SEQ ID NO 9
<211> LENGTH: 276
<212> TYPE: DNA
<213> ORGANISM: Homo sapiens

<400> SEQUENCE: 9

| | |
|---|---:|
| ctcaagccat aaaagccaaa ggtccggtga cgatcccgta ccctcttttc cagtctcatg | 60 |
| ttgaagatct ttatgtagaa ggacttcctg aaggaattcc ttttagaagg ccatctactt | 120 |
| acggaattcc tcgcctggag aggatattac atgcaaagga aggattcgt tttgtgatta | 180 |
| agaagtaaga ctcttggatt cctgttgaac tcttgtctct tttctgagta atacgtcttt | 240 |
| tttattgttg accaatattc attcaccact aggttc | 276 |

<210> SEQ ID NO 10
<211> LENGTH: 2934
<212> TYPE: DNA
<213> ORGANISM: Homo sapiens

<400> SEQUENCE: 10

| | |
|---|---:|
| atggcccaag ttgcaatgtc caccctcccc gttgaagatg aggagtcctc ggagagcagg | 60 |
| atggtggtga cattcctcat gtcagctctc gagtccatgt gtaaagaact ggccaagtcc | 120 |
| aaagccgaag tggcctgcat tgcagtgtat gaaacagacg tgtttgtcgt cggaactgaa | 180 |
| agaggacgtg cttttgtcaa taccagaaag gatttttcaaa aagatttgt aaaatattgt | 240 |
| gttgaagaag aagaaaaagc tgcagagatg cataaaatga atctacaac ccaggcaaat | 300 |
| cggatgagtg tagatgctgt agaaattgaa acactcagaa aaacagttga ggactatttc | 360 |
| tgcttttgct atgggaaagc tttaggcaaa tccacagtgg tacctgtacc atatgagaag | 420 |
| atgctgcgag accagtcggc tgtggtagtg caggggcttc ggaaggtgt tgcctttaaa | 480 |
| caccccgaga actatgatct tgcaaccctg aaatggattt tggagaacaa agcagggatt | 540 |
| tcattcatca ttaagagacc ttttttagag ccaaagaagc atgtaggtgg tcgtgtgatg | 600 |
| gtaacagatg ctgacaggtc aatactatct ccaggtggaa gttgtggccc catcaaagtg | 660 |

```
aaaactgaac ccacagaaga ttctggcatt tccctggaaa tggcagctgt gacagtaaag    720
gaagaatcag aagatcctga ttattatcaa tataacattc aagcaggccc ttctgaaact    780
gatgatgttg atgaaaaaca gcccctatcg aagcctttgc aaggaagcca ccattcttca    840
gagggcaatg aaggcacaga aatggaagta ccagcagaag atgatgatta ttctccaccg    900
tctaagagac caaaggccaa tgagctaccg cagccaccag tcccggaacc cgccaatgct    960
gggaagcgga aagtgaggga gttcaacttc gagaaatgga atgctcgcat cactgatcta   1020
cgtaaacaag ttgaagaatt gtttgaaagg aaatatgctc aagccataaa agccaaaggt   1080
ccggtgacga tcccgtaccc tcttttccag tctcatgttg aagatcttta tgtagaagga   1140
cttcctgaag gaattccttt tagaaggcca tctacttacg gaattcctcg cctggagagg   1200
atattacatg caaaggaaag gattcgtttt gtgattaaga aacatgagct tctgaattca   1260
acacgtgaag atttacagct tgataagcca gcttcaggag taaaggaaga atggtatgcc   1320
agaatcacta aattaagaaa gatggtggat cagcttttct gcaaaaaatt tgcggaagcc   1380
ttggggagca ctgaagccaa ggctgtaccg taccaaaaat ttgaggcaca cccgaatgat   1440
ctgtacgtgg aaggactgcc agaaaacatt cctttccgaa gtccctcatg gtatggaatc   1500
ccaaggctgg aaaaaatcat tcaagtgggc aatcgaatta aatttgttat taaaagacca   1560
gaacttctga ctcacagtac cactgaagtt actcagccaa gaacgaatac accagtcaaa   1620
gaagattgga atgtcagaat taccaagcta cggaagcaag tggaagagat ttttaatttg   1680
aaatttgctc aagctcttgg actcaccgag gcagtaaaag taccatatcc tgtgtttgaa   1740
tcaaacccgg agttcttgta tgtggaaggc ttgccagagg ggattccctt ccgaagccct   1800
acctggtttg gaattccacg acttgaaagg atcgtccgcg ggagtaataa aatcaagttc   1860
gttgttaaaa aacctgaact agttatttcc tacttgcctc ctgggatggc tagtaaaata   1920
aacactaaag ctttgcagtc ccccaaaaga ccacgaagtc ctgggagtaa ttcaaaggtt   1980
cctgaaattg aggtcaccgt ggaaggccct aataacaaca atcctcaaac ctcagctgtt   2040
cgaaccccga cccagactaa cggttctaac gttcccttca agccacgagg gagagagttt   2100
tcctttgagg cctggaatgc caaaatcacg gacctaaaac agaaagttga aaatctcttc   2160
aatgagaaat gtggggaagc tcttggcctt aaacaagctg tgaaggtgcc gttcgcgtta   2220
tttgagtctt tcccggaaga cttttatgtg gaaggcttac ctgagggtgt gccattccga   2280
agaccatcga cttttggcat tccgaggctg gagaagatac tcagaaacaa agccaaaatt   2340
aagttcatca ttaaaaagcc cgaaatgttt gagacggcga ttaaggagag cacctcctct   2400
aagagccctc ccagaaaaat aaattcatca cccaatgtta atactactgc atcaggtgtt   2460
gaagacctta acatcattca ggtgacaatt ccagatgatg ataatgaaag actctcgaaa   2520
gttgaaaaag ctagacagct aagagaacaa gtgaatgacc tctttagtcg gaaatttggt   2580
gaagctattg gtatgggttt tcctgtgaaa gttccctaca ggaaaatcac aattaaccct   2640
ggctgtgtgg tggttgatgg catgcccccg ggggtgtcct tcaaagcccc cagctacctg   2700
gaaatcagct ccatgagaag gatcttagac tctgccgagt ttatcaaatt cacggtcatt   2760
agaccatttc caggacttgt gattaataac cagctggttg atcagagtga gtcagaaggc   2820
cccgtgatac aagaatcagc tgaaccaagc cagttggaag ttccagccac agaagaaata   2880
aaagagactg atggaagctc tcagatcaag caagaaccag accccacgtg gtag         2934
```

<210> SEQ ID NO 11

<211> LENGTH: 2937
<212> TYPE: DNA
<213> ORGANISM: Homo sapiens

<400> SEQUENCE: 11

```
atggcccaag ttgcaatgtc caccctcccc gttgaagatg aggagtcctc ggagagcagg      60
atggtggtga cattcctcat gtcagctctc gagtccatgt gtaaagaact ggccaagtcc     120
aaagccgaag tggcctgcat tgcagtgtat gaaacagacg tgtttgtcgt cggaactgaa     180
agaggacgtg cttttgtcaa taccagaaag gattttcaaa agatttttgt aaaatattgt     240
gttgaagaag aagaaaaagc tgcagagatg cataaaatga atctacaac ccaggcaaat     300
cggatgagtg tagatgctgt agaaattgaa acactcagaa aaacagttga ggactatttc     360
tgcttttgct atgggaaagc tttaggcaaa tccacagtgg tacctgtacc atatgagaag     420
atgctgcgag accagtcggc tgtggtagtg caggggcttc cggaaggtgt tgcctttaaa     480
cacccccgaga actatgatct tgcaaccctg aaatggattt tggagaacaa agcagggatt     540
tcattcatca ttaagagacc ttttttagag ccaaagaagc atgtaggtgg tcgtgtgatg     600
gtaacagatg ctgacaggtc aatactatct ccaggtggaa gttgtggccc catcaaagtg     660
aaaactgaac ccacagaaga ttctggcatt tccctgaaaa tggcagctgt gacagtaaag     720
gaagaatcag aagatcctga ttattatcaa tataacattc aaggaagcca ccattcttca     780
gagggcaatg aaggcacaga atggaagta ccagcagaag attctactca acatgtccct     840
tcagaaacaa gtgaggaccc tgaagttgag gtgactattg aagatgatga ttattctcca     900
ccgtctaaga gaccaaaggc caatgagcta ccgcagccac cagtcccgga acccgccaat     960
gctgggaagc ggaaagtgag ggagttcaac ttcgagaaat ggaatgctcg catcactgat    1020
ctacgtaaac aagttgaaga attgtttgaa aggaaatatg ctcaagccat aaaagccaaa    1080
ggtccggtga cgatcccgta ccctcttttc cagtctcatg ttgaagatct ttatgtagaa    1140
ggacttcctg aaggaattcc ttttagaagg ccatctactt acggaattcc tcgcctggag    1200
aggatattac atgcaaagga aaggattcgt tttgtgatta agaaacatga gcttctgaat    1260
tcaacacgtg aagatttaca gcttgataag ccagcttcag gagtaaagga agaatggtat    1320
gccagaatca ctaaattaag aaagatggtg gatcagcttt tctgcaaaaa atttgcggaa    1380
gccttgggga gcactgaagc caaggctgta ccgtaccaaa aatttgaggc acacccgaat    1440
gatctgtacg tggaaggact gccagaaaac attccttttcc gaagtccctc atggtatgga    1500
atcccaaggc tggaaaaaat cattcaagtg gcaatcgaa ttaaatttgt tattaaaaga    1560
ccagaacttc tgactcacag taccactgaa gttactcagc caagaacgaa tacaccagtc    1620
aaagaagatt ggaatgtcag aattaccaag ctacggaagc aagtggaaga gattttttaat    1680
ttgaaatttg ctcaagctct tggactcacc gaggcagtaa agtaccata tcctgtgttt    1740
gaatcaaacc cggagttctt gtatgtgaa ggcttgccag aggggattcc cttccgaagc    1800
cctacctggt ttggaattcc acgacttgaa aggatcgtcc gcgggagtaa taaatcaag    1860
ttcgttgtta aaaaacctga actagttatt tcctacttgc ctcctgggat ggctagtaaa    1920
ataaacacta agctttgca gtcccccaaa agaccacgaa gtcctgggag taattcaaag    1980
gttcctgaaa ttgaggtcac cgtggaaggc cctaataaca caatcctca acctcagct    2040
gttcgaaccc cgacccagac taacggttct aacgttccct tcaagccacg agggagagag    2100
ttttcctttg aggcctggaa tgccaaaatc acggacctaa aacagaaagt tgaaaatctc    2160
ttcaatgaga aatgtgggga agctcttggc cttaaacaag ctgtgaaggt gccgttcgcg    2220
```

```
ttatttgagt ctttcccgga agactttat gtggaaggct tacctgaggg tgtgccattc    2280
cgaagaccat cgacttttgg cattccgagg ctggagaaga tactcagaaa caaagccaaa    2340
attaagttca tcattaaaaa gcccgaaatg tttgagacgg cgattaagga gagcacctcc    2400
tctaagagcc ctcccagaaa aataaattca tcacccaatg ttaatactac tgcatcaggt    2460
gttgaagacc ttaacatcat tcaggtgaca attccagatg atgataatga aagactctcg    2520
aaagttgaaa aagctagaca gctaagagaa caagtgaatg acctctttag tcggaaattt    2580
ggtgaagcta ttggtatggg ttttcctgtg aaagttccct acaggaaaat cacaattaac    2640
cctggctgtg tggtggttga tggcatgccc ccggggggtgt ccttcaaagc ccccagctac    2700
ctggaaatca gctccatgag aaggatctta gactctgccg agtttatcaa attcacggtc    2760
attagaccat ttccaggact tgtgattaat aaccagctgg ttgatcagag tgagtcagaa    2820
ggccccgtga tacaagaatc agctgaacca agccagttgg aagttccagc cacagaagaa    2880
ataaaagaga ctgatggaag ctctcagatc aagcaagaac cagaccccac gtggtag      2937
```

<210> SEQ ID NO 12
<211> LENGTH: 2997
<212> TYPE: DNA
<213> ORGANISM: Homo sapiens

<400> SEQUENCE: 12

```
atggcccaag ttgcaatgtc caccctcccc gttgaagatg aggagtcctc ggagagcagg     60
atggtggtga cattcctcat gtcagctctc gagtccatgt gtaaagaact ggccaagtcc    120
aaagccgaag tggcctgcat tgcagtgtat gaaacagacg tgtttgtcgt cggaactgaa    180
agaggacgtg cttttgtcaa taccagaaag gattttcaaa aagattttgt aaaatattgt    240
gttgaagaag aagaaaaagc tgcagagatg cataaaatga atctacaac ccaggcaaat    300 cggatgagtg tagatgctgt agaaattgaa acactcagaa aaacagttga ggactatttc    360
tgcttttgct atgggaaagc tttaggcaaa tccacagtgg tacctgtacc atatgagaag    420
atgctgcgag accagtcggc tgtggtagtc aggggcttc cggaaggtgt tgcctttaaa    480 cacccccgaga actatgatct tgcaaccctg aaatggattt tggagaacaa agcagggatt    540
tcattcatca ttaagagacc ttttttagag ccaaagaagc atgtaggtgg tcgtgtgatg    600
gtaacagatg ctgacaggtc aatactatct ccaggtggaa gttgtggccc catcaaagtg    660
aaaactgaac ccacagaaga ttctggcatt tccctggaaa tggcagctgt gacagtaaag    720
gaagaatcag aagatcctga ttattatcaa tataacattc aagcaggccc ttctgaaact    780
gatgatgttg atgaaaaaca gccccctatcg aagcctttgc aaggaagcca ccattcttca    840
gagggcaata aaggcacaga aatggaagta ccagcagaaa attctactca acatgtccct    900
tcagaaacaa gtgaggaccc tgaagttgag gtgactattg aagatgatga ttattctcca    960
ccgtctaaga gaccaaaggc caatgagcta ccgcagccac cagtcccgga acccgccaat   1020
gctgggaagc ggaaagtgag ggagttcaac ttcgagaaat ggaatgctcg catcactgat   1080
ctacgtaaac aagttgaaga attgttttgaa aggaaatatg ctcaagccat aaaagccaaa   1140
ggtccggtga cgatcccgta ccctcttttc cagtctcatg ttgaagatct ttatgtgaaa   1200
ggacttcctg aaggaattcc ttttagaagg ccatctactt acggaattcc tcgcctggag   1260
aggatattac atgcaaagga aaggattcgt tttgtgatta gaaacatga gcttctgaat   1320 tcaacacgtg aagatttaca gcttgataag ccagcttcag gagtaaagga agaatggtat   1380
```

```
gccagaatca ctaaattaag aaagatggtg gatcagcttt tctgcaaaaa atttgcggaa    1440
gccttgggga gcactgaagc caaggctgta ccgtaccaaa aatttgaggc acacccgaat    1500
gatctgtacg tggaaggact gccagaaaac attcctttcc gaagtccctc atggtatgga    1560
atcccaaggc tggaaaaaat cattcaagtg ggcaatcgaa ttaaatttgt tattaaaaga    1620
ccagaacttc tgactcacag taccactgaa gttactcagc caagaacgaa tacaccagtc    1680
aaagaagatt ggaatgtcag aattaccaag ctacggaagc aagtggaaga gattttttaat   1740
ttgaaatttg ctcaagctct tggactcacc gaggcagtaa aagtaccata tcctgtgttt    1800
gaatcaaacc cggagttctt gtatgtggaa ggcttgccag aggggattcc cttccgaagc    1860
cctacctggt ttggaattcc acgacttgaa aggatcgtcc gcgggagtaa taaaatcaag    1920
ttcgttgtta aaaaacctga actagttatt tcctacttgc tcctgggat ggctagtaaa    1980
ataaacacta agctttgca gtcccccaaa agaccacga gtcctgggag taattcaaag    2040
gttcctgaaa ttgaggtcac cgtggaaggc cctaataaca acaatcctca aacctcagct    2100
gttcgaaccc cgacccagac taacggttct aacgttccct tcaagccacg agggagagag    2160
ttttcctttg aggcctggaa tgccaaaatc acggacctaa aacagaaagt tgaaaatctc    2220
ttcaatgaga atgtgggga agctcttggc cttaaacaag ctgtgaaggt gccgttcgcg    2280
ttatttgagt cttctccgga agacttttat gtggaaggct tacctgaggg tgtgccattc    2340
cgaagaccat cgacttttgg cattccgagg ctggagaaga tactcagaaa caagccaaa    2400
attaagttca tcattaaaaa gcccgaaatg tttgagacgg cgattaagga gagcacctcc    2460
tctaagagcc ctcccagaaa aataaattca tcacccaatg ttaatactac tgcatcaggt    2520
gttgaagacc ttaacatcat tcaggtgaca attccagatg atgataatga aagactctcg    2580
aaagttgaaa aagctagaca gctaagagaa caagtgaatg acctctttag tcggaaattt    2640
ggtgaagcta ttggtatggg ttttcctgtg aaagttccct acaggaaaat cacaattaac    2700
cctggctgtg tggtggttga tggcatgccc ccggggggtgt ccttcaaagc ccccagctac    2760
ctggaaatca gctccatgag aaggatctta gactctgccg agtttatcaa attcacggtc    2820
attagaccat ttccaggact tgtgattaat aaccagctgg ttgatcagag tgagtcagaa    2880
ggccccgtga tacaagaatc agctgaacca agccagttgg aagttccagc cacagaagaa    2940
ataaaagaga ctgatggaag ctctcagatc aagcaagaac cagaccccac gtggtag      2997
```

<210> SEQ ID NO 13
<211> LENGTH: 2874
<212> TYPE: DNA
<213> ORGANISM: Homo sapiens

<400> SEQUENCE: 13

```
atgggcccaag ttgcaatgtc caccctcccc gttgaagatg aggagtcctc ggagagcagg     60
atggtggtga cattcctcat gtcagctctc gagtccatgt gtaaagaact ggccaagtcc    120
aaagccgaag tggcctgcat tgcagtgtat gaaacagacg tgtttgtcgt cggaactgaa    180
agaggacgtg cttttgtcaa taccagaaag gattttcaaa aagattttgt aaaatattgt    240
gttgaagaag aagaaaaagc tgcagagatg cataaaatga atctacaac ccaggcaaat    300
cggatgagtg tagatgctgt agaaattgaa acactcagaa aaacagttga ggactatttc    360
tgcttttgct atgggaaagc tttaggcaaa tccacagtgg tacctgtacc atatgagaag    420
atgctgcgag accagtcggc tgtggtagtg caggggcttc cggaaggtgt tgccttttaaa    480
caccccgaga actatgatct tgcaaccctg aaatggattt tggagaacaa agcagggatt    540
```

```
tcattcatca ttaagagacc ttttttagag ccaaagaagc atgtaggtgg tcgtgtgatg      600
gtaacagatg ctgacaggtc aatactatct ccaggtggaa gttgtggccc catcaaagtg      660
aaaactgaac ccacagaaga ttctggcatt tccctggaaa tggcagctgt gacagtaaag      720
gaagaatcag aagatcctga ttattatcaa tataacattc aaggaagcca ccattcttca      780
gagggcaatg aaggcacaga atggaagta  ccagcagaag atgatgatta ttctccaccg      840
tctaagagac caaaggccaa tgagctaccg cagccaccag tcccggaacc cgccaatgct      900
gggaagcgga aagtgaggga gttcaacttc gagaaatgga atgctcgcat cactgatcta      960
cgtaaacaag ttgaagaatt gtttgaaagg aaatatgctc aagccataaa agccaaaggt     1020
ccggtgacga tcccgtaccc tcttttccag tctcatgttg aagatcttta tgtagaagga     1080
cttcctgaag gaattccttt tagaaggcca tctacttacg gaattcctcg cctgagaggg     1140
atattacatg caaaggaaag gattcgtttt gtgattaaga acatgagct  tctgaattca     1200 acacgtgaag atttacagct tgataagcca gcttcaggag taaaggaaga atggtatgcc     1260
agaatcacta aattaagaaa gatggtggat cagcttttct gcaaaaaatt tgcggaagcc     1320
ttggggagca ctgaagccaa ggctgtaccg taccaaaaat ttgaggcaca cccgaatgat     1380
ctgtacgtgg aaggactgcc agaaaacatt cctttccgaa gtccctcatg gtatggaatc     1440
ccaaggctgg aaaaaatcat tcaagtgggc aatcgaatta aatttgttat taaaagacca     1500
gaacttctga ctcacagtac cactgaagtt actcagccaa gaacgaatac accagtcaaa     1560
gaagattgga atgtcagaat taccaagcta cggaagcaag tggaagagat ttttaatttg     1620
aaatttgctc aagctcttgg actcaccgag gcagtaaaag taccatatcc tgtgtttgaa     1680
tcaaacccgg agttcttgta tgtggaaggc ttgccagagg ggattccctt ccgaagccct     1740
acctggtttg gaattccacg acttgaaagg atcgtccgcg ggagtaataa aatcaagttc     1800
gttgttaaaa aacctgaact agttatttcc tacttgcctc ctgggatggc tagtaaaata     1860
aacactaaag ctttgcagtc ccccaaaaga ccacgaagtc ctgggagtaa ttcaaaggtt     1920
cctgaaattg aggtcaccgt ggaaggccct aataacaaca atcctcaaac ctcagctgtt     1980
cgaaccccga cccagactaa cggttctaac gttcccttca agccacgagg gagagagttt     2040
tcctttgagg cctggaatgc caaaatcacg gacctaaaac agaaagttga aaatctcttc     2100
aatgagaaat gtggggaagc tcttggcctt aaacaagctg tgaaggtgcc gttcgcgtta     2160
tttgagtctt tcccggaaga cttttatgtg gaaggcttac ctgagggtgt gccattccga     2220
agaccatcga cttttggcat tccgaggctg agaagatac  tcagaaacaa agccaaaatt     2280
aagttcatca ttaaaaagcc cgaaatgttt gagacggcga ttaaggagag cacctcctct     2340
aagagccctc ccagaaaaat aaattcatca cccaatgtta atactactgc atcaggtgtt     2400
gaagacctta acatcattca ggtgacaatt ccagatgatg ataatgaaag actctcgaaa     2460
gttgaaaaag ctagacagct aagagaacaa gtgaatgacc tctttagtcg gaaatttggt     2520
gaagctattg gtatgggttt tcctgtgaaa gttccctaca ggaaaatcac aattaaccct     2580
ggctgtgtgg tggttgatgg catgcccccg ggggtgtcct tcaaagcccc cagctacctg     2640
gaaatcagct ccatgagaag gatcttagac tctgccgagt ttatcaaatt cacggtcatt     2700
agaccatttc caggacttgt gattaataac cagctggttg atcagagtga gtcagaaggc     2760
cccgtgatac aagaatcagc tgaaccaagc cagttggaag ttccagccac agaagaaata     2820
aaagagactg atggaagctc tcagatcaag caagaaccag accccacgtg gtag          2874
```

<210> SEQ ID NO 14
<211> LENGTH: 2931
<212> TYPE: DNA
<213> ORGANISM: Homo sapiens

<400> SEQUENCE: 14

```
atggcccaag ttgcaatgtc caccctcccc gttgaagatg aggagtcctc ggagagcagg      60
atggtggtga cattcctcat gtcagctctc gagtccatgt gtaaagaact ggccaagtcc     120
aaagccgaag tggcctgcat tgcagtgtat gaaacagacg tgtttgtcgt cggaactgaa     180
agaggacgtg cttttgtcaa taccagaaag gattttcaaa aagattttgt aaaatattgt     240
gttgaagaag aagaaaaagc tgcagagatg cataaaatga atctacaac ccaggcaaat     300
cggatgagtg tagatgctgt agaaattgaa acactcagaa aaacagttga ggactatttc     360
tgcttttgct atgggaaagc tttaggcaaa tccacagtgg tacctgtacc atatgagaag     420
atgctgcgag accagtcggc tgtggtagtc aggggcttc cggaaggtgt tgcctttaaa     480
cacccccgaga actatgatct tgcaaccctg aaatggattt tggagaacaa gcagggatt     540
tcattcatca ttaagagacc ttttttagag ccaaagaagc atgtaggtgg tcgtgtgatg     600
gtaacagatg ctgacaggtc aatactatct ccaggtggaa gttgtggccc catcaaagtg     660
aaaactgaac ccacagaaga ttctggcatt tccctggaaa tggcagctgt gacagtaaag     720
gaagaatcag aagatcctga ttattatcaa tataacattc aaggcccttc tgaaactgat     780
gatgttgatg aaaaacagcc cctatcgaag cctttgcaag aagccacca ttcttcagag     840
ggcaatgaag gcacagaaat ggaagtacca gcagaagatg atgattattc tccaccgtct     900
aagagaccaa aggccaatga gctaccgcag ccaccagtcc cggaacccgc caatgctggg     960
aagcggaaag tgagggagtt caacttcgag aaatggaatg ctcgcatcac tgatctacgt    1020
aaacaagttg aagaattgtt tgaaaggaaa tatgctcaag ccataaaagc caaaggtccg    1080
gtgacgatcc cgtaccctct tttccagtct catgttgaag atctttatgt agaaggactt    1140
cctgaaggaa ttccttttag aaggccatct acttacggaa ttcctcgcct ggagaggata    1200
ttacatgcaa aggaaaggat tcgttttgtg attaagaaac atgagcttct gaattcaaca    1260
cgtgaagatt tacagcttga taagccagct tcaggagtaa aggaagaatg gtatgccaga    1320
atcactaaat taagaaagat ggtggatcag cttttctgca aaaaatttgc ggaagccttg    1380
gggagcactg aagccaaggc tgtaccgtac caaaaatttg aggcacaccc gaatgatctg    1440
tacgtggaag gactgccaga aaacattcct ttccgaagtc cctcatggta tggaatccca    1500
aggctggaaa aaatcattca gtgggcaat cgaattaaat ttgttattaa aagaccagaa    1560
cttctgactc acagtaccac tgaagttact cagccaagaa cgaatacacc agtcaaagaa    1620
gattggaatg tcagaattac caagctacgg aagcaagtgg aagagatttt taatttgaaa    1680
tttgctcaag ctcttggact caccgaggca gtaaaagtac catatcctgt gtttgaatca    1740
aacccggagt tcttgtatgt ggaaggcttg ccagagggga ttcccttccg aagccctacc    1800
tggtttggaa ttccacgact tgaaaggatc gtccgcggga gtaataaaat caagttcgtt    1860
gttaaaaaac tgaactagt tatttcctac ttgcctcctg ggatggctag taaaataaac    1920
actaaagctt tgcagtcccc caaaagacca cgaagtcctg ggagtaattc aaaggttcct    1980
gaaattgagg tcaccgtgga aggccctaat aacaacaatc ctcaaacctc agctgttcga    2040
accccgaccc agactaacgg ttctaacgtt cccttcaagc cacgagggag agagtttttcc    2100
tttgaggcct ggaatgccaa aatcacggac ctaaaacaga agttgaaaaa tctcttcaat    2160
```

-continued

```
gagaaatgtg gggaagctct tggccttaaa caagctgtga aggtgccgtt cgcgttattt    2220
gagtctttcc cggaagactt ttatgtggaa ggcttacctg agggtgtgcc attccgaaga    2280
ccatcgactt ttggcattcc gaggctggag aagatactca gaaacaaagc caaaattaag    2340
ttcatcatta aaaagcccga atgtttgag  acggcgatta aggagagcac ctcctctaag    2400
agccctccca gaaaaataaa ttcatcaccc aatgttaata ctactgcatc aggtgttgaa    2460
gaccttaaca tcattcaggt gacaattcca gatgatgata atgaaagact ctcgaaagtt    2520
gaaaaagcta gacagctaag agaacaagtg aatgacctct ttagtcggaa atttggtgaa    2580
gctattggta tgggttttcc tgtgaaagtt ccctacagga aaatcacaat taaccctggc    2640
tgtgtggtgg ttgatggcat gccccegggg gtgtccttca agcccccag ctacctggaa     2700 atcagctcca tgagaaggat cttagactct gccgagttta tcaaattcac ggtcattaga    2760
ccatttccag gacttgtgat taataaccag ctggttgatc agagtgagtc agaaggcccc    2820
gtgatacaag aatcagctga accaagccag ttggaagttc cagccacaga agaaataaaa    2880
gagactgatg gaagctctca gatcaagcaa gaaccagacc ccacgtggta g             2931
```

<210> SEQ ID NO 15
<211> LENGTH: 977
<212> TYPE: PRT
<213> ORGANISM: Homo sapiens

<400> SEQUENCE: 15

```
Met Ala Gln Val Ala Met Ser Thr Leu Pro Val Glu Asp Glu Glu Ser
1               5                   10                  15

Ser Glu Ser Arg Met Val Val Thr Phe Leu Met Ser Ala Leu Glu Ser
                20                  25                  30

Met Cys Lys Glu Leu Ala Lys Ser Lys Ala Glu Val Ala Cys Ile Ala
            35                  40                  45

Val Tyr Glu Thr Asp Val Phe Val Val Gly Thr Glu Arg Gly Arg Ala
        50                  55                  60

Phe Val Asn Thr Arg Lys Asp Phe Gln Lys Asp Phe Val Lys Tyr Cys
65                  70                  75                  80

Val Glu Glu Glu Lys Ala Ala Glu Met His Lys Met Lys Ser Thr
                85                  90                  95

Thr Gln Ala Asn Arg Met Ser Val Asp Ala Val Glu Ile Glu Thr Leu
            100                 105                 110

Arg Lys Thr Val Glu Asp Tyr Phe Cys Phe Cys Tyr Gly Lys Ala Leu
        115                 120                 125

Gly Lys Ser Thr Val Val Pro Val Pro Tyr Glu Lys Met Leu Arg Asp
    130                 135                 140

Gln Ser Ala Val Val Val Gln Gly Leu Pro Glu Gly Val Ala Phe Lys
145                 150                 155                 160

His Pro Glu Asn Tyr Asp Leu Ala Thr Leu Lys Trp Ile Leu Glu Asn
                165                 170                 175

Lys Ala Gly Ile Ser Phe Ile Ile Lys Arg Pro Phe Leu Glu Pro Lys
            180                 185                 190

Lys His Val Gly Gly Arg Val Met Val Thr Asp Ala Asp Arg Ser Ile
        195                 200                 205

Leu Ser Pro Gly Gly Ser Cys Gly Pro Ile Lys Val Lys Thr Glu Pro
    210                 215                 220

Thr Glu Asp Ser Gly Ile Ser Leu Glu Met Ala Ala Val Thr Val Lys
225                 230                 235                 240
```

-continued

Glu Glu Ser Glu Asp Pro Asp Tyr Tyr Gln Tyr Asn Ile Gln Ala Gly
            245                 250                 255

Pro Ser Glu Thr Asp Asp Val Asp Glu Lys Gln Pro Leu Ser Lys Pro
            260                 265                 270

Leu Gln Gly Ser His His Ser Ser Glu Gly Asn Glu Gly Thr Glu Met
            275                 280                 285

Glu Val Pro Ala Glu Asp Asp Asp Tyr Ser Pro Pro Ser Lys Arg Pro
        290                 295                 300

Lys Ala Asn Glu Leu Pro Gln Pro Val Pro Glu Pro Ala Asn Ala
305                 310                 315                 320

Gly Lys Arg Lys Val Arg Glu Phe Asn Phe Lys Trp Asn Ala Arg
            325                 330                 335

Ile Thr Asp Leu Arg Lys Gln Val Glu Glu Leu Phe Glu Arg Lys Tyr
            340                 345                 350

Ala Gln Ala Ile Lys Ala Lys Gly Pro Val Thr Ile Pro Tyr Pro Leu
            355                 360                 365

Phe Gln Ser His Val Glu Asp Leu Tyr Val Glu Gly Leu Pro Glu Gly
            370                 375                 380

Ile Pro Phe Arg Arg Pro Ser Thr Tyr Gly Ile Pro Arg Leu Glu Arg
385                 390                 395                 400

Ile Leu His Ala Lys Glu Arg Ile Arg Phe Val Ile Lys Lys His Glu
            405                 410                 415

Leu Leu Asn Ser Thr Arg Glu Asp Leu Gln Leu Asp Lys Pro Ala Ser
            420                 425                 430

Gly Val Lys Glu Glu Trp Tyr Ala Arg Ile Thr Lys Leu Arg Lys Met
            435                 440                 445

Val Asp Gln Leu Phe Cys Lys Lys Phe Ala Glu Ala Leu Gly Ser Thr
        450                 455                 460

Glu Ala Lys Ala Val Pro Tyr Gln Lys Phe Glu Ala His Pro Asn Asp
465                 470                 475                 480

Leu Tyr Val Glu Gly Leu Pro Glu Asn Ile Pro Phe Arg Ser Pro Ser
            485                 490                 495

Trp Tyr Gly Ile Pro Arg Leu Glu Lys Ile Ile Gln Val Gly Asn Arg
            500                 505                 510

Ile Lys Phe Val Ile Lys Arg Pro Glu Leu Leu Thr His Ser Thr Thr
            515                 520                 525

Glu Val Thr Gln Pro Arg Thr Asn Thr Pro Val Lys Glu Asp Trp Asn
        530                 535                 540

Val Arg Ile Thr Lys Leu Arg Lys Gln Val Glu Ile Phe Asn Leu
545                 550                 555                 560

Lys Phe Ala Gln Ala Leu Gly Leu Thr Glu Ala Val Lys Val Pro Tyr
            565                 570                 575

Pro Val Phe Glu Ser Asn Pro Glu Phe Leu Tyr Val Glu Gly Leu Pro
            580                 585                 590

Glu Gly Ile Pro Phe Arg Ser Pro Thr Trp Phe Gly Ile Pro Arg Leu
            595                 600                 605

Glu Arg Ile Val Arg Gly Ser Asn Lys Ile Lys Phe Val Val Lys Lys
        610                 615                 620

Pro Glu Leu Val Ile Ser Tyr Leu Pro Pro Gly Met Ala Ser Lys Ile
625                 630                 635                 640

Asn Thr Lys Ala Leu Gln Ser Pro Lys Arg Pro Arg Ser Pro Gly Ser
            645                 650                 655

```
Asn Ser Lys Val Pro Glu Ile Glu Val Thr Val Glu Gly Pro Asn Asn
            660                 665                 670

Asn Asn Pro Gln Thr Ser Ala Val Arg Thr Pro Thr Gln Thr Asn Gly
        675                 680                 685

Ser Asn Val Pro Phe Lys Pro Arg Gly Arg Glu Phe Ser Phe Glu Ala
    690                 695                 700

Trp Asn Ala Lys Ile Thr Asp Leu Lys Gln Lys Val Glu Asn Leu Phe
705                 710                 715                 720

Asn Glu Lys Cys Gly Glu Ala Leu Gly Leu Lys Gln Ala Val Lys Val
                725                 730                 735

Pro Phe Ala Leu Phe Glu Ser Phe Pro Glu Asp Phe Tyr Val Glu Gly
            740                 745                 750

Leu Pro Glu Gly Val Pro Phe Arg Arg Pro Ser Thr Phe Gly Ile Pro
        755                 760                 765

Arg Leu Glu Lys Ile Leu Arg Asn Lys Ala Lys Ile Lys Phe Ile Ile
    770                 775                 780

Lys Lys Pro Glu Met Phe Glu Thr Ala Ile Lys Glu Ser Thr Ser Ser
785                 790                 795                 800

Lys Ser Pro Pro Arg Lys Ile Asn Ser Ser Pro Asn Val Asn Thr Thr
                805                 810                 815

Ala Ser Gly Val Glu Asp Leu Asn Ile Ile Gln Val Thr Ile Pro Asp
            820                 825                 830

Asp Asp Asn Glu Arg Leu Ser Lys Val Glu Lys Ala Arg Gln Leu Arg
        835                 840                 845

Glu Gln Val Asn Asp Leu Phe Ser Arg Lys Phe Gly Glu Ala Ile Gly
    850                 855                 860

Met Gly Phe Pro Val Lys Val Pro Tyr Arg Lys Ile Thr Ile Asn Pro
865                 870                 875                 880

Gly Cys Val Val Val Asp Gly Met Pro Pro Gly Val Ser Phe Lys Ala
                885                 890                 895

Pro Ser Tyr Leu Glu Ile Ser Ser Met Arg Arg Ile Leu Asp Ser Ala
            900                 905                 910

Glu Phe Ile Lys Phe Thr Val Ile Arg Pro Phe Pro Gly Leu Val Ile
        915                 920                 925

Asn Asn Gln Leu Val Asp Gln Ser Glu Ser Glu Gly Pro Val Ile Gln
    930                 935                 940

Glu Ser Ala Glu Pro Ser Gln Leu Glu Val Pro Ala Thr Glu Glu Ile
945                 950                 955                 960

Lys Glu Thr Asp Gly Ser Ser Gln Ile Lys Gln Glu Pro Asp Pro Thr
                965                 970                 975

Trp

<210> SEQ ID NO 16
<211> LENGTH: 978
<212> TYPE: PRT
<213> ORGANISM: Homo sapiens

<400> SEQUENCE: 16

Met Ala Gln Val Ala Met Ser Thr Leu Pro Val Glu Asp Glu Glu Ser
1               5                   10                  15

Ser Glu Ser Arg Met Val Val Thr Phe Leu Met Ser Ala Leu Glu Ser
            20                  25                  30

Met Cys Lys Glu Leu Ala Lys Ser Lys Ala Glu Val Ala Cys Ile Ala
        35                  40                  45
```

```
Val Tyr Glu Thr Asp Val Phe Val Gly Thr Glu Arg Gly Arg Ala
 50                  55                  60

Phe Val Asn Thr Arg Lys Asp Phe Gln Lys Asp Phe Val Lys Tyr Cys
 65                  70                  75                  80

Val Glu Glu Glu Lys Ala Ala Glu Met His Lys Met Lys Ser Thr
                 85                  90                  95

Thr Gln Ala Asn Arg Met Ser Val Asp Ala Val Glu Ile Glu Thr Leu
                100                 105                 110

Arg Lys Thr Val Glu Asp Tyr Phe Cys Phe Cys Tyr Gly Lys Ala Leu
            115                 120                 125

Gly Lys Ser Thr Val Val Pro Val Pro Tyr Glu Lys Met Leu Arg Asp
130                 135                 140

Gln Ser Ala Val Val Gln Gly Leu Pro Glu Gly Val Ala Phe Lys
145                 150                 155                 160

His Pro Glu Asn Tyr Asp Leu Ala Thr Leu Lys Trp Ile Leu Glu Asn
                165                 170                 175

Lys Ala Gly Ile Ser Phe Ile Ile Lys Arg Pro Phe Leu Glu Pro Lys
            180                 185                 190

Lys His Val Gly Gly Arg Val Met Val Thr Asp Ala Asp Arg Ser Ile
        195                 200                 205

Leu Ser Pro Gly Gly Ser Cys Gly Pro Ile Lys Val Lys Thr Glu Pro
    210                 215                 220

Thr Glu Asp Ser Gly Ile Ser Leu Glu Met Ala Ala Val Thr Val Lys
225                 230                 235                 240

Glu Glu Ser Glu Asp Pro Asp Tyr Tyr Gln Tyr Asn Ile Gln Gly Ser
                245                 250                 255

His His Ser Ser Glu Gly Asn Glu Gly Thr Glu Met Glu Val Pro Ala
            260                 265                 270

Glu Asp Ser Thr Gln His Val Pro Ser Glu Thr Ser Glu Asp Pro Glu
        275                 280                 285

Val Glu Val Thr Ile Glu Asp Asp Tyr Ser Pro Pro Ser Lys Arg
    290                 295                 300

Pro Lys Ala Asn Glu Leu Pro Gln Pro Pro Val Pro Glu Pro Ala Asn
305                 310                 315                 320

Ala Gly Lys Arg Lys Val Arg Glu Phe Asn Phe Glu Lys Trp Asn Ala
                325                 330                 335

Arg Ile Thr Asp Leu Arg Lys Gln Val Glu Glu Leu Phe Glu Arg Lys
            340                 345                 350

Tyr Ala Gln Ala Ile Lys Ala Lys Gly Pro Val Thr Ile Pro Tyr Pro
        355                 360                 365

Leu Phe Gln Ser His Val Glu Asp Leu Tyr Val Glu Gly Leu Pro Glu
    370                 375                 380

Gly Ile Pro Phe Arg Arg Pro Ser Thr Tyr Gly Ile Pro Arg Leu Glu
385                 390                 395                 400

Arg Ile Leu His Ala Lys Glu Arg Ile Arg Phe Val Ile Lys Lys His
                405                 410                 415

Glu Leu Leu Asn Ser Thr Arg Glu Asp Leu Gln Leu Asp Lys Pro Ala
            420                 425                 430

Ser Gly Val Lys Glu Glu Trp Tyr Ala Arg Ile Thr Lys Leu Arg Lys
        435                 440                 445

Met Val Asp Gln Leu Phe Cys Lys Lys Phe Ala Glu Ala Leu Gly Ser
    450                 455                 460

Thr Glu Ala Lys Ala Val Pro Tyr Gln Lys Phe Glu Ala His Pro Asn
```

```
            465                 470                 475                 480
Asp Leu Tyr Val Glu Gly Leu Pro Glu Asn Ile Pro Phe Arg Ser Pro
                485                 490                 495
Ser Trp Tyr Gly Ile Pro Arg Leu Glu Lys Ile Ile Gln Val Gly Asn
                500                 505                 510
Arg Ile Lys Phe Val Ile Lys Arg Pro Glu Leu Leu Thr His Ser Thr
                515                 520                 525
Thr Glu Val Thr Gln Pro Arg Thr Asn Thr Pro Val Lys Glu Asp Trp
    530                 535                 540
Asn Val Arg Ile Thr Lys Leu Arg Lys Gln Val Glu Glu Ile Phe Asn
545                 550                 555                 560
Leu Lys Phe Ala Gln Ala Leu Gly Leu Thr Glu Ala Val Lys Val Pro
                565                 570                 575
Tyr Pro Val Phe Glu Ser Asn Pro Glu Phe Leu Tyr Val Glu Gly Leu
                580                 585                 590
Pro Glu Gly Ile Pro Phe Arg Ser Pro Thr Trp Phe Gly Ile Pro Arg
            595                 600                 605
Leu Glu Arg Ile Val Arg Gly Ser Asn Lys Ile Lys Phe Val Val Lys
            610                 615                 620
Lys Pro Glu Leu Val Ile Ser Tyr Leu Pro Pro Gly Met Ala Ser Lys
625                 630                 635                 640
Ile Asn Thr Lys Ala Leu Gln Ser Pro Lys Arg Pro Arg Ser Pro Gly
                645                 650                 655
Ser Asn Ser Lys Val Pro Glu Ile Glu Val Thr Val Glu Gly Pro Asn
                660                 665                 670
Asn Asn Asn Pro Gln Thr Ser Ala Val Arg Thr Pro Thr Gln Thr Asn
            675                 680                 685
Gly Ser Asn Val Pro Phe Lys Pro Arg Gly Arg Glu Phe Ser Phe Glu
            690                 695                 700
Ala Trp Asn Ala Lys Ile Thr Asp Leu Lys Gln Lys Val Glu Asn Leu
705                 710                 715                 720
Phe Asn Glu Lys Cys Gly Glu Ala Leu Gly Leu Lys Gln Ala Val Lys
                725                 730                 735
Val Pro Phe Ala Leu Phe Glu Ser Phe Pro Glu Asp Phe Tyr Val Glu
                740                 745                 750
Gly Leu Pro Glu Gly Val Pro Phe Arg Arg Pro Ser Thr Phe Gly Ile
                755                 760                 765
Pro Arg Leu Glu Lys Ile Leu Arg Asn Lys Ala Lys Ile Lys Phe Ile
            770                 775                 780
Ile Lys Lys Pro Glu Met Phe Glu Thr Ala Ile Lys Glu Ser Thr Ser
785                 790                 795                 800
Ser Lys Ser Pro Pro Arg Lys Ile Asn Ser Ser Pro Asn Val Asn Thr
                805                 810                 815
Thr Ala Ser Gly Val Glu Asp Leu Asn Ile Ile Gln Val Thr Ile Pro
                820                 825                 830
Asp Asp Asp Asn Glu Arg Leu Ser Lys Val Glu Lys Ala Arg Gln Leu
            835                 840                 845
Arg Glu Gln Val Asn Asp Leu Phe Ser Arg Lys Phe Gly Glu Ala Ile
            850                 855                 860
Gly Met Gly Phe Pro Val Lys Val Pro Tyr Arg Lys Ile Thr Ile Asn
865                 870                 875                 880
Pro Gly Cys Val Val Val Asp Gly Met Pro Pro Gly Val Ser Phe Lys
                885                 890                 895
```

```
Ala Pro Ser Tyr Leu Glu Ile Ser Ser Met Arg Arg Ile Leu Asp Ser
            900                 905                 910

Ala Glu Phe Ile Lys Phe Thr Val Ile Arg Pro Phe Pro Gly Leu Val
            915                 920                 925

Ile Asn Asn Gln Leu Val Asp Gln Ser Glu Ser Glu Gly Pro Val Ile
930                 935                 940

Gln Glu Ser Ala Glu Pro Ser Gln Leu Glu Val Pro Ala Thr Glu Glu
945                 950                 955                 960

Ile Lys Glu Thr Asp Gly Ser Ser Gln Ile Lys Gln Glu Pro Asp Pro
            965                 970                 975

Thr Trp

<210> SEQ ID NO 17
<211> LENGTH: 998
<212> TYPE: PRT
<213> ORGANISM: Homo sapiens

<400> SEQUENCE: 17

Met Ala Gln Val Ala Met Ser Thr Leu Pro Val Glu Asp Glu Glu Ser
1               5                   10                  15

Ser Glu Ser Arg Met Val Val Thr Phe Leu Met Ser Ala Leu Glu Ser
            20                  25                  30

Met Cys Lys Glu Leu Ala Lys Ser Lys Ala Glu Val Ala Cys Ile Ala
        35                  40                  45

Val Tyr Glu Thr Asp Val Phe Val Gly Thr Glu Arg Gly Arg Ala
    50                  55                  60

Phe Val Asn Thr Arg Lys Asp Phe Gln Lys Asp Phe Val Lys Tyr Cys
65                  70                  75                  80

Val Glu Glu Glu Lys Ala Ala Glu Met His Lys Met Lys Ser Thr
                85                  90                  95

Thr Gln Ala Asn Arg Met Ser Val Asp Ala Val Glu Ile Glu Thr Leu
            100                 105                 110

Arg Lys Thr Val Glu Asp Tyr Phe Cys Phe Cys Tyr Gly Lys Ala Leu
        115                 120                 125

Gly Lys Ser Thr Val Val Pro Val Pro Tyr Glu Lys Met Leu Arg Asp
    130                 135                 140

Gln Ser Ala Val Val Val Gln Gly Leu Pro Glu Gly Val Ala Phe Lys
145                 150                 155                 160

His Pro Glu Asn Tyr Asp Leu Ala Thr Leu Lys Trp Ile Leu Glu Asn
                165                 170                 175

Lys Ala Gly Ile Ser Phe Ile Ile Lys Arg Pro Phe Leu Glu Pro Lys
            180                 185                 190

Lys His Val Gly Gly Arg Val Met Val Thr Asp Ala Asp Arg Ser Ile
        195                 200                 205

Leu Ser Pro Gly Gly Ser Cys Gly Pro Ile Lys Val Lys Thr Glu Pro
    210                 215                 220

Thr Glu Asp Ser Gly Ile Ser Leu Glu Met Ala Ala Val Thr Val Lys
225                 230                 235                 240

Glu Glu Ser Glu Asp Pro Asp Tyr Tyr Gln Tyr Asn Ile Gln Ala Gly
                245                 250                 255

Pro Ser Glu Thr Asp Asp Val Asp Glu Lys Gln Pro Leu Ser Lys Pro
            260                 265                 270

Leu Gln Gly Ser His His Ser Ser Glu Gly Asn Glu Gly Thr Glu Met
        275                 280                 285
```

```
Glu Val Pro Ala Glu Asp Ser Thr Gln His Val Pro Ser Glu Thr Ser
    290                 295                 300
Glu Asp Pro Glu Val Glu Val Thr Ile Glu Asp Asp Tyr Ser Pro
305                 310                 315                 320
Pro Ser Lys Arg Pro Lys Ala Asn Glu Leu Pro Gln Pro Pro Val Pro
                325                 330                 335
Glu Pro Ala Asn Ala Gly Lys Arg Lys Val Arg Glu Phe Asn Phe Glu
            340                 345                 350
Lys Trp Asn Ala Arg Ile Thr Asp Leu Arg Lys Gln Val Glu Glu Leu
        355                 360                 365
Phe Glu Arg Lys Tyr Ala Gln Ala Ile Lys Ala Lys Gly Pro Val Thr
    370                 375                 380
Ile Pro Tyr Pro Leu Phe Gln Ser His Val Glu Asp Leu Tyr Val Glu
385                 390                 395                 400
Gly Leu Pro Glu Gly Ile Pro Phe Arg Arg Pro Ser Thr Tyr Gly Ile
                405                 410                 415
Pro Arg Leu Glu Arg Ile Leu His Ala Lys Glu Arg Ile Arg Phe Val
            420                 425                 430
Ile Lys Lys His Glu Leu Leu Asn Ser Thr Arg Glu Asp Leu Gln Leu
        435                 440                 445
Asp Lys Pro Ala Ser Gly Val Lys Glu Glu Trp Tyr Ala Arg Ile Thr
    450                 455                 460
Lys Leu Arg Lys Met Val Asp Gln Leu Phe Cys Lys Lys Phe Ala Glu
465                 470                 475                 480
Ala Leu Gly Ser Thr Glu Ala Lys Ala Val Pro Tyr Gln Lys Phe Glu
                485                 490                 495
Ala His Pro Asn Asp Leu Tyr Val Glu Gly Leu Pro Glu Asn Ile Pro
            500                 505                 510
Phe Arg Ser Pro Ser Trp Tyr Gly Ile Pro Arg Leu Glu Lys Ile Ile
        515                 520                 525
Gln Val Gly Asn Arg Ile Lys Phe Val Ile Lys Arg Pro Glu Leu Leu
    530                 535                 540
Thr His Ser Thr Thr Glu Val Thr Gln Pro Arg Thr Asn Thr Pro Val
545                 550                 555                 560
Lys Glu Asp Trp Asn Val Arg Ile Thr Lys Leu Arg Lys Gln Val Glu
                565                 570                 575
Glu Ile Phe Asn Leu Lys Phe Ala Gln Ala Leu Gly Leu Thr Glu Ala
            580                 585                 590
Val Lys Val Pro Tyr Pro Val Phe Glu Ser Asn Pro Glu Phe Leu Tyr
        595                 600                 605
Val Glu Gly Leu Pro Glu Gly Ile Pro Phe Arg Ser Pro Thr Trp Phe
    610                 615                 620
Gly Ile Pro Arg Leu Glu Arg Ile Val Arg Gly Ser Asn Lys Ile Lys
625                 630                 635                 640
Phe Val Val Lys Lys Pro Glu Leu Val Ile Ser Tyr Leu Pro Pro Gly
                645                 650                 655
Met Ala Ser Lys Ile Asn Thr Lys Ala Leu Gln Ser Pro Lys Arg Pro
            660                 665                 670
Arg Ser Pro Gly Ser Asn Ser Lys Val Pro Glu Ile Glu Val Thr Val
        675                 680                 685
Glu Gly Pro Asn Asn Asn Pro Gln Thr Ser Ala Val Arg Thr Pro
    690                 695                 700
```

Thr Gln Thr Asn Gly Ser Asn Val Pro Phe Lys Pro Arg Gly Arg Glu
705                 710                 715                 720

Phe Ser Phe Glu Ala Trp Asn Ala Lys Ile Thr Asp Leu Lys Gln Lys
            725                 730                 735

Val Glu Asn Leu Phe Asn Glu Lys Cys Gly Glu Ala Leu Gly Leu Lys
        740                 745                 750

Gln Ala Val Lys Val Pro Phe Ala Leu Phe Glu Ser Phe Pro Glu Asp
    755                 760                 765

Phe Tyr Val Glu Gly Leu Pro Glu Gly Val Pro Phe Arg Arg Pro Ser
770                 775                 780

Thr Phe Gly Ile Pro Arg Leu Glu Lys Ile Leu Arg Asn Lys Ala Lys
785                 790                 795                 800

Ile Lys Phe Ile Ile Lys Lys Pro Glu Met Phe Glu Thr Ala Ile Lys
            805                 810                 815

Glu Ser Thr Ser Ser Lys Ser Pro Pro Arg Lys Ile Asn Ser Ser Pro
        820                 825                 830

Asn Val Asn Thr Thr Ala Ser Gly Val Glu Asp Leu Asn Ile Ile Gln
        835                 840                 845

Val Thr Ile Pro Asp Asp Asn Glu Arg Leu Ser Lys Val Glu Lys
850                 855                 860

Ala Arg Gln Leu Arg Glu Gln Val Asn Asp Leu Phe Ser Arg Lys Phe
865                 870                 875                 880

Gly Glu Ala Ile Gly Met Gly Phe Pro Val Lys Val Pro Tyr Arg Lys
            885                 890                 895

Ile Thr Ile Asn Pro Gly Cys Val Val Val Asp Gly Met Pro Pro Gly
        900                 905                 910

Val Ser Phe Lys Ala Pro Ser Tyr Leu Glu Ile Ser Ser Met Arg Arg
        915                 920                 925

Ile Leu Asp Ser Ala Glu Phe Ile Lys Phe Thr Val Ile Arg Pro Phe
930                 935                 940

Pro Gly Leu Val Ile Asn Asn Gln Leu Val Asp Gln Ser Glu Ser Glu
945                 950                 955                 960

Gly Pro Val Ile Gln Glu Ser Ala Glu Pro Gln Leu Glu Val Pro
            965                 970                 975

Ala Thr Glu Glu Ile Lys Glu Thr Asp Gly Ser Ser Gln Ile Lys Gln
        980                 985                 990

Glu Pro Asp Pro Thr Trp
        995

<210> SEQ ID NO 18
<211> LENGTH: 957
<212> TYPE: PRT
<213> ORGANISM: Homo sapiens

<400> SEQUENCE: 18

Met Ala Gln Val Ala Met Ser Thr Leu Pro Val Glu Asp Glu Glu Ser
1               5                   10                  15

Ser Glu Ser Arg Met Val Val Thr Phe Leu Met Ser Ala Leu Glu Ser
            20                  25                  30

Met Cys Lys Glu Leu Ala Lys Ser Lys Ala Glu Val Ala Cys Ile Ala
        35                  40                  45

Val Tyr Glu Thr Asp Val Phe Val Gly Thr Glu Arg Gly Arg Ala
    50                  55                  60

Phe Val Asn Thr Arg Lys Asp Phe Gln Lys Asp Phe Val Lys Tyr Cys
65                  70                  75                  80

```
Val Glu Glu Glu Glu Lys Ala Ala Glu Met His Lys Met Lys Ser Thr
                85                  90                  95

Thr Gln Ala Asn Arg Met Ser Val Asp Ala Val Glu Ile Glu Thr Leu
                100                 105                 110

Arg Lys Thr Val Glu Asp Tyr Phe Cys Phe Cys Tyr Gly Lys Ala Leu
            115                 120                 125

Gly Lys Ser Thr Val Val Pro Val Pro Tyr Glu Lys Met Leu Arg Asp
        130                 135                 140

Gln Ser Ala Val Val Gln Gly Leu Pro Glu Gly Val Ala Phe Lys
145                 150                 155                 160

His Pro Glu Asn Tyr Asp Leu Ala Thr Leu Lys Trp Ile Leu Glu Asn
                165                 170                 175

Lys Ala Gly Ile Ser Phe Ile Ile Lys Arg Pro Phe Leu Glu Pro Lys
                180                 185                 190

Lys His Val Gly Gly Arg Val Met Val Thr Asp Ala Asp Arg Ser Ile
                195                 200                 205

Leu Ser Pro Gly Gly Ser Cys Gly Pro Ile Lys Val Lys Thr Glu Pro
        210                 215                 220

Thr Glu Asp Ser Gly Ile Ser Leu Glu Met Ala Ala Val Thr Val Lys
225                 230                 235                 240

Glu Glu Ser Glu Asp Pro Asp Tyr Tyr Gln Tyr Asn Ile Gln Gly Ser
                245                 250                 255

His His Ser Ser Glu Gly Asn Glu Gly Thr Glu Met Glu Val Pro Ala
                260                 265                 270

Glu Asp Asp Asp Tyr Ser Pro Pro Ser Lys Arg Pro Lys Ala Asn Glu
                275                 280                 285

Leu Pro Gln Pro Pro Val Pro Glu Pro Ala Asn Ala Gly Lys Arg Lys
        290                 295                 300

Val Arg Glu Phe Asn Phe Glu Lys Trp Asn Ala Arg Ile Thr Asp Leu
305                 310                 315                 320

Arg Lys Gln Val Glu Glu Leu Phe Glu Arg Lys Tyr Ala Gln Ala Ile
                325                 330                 335

Lys Ala Lys Gly Pro Val Thr Ile Pro Tyr Pro Leu Phe Gln Ser His
                340                 345                 350

Val Glu Asp Leu Tyr Val Glu Gly Leu Pro Glu Gly Ile Pro Phe Arg
                355                 360                 365

Arg Pro Ser Thr Tyr Gly Ile Pro Arg Leu Glu Arg Ile Leu His Ala
        370                 375                 380

Lys Glu Arg Ile Arg Phe Val Ile Lys Lys His Glu Leu Leu Asn Ser
385                 390                 395                 400

Thr Arg Glu Asp Leu Gln Leu Asp Lys Pro Ala Ser Gly Val Lys Glu
                405                 410                 415

Glu Trp Tyr Ala Arg Ile Thr Lys Leu Arg Lys Met Val Asp Gln Leu
                420                 425                 430

Phe Cys Lys Lys Phe Ala Glu Ala Leu Gly Ser Thr Glu Ala Lys Ala
                435                 440                 445

Val Pro Tyr Gln Lys Phe Glu Ala His Pro Asn Asp Leu Tyr Val Glu
        450                 455                 460

Gly Leu Pro Glu Asn Ile Pro Phe Arg Ser Pro Ser Trp Tyr Gly Ile
465                 470                 475                 480

Pro Arg Leu Glu Lys Ile Ile Gln Val Gly Asn Arg Ile Lys Phe Val
                485                 490                 495
```

-continued

```
Ile Lys Arg Pro Glu Leu Leu Thr His Ser Thr Thr Glu Val Thr Gln
            500                 505                 510
Pro Arg Thr Asn Thr Pro Val Lys Glu Asp Trp Asn Val Arg Ile Thr
        515                 520                 525
Lys Leu Arg Lys Gln Val Glu Glu Ile Phe Asn Leu Lys Phe Ala Gln
    530                 535                 540
Ala Leu Gly Leu Thr Glu Ala Val Lys Val Pro Tyr Pro Val Phe Glu
545                 550                 555                 560
Ser Asn Pro Glu Phe Leu Tyr Val Glu Gly Leu Pro Glu Gly Ile Pro
                565                 570                 575
Phe Arg Ser Pro Thr Trp Phe Gly Ile Pro Arg Leu Glu Arg Ile Val
            580                 585                 590
Arg Gly Ser Asn Lys Ile Lys Phe Val Val Lys Lys Pro Glu Leu Val
        595                 600                 605
Ile Ser Tyr Leu Pro Pro Gly Met Ala Ser Lys Ile Asn Thr Lys Ala
    610                 615                 620
Leu Gln Ser Pro Lys Arg Pro Arg Ser Pro Gly Ser Asn Ser Lys Val
625                 630                 635                 640
Pro Glu Ile Glu Val Thr Val Glu Gly Pro Asn Asn Asn Asn Pro Gln
                645                 650                 655
Thr Ser Ala Val Arg Thr Pro Thr Gln Thr Asn Gly Ser Asn Val Pro
            660                 665                 670
Phe Lys Pro Arg Gly Arg Glu Phe Ser Phe Glu Ala Trp Asn Ala Lys
        675                 680                 685
Ile Thr Asp Leu Lys Gln Lys Val Glu Asn Leu Phe Asn Glu Lys Cys
    690                 695                 700
Gly Glu Ala Leu Gly Leu Lys Gln Ala Val Lys Val Pro Phe Ala Leu
705                 710                 715                 720
Phe Glu Ser Phe Pro Glu Asp Phe Tyr Val Glu Gly Leu Pro Glu Gly
                725                 730                 735
Val Pro Phe Arg Arg Pro Ser Thr Phe Gly Ile Pro Arg Leu Glu Lys
            740                 745                 750
Ile Leu Arg Asn Lys Ala Lys Ile Lys Phe Ile Ile Lys Lys Pro Glu
        755                 760                 765
Met Phe Glu Thr Ala Ile Lys Glu Ser Thr Ser Ser Lys Ser Pro Pro
    770                 775                 780
Arg Lys Ile Asn Ser Ser Pro Asn Val Asn Thr Thr Ala Ser Gly Val
785                 790                 795                 800
Glu Asp Leu Asn Ile Ile Gln Val Thr Ile Pro Asp Asp Asn Glu
                805                 810                 815
Arg Leu Ser Lys Val Glu Lys Ala Arg Gln Leu Arg Glu Gln Val Asn
            820                 825                 830
Asp Leu Phe Ser Arg Lys Phe Gly Glu Ala Ile Gly Met Gly Phe Pro
        835                 840                 845
Val Lys Val Pro Tyr Arg Lys Ile Thr Ile Asn Pro Gly Cys Val Val
    850                 855                 860
Val Asp Gly Met Pro Pro Gly Val Ser Phe Lys Ala Pro Ser Tyr Leu
865                 870                 875                 880
Glu Ile Ser Ser Met Arg Arg Ile Leu Asp Ser Ala Glu Phe Ile Lys
                885                 890                 895
Phe Thr Val Ile Arg Pro Phe Pro Gly Leu Val Ile Asn Asn Gln Leu
            900                 905                 910
Val Asp Gln Ser Glu Ser Glu Gly Pro Val Ile Gln Glu Ser Ala Glu
```

```
                915                 920                 925
Pro Ser Gln Leu Glu Val Pro Ala Thr Glu Glu Ile Lys Glu Thr Asp
        930                 935                 940

Gly Ser Ser Gln Ile Lys Gln Glu Pro Asp Pro Thr Trp
945                 950                 955

<210> SEQ ID NO 19
<211> LENGTH: 976
<212> TYPE: PRT
<213> ORGANISM: Homo sapiens

<400> SEQUENCE: 19

Met Ala Gln Val Ala Met Ser Thr Leu Pro Val Glu Asp Glu Glu Ser
1               5                   10                  15

Ser Glu Ser Arg Met Val Val Thr Phe Leu Met Ser Ala Leu Glu Ser
                20                  25                  30

Met Cys Lys Glu Leu Ala Lys Ser Lys Ala Glu Val Ala Cys Ile Ala
            35                  40                  45

Val Tyr Glu Thr Asp Val Phe Val Val Gly Thr Glu Arg Gly Arg Ala
        50                  55                  60

Phe Val Asn Thr Arg Lys Asp Phe Gln Lys Asp Phe Val Lys Tyr Cys
65                  70                  75                  80

Val Glu Glu Glu Lys Ala Ala Glu Met His Lys Met Lys Ser Thr
                85                  90                  95

Thr Gln Ala Asn Arg Met Ser Val Asp Ala Val Glu Ile Glu Thr Leu
                100                 105                 110

Arg Lys Thr Val Glu Asp Tyr Phe Cys Phe Cys Tyr Gly Lys Ala Leu
            115                 120                 125

Gly Lys Ser Thr Val Val Pro Val Pro Tyr Glu Lys Met Leu Arg Asp
        130                 135                 140

Gln Ser Ala Val Val Gln Gly Leu Pro Glu Gly Val Ala Phe Lys
145                 150                 155                 160

His Pro Glu Asn Tyr Asp Leu Ala Thr Leu Lys Trp Ile Leu Glu Asn
                165                 170                 175

Lys Ala Gly Ile Ser Phe Ile Ile Lys Arg Pro Phe Leu Glu Pro Lys
            180                 185                 190

Lys His Val Gly Gly Arg Val Met Val Thr Asp Ala Asp Arg Ser Ile
        195                 200                 205

Leu Ser Pro Gly Gly Ser Cys Gly Pro Ile Lys Val Lys Thr Glu Pro
    210                 215                 220

Thr Glu Asp Ser Gly Ile Ser Leu Glu Met Ala Ala Val Thr Val Lys
225                 230                 235                 240

Glu Glu Ser Glu Asp Pro Asp Tyr Tyr Gln Tyr Asn Ile Gln Gly Pro
                245                 250                 255

Ser Glu Thr Asp Asp Val Asp Glu Lys Gln Pro Leu Ser Lys Pro Leu
            260                 265                 270

Gln Gly Ser His His Ser Ser Glu Gly Asn Glu Gly Thr Glu Met Glu
        275                 280                 285

Val Pro Ala Glu Asp Asp Asp Tyr Ser Pro Ser Lys Arg Pro Lys
    290                 295                 300

Ala Asn Glu Leu Pro Gln Pro Pro Val Pro Glu Pro Ala Asn Ala Gly
305                 310                 315                 320

Lys Arg Lys Val Arg Glu Phe Asn Phe Glu Lys Trp Asn Ala Arg Ile
                325                 330                 335
```

Thr Asp Leu Arg Lys Gln Val Glu Glu Leu Phe Glu Arg Lys Tyr Ala
            340                 345                 350

Gln Ala Ile Lys Ala Lys Gly Pro Val Thr Ile Pro Tyr Pro Leu Phe
            355                 360                 365

Gln Ser His Val Glu Asp Leu Tyr Val Glu Gly Leu Pro Glu Gly Ile
            370                 375                 380

Pro Phe Arg Arg Pro Ser Thr Tyr Gly Ile Pro Arg Leu Glu Arg Ile
385                 390                 395                 400

Leu His Ala Lys Glu Arg Ile Arg Phe Val Ile Lys Lys His Glu Leu
            405                 410                 415

Leu Asn Ser Thr Arg Glu Asp Leu Gln Leu Asp Lys Pro Ala Ser Gly
            420                 425                 430

Val Lys Glu Glu Trp Tyr Ala Arg Ile Thr Lys Leu Arg Lys Met Val
            435                 440                 445

Asp Gln Leu Phe Cys Lys Lys Phe Ala Glu Ala Leu Gly Ser Thr Glu
            450                 455                 460

Ala Lys Ala Val Pro Tyr Gln Lys Phe Glu Ala His Pro Asn Asp Leu
465                 470                 475                 480

Tyr Val Glu Gly Leu Pro Glu Asn Ile Pro Phe Arg Ser Pro Ser Trp
            485                 490                 495

Tyr Gly Ile Pro Arg Leu Glu Lys Ile Gln Val Gly Asn Arg Ile
            500                 505                 510

Lys Phe Val Ile Lys Arg Pro Glu Leu Leu Thr His Ser Thr Thr Glu
            515                 520                 525

Val Thr Gln Pro Arg Thr Asn Thr Pro Val Lys Glu Asp Trp Asn Val
530                 535                 540

Arg Ile Thr Lys Leu Arg Lys Gln Val Glu Glu Ile Phe Asn Leu Lys
545                 550                 555                 560

Phe Ala Gln Ala Leu Gly Leu Thr Glu Ala Val Lys Val Pro Tyr Pro
            565                 570                 575

Val Phe Glu Ser Asn Pro Glu Phe Leu Tyr Val Glu Gly Leu Pro Glu
            580                 585                 590

Gly Ile Pro Phe Arg Ser Pro Thr Trp Phe Gly Ile Pro Arg Leu Glu
            595                 600                 605

Arg Ile Val Arg Gly Ser Asn Lys Ile Lys Phe Val Val Lys Lys Pro
610                 615                 620

Glu Leu Val Ile Ser Tyr Leu Pro Pro Gly Met Ala Ser Lys Ile Asn
625                 630                 635                 640

Thr Lys Ala Leu Gln Ser Pro Lys Arg Pro Arg Ser Pro Gly Ser Asn
            645                 650                 655

Ser Lys Val Pro Glu Ile Glu Val Thr Val Glu Gly Pro Asn Asn Asn
            660                 665                 670

Asn Pro Gln Thr Ser Ala Val Arg Thr Pro Thr Gln Thr Asn Gly Ser
            675                 680                 685

Asn Val Pro Phe Lys Pro Arg Gly Arg Glu Phe Ser Phe Glu Ala Trp
            690                 695                 700

Asn Ala Lys Ile Thr Asp Leu Lys Gln Lys Val Glu Asn Leu Phe Asn
705                 710                 715                 720

Glu Lys Cys Gly Glu Ala Leu Gly Leu Lys Gln Ala Val Lys Val Pro
            725                 730                 735

Phe Ala Leu Phe Glu Ser Phe Pro Glu Asp Phe Tyr Val Glu Gly Leu
            740                 745                 750

Pro Glu Gly Val Pro Phe Arg Arg Pro Ser Thr Phe Gly Ile Pro Arg

```
                755                 760                 765
Leu Glu Lys Ile Leu Arg Asn Lys Ala Lys Ile Lys Phe Ile Ile Lys
770                 775                 780
Lys Pro Glu Met Phe Glu Thr Ala Ile Lys Glu Ser Thr Ser Ser Lys
785                 790                 795                 800
Ser Pro Pro Arg Lys Ile Asn Ser Ser Pro Asn Val Asn Thr Thr Ala
                805                 810                 815
Ser Gly Val Glu Asp Leu Asn Ile Ile Gln Val Thr Ile Pro Asp Asp
            820                 825                 830
Asp Asn Glu Arg Leu Ser Lys Val Glu Lys Ala Arg Gln Leu Arg Glu
        835                 840                 845
Gln Val Asn Asp Leu Phe Ser Arg Lys Phe Gly Glu Ala Ile Gly Met
    850                 855                 860
Gly Phe Pro Val Lys Val Pro Tyr Arg Lys Ile Thr Ile Asn Pro Gly
865                 870                 875                 880
Cys Val Val Val Asp Gly Met Pro Pro Gly Val Ser Phe Lys Ala Pro
                885                 890                 895
Ser Tyr Leu Glu Ile Ser Ser Met Arg Arg Ile Leu Asp Ser Ala Glu
            900                 905                 910
Phe Ile Lys Phe Thr Val Ile Arg Pro Phe Pro Gly Leu Val Ile Asn
        915                 920                 925
Asn Gln Leu Val Asp Gln Ser Glu Ser Glu Gly Pro Val Ile Gln Glu
    930                 935                 940
Ser Ala Glu Pro Ser Gln Leu Glu Val Pro Ala Thr Glu Glu Ile Lys
945                 950                 955                 960
Glu Thr Asp Gly Ser Ser Gln Ile Lys Gln Glu Pro Asp Pro Thr Trp
                965                 970                 975

<210> SEQ ID NO 20
<211> LENGTH: 19
<212> TYPE: DNA
<213> ORGANISM: Artificial Sequence
<220> FEATURE:
<223> OTHER INFORMATION: Synthetic

<400> SEQUENCE: 20
atcccgtacc ctcttttcc                                                    19

<210> SEQ ID NO 21
<211> LENGTH: 18
<212> TYPE: DNA
<213> ORGANISM: Artificial Sequence
<220> FEATURE:
<223> OTHER INFORMATION: Synthetic

<400> SEQUENCE: 21
agacaagagt tcaacagg                                                     18

<210> SEQ ID NO 22
<211> LENGTH: 38
<212> TYPE: DNA
<213> ORGANISM: Artificial Sequence
<220> FEATURE:
<223> OTHER INFORMATION: Synthetic

<400> SEQUENCE: 22
cgcctggaga ggatattaca tgcaaaggaa aggattcg                               38

<210> SEQ ID NO 23
```

```
<211> LENGTH: 38
<212> TYPE: DNA
<213> ORGANISM: Artificial Sequence
<220> FEATURE:
<223> OTHER INFORMATION: Synthetic

<400> SEQUENCE: 23
cgaatccttt cctttgcatg taatatcctc tccaggcg                              38

<210> SEQ ID NO 24
<211> LENGTH: 36
<212> TYPE: DNA
<213> ORGANISM: Artificial Sequence
<220> FEATURE:
<223> OTHER INFORMATION: Synthetic

<400> SEQUENCE: 24
tgtaaaacga cggccagttg aaggcacaga aatgga                                36

<210> SEQ ID NO 25
<211> LENGTH: 37
<212> TYPE: DNA
<213> ORGANISM: Artificial Sequence
<220> FEATURE:
<223> OTHER INFORMATION: Synthetic

<400> SEQUENCE: 25
caggaaacag ctatgaccac cattcttcct ttactcc                               37

<210> SEQ ID NO 26
<211> LENGTH: 18
<212> TYPE: DNA
<213> ORGANISM: Artificial Sequence
<220> FEATURE:
<223> OTHER INFORMATION: Synthetic

<400> SEQUENCE: 26
ctcaagccat aaaagcca                                                    18

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27
agacaagagt tcaacagg                                                    18

<210> SEQ ID NO 28
<211> LENGTH: 7
<212> TYPE: PRT
<213> ORGANISM: Homo sapiens

<400> SEQUENCE: 28

Arg Ile Leu Leu Ala Lys Glu
1               5

<210> SEQ ID NO 29
<211> LENGTH: 7
<212> TYPE: PRT
<213> ORGANISM: Homo sapiens
<220> FEATURE:
<221> NAME/KEY: MISC_FEATURE
<222> LOCATION: (2)..(3)
<223> OTHER INFORMATION: "Xaa"s are any amino acid
<220> FEATURE:
```

```
<221> NAME/KEY: MISC_FEATURE
<222> LOCATION: (5)..(6)
<223> OTHER INFORMATION: "Xaa"s are any amino acid
<220> FEATURE:
<221> NAME/KEY: MISC_FEATURE
<222> LOCATION: (7)..(7)
<223> OTHER INFORMATION: "Xaa" can be any amino acid

<400> SEQUENCE: 29

Arg Xaa Xaa Leu Xaa Xaa Xaa
1               5

<210> SEQ ID NO 30
<211> LENGTH: 7
<212> TYPE: PRT
<213> ORGANISM: Homo sapiens

<400> SEQUENCE: 30

Arg Ile Leu His Ala Lys Glu
1               5

<210> SEQ ID NO 31
<211> LENGTH: 977
<212> TYPE: PRT
<213> ORGANISM: Homo sapiens

<400> SEQUENCE: 31

Met Ala Gln Val Ala Met Ser Thr Leu Pro Val Glu Asp Glu Glu Ser
1               5                   10                  15

Ser Glu Ser Arg Met Val Val Thr Phe Leu Met Ser Ala Leu Glu Ser
            20                  25                  30

Met Cys Lys Glu Leu Ala Lys Ser Lys Ala Glu Val Ala Cys Ile Ala
        35                  40                  45

Val Tyr Glu Thr Asp Val Phe Val Val Gly Thr Glu Arg Gly Arg Ala
    50                  55                  60

Phe Val Asn Thr Arg Lys Asp Phe Gln Lys Asp Phe Val Lys Tyr Cys
65                  70                  75                  80

Val Glu Glu Glu Glu Lys Ala Ala Glu Met His Lys Met Lys Ser Thr
                85                  90                  95

Thr Gln Ala Asn Arg Met Ser Val Asp Ala Val Glu Ile Glu Thr Leu
            100                 105                 110

Arg Lys Thr Val Glu Asp Tyr Phe Cys Phe Cys Tyr Gly Lys Ala Leu
        115                 120                 125

Gly Lys Ser Thr Val Val Pro Val Pro Tyr Glu Lys Met Leu Arg Asp
    130                 135                 140

Gln Ser Ala Val Val Val Gln Gly Leu Pro Glu Gly Val Ala Phe Lys
145                 150                 155                 160

His Pro Glu Asn Tyr Asp Leu Ala Thr Leu Lys Trp Ile Leu Glu Asn
                165                 170                 175

Lys Ala Gly Ile Ser Phe Ile Ile Lys Arg Pro Phe Leu Glu Pro Lys
            180                 185                 190

Lys His Val Gly Gly Arg Val Met Val Thr Asp Ala Asp Arg Ser Ile
        195                 200                 205

Leu Ser Pro Gly Gly Ser Cys Gly Pro Ile Lys Val Lys Thr Glu Pro
    210                 215                 220

Thr Glu Asp Ser Gly Ile Ser Leu Glu Met Ala Ala Val Thr Val Lys
225                 230                 235                 240

Glu Glu Ser Glu Asp Pro Asp Tyr Tyr Gln Tyr Asn Ile Gln Ala Gly
                245                 250                 255
```

```
Pro Ser Glu Thr Asp Asp Val Asp Glu Lys Gln Pro Leu Ser Lys Pro
            260                 265                 270

Leu Gln Gly Ser His His Ser Glu Gly Asn Glu Gly Thr Glu Met
        275                 280                 285

Glu Val Pro Ala Glu Asp Asp Tyr Ser Pro Pro Ser Lys Arg Pro
    290                 295                 300

Lys Ala Asn Glu Leu Pro Gln Pro Val Pro Glu Pro Ala Asn Ala
305                 310                 315                 320

Gly Lys Arg Lys Val Arg Glu Phe Asn Phe Glu Lys Trp Asn Ala Arg
                325                 330                 335

Ile Thr Asp Leu Arg Lys Gln Val Glu Glu Leu Phe Glu Arg Lys Tyr
                340                 345                 350

Ala Gln Ala Ile Lys Ala Lys Gly Pro Val Thr Ile Pro Tyr Pro Leu
                355                 360                 365

Phe Gln Ser His Val Glu Asp Leu Tyr Val Glu Gly Leu Pro Glu Gly
            370                 375                 380

Ile Pro Phe Arg Arg Pro Ser Thr Tyr Gly Ile Pro Arg Leu Glu Arg
385                 390                 395                 400

Ile Leu Leu Ala Lys Glu Arg Ile Arg Phe Val Ile Lys Lys His Glu
                405                 410                 415

Leu Leu Asn Ser Thr Arg Glu Asp Leu Gln Leu Asp Lys Pro Ala Ser
                420                 425                 430

Gly Val Lys Glu Glu Trp Tyr Ala Arg Ile Thr Lys Leu Arg Lys Met
                435                 440                 445

Val Asp Gln Leu Phe Cys Lys Lys Phe Ala Glu Ala Leu Gly Ser Thr
            450                 455                 460

Glu Ala Lys Ala Val Pro Tyr Gln Lys Phe Glu Ala His Pro Asn Asp
465                 470                 475                 480

Leu Tyr Val Glu Gly Leu Pro Glu Asn Ile Pro Phe Arg Ser Pro Ser
                485                 490                 495

Trp Tyr Gly Ile Pro Arg Leu Glu Lys Ile Ile Gln Val Gly Asn Arg
                500                 505                 510

Ile Lys Phe Val Ile Lys Arg Pro Glu Leu Leu Thr His Ser Thr Thr
            515                 520                 525

Glu Val Thr Gln Pro Arg Thr Asn Thr Pro Val Lys Glu Asp Trp Asn
            530                 535                 540

Val Arg Ile Thr Lys Leu Arg Lys Gln Val Glu Glu Ile Phe Asn Leu
545                 550                 555                 560

Lys Phe Ala Gln Ala Leu Gly Leu Thr Glu Ala Val Lys Val Pro Tyr
                565                 570                 575

Pro Val Phe Glu Ser Asn Pro Glu Phe Leu Tyr Val Glu Gly Leu Pro
            580                 585                 590

Glu Gly Ile Pro Phe Arg Ser Pro Thr Trp Phe Gly Ile Pro Arg Leu
            595                 600                 605

Glu Arg Ile Val Arg Gly Ser Asn Lys Ile Lys Phe Val Val Lys Lys
            610                 615                 620

Pro Glu Leu Val Ile Ser Tyr Leu Pro Pro Gly Met Ala Ser Lys Ile
625                 630                 635                 640

Asn Thr Lys Ala Leu Gln Ser Pro Lys Arg Pro Arg Ser Pro Gly Ser
                645                 650                 655

Asn Ser Lys Val Pro Glu Ile Glu Val Thr Val Glu Gly Pro Asn Asn
                660                 665                 670
```

```
Asn Asn Pro Gln Thr Ser Ala Val Arg Thr Pro Thr Gln Thr Asn Gly
            675                 680                 685

Ser Asn Val Pro Phe Lys Pro Arg Gly Arg Glu Phe Ser Phe Glu Ala
        690                 695                 700

Trp Asn Ala Lys Ile Thr Asp Leu Lys Gln Lys Val Glu Asn Leu Phe
705                 710                 715                 720

Asn Glu Lys Cys Gly Glu Ala Leu Gly Leu Lys Gln Ala Val Lys Val
                725                 730                 735

Pro Phe Ala Leu Phe Glu Ser Phe Pro Glu Asp Phe Tyr Val Glu Gly
            740                 745                 750

Leu Pro Glu Gly Val Pro Phe Arg Arg Pro Ser Thr Phe Gly Ile Pro
        755                 760                 765

Arg Leu Glu Lys Ile Leu Arg Asn Lys Ala Lys Ile Lys Phe Ile Ile
        770                 775                 780

Lys Lys Pro Glu Met Phe Glu Thr Ala Ile Lys Glu Ser Thr Ser Ser
785                 790                 795                 800

Lys Ser Pro Pro Arg Lys Ile Asn Ser Ser Pro Asn Val Asn Thr Thr
                805                 810                 815

Ala Ser Gly Val Glu Asp Leu Asn Ile Ile Gln Val Thr Ile Pro Asp
            820                 825                 830

Asp Asp Asn Glu Arg Leu Ser Lys Val Glu Lys Ala Arg Gln Leu Arg
        835                 840                 845

Glu Gln Val Asn Asp Leu Phe Ser Arg Lys Phe Gly Glu Ala Ile Gly
        850                 855                 860

Met Gly Phe Pro Val Lys Val Pro Tyr Arg Lys Ile Thr Ile Asn Pro
865                 870                 875                 880

Gly Cys Val Val Val Asp Gly Met Pro Pro Gly Val Ser Phe Lys Ala
                885                 890                 895

Pro Ser Tyr Leu Glu Ile Ser Ser Met Arg Arg Ile Leu Asp Ser Ala
            900                 905                 910

Glu Phe Ile Lys Phe Thr Val Ile Arg Pro Phe Pro Gly Leu Val Ile
        915                 920                 925

Asn Asn Gln Leu Val Asp Gln Ser Glu Ser Glu Gly Pro Val Ile Gln
        930                 935                 940

Glu Ser Ala Glu Pro Ser Gln Leu Glu Val Pro Ala Thr Glu Glu Ile
945                 950                 955                 960

Lys Glu Thr Asp Gly Ser Ser Gln Ile Lys Gln Glu Pro Asp Pro Thr
                965                 970                 975

Trp

<210> SEQ ID NO 32
<211> LENGTH: 978
<212> TYPE: PRT
<213> ORGANISM: Homo sapiens

<400> SEQUENCE: 32

Met Ala Gln Val Ala Met Ser Thr Leu Pro Val Glu Asp Glu Glu Ser
1               5                   10                  15

Ser Glu Ser Arg Met Val Val Thr Phe Leu Met Ser Ala Leu Glu Ser
            20                  25                  30

Met Cys Lys Glu Leu Ala Lys Ser Lys Ala Glu Val Ala Cys Ile Ala
        35                  40                  45

Val Tyr Glu Thr Asp Val Phe Val Val Gly Thr Glu Arg Gly Arg Ala
    50                  55                  60
```

-continued

Phe Val Asn Thr Arg Lys Asp Phe Gln Lys Asp Phe Val Lys Tyr Cys
65                  70                  75                  80

Val Glu Glu Glu Lys Ala Ala Glu Met His Lys Met Lys Ser Thr
            85                  90                  95

Thr Gln Ala Asn Arg Met Ser Val Asp Ala Val Glu Ile Glu Thr Leu
        100                 105                 110

Arg Lys Thr Val Glu Asp Tyr Phe Cys Phe Cys Tyr Gly Lys Ala Leu
        115                 120                 125

Gly Lys Ser Thr Val Val Pro Val Pro Tyr Glu Lys Met Leu Arg Asp
        130                 135                 140

Gln Ser Ala Val Val Gln Gly Leu Pro Glu Gly Val Ala Phe Lys
145                 150                 155                 160

His Pro Glu Asn Tyr Asp Leu Ala Thr Leu Lys Trp Ile Leu Glu Asn
                165                 170                 175

Lys Ala Gly Ile Ser Phe Ile Ile Lys Arg Pro Phe Leu Glu Pro Lys
            180                 185                 190

Lys His Val Gly Gly Arg Val Met Val Thr Asp Ala Asp Arg Ser Ile
        195                 200                 205

Leu Ser Pro Gly Gly Ser Cys Gly Pro Ile Lys Val Lys Thr Glu Pro
210                 215                 220

Thr Glu Asp Ser Gly Ile Ser Leu Glu Met Ala Ala Val Thr Val Lys
225                 230                 235                 240

Glu Glu Ser Glu Asp Pro Asp Tyr Tyr Gln Tyr Asn Ile Gln Gly Ser
            245                 250                 255

His His Ser Ser Glu Gly Asn Glu Gly Thr Glu Met Glu Val Pro Ala
        260                 265                 270

Glu Asp Ser Thr Gln His Val Pro Ser Glu Thr Ser Glu Asp Pro Glu
        275                 280                 285

Val Glu Val Thr Ile Glu Asp Asp Tyr Ser Pro Pro Ser Lys Arg
290                 295                 300

Pro Lys Ala Asn Glu Leu Pro Gln Pro Val Pro Glu Pro Ala Asn
305                 310                 315                 320

Ala Gly Lys Arg Lys Val Arg Glu Phe Asn Phe Glu Lys Trp Asn Ala
            325                 330                 335

Arg Ile Thr Asp Leu Arg Lys Gln Val Glu Glu Leu Phe Glu Arg Lys
        340                 345                 350

Tyr Ala Gln Ala Ile Lys Ala Lys Gly Pro Val Thr Ile Pro Tyr Pro
        355                 360                 365

Leu Phe Gln Ser His Val Glu Asp Leu Tyr Val Glu Gly Leu Pro Glu
    370                 375                 380

Gly Ile Pro Phe Arg Arg Pro Ser Thr Tyr Gly Ile Pro Arg Leu Glu
385                 390                 395                 400

Arg Ile Leu Leu Ala Lys Glu Arg Ile Arg Phe Val Ile Lys Lys His
            405                 410                 415

Glu Leu Leu Asn Ser Thr Arg Glu Asp Leu Gln Leu Asp Lys Pro Ala
        420                 425                 430

Ser Gly Val Lys Glu Glu Trp Tyr Ala Arg Ile Thr Lys Leu Arg Lys
        435                 440                 445

Met Val Asp Gln Leu Phe Cys Lys Lys Phe Ala Glu Ala Leu Gly Ser
    450                 455                 460

Thr Glu Ala Lys Ala Val Pro Tyr Gln Lys Phe Glu Ala His Pro Asn
465                 470                 475                 480

Asp Leu Tyr Val Glu Gly Leu Pro Glu Asn Ile Pro Phe Arg Ser Pro

```
                485             490             495
Ser Trp Tyr Gly Ile Pro Arg Leu Glu Lys Ile Ile Gln Val Gly Asn
                500             505             510

Arg Ile Lys Phe Val Ile Lys Arg Pro Glu Leu Leu Thr His Ser Thr
            515             520             525

Thr Glu Val Thr Gln Pro Arg Thr Asn Thr Pro Val Lys Glu Asp Trp
        530             535             540

Asn Val Arg Ile Thr Lys Leu Arg Lys Gln Val Glu Glu Ile Phe Asn
545             550             555             560

Leu Lys Phe Ala Gln Ala Leu Gly Leu Thr Glu Ala Val Lys Val Pro
                565             570             575

Tyr Pro Val Phe Glu Ser Asn Pro Glu Phe Leu Tyr Val Glu Gly Leu
            580             585             590

Pro Glu Gly Ile Pro Phe Arg Ser Pro Thr Trp Phe Gly Ile Pro Arg
        595             600             605

Leu Glu Arg Ile Val Arg Gly Ser Asn Lys Ile Lys Phe Val Val Lys
    610             615             620

Lys Pro Glu Leu Val Ile Ser Tyr Leu Pro Pro Gly Met Ala Ser Lys
625             630             635             640

Ile Asn Thr Lys Ala Leu Gln Ser Pro Lys Arg Pro Arg Ser Pro Gly
                645             650             655

Ser Asn Ser Lys Val Pro Glu Ile Glu Val Thr Val Glu Gly Pro Asn
            660             665             670

Asn Asn Asn Pro Gln Thr Ser Ala Val Arg Thr Pro Thr Gln Thr Asn
        675             680             685

Gly Ser Asn Val Pro Phe Lys Pro Arg Gly Arg Glu Phe Ser Phe Glu
    690             695             700

Ala Trp Asn Ala Lys Ile Thr Asp Leu Lys Gln Lys Val Glu Asn Leu
705             710             715             720

Phe Asn Glu Lys Cys Gly Glu Ala Leu Gly Leu Lys Gln Ala Val Lys
                725             730             735

Val Pro Phe Ala Leu Phe Glu Ser Phe Pro Glu Asp Phe Tyr Val Glu
            740             745             750

Gly Leu Pro Glu Gly Val Pro Phe Arg Arg Pro Ser Thr Phe Gly Ile
        755             760             765

Pro Arg Leu Glu Lys Ile Leu Arg Asn Lys Ala Lys Ile Lys Phe Ile
    770             775             780

Ile Lys Lys Pro Glu Met Phe Glu Thr Ala Ile Lys Glu Ser Thr Ser
785             790             795             800

Ser Lys Ser Pro Pro Arg Lys Ile Asn Ser Ser Pro Asn Val Asn Thr
                805             810             815

Thr Ala Ser Gly Val Glu Asp Leu Asn Ile Ile Gln Val Thr Ile Pro
            820             825             830

Asp Asp Asp Asn Glu Arg Leu Ser Lys Val Glu Lys Ala Arg Gln Leu
        835             840             845

Arg Glu Gln Val Asn Asp Leu Phe Ser Arg Lys Phe Gly Glu Ala Ile
    850             855             860

Gly Met Gly Phe Pro Val Lys Val Pro Tyr Arg Lys Ile Thr Ile Asn
865             870             875             880

Pro Gly Cys Val Val Val Asp Gly Met Pro Pro Gly Val Ser Phe Lys
                885             890             895

Ala Pro Ser Tyr Leu Glu Ile Ser Ser Met Arg Arg Ile Leu Asp Ser
            900             905             910
```

```
Ala Glu Phe Ile Lys Phe Thr Val Ile Arg Pro Phe Pro Gly Leu Val
            915                 920                 925

Ile Asn Asn Gln Leu Val Asp Gln Ser Glu Ser Glu Gly Pro Val Ile
        930                 935                 940

Gln Glu Ser Ala Glu Pro Ser Gln Leu Glu Val Pro Ala Thr Glu Glu
945                 950                 955                 960

Ile Lys Glu Thr Asp Gly Ser Ser Gln Ile Lys Gln Glu Pro Asp Pro
                965                 970                 975

Thr Trp

<210> SEQ ID NO 33
<211> LENGTH: 998
<212> TYPE: PRT
<213> ORGANISM: Homo sapiens

<400> SEQUENCE: 33

Met Ala Gln Val Ala Met Ser Thr Leu Pro Val Glu Asp Glu Glu Ser
1               5                   10                  15

Ser Glu Ser Arg Met Val Val Thr Phe Leu Met Ser Ala Leu Glu Ser
                20                  25                  30

Met Cys Lys Glu Leu Ala Lys Ser Lys Ala Glu Val Ala Cys Ile Ala
            35                  40                  45

Val Tyr Glu Thr Asp Val Phe Val Gly Thr Glu Arg Gly Arg Ala
50                  55                  60

Phe Val Asn Thr Arg Lys Asp Phe Gln Lys Asp Phe Val Lys Tyr Cys
65                  70                  75                  80

Val Glu Glu Glu Glu Lys Ala Ala Glu Met His Lys Met Lys Ser Thr
                85                  90                  95

Thr Gln Ala Asn Arg Met Ser Val Asp Ala Val Glu Ile Glu Thr Leu
            100                 105                 110

Arg Lys Thr Val Glu Asp Tyr Phe Cys Phe Cys Tyr Gly Lys Ala Leu
        115                 120                 125

Gly Lys Ser Thr Val Val Pro Val Pro Tyr Glu Lys Met Leu Arg Asp
130                 135                 140

Gln Ser Ala Val Val Val Gln Gly Leu Pro Glu Gly Val Ala Phe Lys
145                 150                 155                 160

His Pro Glu Asn Tyr Asp Leu Ala Thr Leu Lys Trp Ile Leu Glu Asn
                165                 170                 175

Lys Ala Gly Ile Ser Phe Ile Ile Lys Arg Pro Phe Leu Glu Pro Lys
            180                 185                 190

Lys His Val Gly Gly Arg Val Met Val Thr Asp Ala Asp Arg Ser Ile
        195                 200                 205

Leu Ser Pro Gly Gly Ser Cys Gly Pro Ile Lys Val Lys Thr Glu Pro
210                 215                 220

Thr Glu Asp Ser Gly Ile Ser Leu Glu Met Ala Ala Val Thr Val Lys
225                 230                 235                 240

Glu Glu Ser Glu Asp Pro Asp Tyr Tyr Gln Tyr Asn Ile Gln Ala Gly
                245                 250                 255

Pro Ser Glu Thr Asp Asp Val Asp Lys Gln Pro Leu Ser Lys Pro
            260                 265                 270

Leu Gln Gly Ser His His Ser Ser Glu Gly Asn Glu Gly Thr Glu Met
        275                 280                 285

Glu Val Pro Ala Glu Asp Ser Thr Gln His Val Pro Ser Glu Thr Ser
290                 295                 300
```

```
Glu Asp Pro Glu Val Glu Val Thr Ile Glu Asp Asp Tyr Ser Pro
305                 310                 315                 320

Pro Ser Lys Arg Pro Lys Ala Asn Glu Leu Pro Gln Pro Pro Val Pro
            325                 330                 335

Glu Pro Ala Asn Ala Gly Lys Arg Lys Val Arg Glu Phe Asn Phe Glu
            340                 345                 350

Lys Trp Asn Ala Arg Ile Thr Asp Leu Arg Lys Gln Val Glu Glu Leu
            355                 360                 365

Phe Glu Arg Lys Tyr Ala Gln Ala Ile Lys Ala Lys Gly Pro Val Thr
370                 375                 380

Ile Pro Tyr Pro Leu Phe Gln Ser His Val Glu Asp Leu Tyr Val Glu
385                 390                 395                 400

Gly Leu Pro Glu Gly Ile Pro Phe Arg Arg Pro Ser Thr Tyr Gly Ile
            405                 410                 415

Pro Arg Leu Glu Arg Ile Leu Leu Ala Lys Glu Arg Ile Arg Phe Val
            420                 425                 430

Ile Lys Lys His Glu Leu Leu Asn Ser Thr Arg Glu Asp Leu Gln Leu
            435                 440                 445

Asp Lys Pro Ala Ser Gly Val Lys Glu Glu Trp Tyr Ala Arg Ile Thr
450                 455                 460

Lys Leu Arg Lys Met Val Asp Gln Leu Phe Cys Lys Lys Phe Ala Glu
465                 470                 475                 480

Ala Leu Gly Ser Thr Glu Ala Lys Ala Val Pro Tyr Gln Lys Phe Glu
            485                 490                 495

Ala His Pro Asn Asp Leu Tyr Val Glu Gly Leu Pro Glu Asn Ile Pro
            500                 505                 510

Phe Arg Ser Pro Ser Trp Tyr Gly Ile Pro Arg Leu Glu Lys Ile Ile
            515                 520                 525

Gln Val Gly Asn Arg Ile Lys Phe Val Ile Lys Arg Pro Glu Leu Leu
            530                 535                 540

Thr His Ser Thr Thr Glu Val Thr Gln Pro Arg Thr Asn Thr Pro Val
545                 550                 555                 560

Lys Glu Asp Trp Asn Val Arg Ile Thr Lys Leu Arg Lys Gln Val Glu
            565                 570                 575

Glu Ile Phe Asn Leu Lys Phe Ala Gln Ala Leu Gly Leu Thr Glu Ala
            580                 585                 590

Val Lys Val Pro Tyr Pro Val Phe Glu Ser Asn Pro Glu Phe Leu Tyr
            595                 600                 605

Val Glu Gly Leu Pro Glu Gly Ile Pro Phe Arg Ser Pro Thr Trp Phe
610                 615                 620

Gly Ile Pro Arg Leu Glu Arg Ile Val Arg Gly Ser Asn Lys Ile Lys
625                 630                 635                 640

Phe Val Val Lys Lys Pro Glu Leu Val Ile Ser Tyr Leu Pro Pro Gly
            645                 650                 655

Met Ala Ser Lys Ile Asn Thr Lys Ala Leu Gln Ser Pro Lys Arg Pro
            660                 665                 670

Arg Ser Pro Gly Ser Asn Ser Lys Val Pro Glu Ile Glu Val Thr Val
            675                 680                 685

Glu Gly Pro Asn Asn Asn Asn Pro Gln Thr Ser Ala Val Arg Thr Pro
            690                 695                 700

Thr Gln Thr Asn Gly Ser Asn Val Pro Phe Lys Pro Arg Gly Arg Glu
705                 710                 715                 720
```

-continued

Phe Ser Phe Glu Ala Trp Asn Ala Lys Ile Thr Asp Leu Lys Gln Lys
            725                 730                 735

Val Glu Asn Leu Phe Asn Glu Lys Cys Gly Glu Ala Leu Gly Leu Lys
        740                 745                 750

Gln Ala Val Lys Val Pro Phe Ala Leu Phe Glu Ser Phe Pro Glu Asp
    755                 760                 765

Phe Tyr Val Glu Gly Leu Pro Glu Gly Val Pro Phe Arg Arg Pro Ser
770                 775                 780

Thr Phe Gly Ile Pro Arg Leu Glu Lys Ile Leu Arg Asn Lys Ala Lys
785                 790                 795                 800

Ile Lys Phe Ile Ile Lys Lys Pro Glu Met Phe Glu Thr Ala Ile Lys
                805                 810                 815

Glu Ser Thr Ser Ser Lys Ser Pro Pro Arg Lys Ile Asn Ser Ser Pro
            820                 825                 830

Asn Val Asn Thr Thr Ala Ser Gly Val Glu Asp Leu Asn Ile Ile Gln
        835                 840                 845

Val Thr Ile Pro Asp Asp Asp Asn Glu Arg Leu Ser Lys Val Glu Lys
    850                 855                 860

Ala Arg Gln Leu Arg Glu Gln Val Asn Asp Leu Phe Ser Arg Lys Phe
865                 870                 875                 880

Gly Glu Ala Ile Gly Met Gly Phe Pro Val Lys Val Pro Tyr Arg Lys
                885                 890                 895

Ile Thr Ile Asn Pro Gly Cys Val Val Val Asp Gly Met Pro Pro Gly
            900                 905                 910

Val Ser Phe Lys Ala Pro Ser Tyr Leu Glu Ile Ser Ser Met Arg Arg
        915                 920                 925

Ile Leu Asp Ser Ala Glu Phe Ile Lys Phe Thr Val Ile Arg Pro Phe
    930                 935                 940

Pro Gly Leu Val Ile Asn Asn Gln Leu Val Asp Gln Ser Glu Ser Glu
945                 950                 955                 960

Gly Pro Val Ile Gln Glu Ser Ala Glu Pro Ser Gln Leu Glu Val Pro
                965                 970                 975

Ala Thr Glu Glu Ile Lys Glu Thr Asp Gly Ser Ser Gln Ile Lys Gln
            980                 985                 990

Glu Pro Asp Pro Thr Trp
        995

<210> SEQ ID NO 34
<211> LENGTH: 957
<212> TYPE: PRT
<213> ORGANISM: Homo sapiens

<400> SEQUENCE: 34

Met Ala Gln Val Ala Met Ser Thr Leu Pro Val Glu Asp Glu Glu Ser
1               5                   10                  15

Ser Glu Ser Arg Met Val Val Thr Phe Leu Met Ser Ala Leu Glu Ser
                20                  25                  30

Met Cys Lys Glu Leu Ala Lys Ser Lys Ala Glu Val Ala Cys Ile Ala
            35                  40                  45

Val Tyr Glu Thr Asp Val Phe Val Gly Thr Glu Arg Gly Arg Ala
    50                  55                  60

Phe Val Asn Thr Arg Lys Asp Phe Gln Lys Asp Phe Val Lys Tyr Cys
65                  70                  75                  80

Val Glu Glu Glu Glu Lys Ala Ala Glu Met His Lys Met Lys Ser Thr
                85                  90                  95

```
Thr Gln Ala Asn Arg Met Ser Val Asp Ala Val Glu Ile Glu Thr Leu
            100                 105                 110

Arg Lys Thr Val Glu Asp Tyr Phe Cys Phe Cys Tyr Gly Lys Ala Leu
            115                 120                 125

Gly Lys Ser Thr Val Val Pro Val Pro Tyr Glu Lys Met Leu Arg Asp
            130                 135                 140

Gln Ser Ala Val Val Gln Gly Leu Pro Glu Gly Val Ala Phe Lys
145                 150                 155                 160

His Pro Glu Asn Tyr Asp Leu Ala Thr Leu Lys Trp Ile Leu Glu Asn
                165                 170                 175

Lys Ala Gly Ile Ser Phe Ile Ile Lys Arg Pro Phe Leu Glu Pro Lys
            180                 185                 190

Lys His Val Gly Gly Arg Val Met Val Thr Asp Ala Asp Arg Ser Ile
            195                 200                 205

Leu Ser Pro Gly Gly Ser Cys Gly Pro Ile Lys Val Lys Thr Glu Pro
    210                 215                 220

Thr Glu Asp Ser Gly Ile Ser Leu Glu Met Ala Ala Val Thr Val Lys
225                 230                 235                 240

Glu Glu Ser Glu Asp Pro Asp Tyr Tyr Gln Tyr Asn Ile Gln Gly Ser
                245                 250                 255

His His Ser Ser Glu Gly Asn Glu Gly Thr Glu Met Glu Val Pro Ala
            260                 265                 270

Glu Asp Asp Asp Tyr Ser Pro Pro Ser Lys Arg Pro Lys Ala Asn Glu
            275                 280                 285

Leu Pro Gln Pro Pro Val Pro Glu Pro Ala Asn Ala Gly Lys Arg Lys
    290                 295                 300

Val Arg Glu Phe Asn Phe Glu Lys Trp Asn Ala Arg Ile Thr Asp Leu
305                 310                 315                 320

Arg Lys Gln Val Glu Glu Leu Phe Glu Arg Lys Tyr Ala Gln Ala Ile
                325                 330                 335

Lys Ala Lys Gly Pro Val Thr Ile Pro Tyr Pro Leu Phe Gln Ser His
            340                 345                 350

Val Glu Asp Leu Tyr Val Glu Gly Leu Pro Glu Gly Ile Pro Phe Arg
            355                 360                 365

Arg Pro Ser Thr Tyr Gly Ile Pro Arg Leu Glu Arg Ile Leu Leu Ala
    370                 375                 380

Lys Glu Arg Ile Arg Phe Val Ile Lys Lys His Glu Leu Leu Asn Ser
385                 390                 395                 400

Thr Arg Glu Asp Leu Gln Leu Asp Lys Pro Ala Ser Gly Val Lys Glu
                405                 410                 415

Glu Trp Tyr Ala Arg Ile Thr Lys Leu Arg Lys Met Val Asp Gln Leu
            420                 425                 430

Phe Cys Lys Lys Phe Ala Glu Ala Leu Gly Ser Thr Glu Ala Lys Ala
            435                 440                 445

Val Pro Tyr Gln Lys Phe Glu Ala His Pro Asn Asp Leu Tyr Val Glu
    450                 455                 460

Gly Leu Pro Glu Asn Ile Pro Phe Arg Ser Pro Ser Trp Tyr Gly Ile
465                 470                 475                 480

Pro Arg Leu Glu Lys Ile Ile Gln Val Gly Asn Arg Ile Lys Phe Val
                485                 490                 495

Ile Lys Arg Pro Glu Leu Leu Thr His Ser Thr Thr Glu Val Thr Gln
            500                 505                 510
```

```
Pro Arg Thr Asn Thr Pro Val Lys Glu Asp Trp Asn Val Arg Ile Thr
            515                 520                 525

Lys Leu Arg Lys Gln Val Glu Glu Ile Phe Asn Leu Lys Phe Ala Gln
    530                 535                 540

Ala Leu Gly Leu Thr Glu Ala Val Lys Val Pro Tyr Pro Val Phe Glu
545                 550                 555                 560

Ser Asn Pro Glu Phe Leu Tyr Val Gly Leu Pro Glu Gly Ile Pro
                565                 570                 575

Phe Arg Ser Pro Thr Trp Phe Gly Ile Pro Arg Leu Glu Arg Ile Val
            580                 585                 590

Arg Gly Ser Asn Lys Ile Lys Phe Val Val Lys Lys Pro Glu Leu Val
    595                 600                 605

Ile Ser Tyr Leu Pro Pro Gly Met Ala Ser Lys Ile Asn Thr Lys Ala
    610                 615                 620

Leu Gln Ser Pro Lys Arg Pro Arg Ser Pro Gly Ser Asn Ser Lys Val
625                 630                 635                 640

Pro Glu Ile Glu Val Thr Val Glu Gly Pro Asn Asn Asn Asn Pro Gln
                645                 650                 655

Thr Ser Ala Val Arg Thr Pro Thr Gln Thr Asn Gly Ser Asn Val Pro
            660                 665                 670

Phe Lys Pro Arg Gly Arg Glu Phe Ser Phe Glu Ala Trp Asn Ala Lys
    675                 680                 685

Ile Thr Asp Leu Lys Gln Lys Val Glu Asn Leu Phe Asn Glu Lys Cys
    690                 695                 700

Gly Glu Ala Leu Gly Leu Lys Gln Ala Val Lys Val Pro Phe Ala Leu
705                 710                 715                 720

Phe Glu Ser Phe Pro Glu Asp Phe Tyr Val Glu Gly Leu Pro Glu Gly
                725                 730                 735

Val Pro Phe Arg Arg Pro Ser Thr Phe Gly Ile Pro Arg Leu Glu Lys
            740                 745                 750

Ile Leu Arg Asn Lys Ala Lys Ile Lys Phe Ile Ile Lys Lys Pro Glu
    755                 760                 765

Met Phe Glu Thr Ala Ile Lys Glu Ser Thr Ser Ser Lys Ser Pro Pro
770                 775                 780

Arg Lys Ile Asn Ser Ser Pro Asn Val Asn Thr Thr Ala Ser Gly Val
785                 790                 795                 800

Glu Asp Leu Asn Ile Ile Gln Val Thr Ile Pro Asp Asp Asp Asn Glu
                805                 810                 815

Arg Leu Ser Lys Val Glu Lys Ala Arg Gln Leu Arg Glu Gln Val Asn
            820                 825                 830

Asp Leu Phe Ser Arg Lys Phe Gly Glu Ala Ile Gly Met Gly Phe Pro
    835                 840                 845

Val Lys Val Pro Tyr Arg Lys Ile Thr Ile Asn Pro Gly Cys Val Val
850                 855                 860

Val Asp Gly Met Pro Pro Gly Val Ser Phe Lys Ala Pro Ser Tyr Leu
865                 870                 875                 880

Glu Ile Ser Ser Met Arg Arg Ile Leu Asp Ser Ala Glu Phe Ile Lys
                885                 890                 895

Phe Thr Val Ile Arg Pro Phe Pro Gly Leu Val Ile Asn Asn Gln Leu
            900                 905                 910

Val Asp Gln Ser Glu Ser Glu Gly Pro Val Ile Gln Glu Ser Ala Glu
    915                 920                 925

Pro Ser Gln Leu Glu Val Pro Ala Thr Glu Glu Ile Lys Glu Thr Asp
```

```
              930                 935                 940
Gly Ser Ser Gln Ile Lys Gln Glu Pro Asp Pro Thr Trp
945                 950                 955
```

<210> SEQ ID NO 35
<211> LENGTH: 976
<212> TYPE: PRT
<213> ORGANISM: Homo sapiens

<400> SEQUENCE: 35

```
Met Ala Gln Val Ala Met Ser Thr Leu Pro Val Asp Glu Glu Ser
1               5                   10                  15

Ser Glu Ser Arg Met Val Val Thr Phe Leu Met Ser Ala Leu Glu Ser
                20                  25                  30

Met Cys Lys Glu Leu Ala Lys Ser Lys Ala Glu Val Ala Cys Ile Ala
            35                  40                  45

Val Tyr Glu Thr Asp Val Phe Val Val Gly Thr Glu Arg Gly Arg Ala
        50                  55                  60

Phe Val Asn Thr Arg Lys Asp Phe Gln Lys Asp Phe Val Lys Tyr Cys
65                  70                  75                  80

Val Glu Glu Glu Lys Ala Ala Glu Met His Lys Met Lys Ser Thr
                85                  90                  95

Thr Gln Ala Asn Arg Met Ser Val Asp Ala Val Glu Ile Glu Thr Leu
            100                 105                 110

Arg Lys Thr Val Glu Asp Tyr Phe Cys Phe Cys Tyr Gly Lys Ala Leu
        115                 120                 125

Gly Lys Ser Thr Val Val Pro Val Pro Tyr Glu Lys Met Leu Arg Asp
    130                 135                 140

Gln Ser Ala Val Val Val Gln Gly Leu Pro Glu Gly Val Ala Phe Lys
145                 150                 155                 160

His Pro Glu Asn Tyr Asp Leu Ala Thr Leu Lys Trp Ile Leu Glu Asn
                165                 170                 175

Lys Ala Gly Ile Ser Phe Ile Ile Lys Arg Pro Phe Leu Glu Pro Lys
            180                 185                 190

Lys His Val Gly Gly Arg Val Met Val Thr Asp Ala Asp Arg Ser Ile
        195                 200                 205

Leu Ser Pro Gly Gly Ser Cys Gly Pro Ile Lys Val Lys Thr Glu Pro
    210                 215                 220

Thr Glu Asp Ser Gly Ile Ser Leu Glu Met Ala Ala Val Thr Val Lys
225                 230                 235                 240

Glu Glu Ser Glu Asp Pro Asp Tyr Tyr Gln Tyr Asn Ile Gln Gly Pro
                245                 250                 255

Ser Glu Thr Asp Asp Val Asp Lys Gln Pro Leu Ser Lys Pro Leu
            260                 265                 270

Gln Gly Ser His His Ser Ser Glu Gly Asn Glu Gly Thr Glu Met Glu
        275                 280                 285

Val Pro Ala Glu Asp Asp Tyr Ser Pro Ser Lys Arg Pro Lys
    290                 295                 300

Ala Asn Glu Leu Pro Gln Pro Val Pro Glu Pro Ala Asn Ala Gly
305                 310                 315                 320

Lys Arg Lys Val Arg Glu Phe Asn Phe Glu Lys Trp Asn Ala Arg Ile
                325                 330                 335

Thr Asp Leu Arg Lys Gln Val Glu Glu Leu Phe Glu Arg Lys Tyr Ala
            340                 345                 350
```

-continued

```
Gln Ala Ile Lys Ala Lys Gly Pro Val Thr Ile Pro Tyr Pro Leu Phe
            355                 360                 365
Gln Ser His Val Glu Asp Leu Tyr Val Glu Gly Leu Pro Glu Gly Ile
        370                 375                 380
Pro Phe Arg Arg Pro Ser Thr Tyr Gly Ile Pro Arg Leu Glu Arg Ile
385                 390                 395                 400
Leu Leu Ala Lys Glu Arg Ile Arg Phe Val Ile Lys Lys His Glu Leu
                405                 410                 415
Leu Asn Ser Thr Arg Glu Asp Leu Gln Leu Asp Lys Pro Ala Ser Gly
            420                 425                 430
Val Lys Glu Glu Trp Tyr Ala Arg Ile Thr Lys Leu Arg Lys Met Val
        435                 440                 445
Asp Gln Leu Phe Cys Lys Lys Phe Ala Glu Ala Leu Gly Ser Thr Glu
450                 455                 460
Ala Lys Ala Val Pro Tyr Gln Lys Phe Glu Ala His Pro Asn Asp Leu
465                 470                 475                 480
Tyr Val Glu Gly Leu Pro Glu Asn Ile Pro Phe Arg Ser Pro Ser Trp
                485                 490                 495
Tyr Gly Ile Pro Arg Leu Glu Lys Ile Ile Gln Val Gly Asn Arg Ile
            500                 505                 510
Lys Phe Val Ile Lys Arg Pro Glu Leu Leu Thr His Ser Thr Thr Glu
        515                 520                 525
Val Thr Gln Pro Arg Thr Asn Thr Pro Val Lys Glu Asp Trp Asn Val
    530                 535                 540
Arg Ile Thr Lys Leu Arg Lys Gln Val Glu Glu Ile Phe Asn Leu Lys
545                 550                 555                 560
Phe Ala Gln Ala Leu Gly Leu Thr Glu Ala Val Lys Val Pro Tyr Pro
                565                 570                 575
Val Phe Glu Ser Asn Pro Glu Phe Leu Tyr Val Glu Gly Leu Pro Glu
            580                 585                 590
Gly Ile Pro Phe Arg Ser Pro Thr Trp Phe Gly Ile Pro Arg Leu Glu
        595                 600                 605
Arg Ile Val Arg Gly Ser Asn Lys Ile Lys Phe Val Val Lys Lys Pro
    610                 615                 620
Glu Leu Val Ile Ser Tyr Leu Pro Pro Gly Met Ala Ser Lys Ile Asn
625                 630                 635                 640
Thr Lys Ala Leu Gln Ser Pro Lys Arg Pro Arg Ser Pro Gly Ser Asn
                645                 650                 655
Ser Lys Val Pro Glu Ile Glu Val Thr Val Glu Gly Pro Asn Asn Asn
            660                 665                 670
Asn Pro Gln Thr Ser Ala Val Arg Thr Pro Thr Gln Thr Asn Gly Ser
        675                 680                 685
Asn Val Pro Phe Lys Pro Arg Gly Arg Glu Phe Ser Phe Glu Ala Trp
    690                 695                 700
Asn Ala Lys Ile Thr Asp Leu Lys Gln Lys Val Glu Asn Leu Phe Asn
705                 710                 715                 720
Glu Lys Cys Gly Glu Ala Leu Gly Leu Lys Gln Ala Val Lys Val Pro
                725                 730                 735
Phe Ala Leu Phe Glu Ser Phe Pro Glu Asp Phe Tyr Val Glu Gly Leu
            740                 745                 750
Pro Glu Gly Val Pro Phe Arg Arg Pro Ser Thr Phe Gly Ile Pro Arg
        755                 760                 765
Leu Glu Lys Ile Leu Arg Asn Lys Ala Lys Ile Lys Phe Ile Ile Lys
```

```
                770              775              780
Lys Pro Glu Met Phe Glu Thr Ala Ile Lys Glu Ser Thr Ser Ser Lys
785              790              795              800

Ser Pro Pro Arg Lys Ile Asn Ser Ser Pro Asn Val Asn Thr Thr Ala
            805              810              815

Ser Gly Val Glu Asp Leu Asn Ile Ile Gln Val Thr Ile Pro Asp Asp
            820              825              830

Asp Asn Glu Arg Leu Ser Lys Val Glu Lys Ala Arg Gln Leu Arg Glu
            835              840              845

Gln Val Asn Asp Leu Phe Ser Arg Lys Phe Gly Glu Ala Ile Gly Met
        850              855              860

Gly Phe Pro Val Lys Val Pro Tyr Arg Lys Ile Thr Ile Asn Pro Gly
865              870              875              880

Cys Val Val Val Asp Gly Met Pro Pro Gly Val Ser Phe Lys Ala Pro
            885              890              895

Ser Tyr Leu Glu Ile Ser Ser Met Arg Arg Ile Leu Asp Ser Ala Glu
            900              905              910

Phe Ile Lys Phe Thr Val Ile Arg Pro Phe Pro Gly Leu Val Ile Asn
        915              920              925

Asn Gln Leu Val Asp Gln Ser Glu Ser Glu Gly Pro Val Ile Gln Glu
        930              935              940

Ser Ala Glu Pro Ser Gln Leu Glu Val Pro Ala Thr Glu Glu Ile Lys
945              950              955              960

Glu Thr Asp Gly Ser Ser Gln Ile Lys Gln Glu Pro Asp Pro Thr Trp
                965              970              975
```